(12) United States Patent
Daily et al.

(10) Patent No.: US 10,451,625 B2
(45) Date of Patent: Oct. 22, 2019

(54) METHODS OF DETECTING CANCER

(71) Applicant: Ascendant Diagnostics, LLC, Springdale, AR (US)

(72) Inventors: Anna Daily, Fayetteville, AR (US); Lindsay Rutherford, Fayetteville, AR (US)

(73) Assignee: Ascendant Diagnostics, LLC, Springdale, AR (US)

( * ) Notice: Subject to any disclaimer, the term of this patent is extended or adjusted under 35 U.S.C. 154(b) by 0 days.

(21) Appl. No.: 14/879,982

(22) Filed: Oct. 9, 2015

(65) Prior Publication Data

US 2016/0161492 A1    Jun. 9, 2016

Related U.S. Application Data

(63) Continuation-in-part of application No. 14/707,089, filed on May 8, 2015.

(60) Provisional application No. 62/061,900, filed on Oct. 9, 2014.

(51) Int. Cl.
| | | |
|---|---|---|
| *G01N 33/574* | (2006.01) | |
| *G01N 30/72* | (2006.01) | |
| *C12Q 1/6886* | (2018.01) | |
| *H01J 49/40* | (2006.01) | |
| *H01J 49/00* | (2006.01) | |

(52) U.S. Cl.
CPC ..... *G01N 33/57415* (2013.01); *C12Q 1/6886* (2013.01); *G01N 30/7233* (2013.01); *G01N 33/57488* (2013.01); *G01N 33/57496* (2013.01); *C12Q 2600/158* (2013.01); *H01J 49/00* (2013.01); *H01J 49/40* (2013.01)

(58) Field of Classification Search
None
See application file for complete search history.

(56) References Cited

U.S. PATENT DOCUMENTS

| | | | |
|---|---|---|---|
| 7,662,580 B2 | 2/2010 | Georges et al. | |
| 7,951,529 B2 | 5/2011 | Li | |
| 2004/0029114 A1* | 2/2004 | Mack ............. | C07K 14/47 435/6.14 |
| 2006/0019256 A1* | 1/2006 | Clarke ........... | C12N 5/0695 435/6.14 |
| 2009/0035801 A1 | 2/2009 | Goldknopf et al. | |
| 2009/0215102 A1* | 8/2009 | Moses ............ | C12Q 1/37 435/23 |
| 2010/0190656 A1 | 7/2010 | Li | |
| 2011/0212851 A1* | 9/2011 | Wong ............. | C12Q 1/6886 506/9 |
| 2012/0183555 A1* | 7/2012 | Chang ............ | C07K 14/4748 424/139.1 |
| 2014/0186332 A1 | 7/2014 | Ezrin et al. | |
| 2015/0141273 A1* | 5/2015 | Bosch ............ | G01N 33/57419 506/9 |
| 2016/0003786 A1 | 1/2016 | Daily | |

FOREIGN PATENT DOCUMENTS

| | | |
|---|---|---|
| WO | WO1998035229 A1 | 8/1998 |
| WO | WO2001013117 A2 | 2/2001 |
| WO | WO2001071357 A2 | 9/2001 |
| WO | WO2008014458 A2 | 1/2008 |
| WO | WO 2008/054764 A2 | 5/2008 |
| WO | WO 2009/097692 A1 | 8/2009 |
| WO | WO2010053816 A2 | 5/2010 |
| WO | WO 2011/100472 A1 | 8/2011 |
| WO | WO2012116979 A1 | 9/2012 |
| WO | WO2013106913 A1 | 7/2013 |
| WO | WO2013154422 A1 | 10/2013 |
| WO | WO2013186639 A2 | 12/2013 |
| WO | WO 2014/133855 A1 | 9/2014 |

OTHER PUBLICATIONS

Wheelan et al, J Proteome Res 11:5034-5045, 2012.*
Storr et al, Ann Oncol, 23:2289-2296, 2012.*
Opstal-van Winden et al, BMC Cancer, 11:381, 2011.*
Armstrong, K., Handorf, E. A., Chen, J., & Bristol Demeter, M. N. (2013). Breast cancer risk prediction and mammography biopsy decisions: a model-based study. American Journal of Preventive Medicine, 44(1), 15-22. doi:10.1016/j.amepre.2012.10.002.
Böhm, D., Keller, K., Pieter, J., Boehm, N., Wolters, D., Siggelkow, W., et al. (2012). Comparison of tear protein levels in breast cancer patients and healthy controls using a de novo proteomic approach. Oncology Reports, 28(2), 429-438. doi:10.3892/or.2012.1849.
Böhm, D., Keller, K., Wehrwein, N., Lebrecht, A., Schmidt, M., Kölbl, H., & Grus, F.-H. (2011). Serum proteome profiling of primary breast cancer indicates a specific biomarker profile. Oncology Reports, 26(5), 1051-1056. doi:10.3892/or.2011.1420.
Brown, M. L., Houn, F., Sickles, E. A., & Kessler, L. G. (1995). Screening Mammography in Community Practice: Positive Predictive. American Journal of Radiology, 165, 1373-1377.
Grady, D. (2012). Study of Breast Biopsies Finds Surgery Used Too Extensively. New York Times, 1-4.
Kolb, T., Lichy, J., & Newhouse, J. (2002). Comparison of the performance of screening mammography, physical examination, and breast US and evaluation of factors that influence them: an analysis of 27,825 patient evaluations. Radiology, 225(1), 165-175.

(Continued)

*Primary Examiner* — Mark Halvorson
(74) *Attorney, Agent, or Firm* — Cooley LLP; Michael Rutherford

(57) ABSTRACT

Method and kits for detecting cancer, and in particular breast cancer, in a subject by measuring the levels of at least one of a series of biomarkers, as compared to a control sample lacking cancer. The expression of the biomarker either increases or decreases in samples from subjects with cancer, as compared to the expression level in subjects without cancer. The sample is optimally an ocular sample, such as an isolated tear sample or ocular wash, but can also be from saliva, or other bodily fluid. Kits can include a collection tube and protease inhibitors or protein stabilizers.

11 Claims, 15 Drawing Sheets

Specification includes a Sequence Listing.

(56) References Cited

OTHER PUBLICATIONS

Lebrecht, A., Boehm, D., Schmidt, M., Koelbl, H., & Grus, F. H. (2009a). Surface-enhanced Laser Desorption/Ionisation Time-of-flight Mass Spectrometry to Detect Breast Cancer 30 Markers in Tears and Serum. Cancer Genomics & Proteomics, 6(2), 75-83.
Lebrecht, A., Boehm, D., Schmidt, M., Koelbl, H., Schwirz, R. L., & Grus, F. H. (2009b). Diagnosis of breast cancer by tear proteomic pattern. Cancer Genomics & Proteomics, 6(3), 177-182.
Li, J., Zhang, Z., Rosenzweig, J., Wang, Y., & Chan, D. (2002). Proteomics and bioinformatics approaches for identification of serum biomarkers to detect breast cancer. Clin Chem, 48(8), 1296-1304.
Luftner, D., & Possinger, K. (2002). Nuclear matrix proteins as biomarkers for breast cancer. Expert Rev Mol Diagn, 2(1), 23-31. doi:ERM020106 [pii] 10.1586/14737159.2.1.23.
Schiess, R., Wollscheid, B., & Aebersold, R. (2009). Targeted proteomic strategy for clinical 10 biomarker discovery. Molecular Oncology, 3(1), 33-44. doi:10.1016/j.molonc.2008.12.001.
Wu, K., & Zhang, Y. (2007). Clinical application of tear proteomics: Present and future prospects. Proteomics. Clinical Applications, 1(9), 972-982. doi:10.1002/prca.200700125.
Klifa, C., Carballido-Gamio, J., Wilmes, L., Laprie, A., Shepherd, J., Gibbs, J., Fan, B., Noworolski, S., Hylton, N. (2010) Magnetic resonance imaging for secondary assessment of breast density in a high-risk cohort. Magnetic Resonance Imaging. 28;8-15.
Bigenwald, R.Z., Warner, E., Gunasekara, A., Hill, K.A., Causer, P.A., Messner, S.J., Eisen, A., Plewes, D.B., Narod, S.A., Zhang, L., Yaffe, M.J. (2008) Is Mammography Adequate for Screening Women with Inherited BRCA Mutations and Low Breast Density?. Cancer Epidemiology Biomarkers Prevention. 17(3); 707-711.
Vachon, C.M., van Gils, C. H., Sellers, T.A., Ghosh, K., Pruthi, S., Brandt, K.R., Pankratz, V.S., (2007) Mammographic density, breast cancer risk and risk prediction. Breast Cancer Research 9:2017 (doi:10.1186/bcr1829).
Pisano, E.D., Gatsonis, C., Hendrick E., Yaffe, M., Baum, J.K., Acharyya, S., Conant, E.F. Fajardo, L.L., Bassett, L., D'Orsi, C. Jong, R., Rebner., M. (2005). Diagnostic Performance of Digital versus Film Mammography for Breast-Cancer Screening. The New England Journal of Medicine. 17(353). 1773-1783.
Tabar, L., Vitak, B., Chen, T.H., Yen, A.M., Cohen, A., Tot, T., Chiu, S., Chen, S. Fann, J. Rosell, J., Fohlin, H., Smith, R. A. , Duffy, S.W., (2011) Swedish Two-County Trial: Impact of Mammographic Screening on Breast Cancer Mortality during 3 Decades. Radiology, 3(260), 658-663.
Braun, Michael, et al. "Down-regulation of microfilamental network-associated proteins in leukocytes of breast cancer patients: potential application to predictive diagnosis." Cancer Genomics-Proteomics 6.1: 31-40 (2009).
Cafferey, B.E., "Sjogren's Syndrome: A Clinical and Biochemical Analysis." Thesis 2009; Waterloo, Ontario, Canada, 248 pages.
Cancemi, Patrizia, et al. "Large-scale proteomic identification of S100 proteins in breast cancer tissues." BMC Cancer 10.1: 476 (2010).
Celis, Julio E., et al. "Molecular pathology of breast apocrine carcinomas: a protein expression signature specific for benign apocrine metaplasia." FEBS Letters 580.12: 2935-2944 (2006).
Chen, Xiang, et al. "Comparative profiling of triple-negative breast carcinomas tissue glycoproteome by sequential purification of glycoproteins and stable isotope labeling." Cellular Physiology and Biochemistry 38.1: 110-121 (2016).
Colak, Dilek, et al. "Age-specific gene expression signatures for breast tumors and cross-species conserved potential cancer progression markers in young women." PLOS ONE 8.5: e63204 (2013).
Cross, S. S., et al. "Expression of S100 proteins in normal human tissues and common cancers using tissue microarrays: S100A6, S100A8, S100A9 and S100A11 are all overexpressed in common cancers." Histopathology 46.3: 256-269 (2005).

European Patent Application No. 16168524.3, Extended European Search Report dated Feb. 6, 2017, 22 pages.
European Patent Application No. 16168524.3, Partial European Search Report dated Oct. 24, 2016, 9 pages.
Fusco, Ornella, et al. "90K (MAC-2 BP) gene expression in breast cancer and evidence for the production of 90K by peripheral-blood mononuclear cells." International Journal of Cancer 79.1: 23-26 (1998).
Gunaldi, Meral, et al. "Diagnostic importance of S100A9 and S100A12 in breast cancer." Biomedicine & Pharmacotherapy 76: 52-56 (2015).
Iacobelli, S., et al. "Prognostic value of a novel circulating serum 90K antigen in breast cancer." British Journal of Cancer 69.1: 172-176 (1994).
Kormelink, Tom Groot, et al. "Immunoglobulin free light chains are biomarkers of poor prognosis in basal-like breast cancer and are potential targets in tumor-associated inflammation." Oncotarget 5.10: 3159-3167 (2014).
Koths, K., et al. "Cloning and characterization of a human Mac-2-binding protein, a new member of the superfamily defined by the macrophage scavenger receptor cysteine-rich domain." Journal of Biological Chemistry 268.19: 14245-14249 (1993).
Lee, Han-Byoel, et al. "Development and Validation of a Novel Plasma Protein Signature for Breast Cancer Diagnosis by Using Multiple Reaction Monitoring-based Mass Spectrometry." Anticancer Research 35.11: 6271-6280 (2015).
Seth, Arun, et al. "Gene expression profiling of ductal carcinomas in situ and invasive breast tumors." Anticancer Research 23.3A: 2043-2051 (2002).
Zhang, Lei, et al. "Discovery and preclinical validation of salivary transcriptomic and proteomic biomarkers for the non-invasive detection of breast cancer." PLOS ONE 5.12 : e15573 (2010).
U.S. Appl. No. 14/707,089, Office Action dated Feb. 7, 2017, 10 pages.
Esmaeli, B., et al., "Docetaxel Secretion in Tears Association With Lacrimal Drainage Obstruction." Arch Ophthalmol. (2002); 120(9): 1180-1182.
U.S. Appl. No. 14/707,089, Office Action dated May 26, 2017, 9 pages.
U.S. Appl. No. 14/707,089, Office Action dated Sep. 11, 2017, 10 pages.
Reifenstein, "The Treament of Advanced Endometrial Cancer with Hydroxyprogesterone Caproate," Gynecologic Oncology, vol. 2, pp. 377-414 (1974), 38 pages.
U.S. Appl. No. 14/707,089, Office Action dated Oct. 24, 2018, 14 pages.
Braidotti, et al., "DMBT1 expression is down-regulated in breast cancer." BMC Cancer (2004); 4: 46, 9 pages.
Bundred, et al., "Is apocrine differentiation in breast carcinoma of prognostic significance?" British Journal of Cancer (1990); 62: 113-117.
Catanzaro, et al., "Oncogenic Ras induces inflammatory cytokine production by upregulating the squamous cell carcinoma antigens SerpinB3/B4." Nature Communications (2014); Article Number: 3729 (2014), 12 pages.
Do, et al., "Associations between the Expression of Mucins (MUC1, MUC2, MUC5AC, and MUC6) and Clinicopathologic Parameters of Human Breast Ductal Carcinomas." J Breast Cancer (2013); 16(2) 152-158.
Freije, et al., "Human Zn-$\alpha_2$-glycoprotein cDNA cloning and expression analysis in benign and malignant breast tissues." FEBS Letters (1991); 290(1-2): 247-249.
Plavina et al., "Increased Plasma Concentrations of Cytoskeletal and Ca2+Binding Proteins and Their Peptides in Psoriasis Patients," Clinical Chemistry, vol. 54, No. 11, Nov. 1, 2008 (Nov. 1, 2008), pp. 1805-1814.
Xue, et al., "Zinc-$\alpha$-2-Glycoprotein: A Candidate Biomarker for Colon Cancer Diagnosis in Chinese Population." Int. J. Mol. Sci. (2015), 16(1): 691-703.
U.S. Appl. No. 14/707,089, Office Action dated Mar. 13, 2018, 10 pages.

* cited by examiner

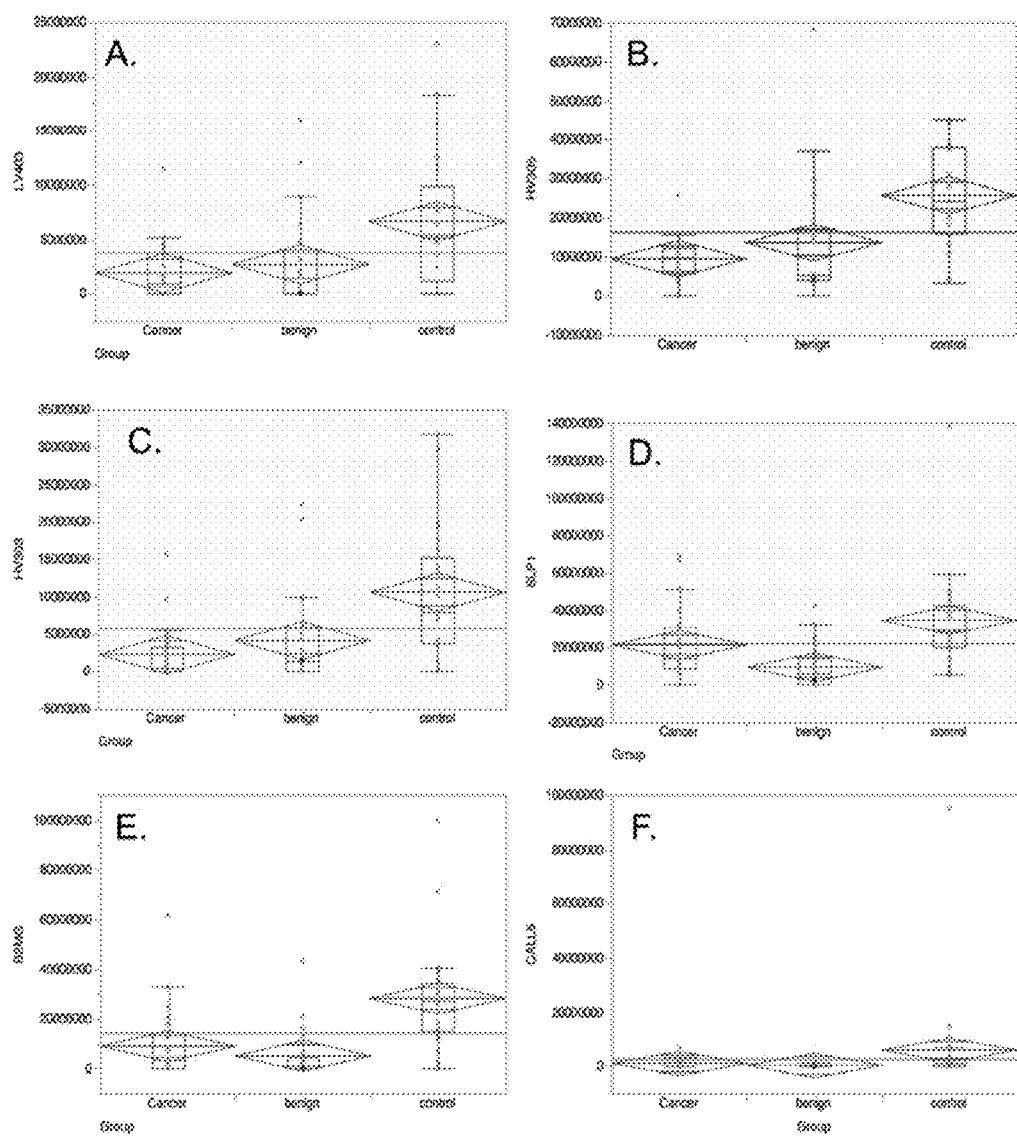

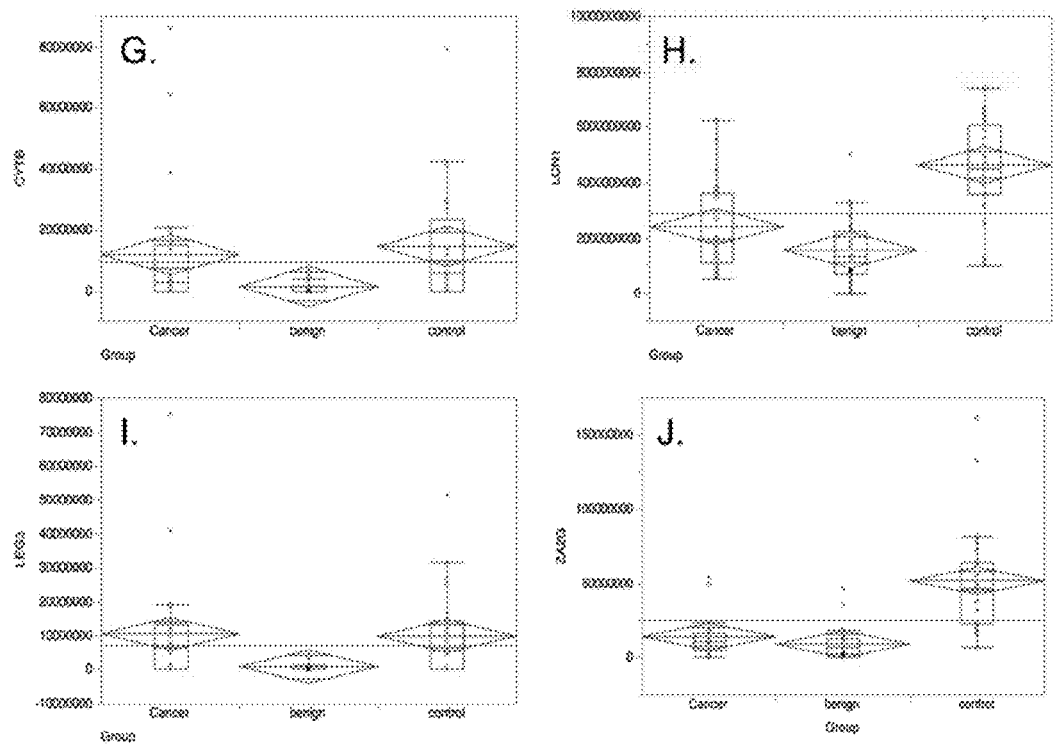
Figure 3 G-J

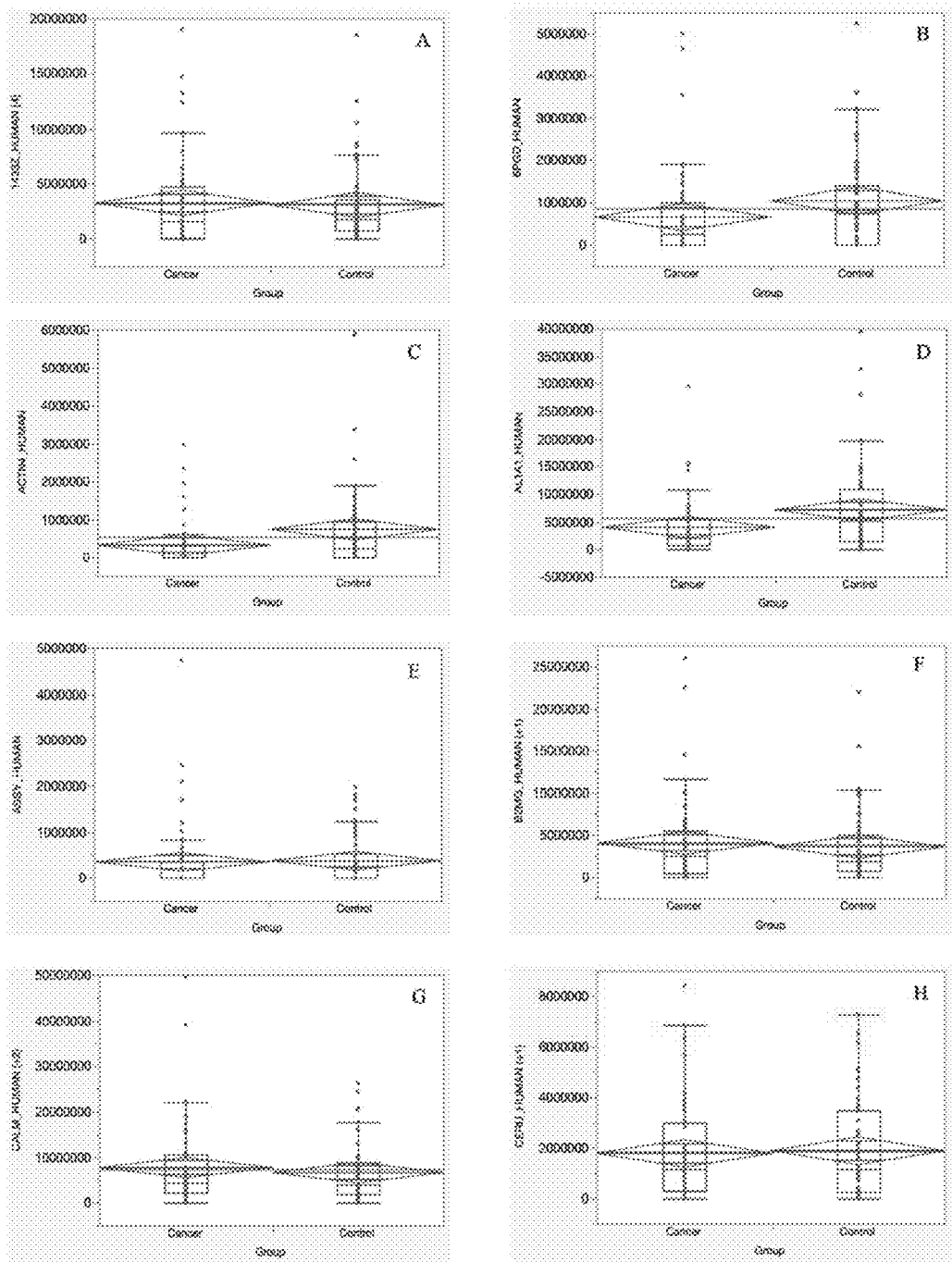
Figure 4 A-H

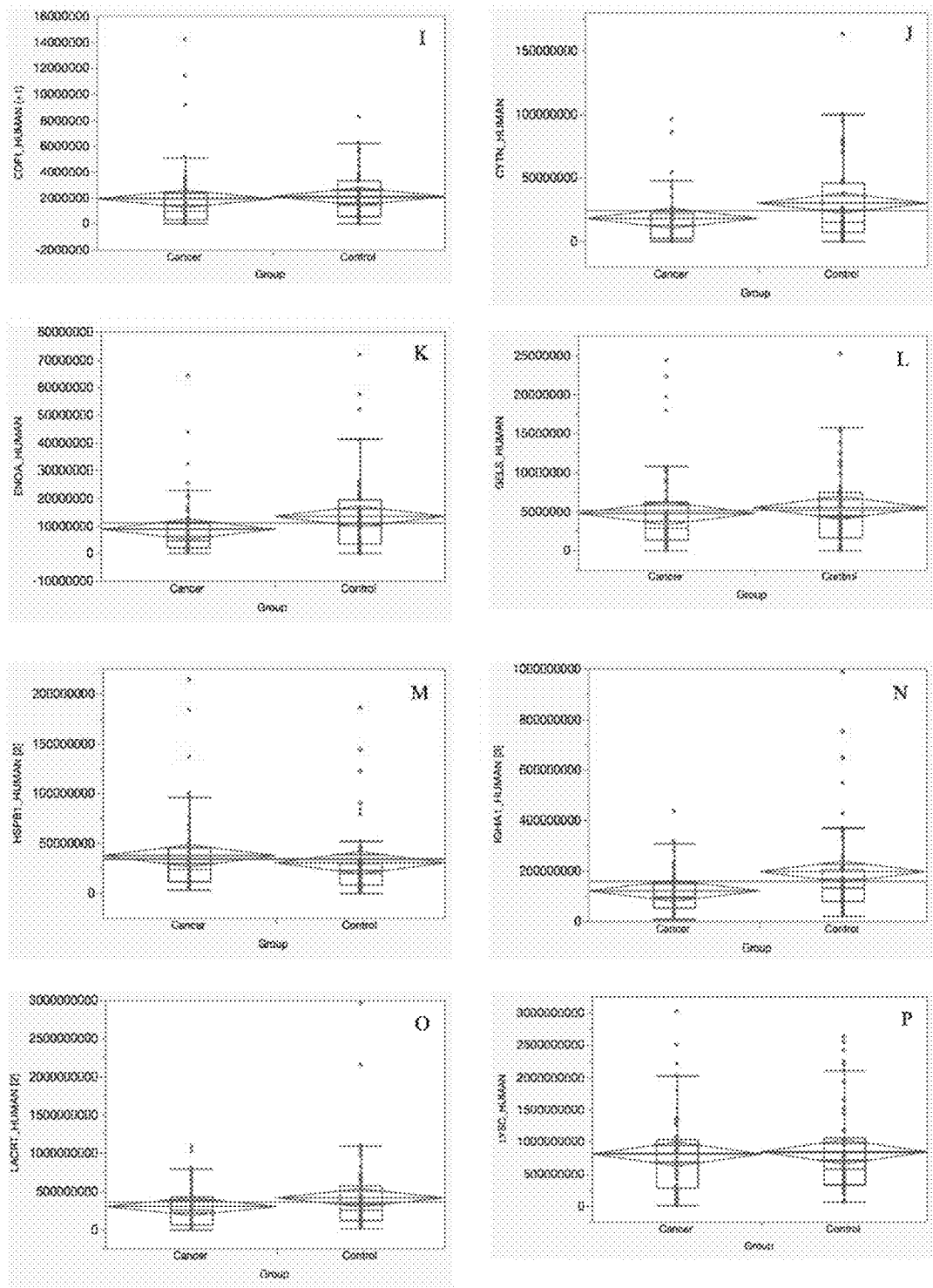
Figure 4 I-P

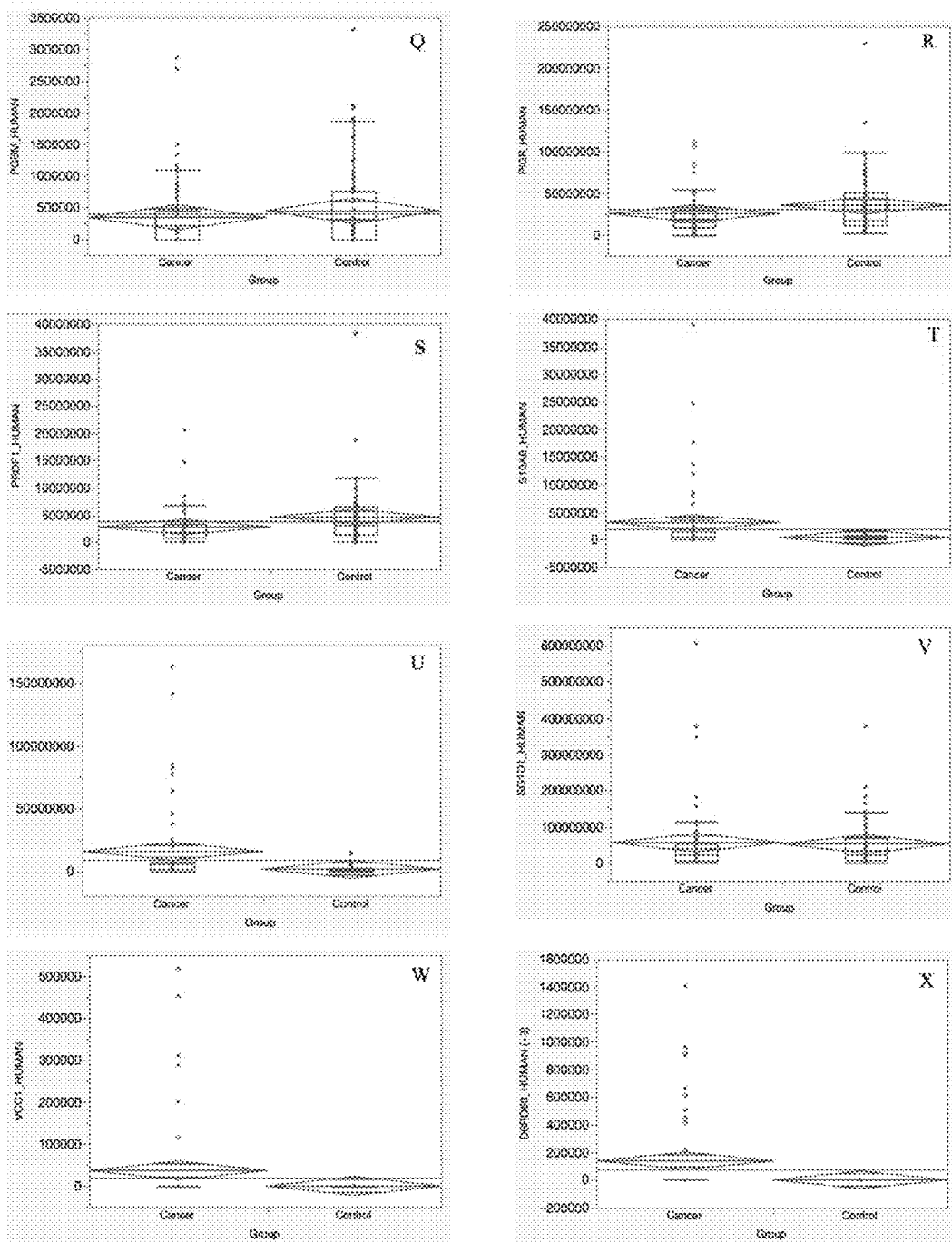

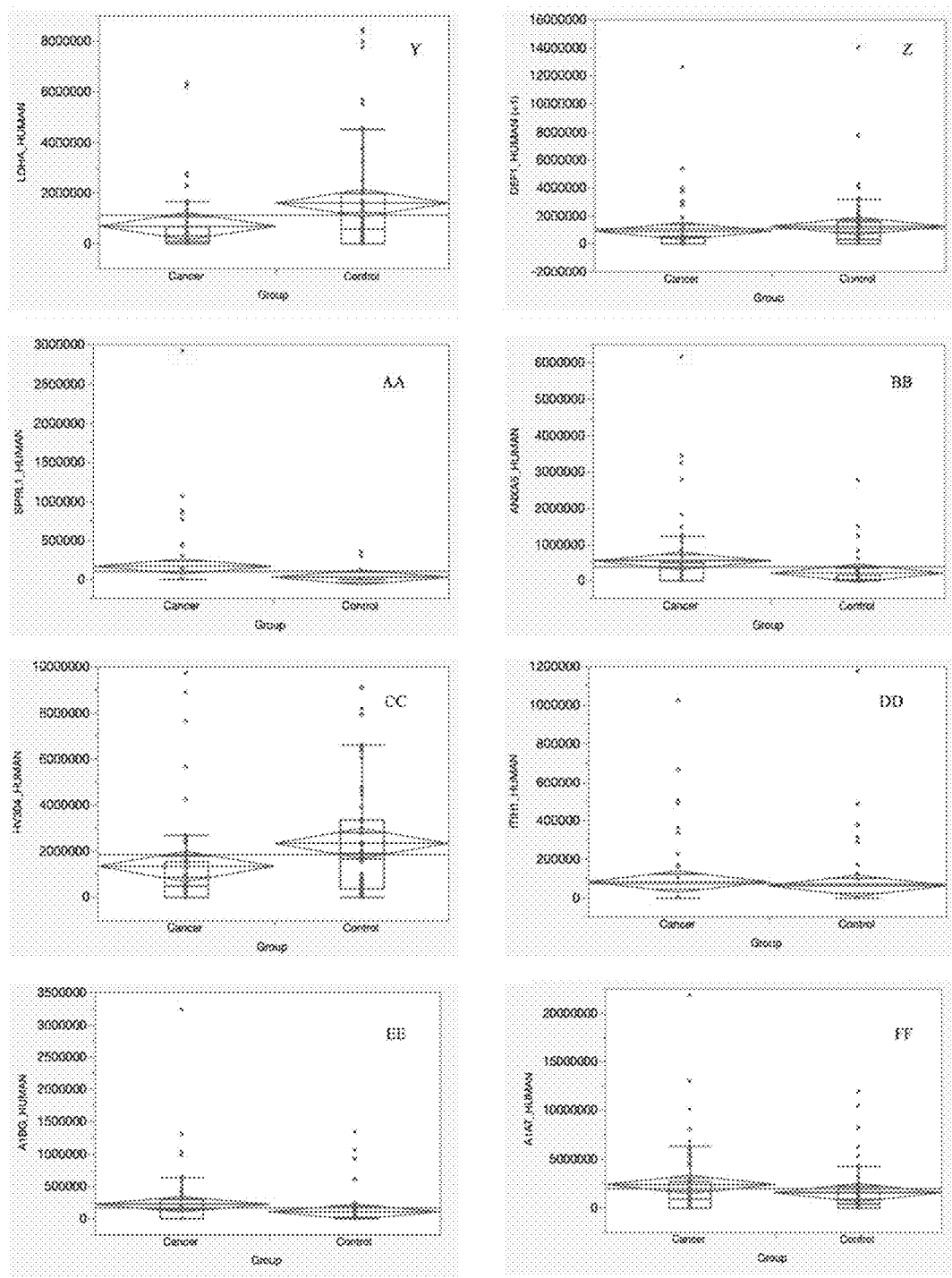
Figure 4 Y-FF

METHODS OF DETECTING CANCER

CROSS REFERENCE TO RELATED APPLICATIONS

This application claims the benefit of U.S. Provisional Patent Application No. 62/061,900, filed on Oct. 9, 2014, which is h ereby incorporated by reference in its entirety. This application claims the benefit as continuation in part to pending U.S. patent application Ser. No. 14/707,089, filed May 8, 2015, which claims priority to U.S. Provisional Application No. 61/991,061 filed May 9, 2014. The disclosures of each of the above-referenced applications are herein incorporated by reference in their entirety.

BACKGROUND

The present application encompasses proteins and peptide fragments of those proteins, which are produced by proteolytic digestion of the proteins, and which both proteins and peptide fragments are useful for diagnosing of cancer or for monitoring for the presence of cancer in an individual.

Screening mammograms typically have a sensitivity of 75% and specificity of around 98% resulting in a false positive rate of roughly 5% per mammogram (Brown, Houn, Sickles, & Kessler, 1995; Kolb, Lichy, & Newhouse, 2002; Luftner & Possinger, 2002). Breast tissue type, more specifically density, also greatly influences the performance of mammography. The degree of breast density is classified using the American College of Radiology Breast Imaging Reporting and Data System (BI-RADS). This system consists of four classifications 1-4; where category 1 is mostly fatty (<25% dense); category 2 is scattered fibroglandular densities (25-50% dense); category 3 is heterogeneously dense (51-75% dense) and category 4 is extremely dense (>75% dense) (Bigenwald, 2008; Klifa, 2010; Scheel, 2014).

For women with fatty breast tissue, mammography can be an effective screening tool, when patients are compliant with yearly screenings (Tabar, 2001; Pisano, 2005). However, as breast density increases, the effectiveness of mammography decreases leading to increased follow up imaging and, more importantly, missed cancer diagnosis. Mammographic sensitivity, for high-risk patients, has been shown to be as low as 31% for category 1, 27% for category 2, 20% for category 3, and 12.5% for category 4 (Bigenwald, 2008). Approximately fifty percent of the female population is in categories 3 and 4, which is considered dense breast tissue (Vachon, 2007). Currently, the best screening option for these women is MRI, which can be up to 10 times more expensive than mammography (Beignwald, 2008). Lack of good screening options is a serious problem as women with 75% or more dense tissue have four to six times greater risk of developing breast cancer than women with less dense tissue (Boyd, 2007).

Follow up imaging to evaluate false positives costs the US over 4 billion dollars with an additional 1.6 billion dollars spent for biopsies alone. In 2010 of the 1.6 million biopsies performed, as few as 16% (only 261,000) were found to have cancer (Grady, 2012). The answer to increasing the diagnostic parameters of imaging can be found in the pre- and post-image diagnostics that focus on genetic and proteomic information, more specifically, biomarkers (Armstrong, Handorf, Chen, & Bristol Demeter, 2013; Li, Zhang, Rosenzweig, Wang, & Chan, 2002).

Tissue and serum are commonly the most logical place for beginning biomarker research, however the large dynamic range of both mediums makes discovery quite difficult (Schiess, Wollscheid, & Aebersold, 2009). The answers may lie in less complex biological fluids, such as saliva and tears. The use of tears as diagnostic medium is not a novel application as the tear proteome has been extensively investigated previously (Böhm et al., 2012; 2011; Lebrecht, Boehm, Schmidt, Koelbl, & Grus, 2009a; Lebrecht et al., 2009b; Wu & Zhang, 2007). In this application a quantitative assay for the detection of a panel of tear-based biomarkers in response to cancer is disclosed. From this quantitative information, the framework for a Certified Laboratory Improvement Amendments (CLIA) protocol will be defined.

SUMMARY

Methods of determining whether a subject has cancer are provided herein. Methods include obtaining a sample from the subject and performing steps of detecting the level of at least one of the markers selected from the following and as listed in Table 1: Ig lambda chain V-IV region Hil (LV403), Ig heavy chain V-III BRO (HV305), Ig heavy chain V-III VH26 (HV303), β-2-microglobulin (B2MG), Lipocalin-1 (LCN1), Zinc-α-2-glycoprotein (ZA2G), Cystatin B (CYTB), Antileukoproteinase (SLP1), Galectin-3 (LEG3), Histidine triad nucleotide-binding protein 1 (D6RD60), S100A9 (S10A9), S100A8 (S10A8), Galectin-3-binding protein (LG3BP), Cluster of Ig alpha-1 chain C region (IGHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (B4E1Z4), Alpha-1-antichymotrypsin (AACT), Superoxide dismutase [Cu—Zn](SODC), SPARC-like protein 1 (SPRL1), Ig heavy chain V-III region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADHIG), Malate dehydrogenase, mitochondrial (MDHM), Calmodulin-like protein 5 (CALL5), Alpha-1-antitrypsin (A1AT), Alpha-1μ-glycoprotein (A1BG), Leucine-rich alpha-2-glycoprotein (A2GL), Small ubiquitin-related modifier 3 (A8MU27), Anterior gradient protein 2 homolog (AGR2), Profilin-1 (PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-I (APOA1), Apolipoprotein A-IV (APOA4), Flavin reductase (NADPH)(BLVRB), Prosaposin (PSAP), Lacritin (LACRT), 60S acidic ribosomal protein P1 (RLA1), Inter-alpha-trypsin inhibitor heavy chain H2 (ITIH2), Mucin-like protein 1 (MUCL1), S100 A6 (S100A6), Na(+)/H(+) exchange regulatory cofactor NHE-RF1 (NHRF1), Thioredoxin domain-containing protein 17 (I3L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-I region EU (KV106), Alcohol dehydrogenase class 4 mu/sigma chain (ADH7), Protein AMBP (AMBP), Angiotensinogen (ANGT), Antithrombin-III (ANT3), Apolipoprotein A-II (APOA2), Calpastatin (B7Z574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), Complement C3 (CO3), Coronin-1A (COR1A), Programmed cell death 6-interacting protein (DCD), Definsin 1 (DEF1), F-box only protein 50 (FBX50), Gamma-glutamylcyclotransferase (GGCT), Glutathione reductase, mitochondrial (GSHR), Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNASET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY). The subject is likely to have cancer if the levels of these markers change in comparison to the levels in a control sample from a subject lacking cancer. The sample is optimally an ocular sample, such as an isolated tear sample or ocular wash, but can also be from saliva, or other bodily fluid. An ocular sample indicates a tear sample encompassing secretions from the lacrimal gland and other tissues that connect with the lymphatic system.

Kits for performing methods described herein are also provided. Kits can contain a sample collection platform, a tube for collection and extraction that can comprise a protease inhibitor or other protein-stabilizing agent, sample extraction reagents and testing apparatus.

BRIEF DESCRIPTION OF THE DRAWINGS

FIG. 3: ANOVA of spectral intensities for the following proteins identified in Experiment 1: (A) Ig Heavy Chain V-IV region HiL, (B) Ig Heavy Chain region V-III region BRO, (C) Ig Heavy Chain V-III region VH26, (D) Antileukoproteinase, (E) β2 Microglobulin, (F) Calmodulin like protein 5, (G) Lipocalin 1, (H) Cystatin B, (I) Galectin 3, (J) Zinc-α 2 glycoprotein.

FIG. 4: ANOVA of spectral intensities for proteins identified in Experiment 2. Proteins shown are: (A) 14-3-3 protein sigma (B) 6-phosphogluconate dehydrogenase, decarboxylating (C) Alpha-actinin-4 (D) Retinal Dehydrogenase (E) Argininosuccinate synthase (F) Beta-2-microglobulin (G) Calmodulin (H) Ceruloplasmin (I) Cofilin (J) Cystatin-SN (K) Enolase 1 (L) Gelsolin (M) Heat shock protein beta-1 (N) Ig alpha-1 chain C region (O) Lacritin (P) Lysozyme (Q) Basement membrane-specific heparin sulfate proteoglycan core protein (R) Polymeric immunoglobulin receptor (S) Profilin 1 (T) S100A8 (U) S100A9 (V) Secretoglobin family 1D member (W) VEGF coregulated chemokine 1 (X) Histidine triad nucleotide-binding protein 1 (Y) Definsin 1 (Z) L-lactate dehydrogenase A chain (AA) SPARC-like protein 1 (BB) Annexin 5 (CC) Ig heavy chain V-III region TIL (DD) Inter-alpha-trypsin inhibitor heavy chain 1 (EE) Alpha-1B-glycoprotein (FF) Alpha-1-antitrypsin.

DETAILED DESCRIPTION

Figure 1:
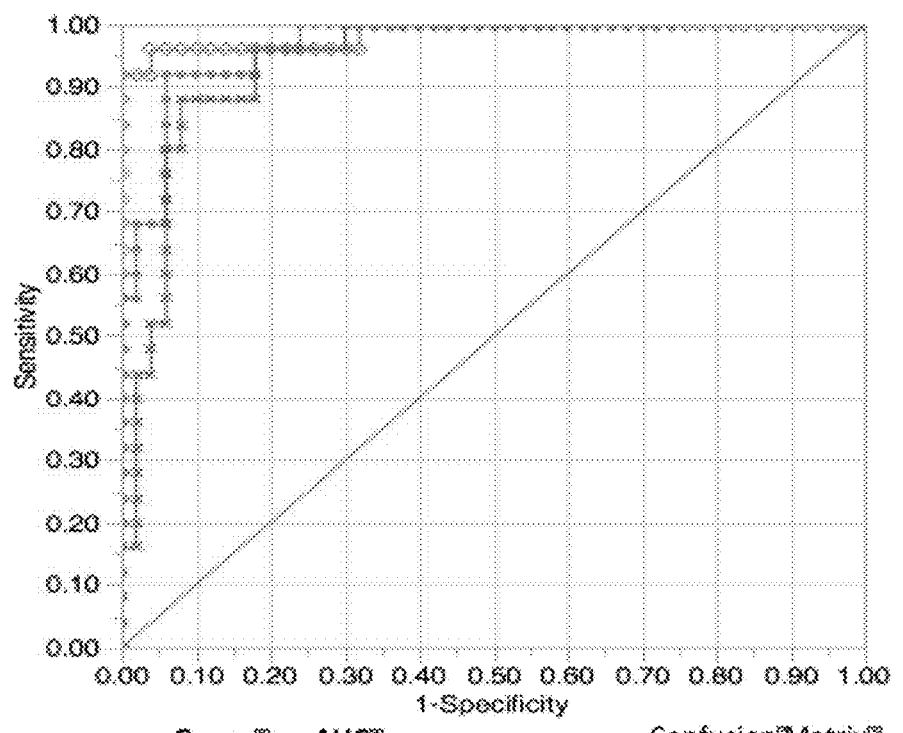
FIG. 1: ROC curves for cancer, benign, and control, from Experiment 1, using Ig Heavy Chain V-IV region HiL, Ig Heavy Chain region V-III region BRO, Ig Heavy Chain V-III region VH26, Antileukoproteinase, β2 Microglobulin, Calmodulin like protein 5, Lipocalin 1, Cystatin B, Galectin 3, Zinc-α 2 glycoprotein.

Provided herein are proteins and peptide fragments obtained by trypsin digestion from ocular samples. The produced polypeptides are selected from the following and as listed in Table 1: Ig lambda chain V-IV region Hil (LV403), Ig heavy chain V-III BRO (HV305), Ig heavy chain V-III VH26 (HV303), β-2-microglobulin (B2MG), Lipocalin-1 (LCN1), Zinc-α-2-glycoprotein (ZA2G), Cystatin B (CYTB), Antileukoproteinase (SLP1), Galectin-3 (LEG3), Histidine triad nucleotide-binding protein 1 (D6RD60), S100A9 (S10A9), S100A8 (S10A8), Galectin-3-binding protein (LG3BP), Cluster of Ig alpha-1 chain C region (IGHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (ALIA1), Uncharacterized Protein (B4E1Z4), Alpha-1-antichymotrypsin (AACT), Superoxide dismutase [Cu—Zn](SODC), SPARC-like protein 1 (SPRL1), Ig heavy chain V-III region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADHIG), Malate dehydrogenase, mitochondrial (MDHM), Calmodulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (A8MU27), Anterior gradient protein 2 homolog (AGR2), Profilin-1(PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-I (APOA1), Apolipoprotein A-IV (APOA4), Flavin reductase (NADPH)(BLVRB), Prosaposin (PSAP), Lacritin (LACRT), 60S acidic ribosomal protein P1 (RLA1), Inter-alpha-trypsin inhibitor heavy chain H2 (ITIH2), Mucin-like protein 1 (MUCL1), S100 A6 (S100A6), Na(+)/H(+) exchange regulatory cofactor NHERF1 (NHRF1), Thioredoxin domain-containing protein 17 (I3L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-I region EU (KV106), Alcohol dehydrogenase class 4 mu/sigma chain (ADH7), Protein AMBP (AMBP), Angiotensinogen (ANGT), Antithrombin-III (ANT3), Apolipoprotein A-II (APOA2), Calpastatin (B7Z574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), Complement C3 (CO3), Coronin-1A (COR1A), Programmed cell death 6-interacting protein (DCD), Definsin 1 (DEF1), F-box only protein 50 (FBX50), Gamma-glutamylcyclotransferase (GGCT), Glutathione reductase, mitochondrial (GSHR), Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNASET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY). The trypsin sequences and full-length amino acid sequences of the proteins identified as being down regulated in cancer samples are provided in Appendix I.

The protein and peptides are shown in the Examples to either increase or decrease in biological samples in response to the presence of breast cancer as compared to controls. These proteins and peptides are biomarkers and will be used to determine the disease state of a patient or other subject.

Subjects include humans, domesticated animals such as cats, dogs, cows, pigs, or other animals susceptible to cancer. A "patient" indicates a subject who is diagnosed with a disease, or with cancer, or is being tested for having cancer. Thus the terms subject and patient can be used interchangeably herein. The subjects can be suspected of having cancer. The subject can be suspected of having cancer, including breast cancer, acoustic neuroma, acute lymphoblastic leukemia, acute myelogenous leukemia, adrenal tumors, AIDS-associated cancers, basal cell carcinoma, benign blood disorders, bladder cancer, bone cancer, brain tumors (metastatic and primary), breast cancer, cancer of unknown primary origin, cervical cancer, chronic lymphocytic leukemia, chronic myelogenous leukemia, colorectal cancer, esophageal cancer, gallbladder and bile duct cancers, gastrointestinal neuroendocrine tumors, GERD, Barrett's esophagus and achalasia, gestational trophoblastic disease, head and neck cancers, Kaposi sarcoma, kidney cancer, leukemias, liver cancer, liver metastases, low-grade glioma, lung cancer, lymphoma, male breast cancer, melanoma, Merkel cell carcinoma, mesothelioma, multiple myeloma, myelodysplastic syndrome, ovarian cancer, pancreatic cancer, pancreatic cysts, pituitary tumors, prostate cancer, pulmonary neuroendocrine tumors, rare blood disorder, skin cancer, soft tissue sarcoma, spine tumors, squamous cell carcinoma, stomach (gastric) cancer, testicular cancer (germ cell tumors), thymoma and other thymic tumors, tracheal diseases, uterine (endometrial) cancer, uterine sarcoma. The subjects can have an increased risk of developing breast cancer. For example, the subject can be at increased risk of cancer, or suspected of having cancer because of a positive mammography result, by detection of a lump in the breast, testing positive for a gene known to increase the risk of cancer such as BRCA, or already had a resection, biopsy, or other procedure to remove the cancer. The subject can be undergoing, or have previously undergone, treatment for cancer and methods and kits herein are used to monitor progression of treatment or alternatively to monitor for recurrence or spread of the cancer.

Also provided herein are methods and kits to collect ocular samples for use in determining the expression levels of the identified proteins or polypeptides in lacrimal secretions. The use of collection strips and tubes containing protease inhibitor or protein stabilizing agents is disclosed. Kits further contain buffers or reagents for the elution of breast cancer biomarkers from the collection strips that have been in contact with an eye to collect lacrimal secretions. The design of devices to collect proteins from the ocular cavity, as well as the packaging of this device with a container to house the collection device and elution buffers, is disclosed.

Methods disclosed herein encompass the use of these cancer biomarkers, singly or in multiples, in a CLIA based protocol utilizing a triple quadrupole LC-MS/MS platform, which will be carried out at a centralized laboratory testing facility. The ocular samples collected from individuals can be shipped to the testing facility in this embodiment. The identified proteins and their subsequent proteolytic fragments, as shown in Appendix I, are used for quantitative analysis of diagnostic peptides produced in the triple quad. A threshold value or a relative or actual value in terms of polypeptide concentration directly relating to the polypeptides selected from the following and as listed in Table 1: Ig lambda chain V-IV region Hil (LV403), Ig heavy chain V-III BRO (HV305), Ig heavy chain V-III VH26 (HV303), β-2-microglobulin (B2MG), Lipocalin-1 (LCN1), Zinc-α-2-glycoprotein (ZA2G), Cystatin B (CYTB), Antileukoproteinase (SLP1), Galectin-3 (LEG3), Histidine triad nucleotide-binding protein 1 (D6RD60), S100A9 (S10A9), S100A8 (S10A8), Galectin-3-binding protein (LG3BP), Cluster of Ig alpha-1 chain C region (IGHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (B4E1Z4), Alpha-1-antichymotrypsin (AACT), Superoxide dismutase [Cu—Zn](SODC), SPARC-like protein 1 (SPRL1), Ig heavy chain V-III region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADHIG), Malate dehydrogenase, mitochondrial (MDHM), Calmodulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (A8MU27), Anterior gradient protein 2 homolog (AGR2), Profilin-1 (PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-I (APOA1), Apolipoprotein A-IV (APOA4), Flavin reductase (NADPH) (BLVRB), Prosaposin (PSAP), Lacritin (LACRT), 60S acidic ribosomal protein P1 (RLA1), Inter-alpha-trypsin inhibitor heavy chain H2 (ITIH2), Mucin-like protein 1 (MUCL1), S100 A6 (S100A6), Na(+)/H(+) exchange regulatory cofactor NHE-RF1 (NHRF1), Thioredoxin domain-containing protein 17 (I3L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-I region EU (KV106), Alcohol dehydrogenase class 4 mu/sigma chain (ADH7), Protein AMBP (AMBP), Angiotensinogen (ANGT), Antithrombin-III (ANT3), Apolipoprotein A-II (APOA2), Calpastatin (B7Z574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), Complement C3 (CO3), Coronin-1A (COR1A), Programmed cell death 6-interacting protein (DCD), Definsin 1 (DEF1), F-box only protein 50 (FBX50), Gamma-glutamylcyclotransferase (GGCT), Glutathione reductase, mitochondrial (GSHR), Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNASET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY) can be defined or samples can be compared directly to non-cancerous controls. The quantitative information in report form can be provided to physicians to help in making decisions regarding the pathway of patient care. Physicians can base treatment decisions on these results and the final step can include administration of an appropriate anti-cancer therapeutic to the subject.

In an alternate embodiment, the polypeptides selected from the following and as listed in Table 1: Ig lambda chain V-IV region Hil (LV403), Ig heavy chain V-III BRO (HV305), Ig heavy chain V-III VH26 (HV303), β-2-microglobulin (B2MG), Lipocalin-1 (LCN1), Zinc-α-2-glycoprotein (ZA2G), Cystatin B (CYTB), Antileukoproteinase (SLP1), Galectin-3 (LEG3), Histidine triad nucleotide-binding protein 1 (D6RD60), S100A9 (S10A9), S100A8 (S10A8), Galectin-3-binding protein (LG3BP), Cluster of Ig alpha-1 chain C region (IGHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (B4E1Z4), Alpha-1-antichymotrypsin (AACT), Superoxide dismutase [Cu—Zn](SODC), SPARC-like protein 1 (SPRL1), Ig heavy chain V-III region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADH1G), Malate dehydrogenase, mitochondrial (MDHM), Calmodulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (A8MU27), Anterior gradient protein 2 homolog (AGR2), Profilin-1, (PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-I (APOA1), Apolipoprotein A-IV (APOA4), Flavin reductase (NADPH) (BLVRB), Prosaposin (PSAP), Lacritin (LACRT), 60S acidic ribosomal protein P1 (RLA1), Inter-alpha-trypsin inhibitor heavy chain H2 (ITIH2), Mucin-like protein 1 (MUCL1), S100 A6 (S100A6), Na(+)/H(+) exchange regulatory cofactor NHE-RF1 (NHRF1), Thioredoxin domain-containing protein 17 (I3L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-I region EU (KV106), Alcohol dehydrogenase class 4 mu/sigma chain (ADH7), Protein AMBP (AMBP), Angiotensinogen (ANGT), Antithrombin-III (ANT3), Apolipoprotein A-II (APOA2), Calpastatin (B7Z574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), Complement C3 (CO3), Coronin-1A (COR1A), Programmed cell death 6-interacting protein (DCD), Definsin 1 (DEF1), F-box only protein 50 (FBX50), Gamma-glutamylcyclotransferase (GGCT), Glutathione reductase, mitochondrial (GSHR), Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNASET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY) can be detected by implementing binding agents, for example antibodies, peptoids, or coated surfaces, and reagents that accommodate a binding interaction specific to these proteins to produce a reaction that can be quantitated based on production of a detectable signal such as florescence, color change, or UV absorbance. Implementing these components in a cartridge with a partnering reading instrument, such as a point-of-care device that can be used at point of care is also provided. Binding agents for these proteins and polypeptides can also be used for detection in a lateral flow device. Thus, methods of detecting the level of protein expression in the samples using a binding partner such as an antibody can be used to detect the markers provided herein in an immunoassay.

The immunoassay typically includes contacting a test sample with an antibody or antigen that specifically binds to, or otherwise recognizes a biomarker, and detecting the presence of a complex of the antibody or antigen bound to the biomarker in the sample. The immunoassay procedure can be selected from a wide variety of immunoassay procedures known in the art involving recognition of antibody/antigen complexes, including enzyme-linked immunosorbent assays (ELISA), radioimmunoassay (RIA), and Western blots, and use of multiplex assays, including use of antibody arrays, wherein several desired antibodies are placed on a support, such as a glass bead or plate, and reacted or otherwise contacted with the test sample. Such assays are well-known to the skilled artisan.

The detection of the biomarkers described herein in a sample can be performed in a variety of ways. In one embodiment, the method provides the reverse-transcription of complementary DNAs from mRNAs obtained from the sample. Fluorescent dye-labeled complementary RNAs can be transcribed from complementary DNAs that are then hybridized to the arrays of oligonucleotide probes. The fluorescent color generated by hybridization can be read by machine, such as a SureScan microarray scanner (Agilent Technologies), and data obtained and processed using software, such as Agilent Feature Extraction Software (9.1). Such array-based methods include microarray analysis to develop a gene expression profile. As used herein, the term "gene expression profile" refers to the expression levels of mRNAs or proteins of a panel of genes in the subject. As used herein, the term "diagnostic panel" refers to a panel of genes, peptides or proteins with an expression level that can be relied on to diagnose or predict the status of the disease. Included in this panel are genes, peptides and proteins selected from the following and as listed in Table 1: Ig lambda chain V-IV region Hil (LV403), Ig heavy chain V-III BRO (HV305), Ig heavy chain V-III VH26 (HV303), β-2-microglobulin (B2MG), Lipocalin-1 (LCN1), Zinc-α-2-glycoprotein (ZA2G), Cystatin B (CYTB), Antileukoproteinase (SLP1), Galectin-3 (LEG3), Histidine triad nucleotide-binding protein 1 (D6RD60), S100A9 (S10A9), S100A8 (S10A8), Galectin-3-binding protein (LG3BP), Cluster of Ig alpha-1 chain C region (IGHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (B4E1Z4), Alpha-1-antichymotrypsin (AACT), Superoxide dismutase [Cu—Zn](SODC), SPARC-like protein 1 (SPRL1), Ig heavy chain V-III region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADHIG), Malate dehydrogenase, mitochondrial (MDHM), Calmodulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (A8MU27), Anterior gradient protein 2 homolog (AGR2), Profilin-1 (PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-I (APOA1), Apolipoprotein A-IV (APOA4), Flavin reductase (NADPH) (BLVRB), Prosaposin (PSAP), Lacritin (LACRT), 60S acidic ribosomal protein P1 (RLA1), Inter-alpha-trypsin inhibitor heavy chain H2 (ITIH2), Mucin-like protein 1 (MUCL1), S100 A6 (S100A6), Na(+)/H(+) exchange regulatory cofactor NHE-RF1 (NHRF1), Thioredoxin domain-containing protein 17 (I3L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-I region EU (KV106), Alcohol dehydrogenase class 4 mu/sigma chain (ADH7), Protein AMBP (AMBP), Angiotensinogen (ANGT), Antithrombin-III (ANT3), Apolipoprotein A-II (APOA2), Calpastatin (B7Z574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), Complement C3 (CO3), Coronin-1A (COR1A), Programmed cell death 6-interacting protein (DCD), Defin-sin 1 (DEF1), F-box only protein 50 (FBX50), Gamma-glutamylcyclotransferase (GGCT), Glutathione reductase, mitochondrial (GSHR), Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNA-SET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY) as well as any combination thereof, as provided herein.

In other embodiments, complementary DNAs are reverse-transcribed from mRNAs obtained from the sample, amplified, and simultaneously quantified by real-time PCR, thereby enabling both detection and quantification (as absolute number of copies or relative amount when normalized to DNA input or additional normalizing genes) of a specific gene product in the complementary DNA sample as well as the original mRNA sample.

The methods of the versions of this invention include detecting at least one biomarker. However, any number of biomarkers can be detected. It is preferred that at least two biomarkers are detected in the analysis. However, it is realized that three, four, or more, including all, of the biomarkers described herein can be utilized in the analysis.

Thus, not only can one or more markers be detected, any number or combination of markers can be used in detection. In addition, other biomarkers not herein described can be combined with any of the presently disclosed biomarkers to aid in the diagnosis of cancer. Moreover, any combination of the above biomarkers can be detected in accordance with versions of the present invention.

The markers selected from the following and as listed in Table 1: Ig lambda chain V-IV region Hil (LV403), Ig heavy chain V-III BRO (HV305), Ig heavy chain V-III VH26 (HV303), β-2-microglobulin (B2MG), Lipocalin-1 (LCN1), Zinc-α-2-glycoprotein (ZA2G), Cystatin B (CYTB), Antileukoproteinase (SLP1), Galectin-3 (LEG3), Histidine triad nucleotide-binding protein 1 (D6RD60), S100A9 (S10A9), S100A8 (S10A8), Galectin-3-binding protein (LG3BP), Cluster of Ig alpha-1 chain C region (IGHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (B4E1Z4), Alpha-1-antichymotrypsin (AACT), Superoxide dismutase [Cu—Zn] (SODC), SPARC-like protein 1 (SPRL1), Ig heavy chain V-III region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADHIG), Malate dehydrogenase, mitochondrial (MDHM), Calmodulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (A8MU27), Anterior gradient protein 2 homolog (AGR2), Profilin-1 (PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-I (APOA1), Apolipoprotein A-IV (APOA4), Flavin reductase (NADPH)(BLVRB), Prosaposin (PSAP), Lacritin (LACRT), 60S acidic ribosomal protein P1 (RLA1), Inter-alpha-trypsin inhibitor heavy chain H2 (ITIH2), Mucin-like protein 1 (MUCL1), S100 A6 (S100A6), Na(+)/H(+) exchange regulatory cofactor NHE-RF1 (NHRF1), Thioredoxin domain-containing protein 17 (I3L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-I region EU (KV106), Alcohol dehydrogenase class 4 mu/sigma chain (ADH7), Protein AMBP (AMBP), Angiotensinogen (ANGT), Antithrombin-III (ANT3), Apolipoprotein A-II (APOA2), Calpastatin (B7Z574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), Complement C3 (CO3), Coronin-1A (COR1A), Programmed cell death 6-interacting protein (DCD), Definsin 1 (DEF1), F-box only protein 50 (FBX50), Gamma-glutamylcyclotransferase (GGCT), Glutathione reductase, mitochondrial (GSHR), Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNASET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY) can increase or decrease at least 1.5 fold, 2 fold, 4 fold, 5 fold, 8 fold, 10 fold or more, relative to the level of the marker in the control sample. The control sample can be a sample from a subject that does not have cancer, a pooled sample from subjects that do not have cancer, or can be a control or baseline expression level known to be the average expression level of subjects without cancer.

Several terms are used throughout this disclosure and should be defined as commonly used in the art, or as specifically provided herein. As provided herein, mass spectrometry or MS refers to an analytical technique generating electrical or magnetic fields to determine mass-to-charge ratio of peptides and chemical compounds in order to identify or determine peptide sequence and chemical structures. LC-MS/MS spectrometry refers to an analytical technique combining the separation capabilities of high performance liquid chromatography (HPLC) with the mass analysis of mass spectrometry. Triple quadrupole mass spectrometry refers to a tandem mass spectrometer with three ionizing chambers (Q1, Q2, & Q3). This technique allows for target detection of molecules of interest. Ion pairs refers to a parent peptide detected in Q1 in its doubly or triply charged form and a resulting y or b ion as generated by Q2 and detected in Q3 of a triple quadrupole mass spectrometry instrument. SIS internal peptide refers to a synthesized isotopically-labeled peptide with the same sequence as the peptide to be monitored in Q1 and used as an internal standard for reference to quantify the peptide of interest. The -y ion refers to an ion generated from the c-terminal of a peptide fragment. The -b ion refers to an ion generated from the n-terminal of a peptide fragment. Quantitative ion refers to the selected highest intensity y or b ion used to determine the quantity of its parent protein in a biological sample. Qualitative Ion refers to ion/ions chosen to ensure the integrity of the Qualitative Ion to selected protein of interest and labeled peptide to selected standards.

CLIA refers to Clinical Laboratory Improvements Amendments, which are federal regulatory standards that apply to all clinical laboratory testing preformed on humans in the United States, except clinical trials and basic research. (*CLIA related Federal Register and Code of Federal Regulation Announcements*). CLIA approved laboratory refers to a clinical lab that preforms laboratory testing on human specimens for diagnosis, prevention, or treatment of disease or impairment and is approved and monitored by a Food and Drug Administration (FDA) approved regulatory organization (CLIA Laws and Regulations, 2013). CLIA-waived test refers to a clinical laboratory test meeting specific criteria for risk, error, and complexity as defined by the FDA.

Point-of-care device refers to an instrument or cartridge available at the location of patient and physician care, which contains binding agents to a biomarker, or series of biomarkers of interest, and which can generate information on the presence, absence, and in some cases concentrations of detected biomarkers. Analyte refers to any measurable biomarker, which can be protein, peptide, macromolecule, metabolite, small molecule, or autoantibody. Biological fluid, as used herein, refers to tears, whole blood, serum, urine, and saliva. Biomarker refers to any substance (e.g. protein, peptide, metabolite, polynucleotide sequence) the concentration level of which changes in the body, for example increased or decreased, as a result of a disease or condition. Marker and biomarker can be used interchangeably used herein.

Lateral flow test refers to a device that measures the presence of an analyte in a biological fluid using porous paper of sintered polymer. ELISA refers to Enzyme-linked immunosorbent assay, which utilizes antibodies or antigens to detect the presence and concentration of an analyte of interest. Diagnostic panel refers to a group of molecules for example proteins or peptides, the combined concentrations of which are used to diagnose a disease state, for example cancer. A breast cancer marker refers to a molecule: for example protein, peptide, metabolite, polynucleotide sequence, the concentration level of which changes in the body: for example increased or decreased, as a result of the presence or absence of cancer.

In addition to being useful to diagnose cancer, and in particular breast cancer, in a subject, kits and methods provided herein can be used to monitor treatment or recurrence of cancer in an individual previously diagnosed with cancer. Thus if the levels of the markers selected from the following and as listed in Table 1: Ig lambda chain V-IV region Hil (LV403), Ig heavy chain V-III BRO (HV305), Ig heavy chain V-III VH26 (HV303), β-2-microglobulin (B2MG), Lipocalin-1 (LCN1), Zinc-α-2-glycoprotein (ZA2G), Cystatin B (CYTB), Antileukoproteinase (SLP1), Galectin-3 (LEG3), Histidine triad nucleotide-binding protein 1 (D6RD60), S100A9 (S10A9), S100A8 (S10A8), Galectin-3-binding protein (LG3BP), Cluster of Ig alpha-1 chain C region (IGHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (B4E1Z4), Alpha-1-antichymotrypsin (AACT), Superoxide dismutase [Cu—Zn](SODC), SPARC-like protein 1 (SPRL1), Ig heavy chain V-III region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADHIG), Malate dehydrogenase, mitochondrial (MDHM), Calmodulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (A8MU27), Anterior gradient protein 2 homolog (AGR2), Profilin-1 (PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-I (APOA1), Apolipoprotein A-IV (APOA4), Flavin reductase (NADPH) (BLVRB), Prosaposin (PSAP), Lacritin (LACRT), 60S acidic ribosomal protein P1 (RLA1), Inter-alpha-trypsin inhibitor heavy chain H2 (ITIH2), Mucin-like protein 1 (MUCL1), S100 A6 (S100A6), Na(+)/H(+) exchange regulatory cofactor NHE-RF1 (NHRF1), Thioredoxin domain-containing protein 17 (I3L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-I region EU (KV106), Alcohol dehydrogenase class 4 mu/sigma chain (ADH7), Protein AMBP (AMBP), Angiotensinogen (ANGT), Antithrombin-III (ANT3), Apolipoprotein A-II (APOA2), Calpastatin (B7Z574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), Complement C3 (CO3), Coronin-1A (COR1A), Programmed cell death 6-interacting protein (DCD), Definsin 1 (DEF1), F-box only protein 50 (FBX50), Gamma-glutamylcyclotransferase (GGCT), Glutathione reductase, mitochondrial (GSHR), Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNASET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY) increases or decreases over time in the same subject after treatment, further chemotherapeutics targeting the cancer can be administered.

Methods and kits can also be used to monitor the effectiveness of a chemotherapeutic treatment. In this alternate embodiment, the levels of the biomarkers selected from the following and as listed in Table 1: Ig lambda chain V-IV region Hil (LV403), Ig heavy chain V-III BRO (HV305), Ig heavy chain V-III VH26 (HV303), β-2-microglobulin (B2MG), Lipocalin-1 (LCN1), Zinc-α-2-glycoprotein (ZA2G), Cystatin B (CYTB), Antileukoproteinase (SLP1), Galectin-3 (LEG3), Histidine triad nucleotide-binding protein 1 (D6RD60), S100A9 (S10A9), S100A8 (S10A8), Galectin-3-binding protein (LG3BP), Cluster of Ig alpha-1 chain C region (IGHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (B4E1Z4), Alpha-1-antichymotrypsin (AACT), Superoxide dismutase [Cu—Zn](SODC), SPARC-like protein 1 (SPRL1), Ig heavy chain V-III region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADHIG), Malate dehydrogenase, mitochondrial (MDHM), Calmodulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (A8MU27), Anterior gradient protein 2 homolog (AGR2), Profilin-1 (PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-I (APOA1), Apolipoprotein A-IV (APOA4), Flavin reductase (NADPH) (BLVRB), Prosaposin (PSAP), Lacritin (LACRT), 60S acidic ribosomal protein P1 (RLA1), Inter-alpha-trypsin inhibitor heavy chain H2 (ITIH2), Mucin-like protein 1 (MUCL1), S100 A6 (S100A6), Na(+)/H(+) exchange regulatory cofactor NHE-RF1 (NHRF1), Thioredoxin domain-containing protein 17 (13L0K2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-I region EU (KV106), Alcohol dehydrogenase class 4 mu/sigma chain (ADH7), Protein AMBP (AMBP), Angiotensinogen (ANGT), Antithrombin-II (ANT3), Apolipoprotein A-II (APOA2), Calpastatin (B7Z574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), Complement C3 (CO3), Coronin-1A (COR1A), Programmed cell death 6-interacting protein (DCD), Definsin 1 (DEF1), F-box only protein 50 (FBX50), Gamma-glutamylcyclotransferase (GGCT), Glutathione reductase, mitochondrial (GSHR), Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNASET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY) can increase or decrease over time if the treatment regime is effective and either would not change or can increase or decrease over time if the treatment regime is not effective in a single subject, depending on which biomarker(s) are being examined in the subject.

Treating cancer includes, but is not limited to, reducing the number of cancer cells or the size of a tumor or mass in the subject, reducing progression of a cancer to a less aggressive form, reducing proliferation of cancer cells or reducing the speed of tumor growth, killing of cancer cells, reducing metastasis of cancer cells or reducing the likelihood of recurrence of a cancer in a subject. Treating a subject, as used herein, refers to any type of treatment that imparts a benefit to a subject afflicted with a disease or at risk of developing the disease, including improvement in the condition of the subject for example in one or more symptoms, delay in the progression of the disease, delay in the onset of symptoms, or delay in the progression of symptoms, etc.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language for example "such as," provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values near to the recited amount are included in that amount, such as values that can or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what that author asserts, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references. Any references mentioned are not admitted to be prior art with respect to the present invention.

The following examples are meant only to be illustrative and are not meant as limitations on the scope embodiments of the invention or of the appended claims.

EXAMPLES

Example 1

Participant Selection

Study participants were recruited from patients being seen at Breast Health and Surgery Centers AR, OK, TN and WA under Institutional Review Board approval. All patients were consented and provided a copy of the informed consent prior to sample collection or completing patient information sheet. Samples were collected by clinic staff (i.e. nurses and technicians) and/or Ascendant Dx staff. Inclusion/exclusion criteria used for patient selection were as follows:

Inclusion Criteria:
Individuals between the ages of 18-100 years of age,
Presenting for a routine check-up, or
Presenting for the evaluation of an abnormal exam or test, or
Presenting for the evaluation of palpable mass, or
Presenting with a mass pre or post biopsy as long as a portion of the mass is remaining, or
Have recently been diagnosed with breast cancer but have not undergone treatment of any kind.
Exclusion Criteria:
Individuals below the age of 18 or over 100
Experiencing a concurrent eye infection or trauma, or
Currently experiencing acute conjunctivitis, or
Have been diagnosed with breast cancer and have undergone treatment.

Control samples were collected from patients being seen for routine screening mammograms and did not receive a call back for additional procedures. Benign samples were collected at the time of biopsy and were included in the benign group once the pathology results were determined. Cancer samples were also collected at time of biopsy and included in the cancer group after pathology results were known, from patients having MRI's prior to surgery, and from patients undergoing sentinel node procedures prior to surgery.

Data collected from participants included the following: age, sex, race, currently taking birth control or on hormone replacement therapy, ophthalmological infections, current or recent chemotherapy treatments, family history of cancer, genetic testing (BRAC1/2) if available, cancer stage (I, II, III, IV), cancer type (Ductal Carcinoma In Situ, Invasive Ductal Carcinoma, Invasive Lobular Carcinoma, Lobular Carcinoma In Situ, and Unknown), hormone receptor status (ER+/−, PR+/−, HER2+/−), size of mass, tumor grade (I, II, III), breast density score (densities identified as category1, 2, 3, or 4) and previous history of cancer.

Example 2

Schirmer Strip Sample Collection Procedure

Institutional review board approval was obtained for the collection of tears using Schirmer strips (GuldenOpthalmics Elkins Park, PA). For collection, the rounded tip of the Schirmer strip was folded over at the 0 mm line forming a lip. The folded portion was placed in the lower eyelid of the participant and they were asked to close their eye and keep it in the closed position for a period of 5 minutes. After five minutes the strip was removed and placed in a sterile 1.5 mL pre-labeled snap top tube and placed at −20° C. or −80° C. depending on availability. Collection criteria stated that if the 35 mm mark was reached prior to the five minute time, the strip can be removed. Samples collected at participating clinics were retrieved by Ascendant Dx staff on a weekly basis and transferred on dry ice to Ascendant Dx's laboratory facility.

Example 3

Schirmer Strip Sample Processing

Protein elution was carried out by first dicing the strips, using sterile tweezers and scissors, into clean sterile 1.5 mL snap top tube. 200 µL of 1X Phosphate-buffered saline (PBS) was added to the diced strip and the sample was incubated at 4° C. with mild shaking for 3 hours. Following elution, the samples were spun briefly in a tabletop centrifuge to collect the strip fragments at the bottom of the tube, and the supernatant was transferred to a new clean 1.5 mL snap top tube. Total protein content was determined using standard bicinchoninic acid (BCA) assay, and the samples were stored at −80° C. until further use.

Total protein content of each pool was determined using a BCA assay kit (Pierce) with a 1:20 (v/v) ratio of standard and unknown to working reagent and an incubation time of 30 min at 37° C. To ensure reliable total protein content calculation, a series of dilutions were made for each sample, for example 1:2, 1:4, 1:6, and all dilutions were plated in triplicate. A standard curve using diluted albumin (2 mg/ml, 1.5 mg/ml, 1 m/ml, 0.75 mg/ml, 0.5 mg/ml, 0.25 mg/ml 0.125 mg/ml 0.025 mg/ml and 0 mg/ml) was generated and blank subtraction was applied to all standards and unknowns. The protein concentration for each unknown was calculated using a four-parameter fit of the standard curve. Concentrations were multiplied by the dilution factor and averaged to give an accurate total protein content calculation. Assays were considered valid if the coefficient of variation (% CV) was 15% or below.

Example 4

Methods and Results for Label Free Quantitation by LC MS/MS

Experiment 1:
In solution trypsin digestion followed by LC MS/MS was carried out on 25 breast cancer samples, 25 benign samples, and 25 control samples by the Proteomic Core at the University of Arkansas for Medical Sciences (UAMS). Solution digests were carried out on all 75 samples in 100 mM ammonium bicarbonate (Sigma-Aldrich), following reduction in 10 mM Tris[2-carboxyethyl]phosphine (Pierce) and alkylation in 50 mM iodoacetamide (Sigma-Aldrich), by addition of 100 rig porcine trypsin (Promega) and incubation at 37° C. for 12-16 hours. Peptide products were then acidified in 0.1% formic acid (Fluka). Tryptic peptides were separated by reverse phase Jupiter Proteo resin (Phenomenex) on a 100×0.075 mm column using a nanoAcquity UPLC system (Waters). Peptides were eluted using an 80 min gradient from 97:3 to 35:65 buffer A:B ratio. [Buffer A=0.1% formic acid, 0.05% acetonitrile; buffer B=0.1% formic acid, 75% acetonitrile.] Eluted peptides were ionized by electrospray (1.8 kV) followed by MS/MS analysis using collision-induced dissociation on an LTQ Orbitrap Velos mass spectrometer (Thermo). MS data were acquired using the FTMS analyzer in profile mode at a resolution of 60,000 over a range of 375 to 1500 m/z. MS/MS data were acquired for the top 15 peaks from each MS scan using the ion trap analyzer in centroid mode and normal mass range with a normalized collision energy of 35.0. Proteins were identified from MS/MS spectra by database searching the Mascot search engine (Matrix Science) or MaxQuant quantitative proteomics software (Max Planck Institute). Mascot search results were compiled using Scaffold (Proteome Software).

The following criteria were set to select a group of proteins that can be indicative of altered breast physiology: 1) protein has a fold change of 1.5 or greater (in either positive or negative direction with respect to cancer). 2) fold change should be accompanied by p value of <0.05. 3) protein is present in 12 out of the 25 cancer samples. Using these criteria, the list of over 500 was reduced to the following proteins: Alpha-1-antitrypsin (A1AT), Antileukoproteinase (SLP1), Cofilin (COF1), Antithrombin-III (ANT3), Beta-2-microglobulin (B2MG), Protein-glutamine-gamma-glutamyltransferase (B4DIT7), Uncharacterized protein (B8ZZQ6), Calmodulin-like protein 5 (CALL5), Cystatin-B (CYTB), Neutrophil defensing-1 (DEF1), Destrin (DEST), Kaliocin-1 (E7ER44), Cluster of Rab GDP dissociation inhibitor beta (E7EU23), Elongation factor 1-alpha (EF1A1), Ezrin (EZRI), Heme-binding protein 2 (HEB2), Heat Shock cognate 71 (HSP7C), Heat shock protein beta 1 (HSPB1), Ig Heavy chain V-III (HV303), Cluster of Ig Heavy chain V-III region BRO (HV305), Lipocalin-1 (LCN1), Galectin-3 (LEG3), Ig lambda chain V-IV (LV403), Isoform 2 of Ig mu chain c region (P01871), Cluster of isoform 2 heat shock protein (P07900-2), Cluster of 14-3-3 protein zeta delta (P63104), Isoform 3 of Perilipin-3 (PLIN3), Proteasome activator complex subunit 1 (Q06323), UMP-CMP kinase (Q5T0D2), Protein S100-A4 (S10A4), S100-A8 (S10A8), Protein S100-A9 (S10A9), Protein S100-A11 (S10AB), Submaxillary gland androgen-regulated protein (SMR3B), Zinc-alpha-2-glycoprotien (ZA2G), Zymogen granule protein 16 homolog B (ZG16B).

Experiment 2:
In solution trypsin digestion followed by LC MS/MS was repeated using fifty samples in each group (breast cancer, benign, control). Identical methods as described for Experiment 1 were used for Experiment 2. The increase in samples size caused some of the trends observed in Experiment 1 to disappear, while making trends emerging in Experiment 1 more prominent in Experiment 2. From this data the list of 500 proteins described in Experiment 1 was further refined down to 103 proteins of interest. This list includes: Histidine triad nucleotide-binding protein 1 (D6RD60), S100A9 (S10A9), S100A8 (S10A8), Galectin-3-binding protein (LG3BP), Cluster of Ig alpha-1 chain C region (IGHA1), Cluster of Ig kappa chain V-III region HAH (KV312), VEGF co-regulated chemokine 1 (VCC1), L-lactate dehydrogenase A chain (LDHA), Aldo-keto reductase family 1 member C (AKR1C1), Rootletin (B1AKD8), L-lactate dehydrogenase B chain (LDHB), Retinal dehydrogenase 1 (AL1A1), Uncharacterized Protein (B4E1Z4), Alpha-1-antichymotrypsin (AACT), Superoxide dismutase [Cu—Zn] (SODC), SPARC-like protein 1 (SPRL1), Ig heavy chain V-III region TIL (HV304), Keratin (K1C9), Cystatin-SN (CYTN), Alpha-actinin-4 (ACTN4), Ig lambda-3 chain C regions (Fragment) (IGLC3), Immunoglobulin lambda-like polypeptide 5 (IGLL5), Alcohol dehydrogenase 1C (ADH1G), Malate dehydrogenase, mitochondrial (MDHM), Calmodulin-like protein 5 (CALL5), Alpha-1-antitrypsin (A1AT), Alpha-1B-glycoprotein (A1BG), Leucine-rich alpha-2-glycoprotein (A2GL), Small ubiquitin-related modifier 3 (A8MU27), Anterior gradient protein 2 homolog (AGR2), Profilin-1 (PROF1), Cluster of Ig lambda chain V-III region LOI (LV302), Prothrombin (E9PIT3), Hemopexin (HEMO), Ig gamma-2 chain C region (IGHG2), Ubiquitin-40S ribosomal protein S27a (RPS27A), Afamin (AFAM), Apolipoprotein A-I (APOA1), Apolipoprotein A-IV (APOA4), Flavin reductase (NADPH)(BLVRB), Prosaposin (PSAP), Lacritin (LACRT), 60S acidic ribosomal protein P1 (RLA1), Inter-alpha-trypsin inhibitor heavy chain H2 (ITIH2), Mucin-like protein 1 (MUCL1), S100 A6 (S100A6), Na(+)/H(+) exchange regulatory cofactor NHE-RF1 (NHRF1), Thioredoxin domain-containing protein 17 (I3LOK2), Lymphocyte-specific protein (LSP1), Cluster of Haptoglobin (H3BS21), Myosin regulatory light chain 12A (J2QRS3), Ribonuclease inhibitor (RINI), Alpha-enolase (ENOA), Cluster of Ig kappa chain V-I region EU (KV106), Alcohol dehydrogenase class 4 mu/sigma chain (ADH7), Protein AMBP (AMBP), Angiotensinogen (ANGT), Antithrombin-III (ANT3), Apolipoprotein A-II (APOA2), Calpastatin (B7Z574), Brain acid soluble protein 1 (BASP1), Alpha-2-HS-glycoprotein (C9JV77), Calreticulin (CALR), Calpain-1 catalytic subunit (CAN1), Cell division control protein 42 homolog (CDC42), Complement C3 (CO3), Coronin-1A (COR1A), Programmed cell death 6-interacting protein (DCD), Definsin 1 (DEF1), F-box only protein 50 (FBX50), Gamma-glutamylcyclotransferase (GGCT), Glutathione reductase, mitochondrial (GSHR), Keratin, type II cytoskeletal 1 (K2C1), UMP-CMP kinase (KCY), Mesothelin (MSLN), N-acetylmuramoyl-L-alanine amidase (PGRP2), Nicotinate phosphoribosyltransferase (PNCB), Inter-alpha-trypsin inhibitor heavy chain H1 (ITIH1), Ribonuclease T2 (RNASET2), Superoxide dismutase [Mn], mitochondrial (SODM), Small proline-rich protein 3 (SPRR3), Src substrate cortactin (SRC8), Cluster of Tubulin beta-4B chain (TBB4B), Tropomyosin alpha-3 chain (TPM3), Serotransferrin (TRFE), Glutathione S-transferase P (THIO), Vitronectin (VTNC), Vitamin D Binding protein (Q6LDC6), Inter-alpha-trypsin inhibitor heavy chain H4 (ITIH4), Metalloprotease inhibitor (TIMP1), Heat Shock protein 90 (HSP90), Cathepsin B (CATB), Ceruloplasmin (CERU), Calprotectin, 14-3-3 sigma (1433S), alpha-2-hs-glycoprotein (FETUA), alpha-2-macroglobulin (A2MG), Transthyretin (TTHY) (Appendix 1). The complete list of proteins identified was exported from Scaffold software for analysis using JMPpro11 statistical software package.

Example 5

Statistical Analysis Using JMPpro11 Software

Experiment 1:
The data was organized by using Microsoft Excel® spreadsheet software with spectral intensities of each of the previously identified proteins for all 75 samples. Also included in the spreadsheet were sample status (cancer, benign, control) cancer type, tumor size grouping (1=0.1 mm-1 cm, 2=1.1-2.9 cm, 3=3 cm or greater) and tumor grade status. This spreadsheet was uploaded into the JMPpro11 software package for analysis.
Binary linear regression was applied between cancer and control samples. Six proteins were identified as significant based on their sigmoidal curve and p-value, they were Ig lambda chain V-IV (LV403), Ig heavy chain V-III region BRO (HV305), Ig heavy chain V-III VH26 (HV303), Lipocallin-1 (LCN1), Beta-2-microglobulin (B2MG), Zinc-alpha-2-glycoprotein (ZA2G). All six proteins appeared to be down-regulated with respect to cancer. To determine if the down regulation of these proteins was specific to breast cancer a binary linear regression was repeated between benign and control. This comparison indicated the six previously identified proteins were also down-regulated in benign samples and an additional four proteins were identified as significant between benign and control; Antileukoproteinase (SLP1), Calmodulin-like-protein 5 (CALL5), Cystatin B (CYTB), and Galectin-3 (LEG3).
Nominal logistic regression was carried out using all three groups and all ten proteins to determine degree of differentiation between all groups. Degree of misclassification was for the group of ten proteins was 12%. Receiver operator curves for each category produced AUC values of 0.96 for cancer, 0.94 for benign, and 0.98 for control (FIG. 1). One way ANOVA analysis was preformed to ensure a shifting mean value for the three categories of samples by each protein (FIG. 3).

Experiment 2:
One-way ANOVA analysis was preformed using spectral intensities recorded for all proteins identified from mass spectrometry. Tryptic peptide products were analyzed for all proteins. Proteins were compared in three ways: 1) control vs cancer, 2) cancer vs benign, 3) benign vs control. An alpha level of 0.05 was used as an indicator of significant expression change between the groups. Variations in spectral intensities of tryptic fragments were compared. A series of proteins was identified where expression level increased in breast cancer samples with respect to control. Proteins were also identified where expression decreased in breast cancer samples with respect to control. To ensure experimental validity, it was established that proteins were present in whose expression remained constant across all groups tested (FIG. 4).
The initial list of 500 proteins was reduced to 103 proteins of interest. Within this group of proteins are proteins with increased expression with respect to breast cancer as well as proteins with decreased expression with respect to breast cancer (FIG. 4). The diagnostic capability of whole protein sequence, tryptic peptides, and sequence anomalies, which can be present as a result of disease, are all of interest.

Example 6

ELISA Analysis

A series of proteins with an increase in expression level in cancer samples relative to control samples were observed by mass spectrometry, and several candidates were selected for further validated using ELISA. S100A9 was selected as a representative example of increased expression in tears of breast cancer patients relative to control. LG3BP is shown as a representative of proteins with a decreased expression level in breast cancer samples relative to control samples. Standard ELISA protocol was used to evaluate the expression level of in tears. Data for S100A9 and LG3BP was obtained using kits purchased as DuoSets from R&D Systems (Minneapolis, Minn.). ELISA procedures were carried out according to instructions provided by R&D systems. Briefly, 100 µL per well of capture antibody, diluted to the recommended working concentration (GAL3BP 1.0 ug/ml; S100A9 0.5 ug/ml) in 1XPBS, was added to a high binding 96 well plate and incubated overnight (~16 hrs) at room temperature. The plate was rinsed with 1XPBS with 0.05% Tween four times, and blotted against clean absorbent paper to remove any traces of liquid following each rinse. Rinse cycles were carried out after each step of the assay. Blocking buffer (1XPBS with 1% BSA) was added to all wells (~200 µL/well) and the plates were incubated for two hours at room temperature. Tear samples were diluted using 1XPBS with 1% BSA at dilutions of 1:10 and 1:50 for S100A9 and 1:100 & 1:500 for Galectin 3 Binding Protein. Dilutions known to fall within the linear region of the standard curve for each assay were selected based on results from previous optimization assays. Samples and standards were tested in duplicate using 100 µL/well and incubated at room temperature for 2 hours. Detection antibody was diluted to the recommended working concentration (GAL3BP 2 ug/ml and S100A9 1 ug/ml) 100 µL was added to each well, and the plate was allowed to incubate for 2 hours at room temperature. Streptavidin-HRP solution was added to each well (100 µL/well) and allowed to incubate for 15 min at room temperature. Visualization was achieved by addition of TMB substrate solution. After 15 minutes, 50 µL of 1M $H_2SO_4$ was added to each well, and the absorbance at 450 nm was determined. ELISA data was analyzed using Prism version 6.0 available from GraphPad.

Figure 5:
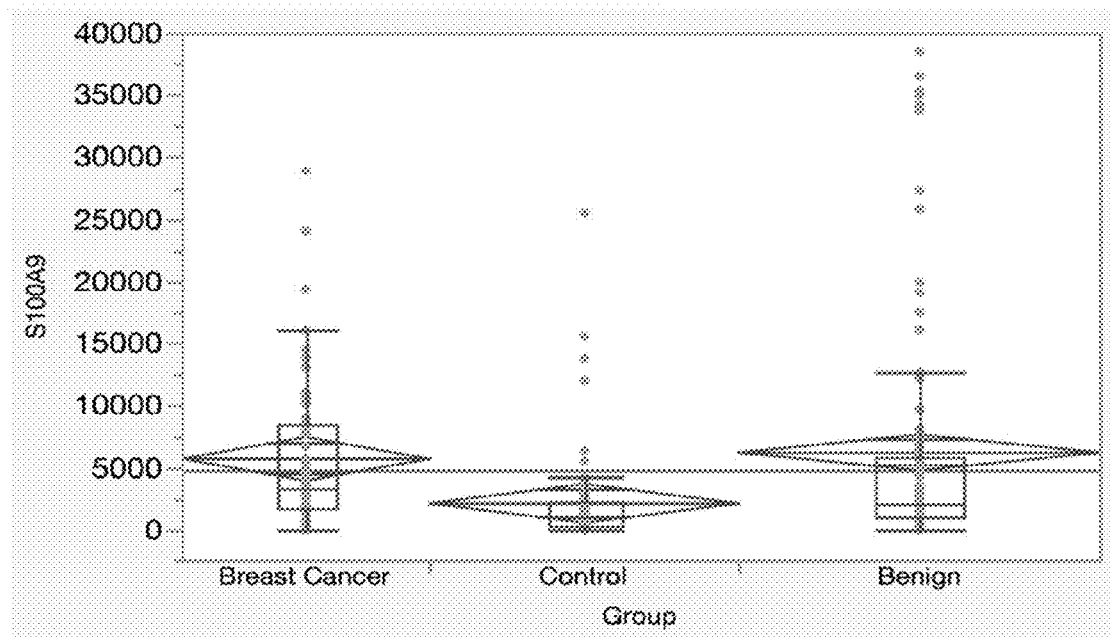
FIG. 5: ANOVA comparing expression levels of S100A9 as determined by ELISA, in breast cancer and control samples.
Figure 6:
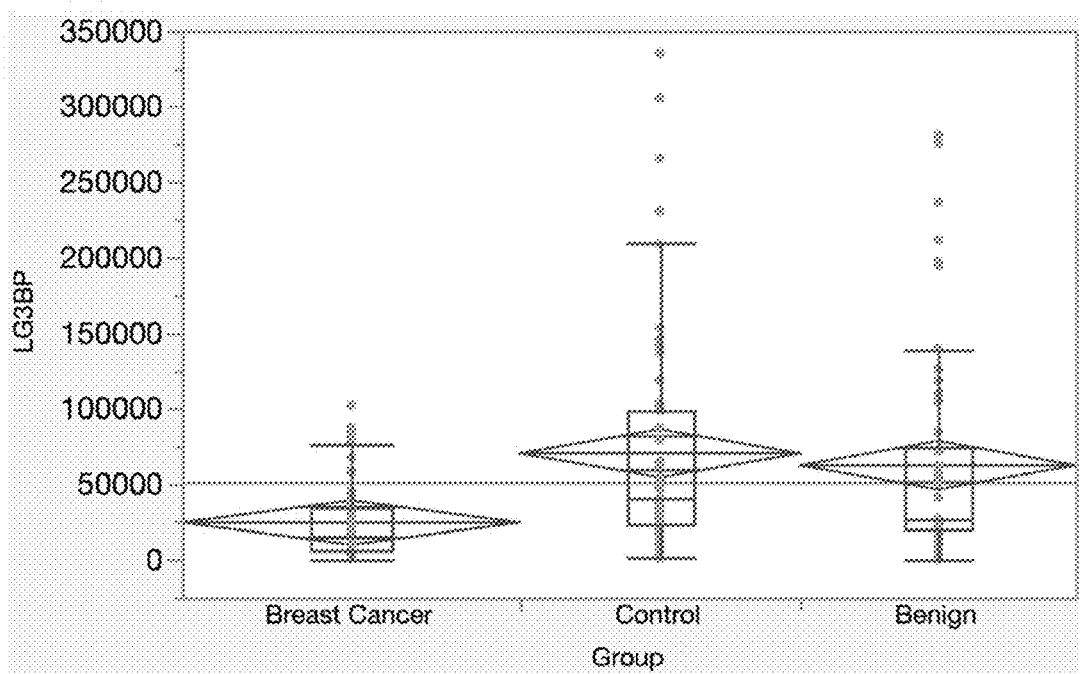
FIG. 6: ANOVA comparing expression levels of LG3BP, as determined by ELISA, in breast cancer and control samples.

Statistical Analysis of ELISA Data:

Concentrations of each protein, as calculated by Prism software, were exported into JMP Pro11 for statistical evaluation. Numerous candidates were selected to be investigated using ELISA assays on Control, Cancer or Benign samples. Results of two proteins (S100A9 and Galectin-3-Binding Protein) are shown (FIG. 5 and FIG. 6, respectively) to provide representative example of increased and decreased protein expression in breast cancer tear samples with respect to control. ANOVA of S100A9 for 63 breast cancer samples, 79 control samples, and 92 benign samples resulted in a p-value of 0.0005 when all three groups were evaluated. Group means for S100A9 were: breast cancer=5673.02 pg/ml; control=2130.18 pg/ml; benign=6179.10 pg/ml. S100A9 expression is increased by 2.6 fold in cancer samples compared to control samples and 2.9 fold increase in benign samples compared to control. ANOVA of Galectin-3 Binding Protein for 66 breast cancer samples, 55 control samples, and 54 benign samples resulted in a p-value of <0.0001 when all three groups were evaluated. Group means for LG3BP were: breast cancer=24448.1 pg/ml; control=70242.2 pg/ml; benign=62329.7 pg/ml. LG3BP has a 2.8 fold increase in control samples compared to cancer samples and a 2.5 fold increase in benign samples compared to cancer.

Figure 7:
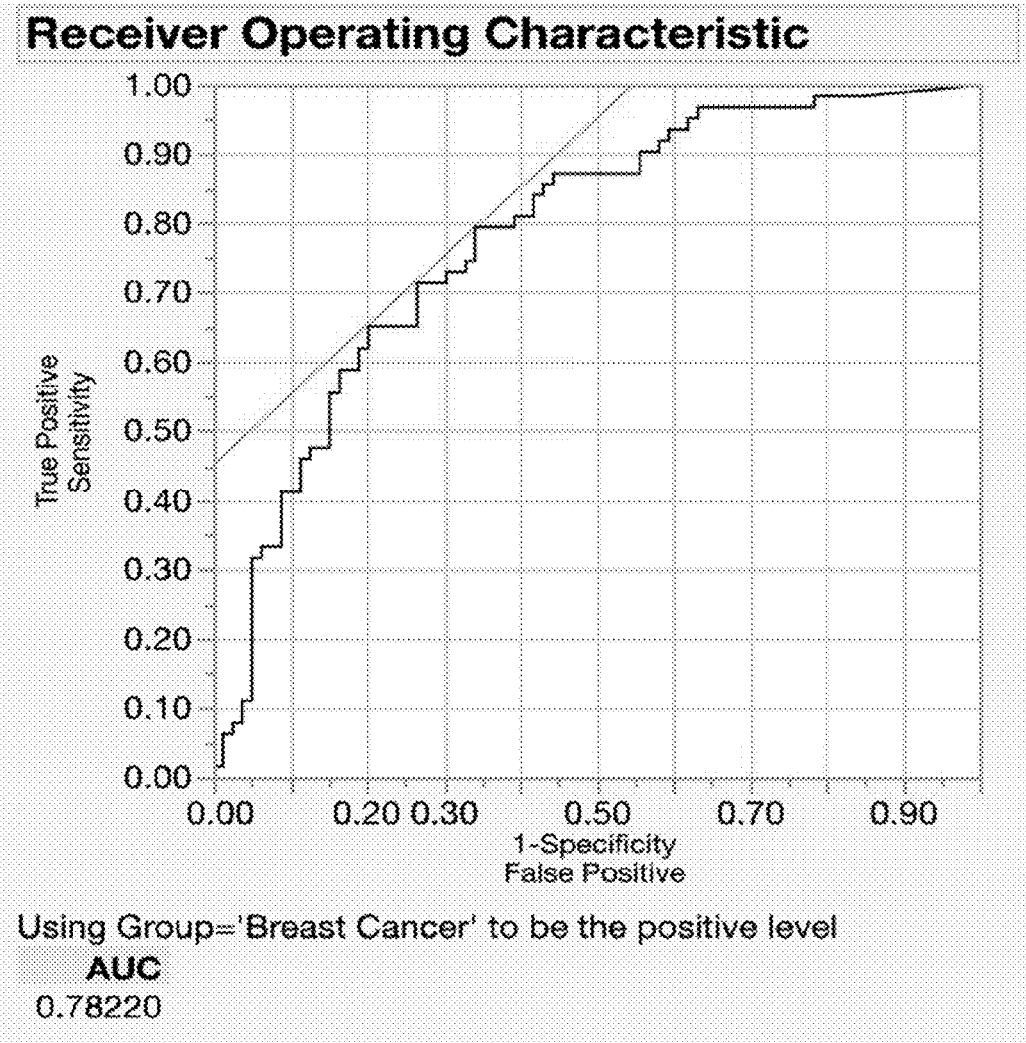
FIG. 7: ROC curve for S100A9
Figure 8:
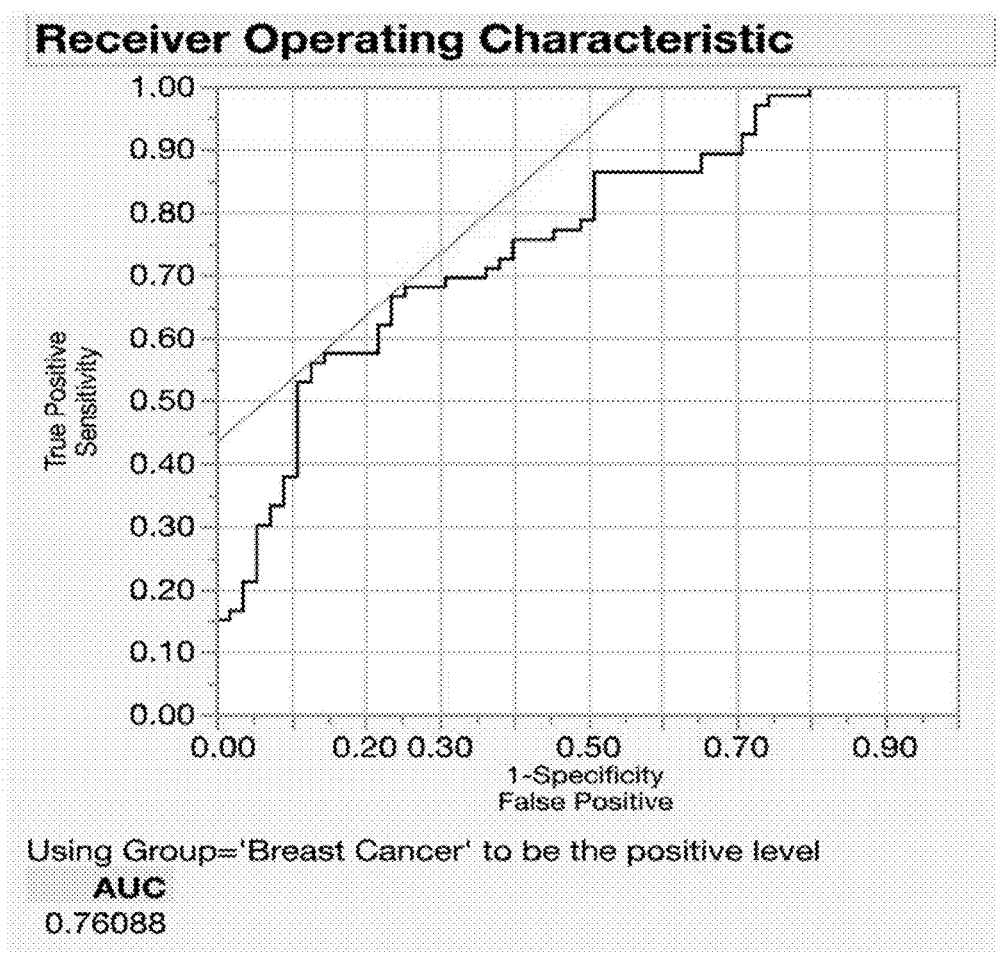
FIG. 8: ROC curve for LG3BP
Figure 9:
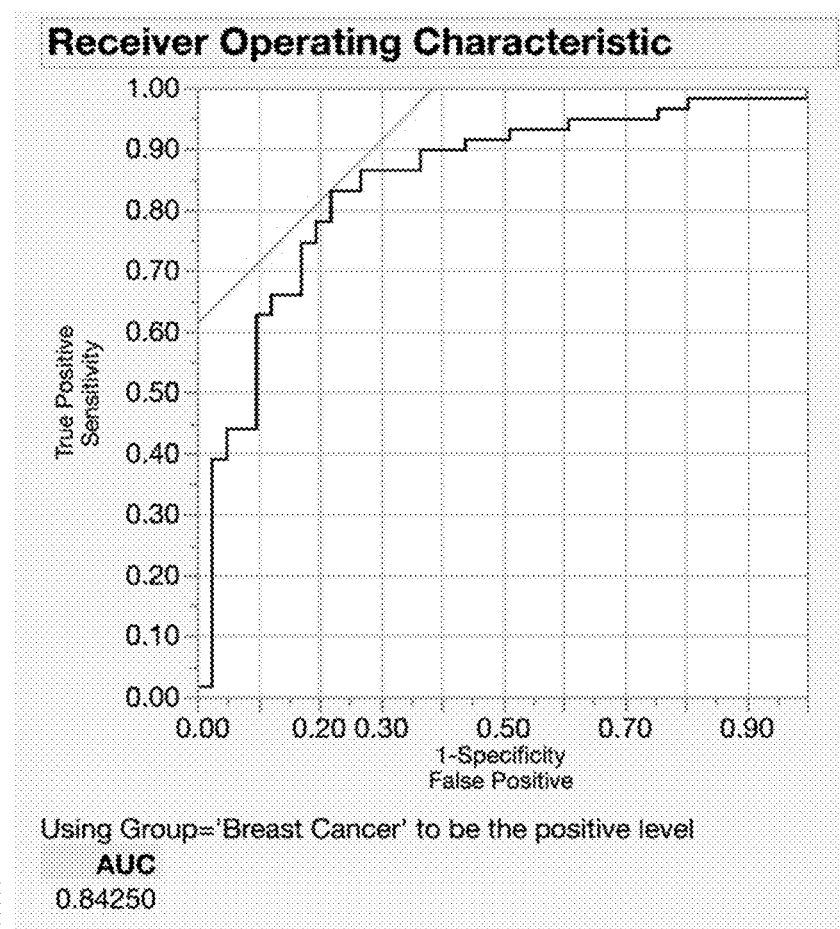
FIG. 9: ROC curve of S100A9 and LG3BP combined.

Nominal logistic regression analysis for breast cancer and control samples, was conducted using the two representative proteins. The generated ROC curve for S100A9 has an AUC of 0.78220 (FIG. 7), and LG3BP has an AUC of 0.76088 (FIG. 8). The analysis was repeated using two proteins and an AUC of 0.84250 was obtained (FIG. 9).

Sample Population Characteristics:

Clinical data such as breast density, cancer type, and tumor size were obtained on as many samples as possible.

Figure 2:
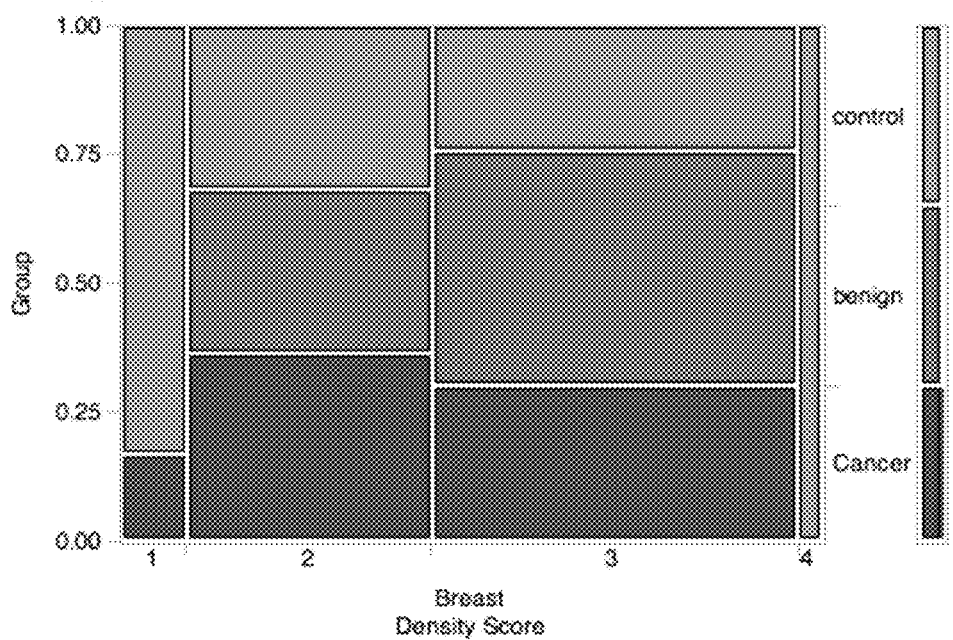
FIG. 2: Mosaic plot of the distribution of breast density for 66 of the 75 samples tested in Experiment 1.

Experiment 1: Out of the 75 samples tested, breast density scores were obtained for 41 of the samples. The break down of the sample population by breast density was 14% category 1, 36.6% category 2, 43.9% category 3, 4.7% category 4 (FIG. 2). Eighteen of the twenty-five cancer samples were collected from patients diagnosed with Intra ductal carcinoma (IDC). Two patients were diagnosed with ductal carcinoma In Situ (DCIS), one patient was diagnosed with lobular carcinoma In Situ (LCIS), and one patient was diagnosed with intra lobular carcinoma (ILC).

For classification a scale was designed where a classification of "small" was given to tumors <20 mm, a classification of "medium" was assigned to tumors between 21 mm-99 mm, and a classification of "large" was assigned to tumors >1 cm. Seventeen of the samples collected from breast cancer patients were classified as large tumors, two samples were classified as medium, and six were classified as small. Pathology information of receptor type was obtained for eight of the cancer samples. One sample was ER-/HER2-, one sample was ER-/PR-, two samples were ER+/HER2-, three samples were ER+/HER2+, and one sample was ER+/PR-.

Figure 10:
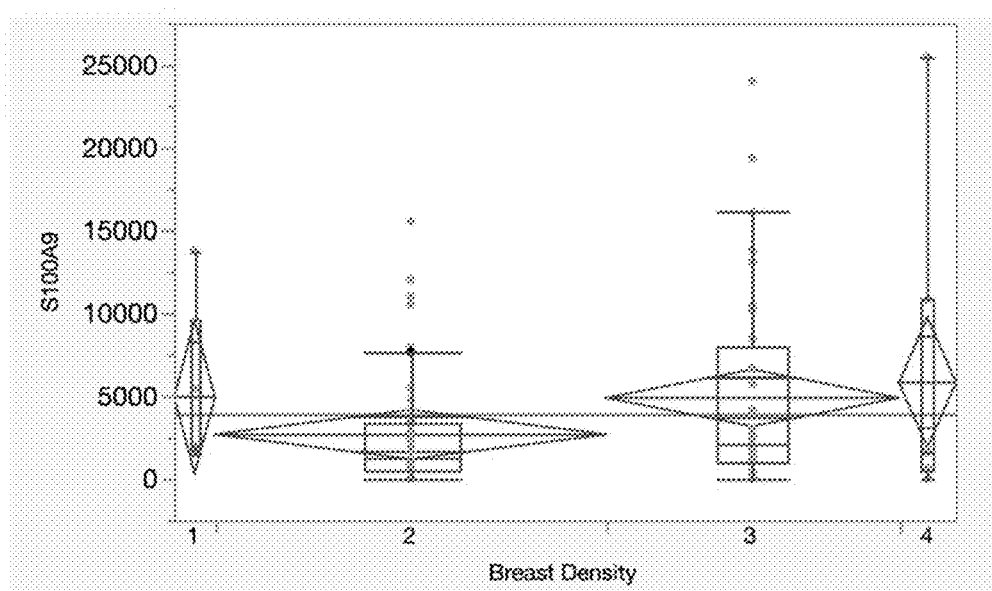
FIG. 10: ANOVA for S100A9 expression based on breast tissue category.
Figure 11:
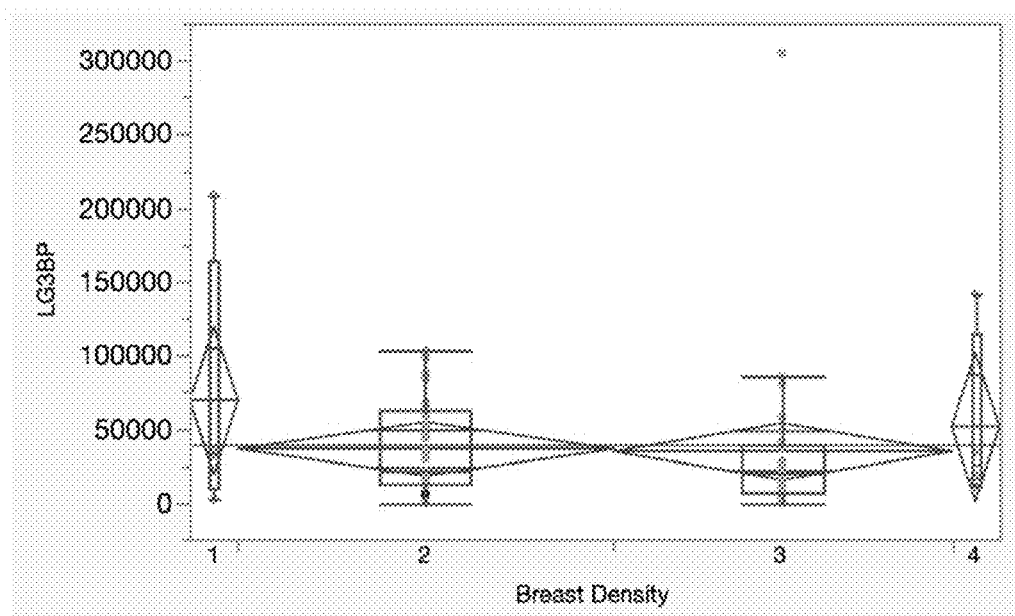
FIG. 11: ANOVA of LG3BP expression based on breast tissue category.

Experiment 2: The sample pool analyzed in this study consisted of 5.9% category 1 breast tissue; 50% category 2, 37.8% category 3, and 5.4% category 4. ANOVA analysis was conducted on several proteins evaluated by ELISA to determine if breast tissue type affects protein expression levels. Representative data is provided for two proteins studied (FIG. 10 and FIG. 11). Using an alpha level of 0.05, no statistically significant difference was observed for the means of the four types of breast tissue for each of the proteins evaluated in the ELISAs shown in FIGS. 10 and 11.

Samples were collected from a variety of breast cancer types resulting in 17 samples from patients diagnosed with DCIS, 44 samples from patients diagnosed with IDC, 4 samples from patients with both DCIS & IDC, and 5 samples from patients with ILC. Tumor size varied tremendously. Using that classification system described for Experiment 1, for the samples where tumor size was provided, 33 samples from patients with large tumors were tested, 9 samples from patients with medium tumor size, and 12 samples from patients with small tumor size. Of the 38 samples where receptor type was provided 1 sample was ER-, 2 samples were ER-/HER2-, 2 samples were triple negative (ER-/HER2-/PR-), 1 sample was ER-/HER2+, 11 samples were ER+, ER+/HER2 16, and 5 samples were ER+/HER2+. To date no distinguishing trend has been observed based on tumor size, cancer type, or receptor status, for the proteins that have been studied.

REFERENCES

Armstrong, K., Handorf, E. A., Chen, J., & Bristol Demeter, M. N. (2013). Breast cancer risk prediction and mammography biopsy decisions: a model-based study. *American Journal of Preventive Medicine*, 44(1), 15-22. doi: 10.1016/j.amepre.2012.10.002

Bigenwald, R. Z., Warner, E., Gunasekara, A., Hill, K. A., Causer, P. A., Messner, S. J., Eisen, A., Plewes, D. B., Narod, S. A., Zhang, L., Yaffe, M. J. (2008) Is Mammography Adequate for Screening Women with Inherited BRCA Mutations and Low Breast Density?. Cancer Epidemiology Biomarkers Prevention. 17(3); 707-711.

Böhm, D., Keller, K., Pieter, J., Boehm, N., Wolters, D., Siggelkow, W., et al. (2012). Comparison of tear protein levels in breast cancer patients and healthy controls using a de novo proteomic approach. *Oncology Reports*, 28(2), 429-438. doi: 10.3892/or.2012.1849

Böhm, D., Keller, K., Wehrwein, N., Lebrecht, A., Schmidt, M., Kölbl, H., & Grus, F.-H. (2011). Serum proteome profiling of primary breast cancer indicates a specific biomarker profile. *Oncology Reports*, 26(5), 1051-1056. doi: 10.3892/or.2011.1420

Boyd, N. F., Guo, H., Martin, L. J., Sun, L., Stone, J., Fishell, E., Jong, R. A., Hislop, G., Chiarelli, A., Minkin, S., Yaffee, M. J., (2007) Mammographic Density and the Risk and Detection of Breast Cancer. *The New England Journal of Medicine.* 356(3): 227-236).

Brown, M. L., Houn, F., Sickles, E. A., & Kessler, L. G. (1995). Screening Mammography in Community Practice: Positive Predictive. *American Journal of Radiology,* 165, 1373-1377.

CLIA Laws and Regulations, 2013, http://wwwn.cdc.gov/CLIA/Regulatory/default.aspx.

Grady, D. (2012). Study of Breast Biopsies Finds Surgery Used Too Extensively. *New York Times,* 1-4.

Klifa, C., Carballido-Gamio, J., Wilmes, L., Laprie, A., Shepherd, J., Gibbs, J., Fan, B., Noworolski, S., Hylton, N. (2010) Magnetic resonance imaging for secondary assessment of breast density in a high-risk cohort. *Magnetic Resonance Imaging.* 28; 8-15.

Kolb, T., Lichy, J., & Newhouse, J. (2002). Comparison of the performance of screening mammography, physical examination, and breast US and evaluation of factors that influence them: an analysis of 27,825 patient evaluations. *Radiology,* 225(1), 165-175.

Lebrecht, A., Boehm, D., Schmidt, M., Koelbl, H., & Grus, F. H. (2009a). Surface-enhanced Laser Desorption/Ionisation Time-of-flight Mass Spectrometry to Detect Breast Cancer Markers in Tears and Serum. *Cancer Genomics & Proteomics,* 6(2), 75-83.

Lebrecht, A., Boehm, D., Schmidt, M., Koelbl, H., Schwirz, R. L., & Grus, F. H. (2009b). Diagnosis of breast cancer by tear proteomic pattern. *Cancer Genomics & Proteomics,* 6(3), 177-182.

Li, J., Zhang, Z., Rosenzweig, J., Wang, Y., & Chan, D. (2002). Proteomics and bioinformatics approaches for identification of serum biomarkers to detect breast cancer. *Clin Chem,* 48(8), 1296-1304.

Luftner, D., & Possinger, K. (2002). Nuclear matrix proteins as biomarkers for breast cancer. *Expert Rev Mol Diagn,* 2(1), 23-31. doi:ERM020106 [pii]10.1586/14737159.2.1.23

Pisano, E. D., Gatsonis, C., Hendrick E., Yaffe, M., Baum, J. K., Acharyya, S., Conant, E. F. Fajardo, L. L., Bassett, L., D'Orsi, C. Jong, R., Rebner., M. (2005). Diagnostic Performance of Digital versus Film Mammography for Breast-Cancer Screening. The *New England Journal of Medicine.* 17(353). 1773-1783.

Scheel, J. R., Lee, J. M., Sprague, B. L., Lee, C. I., Lehman, C. D. (2015) Screening ultrasound as an adjunct to mammography in women with mammographically dense breasts. *Gynecology.* 212(1); 9-17.

Schiess, R., Wollscheid, B., & Aebersold, R. (2009). Targeted proteomic strategy for clinical biomarker discovery. *Molecular Oncology,* 3(1), 33-44. doi: 10.1016/j.molonc.2008.12.001

Tabar, L., Vitak, B., Chen, T. H., Yen, A. M., Cohen, A., Tot, T., Chiu, S., Chen, S. Fann, J. Rosell, J., Fohlin, H., Smith, R. A., Duffy, S. W., (2011) Swedish Two-County Trial: Impact of Mammographic Screening on Breast Cancer Mortality during 3 Decades. *Radiology,* 3(260), 658-663.

Vachon, C. M., van Gils, C. H., Sellers, T. A., Ghosh, K., Pruthi, S., Brandt, K. R., Pankratz, V. S., (2007) Mammographic density, breast cancer risk and risk prediction. *Breast Cancer Research* 9:2017 (doi: 10.1186/bcr1829).

Wu, K., & Zhang, Y. (2007). Clinical application of tear proteomics: Present and future prospects. *Proteomics. Clinical Applications,* 1(9), 972-982. doi: 10.1002/prca.200700125

APPENDIX I

| Protein Name | UniProt | IPI | Gene Name |
|---|---|---|---|
| Lipocalin 1 | P10325 | | LCN1_Human |
| Trypsin Fragments | | | |

| | | |
|---|---|---|
| 1. QSETCSPGSD | 2. VTMLISGR | 3. AVLEKTDEPGK |
| 4. AVLEKTDEPGKYTADGGK | 5. TDEPGKYTADGGK | 6. HVAYIIR |
| 7. DPKNNLEALEDFEK | 8. SHVKDHYIFYCEGELHGKPVR | 9. DHYIFYCEGELHGKPVR |
| 10. SHVKDHYIFYCEGELHGK | 11. LVGRDPKNNLEALEDFEK | 12. GLSTESILIPR |
| 13. NNLEALEDFEKAAGAR | 14. YTADGGKHVAYIIR | 15. AAGARGLSTESILIPR |
| 16. TDEPGKYTADGGKHVAYIIR | 17. AAGARGLSTESILIPRQSETCSPGSD | 18. DHYIFYCEGELHGK |
| 19. NNLEALEDFEK | 20. AMTVDREFPEMNLESVTPMTLTTLEGGN | 21. GLSTESILIPRQSETCSPGSD |

Proteins selected through Experiment 1:

```
        10          20          30          40
MKPLLLAVSL GLIAALQAHH LLASDEEIQD VSGTWYLK20AM 50          60          70          80
TVDREFPEMN LESVTPMTLT TLEGGNLEAK 7VTMLISGRCQ 90          100         110
EVK3,4AVLEK5,16TD EPGK14YTADGG K6HVAYIIR8SH 120         130         140
VK9,10,18DHYIFYCE GELHGKPVRG VR11LVGR7DPK13,19N 150         160         170
NLEALEDFEK 15,17AAGAR12,21GLSTE SILIPR1QSET CSPGSD
```

| Protein Name | UniProt | IPI | Gene Name |
|---|---|---|---|
| Zinc-α-2-glycoprotein | P25311 | | ZA2G_Human |
| Trypsin Fragments | | | |

| | | |
|---|---|---|
| 1. AGEVQEPELR | 2. AYLEEECPATLR | 3. CLAYDFYPGK |
| 4. EIPAWVPFDPAAQITK | 5. HVEDVPAFQALGSLNDLQFFR | 6. LKCLAYDFYPGK |
| 7. NILDRQDPPSVVVTSHQAPGEK | 8. QDPPSVVVTSHQAPGEK | 9. QKWEAEPVYVQR |

25

-continued

| | | |
|---|---|---|
| 10. WEAEPVYVQR | 11. YSKNILDRQDPPSVVVTSHQAPGEK | 12. YSLTYIYTGLSK |
| 13. YYYDGKDYIEFNK | 14. AYLEEECPATLRK | 15. AKAYLEEECPATLRK |
| 16. QVEGMEDWKQDSQLQK | 17. CLAYDFYPGKIDVHWTR | |

```
         10         20         30         40
MVRMVPVLLS LLLLLGPAVP QENQDGR¹²YSL TYIYTGLSK⁵H
         50         60         70         80
VEDVPAFQAL GSLNDLQFFR YNSKDRKSQP MGLWR¹⁶QVEGM
         90        100        110        120
EDWKQDSQLQ KAREDIFMET LKDIVEYYND SNGSHVLQGR
        130        140        150        160
FGCEIENNRS SGAFWK¹³YYYD GKDYIEFNK⁴E IPAWVPFDPA
        170        180        190        200
AQITK⁹QK¹⁰WEA EPVYVQR¹⁵AK²,¹⁴A YLEEECPATL RK¹¹YLKYS³KNI
        210        220        230        240
LDR⁸QDPPSVV VTSHQAPGEK KK⁶LK³,¹⁷CLAYDF YPGKIDVHWT
        250        260        270        280
R¹AGEVQEPEL RGDVLHNGNG TYQSWVVAV PPQDTAPYSC
        290
HVQHSSLAQP LVVPWEAS
```

```
         10         20         30         40
¹EVQLVESGGG LVQPGGSLRL SCAASGFTFS YYNMNWVRQV
         50         60         70         80
TGKGLEWVSA IGTAGDQYYA DSVKGRFTIS RNDSKNTLYL
         90        100        110        120
NMNSLR²AEDT AVYYCARSPV SLVDGWLYYY YGSVWGQGTL
```

| Protein Name | UniProt | IPI | Gene Name |
|---|---|---|---|

```
                20         30         40
MSRSVALAVL ALLSLSGLEA IQRTPK³IQVY SRHPAENGK²S
         50         60         70         80
NFLNCYVSGF HPSDIEVDLL KNGER⁴IEK³VE HSDLSFSKDW
         90        100        110
SFYLLYYTEF TPTER⁶DEYAC R⁵VNHVTLSQP KIVKWDRDM
```

| Protein Name | UniProt | IPI | Gene Name |
|---|---|---|---|
| Ig heavy chain V-III region BRO | P01766 | | HV305_Human |

Trypsin Fragments

| | | |
|---|---|---|
| 1. EVQLVESGGGLVQPGGSLR | 2. AEDTAVYYCAR | 3. |

26

| Protein Name | UniProt | IPI | Gene Name |
|---|---|---|---|
| Beta-2-microglobulin | P61769 | | B2MG_Human |

Trypsin Fragments

| | | |
|---|---|---|
| 1. IQVYSRHPAENGK | 2. SNFLNCYVSGFHPSDIEVDLLK | 3. IEKVEHHSDLSFSK |
| 4. VEHSDLSFSK | 5. VNHVTLSQPK | 6. DEYACRVNHVTLSQPK |

```
                20         30         40
MKSSGLFPFL VLLALGTLAP WAVEGSGKSF K²AGVCPPKKS
         50         60         70         80
AQCLR⁴YK⁶KPE CQSDWQCPGK KR²CCPDTCGI K³CLDPVDTPN
         90        100        110        120
PTRRKPGKCP VTYGQCLMLN PPNFCEMDGQ CKRDLKCCMG
        130
MCGK⁵SCVSPV KA
```

| Protein Name | UniProt | IPI | Gene Name |
|---|---|---|---|
| Cystatin-B | P04080 | | CYTB_Human |

Trypsin Fragments

| | | |
|---|---|---|
| 1. AVSFSQVVAGTNFIK | 2. SQVVAGTNYFIK | 3. VFQSLPHENKPLETLSNYQTNK |
| 4. VHVGDEDFVHLR | | |

```
         10         20         30         40
MMCGAPSATQ PATAETQHIA DQVRSQLEEK ENKKFPVFK²A
         50         60         70         80
VSFK²SQVVAG TNYFIK⁴VHVG DEDFVHLR³VF QSLPHENKPL
         90
TLSNYQTNKA KHDELTYF
```

| Protein Name | UniProt | IPI | Gene Name |
|---|---|---|---|
| Ig Heavy Chain V-III VH26 | P01764 | | HV303_Human |

Trypsin Fragments

| | | |
|---|---|---|
| 1. EVQLLESGGGLVQPGGSLR | 2. AEDTAVYYCAK | 3. |

```
GKGLEWVSAI SGSGGSTYYG DSVKGRFTIS RNDSKNTLYL
QMNSLR²AEDT AVYYCAK
```

| Antileukoproteinase P03972 | | SLP1_Human |
|---|---|---|
| Trypsin Fragments ||| 
| 1. AGVCPPKK SAQCLR | 2. CCPDTCGIKCL DPVDTPNPTR | 3. CLDPVDTP NPTR |
| 4. YKKPECQS DWQCPGK | 5. SCVSPVKA | 6. KPECQSDW QCPGK |

```
10         20         30         40
MEFGLSWLFL VAILKGVQC¹E VQLLESGGGL VQPGGSLRLS 50         60
CAASGFTFSS YAMSWVRQAP 70         80         90         100        110
```

| Protein Name | UniProt | IPI | Gene Name |
|---|---|---|---|
| Ig Lambda Chain V-IV region HiL | P01717 | | LV403_Human |
| Trypsin Fragments ||||
| 1. SYELTQP PSVSVSP GQTAR | 2. | 3. ||

```
10         20         30         40
SYELTQPPSV SVSPGQTARI TCSANALPNQ YAYWYQQKPG 50         60
RAPVMVIYKD TQRPSGIPQR
```

| Protein Name | UniProt | IPI | Gene Name |
|---|---|---|---|
| Galectin-3 | P17931 | | LEG3_Human |
| Trypsin Fragments ||||
| 1. IQVLVEP DHFK | 2. QSVFPFE ESGKPFK | 3. VIVCNTK LDNNWGR |
| 4. IALDFQR | 5. VAVNDAH LLQYNHR | 6. GNDVAFH FNPR |
| 7. MLITILG TVKPNAN R | 8. RVIVCNT KLDNNWG R | 9. KLNEISK |

```
70         80         90         100
FSSSTSGTTV TLTISGVQAE DEADYYCQAW DNSASIFGGG

TKLTVLG 10         20         30         40
MADNFSLHDA LSGSGNPNPQ GWPGAWGNQP AGAGGYPGAS 50         60         70         80
YPGAYPGQAP PGAYPGQAPP GAYPGAPGAY PGAPAPGVYP 90         100        110        120
GPPSGPGAYP SSGQPSATGA YPATGPYGAP AGPLIVPYNL 130        140        150        160
PLPGGVVPR⁷M LITILGTVKP NANR⁴IALDFQ R⁶GNDVAFHFN 170        180        190        200
PRFNENNR⁸R³V IVCNTKLDNN WGREER²QSVF PFESGKPFK¹I 210        220        230        240
QVLVEPDHFK ⁵VAVNDAHLLQ YNHRVK³KLNE ISKLGISGDI

250
DLTSASYTMI 10         20         30         40
M¹AGELTPEEE AQYK²K³AFSAV DTDGNGTINA QELGAALKAT 50         60         70         80
GK⁶NLSEAQLR KLISEVDSDG DGEISFQEFL TAAKKAR⁴AGL 90         100        110        120
EDLQVAFRAF DQDGDGHITV DELRRAMAGL GQPLPQEELD 130        140
AMIR⁵EADVDQ DGRVNYEEFA RMLAQE
```

Proteins selected from Experiment 2:

| Protein Name | uniProt | IPI | Gene Name |
|---|---|---|---|
| Calmodulin-like protein 5 | Q9NZT1 | | CALL5_Human |
| Trypsin Fragments ||||
| 1. AGELTPEEEAQYKK  2. KAFSAVDTDGNGTINAQELGAALK  3. AFSAVDTDGNGTINAQELGAALK ||||
| 4. AGLEDLQVAFR    5. EADVDQDGRVNYEEFAR    6. NLSEAQLR ||||

| Protein Name | Gene |
|---|---|
| Ig lambda chain V-IV region Hil | LV403 |
| Ig heavy chain V-III BRO | HV305 |
| Ig heavy chain V-III VH26 | HV303 |
| Beta-2-microglobulin | B2MG |
| Lipocalin-1 | LCN1 |
| Zinc-⍺-2-glycoprotein | ZA2G |
| Cystatin B | CYTB |
| Antileukoproteinase | SLP1 |
| Galectin-3 | LEG3 |
| Histidine triad nucleotide-binditig protein 1 | D6RD60 |
| S100A9 | S10A9 |
| S100A8 | S10A8 |
| Galectin- 3-binding protein | LG3BP |
| Cluster of Ig alpha- 1 chain C region | IGHA1 |
| Cluster of Ig kappa chain V-III region HAH | KV312 |
| VEGF co-regulated chemokine | VCC1 |
| L-lactate dehydrogenase A chain | LDHA |
| Aldo-keto reductase family 1 member C | AKR1C1 |
| Rootletin | B1AKD8 |
| L-lactate dehydrogenase B chain | LDHB |
| Retinal dehydrogenase 1 | AL1A1 |
| Uncharacterized Protein | B4E1Z4 |
| Alpha-1-antichymotrypsin | AACT |
| Superoxide dismutase [Cu—Zn] | SODC |

| Protein Name | Gene |
|---|---|
| SPARC-like protein 1 | SPRL1 |
| Ig heavy chain V-III region TIL | HV304 |
| Keratin | K1C9 |
| Cystatin-SN | CYTN |
| Alpha-actinin-4 | ACTN4 |
| Ig lambda-3 chain C regions (Fragment) | IGLC3 |
| Immunoglobulin lambda-like polypeptide 5 | IGLL5 |
| Alcohol dehydrogenase 1C | ADH1G |
| Malate dehydrogenase, mitochondrial | MDHM |
| Calmodulin-like protein 5 | CALL5 |
| Alpha-1-antitrypsin | A1AT |
| Alpha-1B-glycoprotein | A1BG |
| Leucine-rich alpha-2-glycoprotein | A2GL |
| Small ubiquitin-related modifier 3 | A8MU27 |
| Anterior gradient protein 2 homolog | AGR2 |
| Profilin-1 | PROF1 |
| Cluster of Ig lambda chain V-III region LOI | LV302 |
| Prothrombin | E9PIT3 |
| Hemopexin | HEMO |
| Ig gamma-2 chain C region | IGHG2 |
| Ubiquitin-40S ribosomal protein S27a | RPS27A |
| Afamin | AFAM |
| Apolipoprotein A-I | APOA1 |
| Apolipoprotein A-IV | APOA4 |
| Flavin reductase (NADPH) | BLVRB |
| Prosaposin | PSAP |
| Lacritin | LACRT |
| 14-3-3 sigma | 1433S |
| alpha-2-lis-glycoprotein | FETUA |
| 60S acidic ribosomal protein P1 | RLA1 |
| Inter-alpha-trypsin inhibitor heavy chain H2 | ITIH2 |
| Mucin-like protein 1 | MUCL1 |
| S100 A6 | S100A6 |
| Na(+)/H(+) exchange regulatory cofactor NHE-RF1 | NHRF1 |
| Thioredoxin domain-containing protein 17 | I3L0K2 |
| Lymphocyte-specific protein | LSP1 |
| Cluster of Haptoglobin | H3BS21 |
| Myosin regulatory light chain 12A | J2QRS3 |
| Ribonuclease inhibitor | RINI |
| Alpha-enolase | ENOA |
| Cluster of Ig kappa chain V-I region EU | KV106 |
| Alcohol dehydrogenase class 4 mu/sigma chain | ADH7 |
| Protein AMBP | AMBP |
| Angiotensinogen | ANGT |
| Antithrombin-III | ANT3 |
| Apolipoprotein A-II | APOA2 |
| Calpastatin | B7Z574 |
| Brain acid soluble protein 1 | BASP1 |
| Alpha-2-HS-glycoprotein | C9JV77 |
| Calreticulin | CALR |
| Calpain-1 catalytic subunit | CAN1 |
| Cell division control protein 42 homolog | CDC42 |
| Complement C3 | CO3 |
| Coronin-1A | COR1A |
| Programmed cell death 6-interacting protein | DCD |
| Defensin 1 | DEF1 |
| F-box only protein 50 | FBX50 |
| Gamma-glutamylcyclotransferase | GGCT |
| Glutathione reductase, mitochondrial | GSHR |
| Keratin, type II cytoskeletal 1 | K2C1 |
| UMP-CMP kinase | KCY |
| Mesothelin | MSLN |
| N-acetylmuramoyl-L-alanine amidase | PGRP2 |
| Nicotinate phosphoribosyltransferase | PNCB |
| Inter-alpha-trypsin inhibitor heavy chain H1 | ITIH1 |
| Ribonuclease T2 | RNASET2 |
| Superoxide dismutase [Mn], mitochondrial | SODM |
| Small proline-rich protein 3 | SPRR3 |
| Sic substrate cortactin | SRC8 |
| Cluster of Tubulin beta-4B chain | TBb4B |
| Tropomyosin alpha-3 chain | TPM3 |
| Serotransferrin | TRFE |
| Glutathione S-transferase P | THIO |
| Vitronectin | VTNC |
| Vitaimn D Binding protein | Q6LDC6 |
| Inter-alpha-trypsin inhibitor heavy chain H4 | ITIH4 |
| Metalloprotease inhibitor | TI MP1 |
| Heat Shock protein 90 | HSP90 |
| Cathepsin B | CATB |
| Ceruloplasmin | CERU |
| Calprotectin | |
| alpha-2 -macroglobulin | A2MG |
| Transthyretin | TTHY |

---

What is claimed is:

1. A method of treating breast cancer in a subject, comprising: obtaining a sample of lacrimal secretions from the subject; detecting levels in the sample of at least three protein markers comprising S100A8, S100A9, and LG3BP; determining the subject has breast cancer if the levels of S100A8 increase, the levels of S100A9 increase, and the levels of LG3BP decrease as compared to the levels of the corresponding protein markers in a control sample lacking cancer; and administering an appropriate anti-cancer therapeutic to the subject if the subject is determined to have breast cancer.

2. The method of claim 1, wherein the subject is a human.

3. The method of claim 1, wherein the levels of the LG3BP protein market are decreased at least, 1.5 fold, 2 fold, 4 fold or more relative to the level of the corresponding marker in the control sample.

4. The method of claim 1, wherein the levels of the S100A8 and S100A9 protein markers are increased at least, 1.5 fold, 2 fold, 4 fold or more relative to the level of the corresponding markers in the control sample.

5. The method of claim 1, wherein the level of the marker is detected by liquid chromatography-mass spectroscopy (LC-MS).

6. The method of claim 1, wherein the levels of the at least three markers are detected by an antibody-based detection method.

7. The method of claim 1, wherein the level of the marker is detected by multiplex protein detection method.

8. The method of claim 1, wherein the breast density of the subject is category 1, category 2, category 3 or category 4.

9. The method of claim 1, wherein the cancer is detected as a stage of breast cancer.

10. The method of claim 1, wherein at least ten markers are used in combination.

11. The method of claim 1, wherein at least five markers are used in combination.

* * * * *

SEQUENCE LISTING

```
<160> NUMBER OF SEQ ID NOS: 1162

<210> SEQ ID NO 1
<211> LENGTH: 599
<212> TYPE: PRT
<213> ORGANISM: Homo sapiens

<400> SEQUENCE: 1

Met Lys Leu Leu Lys Leu Thr Gly Phe Ile Phe Phe Leu Phe Phe Leu
1               5                   10                  15

Thr Glu Ser Leu Thr Leu Pro Thr Gln Pro Arg Asp Ile Glu Asn Phe
            20                  25                  30

Asn Ser Thr Gln Lys Phe Ile Glu Asp Asn Ile Glu Tyr Ile Thr Ile
        35                  40                  45

Ile Ala Phe Ala Gln Tyr Val Gln Glu Ala Thr Phe Glu Glu Met Glu
    50                  55                  60

Lys Leu Val Lys Asp Met Val Glu Tyr Lys Asp Arg Cys Met Ala Asp
65                  70                  75                  80

Lys Thr Leu Pro Glu Cys Ser Lys Leu Pro Asn Asn Val Leu Gln Glu
                85                  90                  95

Lys Ile Cys Ala Met Glu Gly Leu Pro Gln Lys His Asn Phe Ser His
            100                 105                 110
```

```
Cys Cys Ser Lys Val Asp Ala Gln Arg Arg Leu Cys Phe Phe Tyr Asn
        115                 120                 125

Lys Lys Ser Asp Val Gly Phe Leu Pro Pro Phe Pro Thr Leu Asp Pro
130                 135                 140

Glu Glu Lys Cys Gln Ala Tyr Glu Ser Asn Arg Glu Ser Leu Leu Asn
145                 150                 155                 160

His Phe Leu Tyr Glu Val Ala Arg Arg Asn Pro Phe Val Phe Ala Pro
                165                 170                 175

Thr Leu Leu Thr Val Ala Val His Phe Glu Glu Val Ala Lys Ser Cys
                180                 185                 190

Cys Glu Glu Gln Asn Lys Val Asn Cys Leu Gln Thr Arg Ala Ile Pro
                195                 200                 205

Val Thr Gln Tyr Leu Lys Ala Phe Ser Ser Tyr Gln Lys His Val Cys
        210                 215                 220

Gly Ala Leu Leu Lys Phe Gly Thr Lys Val Val His Phe Ile Tyr Ile
225                 230                 235                 240

Ala Ile Leu Ser Gln Lys Phe Pro Lys Ile Glu Phe Lys Glu Leu Ile
                245                 250                 255

Ser Leu Val Glu Asp Val Ser Ser Asn Tyr Asp Gly Cys Cys Glu Gly
        260                 265                 270

Asp Val Val Gln Cys Ile Arg Asp Thr Ser Lys Val Met Asn His Ile
        275                 280                 285

Cys Ser Lys Gln Asp Ser Ile Ser Ser Lys Ile Lys Glu Cys Cys Glu
        290                 295                 300

Lys Lys Ile Pro Glu Arg Gly Gln Cys Ile Ile Asn Ser Asn Lys Asp
305                 310                 315                 320

Asp Arg Pro Lys Asp Leu Ser Leu Arg Glu Gly Lys Phe Thr Asp Ser
                325                 330                 335

Glu Asn Val Cys Gln Glu Arg Asp Ala Asp Pro Asp Thr Phe Phe Ala
                340                 345                 350

Lys Phe Thr Phe Glu Tyr Ser Arg Arg His Pro Asp Leu Ser Ile Pro
                355                 360                 365

Glu Leu Leu Arg Ile Val Gln Ile Tyr Lys Asp Leu Leu Arg Asn Cys
        370                 375                 380

Cys Asn Thr Glu Asn Pro Pro Gly Cys Tyr Arg Tyr Ala Glu Asp Lys
385                 390                 395                 400

Phe Asn Glu Thr Thr Glu Lys Ser Leu Lys Met Val Gln Gln Glu Cys
                405                 410                 415

Lys His Phe Gln Asn Leu Gly Lys Asp Gly Leu Lys Tyr His Tyr Leu
                420                 425                 430

Ile Arg Leu Thr Lys Ile Ala Pro Gln Leu Ser Thr Glu Glu Leu Val
                435                 440                 445

Ser Leu Gly Glu Lys Met Val Thr Ala Phe Thr Thr Cys Cys Thr Leu
        450                 455                 460

Ser Glu Glu Phe Ala Cys Val Asp Asn Leu Ala Asp Leu Val Phe Gly
465                 470                 475                 480

Glu Leu Cys Gly Val Asn Glu Asn Arg Thr Ile Asn Pro Ala Val Asp
                485                 490                 495

His Cys Cys Lys Thr Asn Phe Ala Phe Arg Arg Pro Cys Phe Glu Ser
                500                 505                 510

Leu Lys Ala Asp Lys Thr Tyr Val Pro Pro Pro Phe Ser Gln Asp Leu
        515                 520                 525
```

Phe Thr Phe His Ala Asp Met Cys Gln Ser Gln Asn Glu Glu Leu Gln
530                 535                 540

Arg Lys Thr Asp Arg Phe Leu Val Asn Leu Val Lys Leu Lys His Glu
545                 550                 555                 560

Leu Thr Asp Glu Glu Leu Gln Ser Leu Phe Thr Asn Phe Ala Asn Val
                565                 570                 575

Val Asp Lys Cys Cys Lys Ala Glu Ser Pro Glu Val Cys Phe Asn Glu
                580                 585                 590

Glu Ser Pro Lys Ile Gly Asn
            595

<210> SEQ ID NO 2
<211> LENGTH: 93
<212> TYPE: PRT
<213> ORGANISM: Homo sapiens

<400> SEQUENCE: 2

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
                20                  25                  30

Asp Leu Lys Lys Leu Leu Glu Thr Glu Cys Pro Gln Tyr Ile Arg Lys
            35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90

<210> SEQ ID NO 3
<211> LENGTH: 103
<212> TYPE: PRT
<213> ORGANISM: Homo sapiens

<400> SEQUENCE: 3

Met Ala Asp Glu Ile Ala Lys Ala Gln Val Ala Arg Pro Gly Gly Asp
1               5                   10                  15

Thr Ile Phe Gly Lys Ile Ile Arg Lys Glu Ile Pro Ala Lys Ile Ile
                20                  25                  30

Phe Glu Asp Asp Arg Cys Leu Ala Phe His Asp Ile Ser Pro Gln Ala
            35                  40                  45

Pro Thr His Phe Leu Val Ile Pro Lys Lys His Ile Ser Gln Ile Ser
    50                  55                  60

Val Ala Glu Asp Asp Asp Glu Ser Val Ile Thr Lys Gly Lys Pro Glu
65                  70                  75                  80

Lys Pro Leu Gly Leu Gln Leu Pro Ser Cys Phe Pro Lys Leu Leu His
                85                  90                  95

His Phe Val Ser His Gln Gln
            100

<210> SEQ ID NO 4
<211> LENGTH: 585
<212> TYPE: PRT
<213> ORGANISM: Homo sapiens

<400> SEQUENCE: 4

Met Thr Pro Pro Arg Leu Phe Trp Val Trp Leu Leu Val Ala Gly Thr

```
1               5                   10                  15
Gln Gly Val Asn Asp Gly Asp Met Arg Leu Ala Asp Gly Ala Thr
                20                  25                  30
Asn Gln Gly Arg Val Glu Ile Phe Tyr Arg Gly Gln Trp Gly Thr Val
                35                  40                  45
Cys Asp Asn Leu Trp Asp Leu Thr Asp Ala Ser Val Cys Arg Ala
                50                  55                  60
Leu Gly Phe Glu Asn Ala Thr Gln Ala Leu Gly Arg Ala Ala Phe Gly
65                  70                  75                  80
Gln Gly Ser Gly Pro Ile Met Leu Asp Glu Val Gln Cys Thr Gly Thr
                85                  90                  95
Glu Ala Ser Leu Ala Asp Cys Lys Ser Leu Gly Trp Leu Lys Ser Asn
                100                 105                 110
Cys Arg His Glu Arg Asp Ala Gly Val Val Cys Thr Asn Glu Thr Arg
                115                 120                 125
Ser Thr His Thr Leu Asp Leu Ser Arg Glu Leu Ser Glu Ala Leu Gly
                130                 135                 140
Gln Ile Phe Asp Ser Gln Arg Gly Cys Asp Leu Ser Ile Ser Val Asn
145                 150                 155                 160
Val Gln Gly Glu Asp Ala Leu Gly Phe Cys Gly His Thr Val Ile Leu
                165                 170                 175
Thr Ala Asn Leu Glu Ala Gln Ala Leu Trp Lys Glu Pro Gly Ser Asn
                180                 185                 190
Val Thr Met Ser Val Asp Ala Glu Cys Val Pro Met Val Arg Asp Leu
                195                 200                 205
Leu Arg Tyr Phe Tyr Ser Arg Arg Ile Asp Ile Thr Leu Ser Ser Val
                210                 215                 220
Lys Cys Phe His Lys Leu Ala Ser Ala Tyr Gly Ala Arg Gln Leu Gln
225                 230                 235                 240
Gly Tyr Cys Ala Ser Leu Phe Ala Ile Leu Leu Pro Gln Asp Pro Ser
                245                 250                 255
Phe Gln Met Pro Leu Asp Leu Tyr Ala Tyr Ala Val Ala Thr Gly Asp
                260                 265                 270
Ala Leu Leu Glu Lys Leu Cys Leu Gln Phe Leu Ala Trp Asn Phe Glu
                275                 280                 285
Ala Leu Thr Gln Ala Glu Ala Trp Pro Ser Val Pro Thr Asp Leu Leu
                290                 295                 300
Gln Leu Leu Leu Pro Arg Ser Asp Leu Ala Val Pro Ser Glu Leu Ala
305                 310                 315                 320
Leu Leu Lys Ala Val Asp Thr Trp Ser Trp Gly Glu Arg Ala Ser His
                325                 330                 335
Glu Glu Val Glu Gly Leu Val Glu Lys Ile Arg Phe Pro Met Met Leu
                340                 345                 350
Pro Glu Glu Leu Phe Glu Leu Gln Phe Asn Leu Ser Leu Tyr Trp Ser
                355                 360                 365
His Glu Ala Leu Phe Gln Lys Lys Thr Leu Gln Ala Leu Glu Phe His
                370                 375                 380
Thr Val Pro Phe Gln Leu Leu Ala Arg Tyr Lys Gly Leu Asn Leu Thr
385                 390                 395                 400
Glu Asp Thr Tyr Lys Pro Arg Ile Tyr Thr Ser Pro Thr Trp Ser Ala
                405                 410                 415
Phe Val Thr Asp Ser Ser Trp Ser Ala Arg Lys Ser Gln Leu Val Tyr
                420                 425                 430
```

```
Gln Ser Arg Arg Gly Pro Leu Val Lys Tyr Ser Ser Asp Tyr Phe Gln
        435                 440                 445

Ala Pro Ser Asp Tyr Arg Tyr Tyr Pro Tyr Gln Ser Phe Gln Thr Pro
450                 455                 460

Gln His Pro Ser Phe Leu Phe Gln Asp Lys Arg Val Ser Trp Ser Leu
465                 470                 475                 480

Val Tyr Leu Pro Thr Ile Gln Ser Cys Trp Asn Tyr Gly Phe Ser Cys
            485                 490                 495

Ser Ser Asp Glu Leu Pro Val Leu Gly Leu Thr Lys Ser Gly Gly Ser
            500                 505                 510

Asp Arg Thr Ile Ala Tyr Glu Asn Lys Ala Leu Met Leu Cys Glu Gly
            515                 520                 525

Leu Phe Val Ala Asp Val Thr Asp Phe Glu Gly Trp Lys Ala Ala Ile
        530                 535                 540

Pro Ser Ala Leu Asp Thr Asn Ser Ser Lys Ser Thr Ser Ser Phe Pro
545                 550                 555                 560

Cys Pro Ala Gly His Phe Asn Gly Phe Arg Thr Val Ile Arg Pro Phe
            565                 570                 575

Tyr Leu Thr Asn Ser Ser Gly Val Asp
        580                 585

<210> SEQ ID NO 5
<211> LENGTH: 353
<212> TYPE: PRT
<213> ORGANISM: Homo sapiens

<400> SEQUENCE: 5

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
            85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
        130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
            165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
```

```
                210                 215                 220
Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
                275                 280                 285

Thr Thr Thr Phe Ala Val Thr Ser Ile Leu Arg Val Ala Ala Glu Asp
            290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
                340                 345                 350

Tyr

<210> SEQ ID NO 6
<211> LENGTH: 334
<212> TYPE: PRT
<213> ORGANISM: Homo sapiens

<400> SEQUENCE: 6

Met Ala Thr Leu Lys Glu Lys Leu Ile Ala Pro Val Ala Glu Glu
1               5                   10                  15

Ala Thr Val Pro Asn Asn Lys Ile Thr Val Val Gly Val Gly Gln Val
                20                  25                  30

Gly Met Ala Cys Ala Ile Ser Ile Leu Gly Lys Ser Leu Ala Asp Glu
            35                  40                  45

Leu Ala Leu Val Asp Val Leu Glu Asp Lys Leu Lys Gly Glu Met Met
    50                  55                  60

Asp Leu Gln His Gly Ser Leu Phe Leu Gln Thr Pro Lys Ile Val Ala
65                  70                  75                  80

Asp Lys Asp Tyr Ser Val Thr Ala Asn Ser Lys Ile Val Val Thr
                85                  90                  95

Ala Gly Val Arg Gln Gln Glu Gly Glu Ser Arg Leu Asn Leu Val Gln
            100                 105                 110

Arg Asn Val Asn Val Phe Lys Phe Ile Ile Pro Gln Ile Val Lys Tyr
        115                 120                 125

Ser Pro Asp Cys Ile Ile Ile Val Val Ser Asn Pro Val Asp Ile Leu
    130                 135                 140

Thr Tyr Val Thr Trp Lys Leu Ser Gly Leu Pro Lys His Arg Val Ile
145                 150                 155                 160

Gly Ser Gly Cys Asn Leu Asp Ser Ala Arg Phe Arg Tyr Leu Met Ala
                165                 170                 175

Glu Lys Leu Gly Ile His Pro Ser Ser Cys His Gly Trp Ile Leu Gly
            180                 185                 190

Glu His Gly Asp Ser Ser Val Ala Val Trp Ser Gly Val Asn Val Ala
        195                 200                 205

Gly Val Ser Leu Gln Glu Leu Asn Pro Glu Met Gly Thr Asp Asn Asp
    210                 215                 220

Ser Glu Asn Trp Lys Glu Val His Lys Met Val Val Glu Ser Ala Tyr
```

```
                    225                 230                 235                 240

Glu Val Ile Lys Leu Lys Gly Tyr Thr Asn Trp Ala Ile Gly Leu Ser
                245                 250                 255

Val Ala Asp Leu Ile Glu Ser Met Leu Lys Asn Leu Ser Arg Ile His
            260                 265                 270

Pro Val Ser Thr Met Val Lys Gly Met Tyr Gly Ile Glu Asn Glu Val
        275                 280                 285

Phe Leu Ser Leu Pro Cys Ile Leu Asn Ala Arg Gly Leu Thr Ser Val
    290                 295                 300

Ile Asn Gln Lys Leu Lys Asp Asp Glu Val Ala Gln Leu Lys Lys Ser
305                 310                 315                 320

Ala Asp Thr Leu Trp Asp Ile Gln Lys Asp Leu Lys Asp Leu
                325                 330

<210> SEQ ID NO 7
<211> LENGTH: 332
<212> TYPE: PRT
<213> ORGANISM: Homo sapiens

<400> SEQUENCE: 7

Met Ala Thr Leu Lys Asp Gln Leu Ile Tyr Asn Leu Leu Lys Glu Glu
1               5                   10                  15

Gln Thr Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Asn Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asn Cys Lys Leu Leu Ile Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Met Asn Val Ala Gly
        195                 200                 205

Val Ser Leu Lys Thr Leu His Pro Asp Leu Gly Thr Asp Lys Asp Lys
    210                 215                 220

Glu Gln Trp Lys Glu Val His Lys Gln Val Val Glu Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270
```

```
Val Ser Thr Met Ile Lys Gly Leu Tyr Gly Ile Lys Asp Val Phe
            275                 280                 285

Leu Ser Val Pro Cys Ile Leu Gly Gln Asn Gly Ile Ser Asp Leu Val
            290                 295                 300

Lys Val Thr Leu Thr Ser Glu Glu Ala Arg Leu Lys Lys Ser Ala
305                 310                 315                 320

Asp Thr Leu Trp Gly Ile Gln Lys Glu Leu Gln Phe
                    325                 330

<210> SEQ ID NO 8
<211> LENGTH: 119
<212> TYPE: PRT
<213> ORGANISM: Homo sapiens

<400> SEQUENCE: 8

Met Lys Val Leu Ile Ser Ser Leu Leu Leu Leu Pro Leu Met Leu
1               5                   10                  15

Met Ser Met Val Ser Ser Ser Leu Asn Pro Gly Val Ala Arg Gly His
                20                  25                  30

Arg Asp Arg Gly Gln Ala Ser Arg Arg Trp Leu Gln Glu Gly Gly Gln
            35                  40                  45

Glu Cys Glu Cys Lys Asp Trp Phe Leu Arg Ala Pro Arg Arg Lys Phe
    50                  55                  60

Met Thr Val Ser Gly Leu Pro Lys Lys Gln Cys Pro Cys Asp His Phe
65                  70                  75                  80

Lys Gly Asn Val Lys Lys Thr Arg His Gln Arg His His Arg Lys Pro
                85                  90                  95

Asn Lys His Ser Arg Ala Cys Gln Gln Phe Leu Lys Gln Cys Gln Leu
            100                 105                 110

Arg Ser Phe Ala Leu Pro Leu
        115

<210> SEQ ID NO 9
<211> LENGTH: 501
<212> TYPE: PRT
<213> ORGANISM: Homo sapiens

<400> SEQUENCE: 9

Met Ser Ser Ser Gly Thr Pro Asp Leu Pro Val Leu Leu Thr Asp Leu
1               5                   10                  15

Lys Ile Gln Tyr Thr Lys Ile Phe Ile Asn Asn Glu Trp His Asp Ser
            20                  25                  30

Val Ser Gly Lys Lys Phe Pro Val Phe Asn Pro Ala Thr Glu Glu Glu
        35                  40                  45

Leu Cys Gln Val Glu Glu Gly Asp Lys Glu Asp Val Asp Lys Ala Val
    50                  55                  60

Lys Ala Ala Arg Gln Ala Phe Gln Ile Gly Ser Pro Trp Arg Thr Met
65                  70                  75                  80

Asp Ala Ser Glu Arg Gly Arg Leu Leu Tyr Lys Leu Ala Asp Leu Ile
                85                  90                  95

Glu Arg Asp Arg Leu Leu Leu Ala Thr Met Glu Ser Met Asn Gly Gly
            100                 105                 110

Lys Leu Tyr Ser Asn Ala Tyr Leu Asn Asp Leu Ala Gly Cys Ile Lys
        115                 120                 125

Thr Leu Arg Tyr Cys Ala Gly Trp Ala Asp Lys Ile Gln Gly Arg Thr
    130                 135                 140
```

```
Ile Pro Ile Asp Gly Asn Phe Phe Thr Tyr Thr Arg His Glu Pro Ile
145                 150                 155                 160

Gly Val Cys Gly Gln Ile Ile Pro Trp Asn Phe Pro Leu Val Met Leu
            165                 170                 175

Ile Trp Lys Ile Gly Pro Ala Leu Ser Cys Gly Asn Thr Val Val
            180                 185                 190

Lys Pro Ala Glu Gln Thr Pro Leu Thr Ala Leu His Val Ala Ser Leu
        195                 200                 205

Ile Lys Glu Ala Gly Phe Pro Pro Gly Val Val Asn Ile Val Pro Gly
    210                 215                 220

Tyr Gly Pro Thr Ala Gly Ala Ala Ile Ser Ser His Met Asp Ile Asp
225                 230                 235                 240

Lys Val Ala Phe Thr Gly Ser Thr Glu Val Gly Lys Leu Ile Lys Glu
                245                 250                 255

Ala Ala Gly Lys Ser Asn Leu Lys Arg Val Thr Leu Glu Leu Gly Gly
            260                 265                 270

Lys Ser Pro Cys Ile Val Leu Ala Asp Ala Asp Leu Asp Asn Ala Val
        275                 280                 285

Glu Phe Ala His His Gly Val Phe Tyr His Gln Gly Gln Cys Cys Ile
    290                 295                 300

Ala Ala Ser Arg Ile Phe Val Glu Glu Ser Ile Tyr Asp Glu Phe Val
305                 310                 315                 320

Arg Arg Ser Val Glu Arg Ala Lys Lys Tyr Ile Leu Gly Asn Pro Leu
                325                 330                 335

Thr Pro Gly Val Thr Gln Gly Pro Gln Ile Asp Lys Glu Gln Tyr Asp
            340                 345                 350

Lys Ile Leu Asp Leu Ile Glu Ser Gly Lys Lys Glu Gly Ala Lys Leu
        355                 360                 365

Glu Cys Gly Gly Gly Pro Trp Gly Asn Lys Gly Tyr Phe Val Gln Pro
    370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Leu Asp Asp
                405                 410                 415

Val Ile Lys Arg Ala Asn Asn Thr Phe Tyr Gly Leu Ser Ala Gly Val
            420                 425                 430

Phe Thr Lys Asp Ile Asp Lys Ala Ile Thr Ile Ser Ser Ala Leu Gln
        435                 440                 445

Ala Gly Thr Val Trp Val Asn Cys Tyr Gly Val Val Ser Ala Gln Cys
    450                 455                 460

Pro Phe Gly Gly Phe Lys Met Ser Gly Asn Gly Arg Glu Leu Gly Glu
465                 470                 475                 480

Tyr Gly Phe His Glu Tyr Thr Glu Val Lys Thr Val Thr Val Lys Ile
                485                 490                 495

Ser Gln Lys Asn Ser
            500

<210> SEQ ID NO 10
<211> LENGTH: 1266
<212> TYPE: PRT
<213> ORGANISM: Homo sapiens

<400> SEQUENCE: 10

Met Gly Pro Leu Met Val Leu Phe Cys Leu Leu Phe Leu Tyr Pro Gly
1               5                   10                  15
```

```
Leu Ala Asp Ser Ala Pro Ser Cys Pro Gln Asn Val Asn Ile Ser Gly
             20                  25                  30
Gly Thr Phe Thr Leu Ser His Gly Trp Ala Pro Gly Ser Leu Leu Thr
                 35                  40                  45
Tyr Ser Cys Pro Gln Gly Leu Tyr Pro Ser Pro Ala Ser Arg Leu Cys
         50                  55                  60
Lys Ser Ser Gly Gln Trp Gln Thr Pro Gly Ala Thr Arg Ser Leu Ser
 65                  70                  75                  80
Lys Ala Val Cys Lys Pro Gly His Cys Pro Asn Pro Gly Ile Ser Leu
                 85                  90                  95
Gly Ala Val Arg Thr Gly Phe Arg Phe Gly His Gly Asp Lys Val Arg
                100                 105                 110
Tyr Arg Cys Ser Ser Asn Leu Val Leu Thr Gly Ser Ser Glu Arg Glu
            115                 120                 125
Cys Gln Gly Asn Gly Val Trp Ser Gly Thr Glu Pro Ile Cys Arg Gln
130                 135                 140
Pro Tyr Ser Tyr Asp Phe Pro Glu Asp Val Ala Pro Ala Leu Gly Thr
145                 150                 155                 160
Ser Phe Ser His Met Leu Gly Ala Thr Asn Pro Thr Gln Lys Thr Lys
                165                 170                 175
Asp His Glu Asn Gly Thr Gly Thr Asn Thr Tyr Ala Ala Leu Asn Ser
            180                 185                 190
Val Tyr Leu Met Met Asn Asn Gln Met Arg Leu Leu Gly Met Glu Thr
            195                 200                 205
Met Ala Trp Gln Glu Ile Arg His Ala Ile Ile Leu Leu Thr Asp Gly
210                 215                 220
Lys Ser Asn Met Gly Gly Ser Pro Lys Thr Ala Val Asp His Ile Arg
225                 230                 235                 240
Glu Ile Leu Asn Ile Asn Gln Lys Arg Asn Asp Tyr Leu Asp Ile Tyr
                245                 250                 255
Ala Ile Gly Val Gly Lys Leu Asp Val Asp Trp Arg Glu Leu Asn Glu
            260                 265                 270
Leu Gly Ser Lys Lys Asp Gly Glu Arg His Ala Phe Ile Leu Gln Asp
            275                 280                 285
Thr Lys Ala Leu His Gln Val Phe Glu His Met Leu Asp Val Ser Lys
290                 295                 300
Leu Thr Asp Thr Ile Cys Gly Val Gly Asn Met Ser Ala Asn Ala Ser
305                 310                 315                 320
Asp Gln Glu Arg Thr Pro Trp His Val Thr Ile Lys Pro Lys Ser Gln
                325                 330                 335
Glu Thr Cys Arg Gly Ala Leu Ile Ser Asp Gln Trp Val Leu Thr Ala
            340                 345                 350
Ala His Cys Phe Arg Asp Gly Asn Asp His Ser Leu Trp Arg Val Asn
            355                 360                 365
Val Gly Asp Pro Lys Ser Gln Trp Gly Lys Glu Phe Leu Ile Glu Lys
            370                 375                 380
Ala Val Ile Ser Pro Gly Phe Asp Val Phe Ala Lys Lys Asn Gln Gly
385                 390                 395                 400
Ile Leu Glu Phe Tyr Gly Asp Asp Ile Ala Leu Leu Lys Leu Ala Gln
                405                 410                 415
Lys Val Lys Met Ser Thr His Ala Arg Pro Ile Cys Leu Pro Cys Thr
            420                 425                 430
```

```
Met Glu Ala Asn Leu Ala Leu Arg Arg Pro Gln Gly Ser Thr Cys Arg
            435                 440                 445

Asp His Glu Asn Glu Leu Leu Asn Lys Gln Ser Val Pro Ala His Phe
        450                 455                 460

Val Ala Leu Asn Gly Ser Lys Leu Asn Ile Asn Leu Lys Met Gly Val
465                 470                 475                 480

Glu Trp Thr Ser Cys Ala Glu Val Val Ser Gln Lys Thr Met Phe
                485                 490                 495

Pro Asn Leu Thr Asp Val Arg Glu Val Thr Asp Gln Phe Leu Cys
                500                 505                 510

Ser Gly Thr Gln Glu Asp Glu Ser Pro Cys Lys Gly Val Thr Thr Thr
            515                 520                 525

Pro Trp Ser Leu Ala Arg Pro Gln Gly Ser Cys Ser Leu Glu Gly Val
        530                 535                 540

Glu Ile Lys Gly Gly Ser Phe Arg Leu Leu Gln Glu Gly Gln Ala Leu
545                 550                 555                 560

Glu Tyr Val Cys Pro Ser Gly Phe Tyr Pro Tyr Pro Val Gln Thr Arg
                565                 570                 575

Thr Cys Arg Ser Thr Gly Ser Trp Ser Thr Leu Lys Thr Gln Asp Gln
            580                 585                 590

Lys Thr Val Arg Lys Ala Glu Cys Arg Ala Ile His Cys Pro Arg Pro
        595                 600                 605

His Asp Phe Glu Asn Gly Glu Tyr Trp Pro Arg Ser Pro Tyr Tyr Asn
        610                 615                 620

Val Ser Asp Glu Ile Ser Phe His Cys Tyr Asp Gly Tyr Thr Leu Arg
625                 630                 635                 640

Gly Ser Ala Asn Arg Thr Cys Gln Val Asn Gly Arg Trp Ser Gly Gln
                645                 650                 655

Thr Ala Ile Cys Asp Asn Gly Ala Gly Tyr Cys Ser Asn Pro Gly Ile
            660                 665                 670

Pro Ile Gly Thr Arg Lys Val Gly Ser Gln Tyr Arg Leu Glu Asp Ser
        675                 680                 685

Val Thr Tyr His Cys Ser Arg Gly Leu Thr Leu Arg Gly Ser Gln Arg
        690                 695                 700

Arg Thr Cys Gln Glu Gly Gly Ser Trp Ser Gly Thr Glu Pro Ser Cys
705                 710                 715                 720

Gln Asp Ser Phe Met Tyr Asp Thr Pro Gln Glu Val Ala Glu Ala Phe
                725                 730                 735

Leu Ser Ser Leu Thr Glu Thr Ile Glu Gly Val Asp Ala Glu Asp Gly
            740                 745                 750

His Gly Pro Gly Glu Gln Gln Lys Arg Lys Ile Val Leu Asp Pro Ser
        755                 760                 765

Gly Ser Met Asn Ile Tyr Leu Val Leu Asp Gly Ser Asp Ser Ile Gly
770                 775                 780

Ala Ser Asn Phe Thr Gly Ala Lys Lys Cys Leu Val Asn Leu Ile Glu
785                 790                 795                 800

Lys Val Ala Ser Tyr Gly Val Lys Pro Arg Tyr Gly Leu Val Thr Tyr
                805                 810                 815

Ala Thr Tyr Pro Lys Ile Trp Val Lys Val Ser Glu Ala Asp Ser Ser
            820                 825                 830

Asn Ala Asp Trp Val Thr Lys Gln Leu Asn Glu Ile Asn Tyr Glu Asp
        835                 840                 845

His Lys Leu Lys Ser Gly Thr Asn Thr Lys Lys Ala Leu Gln Ala Val
```

-continued

```
            850                 855                 860
Tyr Ser Met Met Ser Trp Pro Asp Asp Val Pro Pro Glu Gly Trp Asn
865                 870                 875                 880

Arg Thr Arg His Val Ile Ile Leu Met Thr Asp Gly Leu His Asn Met
                885                 890                 895

Gly Gly Asp Pro Ile Thr Val Ile Asp Glu Ile Arg Asp Leu Leu Tyr
                900                 905                 910

Ile Gly Lys Asp Arg Lys Asn Pro Arg Glu Asp Tyr Leu Asp Val Tyr
                915                 920                 925

Val Phe Gly Val Gly Pro Leu Val Asn Gln Val Asn Ile Asn Ala Leu
        930                 935                 940

Ala Ser Lys Lys Asp Asn Glu Gln His Val Phe Lys Val Lys Asp Met
945                 950                 955                 960

Glu Asn Leu Glu Asp Val Phe Tyr Gln Met Ile Asp Glu Ser Gln Ser
                965                 970                 975

Leu Ser Leu Cys Gly Met Val Trp Glu His Arg Lys Gly Thr Asp Tyr
                980                 985                 990

His Lys Gln Pro Trp Gln Ala Lys Ile Ser Val Ile Arg Pro Ser Lys
        995                 1000                1005

Gly His Glu Ser Cys Met Gly Ala Val Val Ser Glu Tyr Phe Val
        1010                1015                1020

Leu Thr Ala Ala His Cys Phe Thr Val Asp Asp Lys Glu His Ser
        1025                1030                1035

Ile Lys Val Ser Val Gly Gly Glu Lys Arg Asp Leu Glu Ile Glu
        1040                1045                1050

Val Val Leu Phe His Pro Asn Tyr Asn Ile Asn Gly Lys Lys Glu
        1055                1060                1065

Ala Gly Ile Pro Glu Phe Tyr Asp Tyr Asp Val Ala Leu Ile Lys
        1070                1075                1080

Leu Lys Asn Lys Leu Lys Tyr Gly Gln Thr Ile Arg Pro Ile Cys
        1085                1090                1095

Leu Pro Cys Thr Glu Gly Thr Thr Arg Ala Leu Arg Leu Pro Pro
        1100                1105                1110

Thr Thr Thr Cys Gln Gln Gln Lys Glu Glu Leu Leu Pro Ala Gln
        1115                1120                1125

Asp Ile Lys Ala Leu Phe Val Ser Glu Glu Glu Lys Lys Leu Thr
        1130                1135                1140

Arg Lys Glu Val Tyr Ile Lys Asn Gly Asp Lys Lys Gly Ser Cys
        1145                1150                1155

Glu Arg Asp Ala Gln Tyr Ala Pro Gly Tyr Asp Lys Val Lys Asp
        1160                1165                1170

Ile Ser Glu Val Val Thr Pro Arg Phe Leu Cys Thr Gly Gly Val
        1175                1180                1185

Ser Pro Tyr Ala Asp Pro Asn Thr Cys Arg Gly Asp Ser Gly Gly
        1190                1195                1200

Pro Leu Ile Val His Lys Arg Ser Arg Phe Ile Gln Val Gly Val
        1205                1210                1215

Ile Ser Trp Gly Val Val Asp Val Cys Lys Asn Gln Lys Arg Gln
        1220                1225                1230

Lys Gln Val Pro Ala His Ala Arg Asp Phe His Ile Asn Leu Phe
        1235                1240                1245

Gln Val Leu Pro Trp Leu Lys Glu Lys Leu Gln Asp Glu Asp Leu
        1250                1255                1260
```

Gly Phe Leu
        1265

<210> SEQ ID NO 11
<211> LENGTH: 423
<212> TYPE: PRT
<213> ORGANISM: Homo sapiens

<400> SEQUENCE: 11

Met Glu Arg Met Leu Pro Leu Ala Leu Gly Leu Leu Ala Ala Gly
1               5                   10                  15

Phe Cys Pro Ala Val Leu Cys His Pro Asn Ser Pro Leu Asp Glu Glu
                20                  25                  30

Asn Leu Thr Gln Glu Asn Gln Asp Arg Gly Thr His Val Asp Leu Gly
            35                  40                  45

Leu Ala Ser Ala Asn Val Asp Phe Ala Phe Ser Leu Tyr Lys Gln Leu
        50                  55                  60

Val Leu Lys Ala Pro Asp Lys Asn Val Ile Phe Ser Pro Leu Ser Ile
65                  70                  75                  80

Ser Thr Ala Leu Ala Phe Leu Ser Leu Gly Ala His Asn Thr Thr Leu
                85                  90                  95

Thr Glu Ile Leu Lys Gly Leu Lys Phe Asn Leu Thr Glu Thr Ser Glu
                100                 105                 110

Ala Glu Ile His Gln Ser Phe Gln His Leu Leu Arg Thr Leu Asn Gln
            115                 120                 125

Ser Ser Asp Glu Leu Gln Leu Ser Met Gly Asn Ala Met Phe Val Lys
        130                 135                 140

Glu Gln Leu Ser Leu Leu Asp Arg Phe Thr Glu Asp Ala Lys Arg Leu
145                 150                 155                 160

Tyr Gly Ser Glu Ala Phe Ala Thr Asp Phe Gln Asp Ser Ala Ala Ala
                165                 170                 175

Lys Lys Leu Ile Asn Asp Tyr Val Lys Asn Gly Thr Arg Gly Lys Ile
                180                 185                 190

Thr Asp Leu Ile Lys Asp Leu Asp Ser Gln Thr Met Met Val Leu Val
            195                 200                 205

Asn Tyr Ile Phe Phe Lys Ala Lys Trp Glu Met Pro Phe Asp Pro Gln
        210                 215                 220

Asp Thr His Gln Ser Arg Phe Tyr Leu Ser Lys Lys Trp Val Met
225                 230                 235                 240

Val Pro Met Met Ser Leu His His Leu Thr Ile Pro Tyr Phe Arg Asp
                245                 250                 255

Glu Glu Leu Ser Cys Thr Val Val Glu Leu Lys Tyr Thr Gly Asn Ala
                260                 265                 270

Ser Ala Leu Phe Ile Leu Pro Asp Gln Asp Lys Met Glu Glu Val Glu
            275                 280                 285

Ala Met Leu Leu Pro Glu Thr Leu Lys Arg Trp Arg Asp Ser Leu Glu
        290                 295                 300

Phe Arg Glu Ile Gly Glu Leu Tyr Leu Pro Lys Phe Ser Ile Ser Arg
305                 310                 315                 320

Asp Tyr Asn Leu Asn Asp Ile Leu Leu Gln Leu Gly Ile Glu Glu Ala
                325                 330                 335

Phe Thr Ser Lys Ala Asp Leu Ser Gly Ile Thr Gly Ala Arg Asn Leu
                340                 345                 350

Ala Val Ser Gln Val Val His Lys Ala Val Leu Asp Val Phe Glu Glu

```
                355                 360                 365
Gly Thr Glu Ala Ser Ala Ala Thr Ala Val Lys Ile Thr Leu Leu Ser
        370                 375                 380

Ala Leu Val Glu Thr Arg Thr Ile Val Arg Phe Asn Arg Pro Phe Leu
385                 390                 395                 400

Met Ile Ile Val Pro Thr Asp Thr Gln Asn Ile Phe Phe Met Ser Lys
                405                 410                 415

Val Thr Asn Pro Lys Gln Ala
            420

<210> SEQ ID NO 12
<211> LENGTH: 664
<212> TYPE: PRT
<213> ORGANISM: Homo sapiens

<400> SEQUENCE: 12

Met Lys Thr Gly Leu Phe Phe Leu Cys Leu Leu Gly Thr Ala Ala Ala
1               5                   10                  15

Ile Pro Thr Asn Ala Arg Leu Leu Ser Asp His Ser Lys Pro Thr Ala
            20                  25                  30

Glu Thr Val Ala Pro Asp Asn Thr Ala Ile Pro Ser Leu Arg Ala Glu
        35                  40                  45

Ala Glu Glu Asn Glu Lys Glu Thr Ala Val Ser Thr Glu Asp Asp Ser
    50                  55                  60

His His Lys Ala Glu Lys Ser Ser Val Leu Lys Ser Lys Glu Glu Ser
65                  70                  75                  80

His Glu Gln Ser Ala Glu Gln Gly Lys Ser Ser Gln Glu Leu Gly
                85                  90                  95

Leu Lys Asp Gln Glu Asp Ser Asp Gly His Leu Ser Val Asn Leu Glu
            100                 105                 110

Tyr Ala Pro Thr Glu Gly Thr Leu Asp Ile Lys Glu Asp Met Ser Glu
        115                 120                 125

Pro Gln Glu Lys Lys Leu Ser Glu Asn Thr Asp Phe Leu Ala Pro Gly
    130                 135                 140

Val Ser Ser Phe Thr Asp Ser Asn Gln Gln Glu Ser Ile Thr Lys Arg
145                 150                 155                 160

Glu Glu Asn Gln Glu Gln Pro Arg Asn Tyr Ser His His Gln Leu Asn
                165                 170                 175

Arg Ser Ser Lys His Ser Gln Gly Leu Arg Asp Gln Gly Asn Gln Glu
            180                 185                 190

Gln Asp Pro Asn Ile Ser Asn Gly Glu Glu Glu Glu Lys Glu Pro
        195                 200                 205

Gly Glu Val Gly Thr His Asn Asp Asn Gln Arg Lys Thr Glu Leu
    210                 215                 220

Pro Arg Glu His Ala Asn Ser Lys Gln Glu Glu Asp Asn Thr Gln Ser
225                 230                 235                 240

Asp Asp Ile Leu Glu Glu Ser Asp Gln Pro Thr Gln Val Ser Lys Met
                245                 250                 255

Gln Glu Asp Glu Phe Asp Gln Gly Asn Gln Glu Gln Glu Asp Asn Ser
            260                 265                 270

Asn Ala Glu Met Glu Glu Glu Asn Ala Ser Asn Val Asn Lys His Ile
        275                 280                 285

Gln Glu Thr Glu Trp Gln Ser Gln Glu Gly Lys Thr Gly Leu Glu Ala
    290                 295                 300
```

```
Ile Ser Asn His Lys Glu Thr Glu Lys Thr Val Ser Glu Ala Leu
305                 310                 315                 320

Leu Met Glu Pro Thr Asp Asp Gly Asn Thr Thr Pro Arg Asn His Gly
            325                 330                 335

Val Asp Asp Asp Gly Asp Asp Gly Asp Asp Gly Thr Asp Gly
        340                 345                 350

Pro Arg His Ser Ala Ser Asp Asp Tyr Phe Ile Pro Ser Gln Ala Phe
            355                 360                 365

Leu Glu Ala Glu Arg Ala Gln Ser Ile Ala Tyr His Leu Lys Ile Glu
        370                 375                 380

Glu Gln Arg Glu Lys Val His Glu Asn Glu Asn Ile Gly Thr Thr Glu
385                 390                 395                 400

Pro Gly Glu His Gln Glu Ala Lys Lys Ala Glu Asn Ser Ser Asn Glu
            405                 410                 415

Glu Glu Thr Ser Ser Glu Gly Asn Met Arg Val His Ala Val Asp Ser
        420                 425                 430

Cys Met Ser Phe Gln Cys Lys Arg Gly His Ile Cys Lys Ala Asp Gln
        435                 440                 445

Gln Gly Lys Pro His Cys Val Cys Gln Asp Pro Val Thr Cys Pro Pro
    450                 455                 460

Thr Lys Pro Leu Asp Gln Val Cys Gly Thr Asp Asn Gln Thr Tyr Ala
465                 470                 475                 480

Ser Ser Cys His Leu Phe Ala Thr Lys Cys Arg Leu Glu Gly Thr Lys
            485                 490                 495

Lys Gly His Gln Leu Gln Leu Asp Tyr Phe Gly Ala Cys Lys Ser Ile
        500                 505                 510

Pro Thr Cys Thr Asp Phe Glu Val Ile Gln Phe Pro Leu Arg Met Arg
    515                 520                 525

Asp Trp Leu Lys Asn Ile Leu Met Gln Leu Tyr Glu Ala Asn Ser Glu
530                 535                 540

His Ala Gly Tyr Leu Asn Glu Lys Gln Arg Asn Lys Val Lys Lys Ile
545                 550                 555                 560

Tyr Leu Asp Glu Lys Arg Leu Leu Ala Gly Asp His Pro Ile Asp Leu
            565                 570                 575

Leu Leu Arg Asp Phe Lys Lys Asn Tyr His Met Tyr Val Tyr Pro Val
        580                 585                 590

His Trp Gln Phe Ser Glu Leu Asp Gln His Pro Met Asp Arg Val Leu
    595                 600                 605

Thr His Ser Glu Leu Ala Pro Leu Arg Ala Ser Leu Val Pro Met Glu
610                 615                 620

His Cys Ile Thr Arg Phe Phe Glu Glu Cys Asp Pro Asn Lys Asp Lys
625                 630                 635                 640

His Ile Thr Leu Lys Glu Trp Gly His Cys Phe Gly Ile Lys Glu Glu
            645                 650                 655

Asp Ile Asp Glu Asn Leu Leu Phe
            660

<210> SEQ ID NO 13
<211> LENGTH: 115
<212> TYPE: PRT
<213> ORGANISM: Homo sapiens

<400> SEQUENCE: 13

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Thr Tyr
             20                  25                  30

Val Met Ser Trp Val Arg Gln Ala Pro Gly Lys Gly Leu Glx Trp Val
         35                  40                  45

Gly Ala Ile Glx Gly Leu Ser Val Ser Glx Ser Tyr Ala Asx Ser Val
     50                  55                  60

Lys Gly Arg Phe Thr Ile Ser Arg Asp Asp Ser Lys Asn Thr Met Asn
65                  70                  75                  80

Ser Leu Arg Ala Glu Asp Thr Ala Val Tyr Tyr Cys Ala Lys Gly Lys
                 85                  90                  95

Val Ser Ala Tyr Tyr Phe Asx Tyr Trp Gly Glx Gly Thr Leu Val Thr
             100                 105                 110

Val Ser Ser
        115

<210> SEQ ID NO 14
<211> LENGTH: 623
<212> TYPE: PRT
<213> ORGANISM: Homo sapiens

<400> SEQUENCE: 14

Met Ser Cys Arg Gln Phe Ser Ser Ser Tyr Leu Ser Arg Ser Gly Gly
1               5                   10                  15

Gly Gly Gly Gly Gly Leu Gly Ser Gly Ser Ile Arg Ser Ser Tyr
             20                  25                  30

Ser Arg Phe Ser Ser Ser Gly Gly Gly Gly Gly Arg Phe Ser
         35                  40                  45

Ser Ser Ser Gly Tyr Gly Gly Ser Ser Arg Val Cys Gly Arg Gly
     50                  55                  60

Gly Gly Gly Ser Phe Gly Tyr Ser Tyr Gly Gly Ser Gly Gly
65                  70                  75                  80

Phe Ser Ala Ser Ser Leu Gly Gly Gly Phe Gly Gly Ser Arg Gly
                 85                  90                  95

Phe Gly Gly Ala Ser Gly Gly Tyr Ser Ser Ser Gly Gly Phe Gly
             100                 105                 110

Gly Gly Phe Gly Gly Gly Ser Gly Gly Phe Gly Gly Gly Tyr Gly
         115                 120                 125

Ser Gly Phe Gly Gly Phe Gly Gly Phe Gly Gly Ala Gly Gly Gly
     130                 135                 140

Asp Gly Gly Ile Leu Thr Ala Asn Glu Lys Ser Thr Met Gln Glu Leu
145                 150                 155                 160

Asn Ser Arg Leu Ala Ser Tyr Leu Asp Lys Val Gln Ala Leu Glu Glu
                165                 170                 175

Ala Asn Asn Asp Leu Glu Asn Lys Ile Gln Asp Trp Tyr Asp Lys Lys
             180                 185                 190

Gly Pro Ala Ala Ile Gln Lys Asn Tyr Ser Pro Tyr Tyr Asn Thr Ile
         195                 200                 205

Asp Asp Leu Lys Asp Gln Ile Val Asp Leu Thr Val Gly Asn Asn Lys
     210                 215                 220

Thr Leu Leu Asp Ile Asp Asn Thr Arg Met Thr Leu Asp Asp Phe Arg
225                 230                 235                 240

Ile Lys Phe Glu Met Glu Gln Asn Leu Arg Gln Gly Val Asp Ala Asp
                245                 250                 255

Ile Asn Gly Leu Arg Gln Val Leu Asp Asn Leu Thr Met Glu Lys Ser

```
                260                 265                 270
Asp Leu Glu Met Gln Tyr Glu Thr Leu Gln Glu Glu Leu Met Ala Leu
    275                 280                 285

Lys Lys Asn His Lys Glu Glu Met Ser Gln Leu Thr Gly Gln Asn Ser
290                 295                 300

Gly Asp Val Asn Val Glu Ile Asn Val Ala Pro Gly Lys Asp Leu Thr
305                 310                 315                 320

Lys Thr Leu Asn Asp Met Arg Gln Glu Tyr Glu Gln Leu Ile Ala Lys
                325                 330                 335

Asn Arg Lys Asp Ile Glu Asn Gln Tyr Glu Thr Gln Ile Thr Gln Ile
                340                 345                 350

Glu His Glu Val Ser Ser Gly Gln Glu Val Gln Ser Ser Ala Lys
        355                 360                 365

Glu Val Thr Gln Leu Arg His Gly Val Gln Glu Leu Glu Ile Glu Leu
        370                 375                 380

Gln Ser Gln Leu Ser Lys Lys Ala Ala Leu Glu Lys Ser Leu Glu Asp
385                 390                 395                 400

Thr Lys Asn Arg Tyr Cys Gly Gln Leu Gln Met Ile Gln Glu Gln Ile
                405                 410                 415

Ser Asn Leu Glu Ala Gln Ile Thr Asp Val Arg Gln Glu Ile Glu Cys
                420                 425                 430

Gln Asn Gln Glu Tyr Ser Leu Leu Leu Ser Ile Lys Met Arg Leu Glu
                435                 440                 445

Lys Glu Ile Glu Thr Tyr His Asn Leu Leu Glu Gly Gly Gln Glu Asp
450                 455                 460

Phe Glu Ser Ser Gly Ala Gly Lys Ile Gly Leu Gly Gly Arg Gly Gly
465                 470                 475                 480

Ser Gly Gly Ser Tyr Gly Arg Gly Ser Arg Gly Gly Ser Gly Gly Ser
                485                 490                 495

Tyr Gly Gly Gly Gly Ser Gly Gly Tyr Gly Gly Gly Ser Gly Ser
            500                 505                 510

Arg Gly Gly Ser Gly Gly Ser Tyr Gly Gly Gly Ser Gly Ser Gly Gly
                515                 520                 525

Gly Ser Gly Gly Gly Tyr Gly Gly Gly Ser Gly Gly Gly His Ser Gly
        530                 535                 540

Gly Ser Gly Gly Gly His Ser Gly Gly Ser Gly Gly Asn Tyr Gly Gly
545                 550                 555                 560

Gly Ser Gly Ser Gly Gly Gly Ser Gly Gly Tyr Gly Gly Gly Ser
                565                 570                 575

Gly Ser Arg Gly Gly Ser Gly Gly Ser His Gly Gly Ser Gly Gly Phe
                580                 585                 590

Gly Gly Glu Ser Gly Gly Ser Tyr Gly Gly Gly Glu Glu Ala Ser Gly
            595                 600                 605

Ser Gly Gly Gly Tyr Gly Gly Gly Ser Gly Lys Ser Ser His Ser
        610                 615                 620

<210> SEQ ID NO 15
<211> LENGTH: 141
<212> TYPE: PRT
<213> ORGANISM: Homo sapiens

<400> SEQUENCE: 15

Met Ala Gln Tyr Leu Ser Thr Leu Leu Leu Leu Leu Ala Thr Leu Ala
1               5                   10                  15
```

```
Val Ala Leu Ala Trp Ser Pro Lys Glu Asp Arg Ile Ile Pro Gly
            20                  25                  30

Gly Ile Tyr Asn Ala Asp Leu Asn Asp Glu Trp Val Gln Arg Ala Leu
        35                  40                  45

His Phe Ala Ile Ser Glu Tyr Asn Lys Ala Thr Lys Asp Asp Tyr Tyr
 50                  55                  60

Arg Arg Pro Leu Arg Val Leu Arg Ala Arg Gln Gln Thr Val Gly Gly
 65                  70                  75                  80

Val Asn Tyr Phe Phe Asp Val Glu Val Gly Arg Thr Ile Cys Thr Lys
                 85                  90                  95

Ser Gln Pro Asn Leu Asp Thr Cys Ala Phe His Glu Gln Pro Glu Leu
            100                 105                 110

Gln Lys Lys Gln Leu Cys Ser Phe Glu Ile Tyr Glu Val Pro Trp Glu
        115                 120                 125

Asn Arg Arg Ser Leu Val Lys Ser Arg Cys Gln Glu Ser
        130                 135                 140
```

<210> SEQ ID NO 16
<211> LENGTH: 911
<212> TYPE: PRT
<213> ORGANISM: Homo sapiens

<400> SEQUENCE: 16

```
Met Val Asp Tyr His Ala Ala Asn Gln Ser Tyr Gln Tyr Gly Pro Ser
 1               5                  10                  15

Ser Ala Gly Asn Gly Ala Gly Gly Gly Ser Met Gly Asp Tyr Met
            20                  25                  30

Ala Gln Glu Asp Asp Trp Asp Arg Asp Leu Leu Leu Asp Pro Ala Trp
        35                  40                  45

Glu Lys Gln Gln Arg Lys Thr Phe Thr Ala Trp Cys Asn Ser His Leu
 50                  55                  60

Arg Lys Ala Gly Thr Gln Ile Glu Asn Ile Asp Glu Asp Phe Arg Asp
 65                  70                  75                  80

Gly Leu Lys Leu Met Leu Leu Leu Glu Val Ile Ser Gly Glu Arg Leu
                 85                  90                  95

Pro Lys Pro Glu Arg Gly Lys Met Arg Val His Lys Ile Asn Asn Val
            100                 105                 110

Asn Lys Ala Leu Asp Phe Ile Ala Ser Lys Gly Val Lys Leu Val Ser
        115                 120                 125

Ile Gly Ala Glu Glu Ile Val Asp Gly Asn Ala Lys Met Thr Leu Gly
    130                 135                 140

Met Ile Trp Thr Ile Ile Leu Arg Phe Ala Ile Gln Asp Ile Ser Val
145                 150                 155                 160

Glu Glu Thr Ser Ala Lys Glu Gly Leu Leu Leu Trp Cys Gln Arg Lys
                165                 170                 175

Thr Ala Pro Tyr Lys Asn Val Asn Val Gln Asn Phe His Ile Ser Trp
            180                 185                 190

Lys Asp Gly Leu Ala Phe Asn Ala Leu Ile His Arg His Arg Pro Glu
        195                 200                 205

Leu Ile Glu Tyr Asp Lys Leu Arg Lys Asp Asp Pro Val Thr Asn Leu
    210                 215                 220

Asn Asn Ala Phe Glu Val Ala Glu Lys Tyr Leu Asp Ile Pro Lys Met
225                 230                 235                 240

Leu Asp Ala Glu Asp Ile Val Asn Thr Ala Arg Pro Asp Glu Lys Ala
                245                 250                 255
```

```
Ile Met Thr Tyr Val Ser Ser Phe Tyr His Ala Phe Ser Gly Ala Gln
            260                 265                 270

Lys Ala Glu Thr Ala Ala Asn Arg Ile Cys Lys Val Leu Ala Val Asn
            275                 280                 285

Gln Glu Asn Glu His Leu Met Glu Asp Tyr Glu Lys Leu Ala Ser Asp
            290                 295                 300

Leu Leu Glu Trp Ile Arg Arg Thr Ile Pro Trp Leu Glu Asp Arg Val
305                 310                 315                 320

Pro Gln Lys Thr Ile Gln Glu Met Gln Gln Lys Leu Glu Asp Phe Arg
            325                 330                 335

Asp Tyr Arg Arg Val His Lys Pro Pro Lys Val Gln Glu Lys Cys Gln
            340                 345                 350

Leu Glu Ile Asn Phe Asn Thr Leu Gln Thr Lys Leu Arg Leu Ser Asn
            355                 360                 365

Arg Pro Ala Phe Met Pro Ser Glu Gly Lys Met Val Ser Asp Ile Asn
            370                 375                 380

Asn Gly Trp Gln His Leu Glu Gln Ala Glu Lys Gly Tyr Glu Glu Trp
385                 390                 395                 400

Leu Leu Asn Glu Ile Arg Arg Leu Glu Arg Leu Asp His Leu Ala Glu
                    405                 410                 415

Lys Phe Arg Gln Lys Ala Ser Ile His Glu Ala Trp Thr Asp Gly Lys
            420                 425                 430

Glu Ala Met Leu Lys His Arg Asp Tyr Glu Thr Ala Thr Leu Ser Asp
            435                 440                 445

Ile Lys Ala Leu Ile Arg Lys His Glu Ala Phe Glu Ser Asp Leu Ala
450                 455                 460

Ala His Gln Asp Arg Val Glu Gln Ile Ala Ala Ile Ala Gln Glu Leu
465                 470                 475                 480

Asn Glu Leu Asp Tyr Tyr Asp Ser His Asn Val Asn Thr Arg Cys Gln
                    485                 490                 495

Lys Ile Cys Asp Gln Trp Asp Ala Leu Gly Ser Leu Thr His Ser Arg
            500                 505                 510

Arg Glu Ala Leu Glu Lys Thr Glu Lys Gln Leu Glu Ala Ile Asp Gln
            515                 520                 525

Leu His Leu Glu Tyr Ala Lys Arg Ala Ala Pro Phe Asn Asn Trp Met
            530                 535                 540

Glu Ser Ala Met Glu Asp Leu Gln Asp Met Phe Ile Val His Thr Ile
545                 550                 555                 560

Glu Glu Ile Glu Gly Leu Ile Ser Ala His Asp Gln Phe Lys Ser Thr
                    565                 570                 575

Leu Pro Asp Ala Asp Arg Glu Arg Glu Ala Ile Leu Ala Ile His Lys
            580                 585                 590

Glu Ala Gln Arg Ile Ala Glu Ser Asn His Ile Lys Leu Ser Gly Ser
            595                 600                 605

Asn Pro Tyr Thr Thr Val Thr Pro Gln Ile Ile Asn Ser Lys Trp Glu
            610                 615                 620

Lys Val Gln Gln Leu Val Pro Lys Arg Asp His Ala Leu Leu Glu Glu
625                 630                 635                 640

Gln Ser Lys Gln Gln Ser Asn Glu His Leu Arg Arg Gln Phe Ala Ser
                    645                 650                 655

Gln Ala Asn Val Val Gly Pro Trp Ile Gln Thr Lys Met Glu Glu Ile
            660                 665                 670
```

Gly Arg Ile Ser Ile Glu Met Asn Gly Thr Leu Glu Asp Gln Leu Ser
            675                 680                 685

His Leu Lys Gln Tyr Glu Arg Ser Ile Val Asp Tyr Lys Pro Asn Leu
690                 695                 700

Asp Leu Leu Glu Gln Gln His Gln Leu Ile Gln Glu Ala Leu Ile Phe
705                 710                 715                 720

Asp Asn Lys His Thr Asn Tyr Thr Met Glu His Ile Arg Val Gly Trp
                725                 730                 735

Glu Gln Leu Leu Thr Thr Ile Ala Arg Thr Ile Asn Glu Val Glu Asn
            740                 745                 750

Gln Ile Leu Thr Arg Asp Ala Lys Gly Ile Ser Gln Glu Gln Met Gln
        755                 760                 765

Glu Phe Arg Ala Ser Phe Asn His Phe Asp Lys Asp His Gly Gly Ala
770                 775                 780

Leu Gly Pro Glu Glu Phe Lys Ala Cys Leu Ile Ser Leu Gly Tyr Asp
785                 790                 795                 800

Val Glu Asn Asp Arg Gln Gly Glu Ala Glu Phe Asn Arg Ile Met Ser
                805                 810                 815

Leu Val Asp Pro Asn His Ser Gly Leu Val Thr Phe Gln Ala Phe Ile
            820                 825                 830

Asp Phe Met Ser Arg Glu Thr Thr Asp Thr Asp Thr Ala Asp Gln Val
        835                 840                 845

Ile Ala Ser Phe Lys Val Leu Ala Gly Asp Lys Asn Phe Ile Thr Ala
850                 855                 860

Glu Glu Leu Arg Arg Glu Leu Pro Pro Asp Gln Ala Glu Tyr Cys Ile
865                 870                 875                 880

Ala Arg Met Ala Pro Tyr Gln Gly Pro Asp Ala Val Pro Gly Ala Leu
                885                 890                 895

Asp Tyr Lys Ser Phe Ser Thr Ala Leu Tyr Gly Glu Ser Asp Leu
            900                 905                 910

<210> SEQ ID NO 17
<211> LENGTH: 235
<212> TYPE: PRT
<213> ORGANISM: Homo sapiens

<400> SEQUENCE: 17

Met Ala Trp Ile Pro Leu Phe Leu Gly Val Leu Ala Tyr Cys Thr Gly
1               5                   10                  15

Ser Val Ala Ser Tyr Glu Leu Thr Gln Pro Pro Ser Val Ser Val Ser
            20                  25                  30

Pro Gly Gln Thr Ala Ser Ile Thr Cys Ser Gly Asp Lys Leu Gly Asp
        35                  40                  45

Lys Tyr Ala Cys Trp Tyr Gln Gln Lys Pro Gly Gln Ser Pro Val Leu
    50                  55                  60

Val Ile Tyr Gln Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Met Asp Glu Ala Asp Tyr Tyr Cys Gln Ala Trp Asp Ser Ser
            100                 105                 110

Ala Ser Gly Pro Val Leu Val Phe Gly Thr Gly Thr Lys Val Thr Val
        115                 120                 125

Leu Gly Gln Pro Lys Ala Asn Pro Thr Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Gly Ser
            165                 170                 175

Pro Val Lys Ala Gly Val Glu Thr Thr Lys Pro Ser Lys Gln Ser Asn
        180                 185                 190

Asn Lys Tyr Ala Ala Ser Ser Tyr Leu Ser Leu Thr Pro Glu Gln Trp
    195                 200                 205

Lys Ser His Arg Ser Tyr Ser Cys Gln Val Thr His Glu Gly Ser Thr
210                 215                 220

Val Glu Lys Thr Val Ala Pro Thr Glu Cys Ser
225                 230                 235

<210> SEQ ID NO 18
<211> LENGTH: 106
<212> TYPE: PRT
<213> ORGANISM: Homo sapiens

<400> SEQUENCE: 18

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Ala Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 19
<211> LENGTH: 138
<212> TYPE: PRT
<213> ORGANISM: Homo sapiens

<400> SEQUENCE: 19

Met Lys Phe Thr Thr Leu Leu Phe Leu Ala Ala Val Ala Gly Ala Leu
1               5                   10                  15

Val Tyr Ala Glu Asp Ala Ser Ser Asp Ser Thr Gly Ala Asp Pro Ala
            20                  25                  30

Gln Glu Ala Gly Thr Ser Lys Pro Asn Glu Glu Ile Ser Gly Pro Ala
        35                  40                  45

Glu Pro Ala Ser Pro Pro Glu Thr Thr Thr Ala Gln Glu Thr Ser
    50                  55                  60

Ala Ala Ala Val Gln Gly Thr Ala Lys Val Thr Ser Ser Arg Gln Glu
65                  70                  75                  80

Leu Asn Pro Leu Lys Ser Ile Val Glu Lys Ser Ile Leu Leu Thr Glu
                85                  90                  95

Gln Ala Leu Ala Lys Ala Gly Lys Gly Met His Gly Val Pro Gly
            100                 105                 110

Gly Lys Gln Phe Ile Glu Asn Gly Ser Glu Phe Ala Gln Lys Leu Leu
        115                 120                 125

```
Lys Lys Phe Ser Leu Leu Lys Pro Trp Ala
        130             135

<210> SEQ ID NO 20
<211> LENGTH: 206
<212> TYPE: PRT
<213> ORGANISM: Homo sapiens

<400> SEQUENCE: 20

Met Ala Val Lys Lys Ile Ala Ile Phe Gly Ala Thr Gly Gln Thr Gly
1               5                   10                  15

Leu Thr Thr Leu Ala Gln Ala Val Gln Ala Gly Tyr Glu Val Thr Val
            20                  25                  30

Leu Val Arg Asp Ser Ser Arg Leu Pro Ser Glu Gly Pro Arg Pro Ala
        35                  40                  45

His Val Val Gly Asp Val Leu Gln Ala Ala Asp Val Asp Lys Thr
    50                  55                  60

Val Ala Gly Gln Asp Ala Val Ile Val Leu Leu Gly Thr Arg Asn Asp
65                  70                  75                  80

Leu Ser Pro Thr Thr Val Met Ser Glu Gly Ala Arg Asn Ile Val Ala
                85                  90                  95

Ala Met Lys Ala His Gly Val Asp Lys Val Val Ala Cys Thr Ser Ala
            100                 105                 110

Phe Leu Leu Trp Asp Pro Thr Lys Val Pro Pro Arg Leu Gln Ala Val
        115                 120                 125

Thr Asp Asp His Ile Arg Met His Lys Val Leu Arg Glu Ser Gly Leu
    130                 135                 140

Lys Tyr Val Ala Val Met Pro Pro His Ile Gly Asp Gln Pro Leu Thr
145                 150                 155                 160

Gly Ala Tyr Thr Val Thr Leu Asp Gly Arg Gly Pro Ser Arg Val Ile
                165                 170                 175

Ser Lys His Asp Leu Gly His Phe Met Leu Arg Cys Leu Thr Thr Asp
            180                 185                 190

Glu Tyr Asp Gly His Ser Thr Tyr Pro Ser His Gln Tyr Gln
        195                 200                 205

<210> SEQ ID NO 21
<211> LENGTH: 396
<212> TYPE: PRT
<213> ORGANISM: Homo sapiens

<400> SEQUENCE: 21

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110
```

```
Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Arg Gly Asn Thr Glu Gly Leu Gln Lys Ser
            275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
            370                 375                 380

Gln Glu Gln Val Gln Met Leu Ala Pro Leu Glu Ser
385                 390                 395

<210> SEQ ID NO 22
<211> LENGTH: 267
<212> TYPE: PRT
<213> ORGANISM: Homo sapiens

<400> SEQUENCE: 22

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
```

```
                       85                  90                  95
Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 23
<211> LENGTH: 326
<212> TYPE: PRT
<213> ORGANISM: Homo sapiens

<400> SEQUENCE: 23

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190
```

```
Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 24
<211> LENGTH: 462
<212> TYPE: PRT
<213> ORGANISM: Homo sapiens

<400> SEQUENCE: 24

Met Ala Arg Val Leu Gly Ala Pro Val Ala Leu Gly Leu Trp Ser Leu
1               5                   10                  15

Cys Trp Ser Leu Ala Ile Ala Thr Pro Leu Pro Pro Thr Ser Ala His
            20                  25                  30

Gly Asn Val Ala Glu Gly Glu Thr Lys Pro Asp Pro Asp Val Thr Glu
            35                  40                  45

Arg Cys Ser Asp Gly Trp Ser Phe Asp Ala Thr Thr Leu Asp Asp Asn
    50                  55                  60

Gly Thr Met Leu Phe Phe Lys Gly Glu Phe Val Trp Lys Ser His Lys
65                  70                  75                  80

Trp Asp Arg Glu Leu Ile Ser Glu Arg Trp Lys Asn Phe Pro Ser Pro
                85                  90                  95

Val Asp Ala Ala Phe Arg Gln Gly His Asn Ser Val Phe Leu Ile Lys
            100                 105                 110

Gly Asp Lys Val Trp Val Tyr Pro Pro Glu Lys Lys Glu Lys Gly Tyr
            115                 120                 125

Pro Lys Leu Leu Gln Asp Glu Phe Pro Gly Ile Pro Ser Pro Leu Asp
            130                 135                 140

Ala Ala Val Glu Cys His Arg Gly Glu Cys Gln Ala Glu Gly Val Leu
145                 150                 155                 160

Phe Phe Gln Gly Asp Arg Glu Trp Phe Trp Asp Leu Ala Thr Gly Thr
                165                 170                 175

Met Lys Glu Arg Ser Trp Pro Ala Val Gly Asn Cys Ser Ser Ala Leu
            180                 185                 190

Arg Trp Leu Gly Arg Tyr Tyr Cys Phe Gln Gly Asn Gln Phe Leu Arg
            195                 200                 205

Phe Asp Pro Val Arg Gly Glu Val Pro Pro Arg Tyr Pro Arg Asp Val
            210                 215                 220

Arg Asp Tyr Phe Met Pro Cys Pro Gly Arg Gly His Gly His Arg Asn
225                 230                 235                 240
```

```
Gly Thr Gly His Gly Asn Ser Thr His Gly Pro Glu Tyr Met Arg
            245                 250                 255

Cys Ser Pro His Leu Val Leu Ser Ala Leu Thr Ser Asp Asn His Gly
        260                 265                 270

Ala Thr Tyr Ala Phe Ser Gly Thr His Tyr Trp Arg Leu Asp Thr Ser
            275                 280                 285

Arg Asp Gly Trp His Ser Trp Pro Ile Ala His Gln Trp Pro Gln Gly
    290                 295                 300

Pro Ser Ala Val Asp Ala Ala Phe Ser Trp Glu Lys Leu Tyr Leu
305                 310                 315                 320

Val Gln Gly Thr Gln Val Tyr Val Phe Leu Thr Lys Gly Gly Tyr Thr
                325                 330                 335

Leu Val Ser Gly Tyr Pro Lys Arg Leu Glu Lys Glu Val Gly Thr Pro
            340                 345                 350

His Gly Ile Ile Leu Asp Ser Val Asp Ala Ala Phe Ile Cys Pro Gly
            355                 360                 365

Ser Ser Arg Leu His Ile Met Ala Gly Arg Arg Leu Trp Trp Leu Asp
    370                 375                 380

Leu Lys Ser Gly Ala Gln Ala Thr Trp Thr Glu Leu Pro Trp Pro His
385                 390                 395                 400

Glu Lys Val Asp Gly Ala Leu Cys Met Glu Lys Ser Leu Gly Pro Asn
                405                 410                 415

Ser Cys Ser Ala Asn Gly Pro Gly Leu Tyr Leu Ile His Gly Pro Asn
            420                 425                 430

Leu Tyr Cys Tyr Ser Asp Val Glu Lys Leu Asn Ala Ala Lys Ala Leu
            435                 440                 445

Pro Gln Pro Gln Asn Val Thr Ser Leu Leu Gly Cys Thr His
    450                 455                 460

<210> SEQ ID NO 25
<211> LENGTH: 583
<212> TYPE: PRT
<213> ORGANISM: Homo sapiens

<400> SEQUENCE: 25

Met Ala His Val Arg Gly Leu Gln Leu Pro Gly Cys Leu Ala Leu
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
    50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140

Thr Thr His Pro Gly Ala Asp Leu Gln Glu Asn Phe Cys Arg Asn Pro
```

```
                  145                 150                 155                 160
Asp Ser Ser Thr Thr Gly Pro Trp Cys Tyr Thr Thr Asp Pro Thr Val
                      165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285

Asn Tyr Cys Glu Glu Ala Val Glu Glu Glu Thr Gly Asp Gly Leu Asp
    290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
        355                 360                 365

Asp Ala Glu Ile Gly Met Ser Pro Trp Gln Val Met Leu Phe Arg Lys
    370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
        435                 440                 445

Ile His Pro Ser Leu Leu Gln Ala Gly Tyr Lys Gly Arg Val Thr Gly
    450                 455                 460

Trp Gly Asn Leu Lys Glu Thr Trp Thr Ala Asn Val Gly Lys Gly Gln
465                 470                 475                 480

Pro Ser Val Leu Gln Val Asn Leu Pro Ile Val Glu Arg Pro Val
                485                 490                 495

Cys Lys Asp Ser Thr Arg Ile Arg Ile Thr Asp Asn Met Phe Cys Ala
            500                 505                 510

Gly Tyr Lys Pro Asp Glu Gly Lys Arg Gly Asp Ala Cys Glu Gly Asp
        515                 520                 525

Ser Gly Gly Pro Phe Val Met Lys Ser Pro Phe Asn Asn Arg Trp Tyr
    530                 535                 540

Gln Met Gly Ile Val Ser Trp Gly Glu Gly Cys Asp Arg Asp Gly Lys
545                 550                 555                 560

Tyr Gly Phe Tyr Thr His Val Phe Arg Leu Lys Lys Trp Ile Gln Lys
                565                 570                 575
```

Val Ile Asp Gln Phe Gly Glu
            580

<210> SEQ ID NO 26
<211> LENGTH: 111
<212> TYPE: PRT
<213> ORGANISM: Homo sapiens

<400> SEQUENCE: 26

Tyr Val Leu Thr Gln Pro Ser Val Ser Val Ala Pro Gly Glu Thr
1               5                   10                  15

Ala Arg Leu Thr Cys Gly Gly Asn Asp Ile Gly Ser Glu Ser Val His
            20                  25                  30

Trp Tyr Gln Gln Lys Pro Gly Gln Ala Pro Val Leu Val Ile Tyr Phe
            35                  40                  45

Asp Arg Asp Arg Pro Ser Gly Ile Pro Glu Arg Phe Ser Gly Ser Asn
            50                  55                  60

Ser Gly Asn Thr Ala Thr Leu Thr Ile Ser Arg Val Glu Ala Gly Asp
65                  70                  75                  80

Glu Ala Asp Tyr Tyr Cys Gln Leu Trp Asp Ser Ser Ser Glu His Val
                    85                  90                  95

Val Phe Gly Gly Gly Thr Lys Leu Thr Val Leu Ser Gln Pro Lys
            100                 105                 110

<210> SEQ ID NO 27
<211> LENGTH: 140
<212> TYPE: PRT
<213> ORGANISM: Homo sapiens

<400> SEQUENCE: 27

Met Ala Gly Trp Asn Ala Tyr Ile Asp Asn Leu Met Ala Asp Gly Thr
1               5                   10                  15

Cys Gln Asp Ala Ala Ile Val Gly Tyr Lys Asp Ser Pro Ser Val Trp
            20                  25                  30

Ala Ala Val Pro Gly Lys Thr Phe Val Asn Ile Thr Pro Ala Glu Val
            35                  40                  45

Gly Val Leu Val Gly Lys Asp Arg Ser Ser Phe Tyr Val Asn Gly Leu
    50                  55                  60

Thr Leu Gly Gly Gln Lys Cys Ser Val Ile Arg Asp Ser Leu Leu Gln
65                  70                  75                  80

Asp Gly Glu Phe Ser Met Asp Leu Arg Thr Lys Ser Thr Gly Gly Ala
                    85                  90                  95

Pro Thr Phe Asn Val Thr Val Thr Lys Thr Asp Lys Thr Leu Val Leu
            100                 105                 110

Leu Met Gly Lys Glu Gly Val His Gly Gly Leu Ile Asn Lys Lys Cys
            115                 120                 125

Tyr Glu Met Ala Ser His Leu Arg Arg Ser Gln Tyr
            130                 135                 140

<210> SEQ ID NO 28
<211> LENGTH: 175
<212> TYPE: PRT
<213> ORGANISM: Homo sapiens

<400> SEQUENCE: 28

Met Glu Lys Ile Pro Val Ser Ala Phe Leu Leu Leu Val Ala Leu Ser
1               5                   10                  15

Tyr Thr Leu Ala Arg Asp Thr Thr Val Lys Pro Gly Ala Lys Lys Asp
            20                  25                  30

Thr Lys Asp Ser Arg Pro Lys Leu Pro Gln Thr Leu Ser Arg Gly Trp
        35                  40                  45

Gly Asp Gln Leu Ile Trp Thr Gln Thr Tyr Glu Glu Ala Leu Tyr Lys
    50                  55                  60

Ser Lys Thr Ser Asn Lys Pro Leu Met Ile Ile His His Leu Asp Glu
65                  70                  75                  80

Cys Pro His Ser Gln Ala Leu Lys Lys Val Phe Ala Glu Asn Lys Glu
                85                  90                  95

Ile Gln Lys Leu Ala Glu Gln Phe Val Leu Leu Asn Leu Val Tyr Glu
            100                 105                 110

Thr Thr Asp Lys His Leu Ser Pro Asp Gly Gln Tyr Val Pro Arg Ile
        115                 120                 125

Met Phe Val Asp Pro Ser Leu Thr Val Arg Ala Asp Ile Thr Gly Arg
    130                 135                 140

Tyr Ser Asn Arg Leu Tyr Ala Tyr Glu Pro Ala Asp Thr Ala Leu Leu
145                 150                 155                 160

Leu Asp Asn Met Lys Lys Ala Leu Lys Leu Leu Lys Thr Glu Leu
                165                 170                 175

<210> SEQ ID NO 29
<211> LENGTH: 147
<212> TYPE: PRT
<213> ORGANISM: Homo sapiens

<400> SEQUENCE: 29

Met Ser Glu Glu Lys Pro Lys Glu Gly Val Lys Thr Glu Asn Asp His
1               5                   10                  15

Ile Asn Leu Lys Val Ala Gly Gln Asp Gly Ser Val Val Gln Phe Lys
            20                  25                  30

Ile Lys Arg His Thr Pro Leu Ser Lys Leu Met Lys Ala Tyr Cys Glu
        35                  40                  45

Arg Gln Gly Leu Ser Met Arg Gln Ile Arg Phe Arg Phe Asp Gly Gln
    50                  55                  60

Pro Ile Asn Glu Thr Asp Thr Pro Ala Gln Gly Ile Ile Leu Ser Trp
65                  70                  75                  80

Lys Glu Leu Trp Thr Trp Lys Gln Thr Phe Phe Phe Glu Thr Glu Ser
                85                  90                  95

Arg Phe Val Ala Gln Ala Arg Met Gln Trp Arg Ser Leu Ser Ser Leu
            100                 105                 110

Cys Lys Leu Cys Leu Leu Ser Ser Arg His Ser Pro Ala Ser Ala Ser
        115                 120                 125

Gln Val Ala Gly Thr Ile Gly Ala His His Ser Arg Leu Ile Phe
    130                 135                 140

Leu Tyr Phe
145

<210> SEQ ID NO 30
<211> LENGTH: 347
<212> TYPE: PRT
<213> ORGANISM: Homo sapiens

<400> SEQUENCE: 30

Met Ser Ser Trp Ser Arg Gln Arg Pro Lys Ser Pro Gly Gly Ile Gln
1               5                   10                  15

-continued

```
Pro His Val Ser Arg Thr Leu Phe Leu Leu Leu Leu Ala Ala Ser
         20                  25                  30

Ala Trp Gly Val Thr Leu Ser Pro Lys Asp Cys Gln Val Phe Arg Ser
         35                  40                  45

Asp His Gly Ser Ser Ile Ser Cys Gln Pro Ala Glu Ile Pro Gly
         50                  55                  60

Tyr Leu Pro Ala Asp Thr Val His Leu Ala Val Glu Phe Phe Asn Leu
65                   70                  75                  80

Thr His Leu Pro Ala Asn Leu Leu Gln Gly Ala Ser Lys Leu Gln Glu
                 85                  90                  95

Leu His Leu Ser Ser Asn Gly Leu Glu Ser Leu Ser Pro Glu Phe Leu
                 100                 105                 110

Arg Pro Val Pro Gln Leu Arg Val Leu Asp Leu Thr Arg Asn Ala Leu
                 115                 120                 125

Thr Gly Leu Pro Pro Gly Leu Phe Gln Ala Ser Ala Thr Leu Asp Thr
         130                 135                 140

Leu Val Leu Lys Glu Asn Gln Leu Glu Val Leu Glu Val Ser Trp Leu
145                 150                 155                 160

His Gly Leu Lys Ala Leu Gly His Leu Asp Leu Ser Gly Asn Arg Leu
                 165                 170                 175

Arg Lys Leu Pro Pro Gly Leu Leu Ala Asn Phe Thr Leu Leu Arg Thr
                 180                 185                 190

Leu Asp Leu Gly Glu Asn Gln Leu Glu Thr Leu Pro Pro Asp Leu Leu
         195                 200                 205

Arg Gly Pro Leu Gln Leu Glu Arg Leu His Leu Glu Gly Asn Lys Leu
         210                 215                 220

Gln Val Leu Gly Lys Asp Leu Leu Pro Gln Pro Asp Leu Arg Tyr
225                 230                 235                 240

Leu Phe Leu Asn Gly Asn Lys Leu Ala Arg Val Ala Ala Gly Ala Phe
                 245                 250                 255

Gln Gly Leu Arg Gln Leu Asp Met Leu Asp Leu Ser Asn Asn Ser Leu
         260                 265                 270

Ala Ser Val Pro Glu Gly Leu Trp Ala Ser Leu Gly Gln Pro Asn Trp
         275                 280                 285

Asp Met Arg Asp Gly Phe Asp Ile Ser Gly Asn Pro Trp Ile Cys Asp
290                 295                 300

Gln Asn Leu Ser Asp Leu Tyr Arg Trp Leu Gln Ala Gln Lys Asp Lys
305                 310                 315                 320

Met Phe Ser Gln Asn Asp Thr Arg Cys Ala Gly Pro Glu Ala Val Lys
                 325                 330                 335

Gly Gln Thr Leu Leu Ala Val Ala Lys Ser Gln
         340                 345
```

<210> SEQ ID NO 31
<211> LENGTH: 495
<212> TYPE: PRT
<213> ORGANISM: Homo sapiens

<400> SEQUENCE: 31

```
Met Ser Met Leu Val Val Phe Leu Leu Leu Trp Gly Val Thr Trp Gly
1               5                   10                  15

Pro Val Thr Glu Ala Ala Ile Phe Tyr Glu Thr Gln Pro Ser Leu Trp
         20                  25                  30

Ala Glu Ser Glu Ser Leu Leu Lys Pro Leu Ala Asn Val Thr Leu Thr
         35                  40                  45
```

-continued

Cys Gln Ala His Leu Glu Thr Pro Asp Phe Gln Leu Phe Lys Asn Gly
        50                  55                  60

Val Ala Gln Glu Pro Val His Leu Asp Ser Pro Ala Ile Lys His Gln
65                  70                  75                  80

Phe Leu Leu Thr Gly Asp Thr Gln Gly Arg Tyr Arg Cys Arg Ser Gly
                85                  90                  95

Leu Ser Thr Gly Trp Thr Gln Leu Ser Lys Leu Leu Glu Leu Thr Gly
                100                 105                 110

Pro Lys Ser Leu Pro Ala Pro Trp Leu Ser Met Ala Pro Val Ser Trp
        115                 120                 125

Ile Thr Pro Gly Leu Lys Thr Thr Ala Val Cys Arg Gly Val Leu Arg
        130                 135                 140

Gly Val Thr Phe Leu Leu Arg Arg Glu Gly Asp His Glu Phe Leu Glu
145                 150                 155                 160

Val Pro Glu Ala Gln Glu Asp Val Glu Ala Thr Phe Pro Val His Gln
                165                 170                 175

Pro Gly Asn Tyr Ser Cys Ser Tyr Arg Thr Asp Gly Glu Gly Ala Leu
                180                 185                 190

Ser Glu Pro Ser Ala Thr Val Thr Ile Glu Glu Leu Ala Ala Pro Pro
        195                 200                 205

Pro Pro Val Leu Met His His Gly Glu Ser Ser Gln Val Leu His Pro
210                 215                 220

Gly Asn Lys Val Thr Leu Thr Cys Val Ala Pro Leu Ser Gly Val Asp
225                 230                 235                 240

Phe Gln Leu Arg Arg Gly Glu Lys Glu Leu Leu Val Pro Arg Ser Ser
                245                 250                 255

Thr Ser Pro Asp Arg Ile Phe Phe His Leu Asn Ala Val Ala Leu Gly
                260                 265                 270

Asp Gly Gly His Tyr Thr Cys Arg Tyr Arg Leu His Asp Asn Gln Asn
        275                 280                 285

Gly Trp Ser Gly Asp Ser Ala Pro Val Glu Leu Ile Leu Ser Asp Glu
        290                 295                 300

Thr Leu Pro Ala Pro Glu Phe Ser Pro Glu Pro Glu Ser Gly Arg Ala
305                 310                 315                 320

Leu Arg Leu Arg Cys Leu Ala Pro Leu Glu Gly Ala Arg Phe Ala Leu
                325                 330                 335

Val Arg Glu Asp Arg Gly Gly Arg Arg Val His Arg Phe Gln Ser Pro
        340                 345                 350

Ala Gly Thr Glu Ala Leu Phe Glu Leu His Asn Ile Ser Val Ala Asp
        355                 360                 365

Ser Ala Asn Tyr Ser Cys Val Tyr Val Asp Leu Lys Pro Pro Phe Gly
        370                 375                 380

Gly Ser Ala Pro Ser Glu Arg Leu Glu Leu His Val Asp Gly Pro Pro
385                 390                 395                 400

Pro Arg Pro Gln Leu Arg Ala Thr Trp Ser Gly Ala Val Leu Ala Gly
                405                 410                 415

Arg Asp Ala Val Leu Arg Cys Glu Gly Pro Ile Pro Asp Val Thr Phe
        420                 425                 430

Glu Leu Leu Arg Glu Gly Glu Thr Lys Ala Val Lys Thr Val Arg Thr
                435                 440                 445

Pro Gly Ala Ala Ala Asn Leu Glu Leu Ile Phe Val Gly Pro Gln His
        450                 455                 460

```
Ala Gly Asn Tyr Arg Cys Arg Tyr Arg Ser Trp Val Pro His Thr Phe
465                 470                 475                 480

Glu Ser Glu Leu Ser Asp Pro Val Glu Leu Leu Val Ala Glu Ser
            485                 490                 495

<210> SEQ ID NO 32
<211> LENGTH: 418
<212> TYPE: PRT
<213> ORGANISM: Homo sapiens

<400> SEQUENCE: 32

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350
```

```
Leu Ser Lys Ala Val His Lys Ala Val Leu Thr Ile Asp Glu Lys Gly
        355                 360                 365
Thr Glu Ala Ala Gly Ala Met Phe Leu Glu Ala Ile Pro Met Ser Ile
    370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415
Gln Lys

<210> SEQ ID NO 33
<211> LENGTH: 146
<212> TYPE: PRT
<213> ORGANISM: Homo sapiens

<400> SEQUENCE: 33

Met Ala Gly Glu Leu Thr Pro Glu Glu Ala Gln Tyr Lys Lys Ala
1               5                   10                  15
Phe Ser Ala Val Asp Thr Asp Gly Asn Gly Thr Ile Asn Ala Gln Glu
                20                  25                  30
Leu Gly Ala Ala Leu Lys Ala Thr Gly Lys Asn Leu Ser Glu Ala Gln
            35                  40                  45
Leu Arg Lys Leu Ile Ser Glu Val Asp Ser Asp Gly Asp Gly Glu Ile
    50                  55                  60
Ser Phe Gln Glu Phe Leu Thr Ala Ala Lys Lys Ala Arg Ala Gly Leu
65                  70                  75                  80
Glu Asp Leu Gln Val Ala Phe Arg Ala Phe Asp Gln Asp Gly Asp Gly
                85                  90                  95
His Ile Thr Val Asp Glu Leu Arg Arg Ala Met Ala Gly Leu Gly Gln
            100                 105                 110
Pro Leu Pro Gln Glu Glu Leu Asp Ala Met Ile Arg Glu Ala Asp Val
    115                 120                 125
Asp Gln Asp Gly Arg Val Asn Tyr Glu Glu Phe Ala Arg Met Leu Ala
130                 135                 140
Gln Glu
145

<210> SEQ ID NO 34
<211> LENGTH: 338
<212> TYPE: PRT
<213> ORGANISM: Homo sapiens

<400> SEQUENCE: 34

Met Leu Ser Ala Leu Ala Arg Pro Ala Ser Ala Ala Leu Arg Arg Ser
1               5                   10                  15
Phe Ser Thr Ser Ala Gln Asn Asn Ala Lys Val Ala Val Leu Gly Ala
                20                  25                  30
Ser Gly Gly Ile Gly Gln Pro Leu Ser Leu Leu Leu Lys Asn Ser Pro
            35                  40                  45
Leu Val Ser Arg Leu Thr Leu Tyr Asp Ile Ala His Thr Pro Gly Val
    50                  55                  60
Ala Ala Asp Leu Ser His Ile Glu Thr Lys Ala Ala Val Lys Gly Tyr
65                  70                  75                  80
Leu Gly Pro Glu Gln Leu Pro Asp Cys Leu Lys Gly Cys Asp Val Val
                85                  90                  95
```

Val Ile Pro Ala Gly Val Pro Arg Lys Pro Gly Met Thr Arg Asp Asp
                100                 105                 110

Leu Phe Asn Thr Asn Ala Thr Ile Val Ala Thr Leu Thr Ala Ala Cys
            115                 120                 125

Ala Gln His Cys Pro Glu Ala Met Ile Cys Val Ile Ala Asn Pro Val
        130                 135                 140

Asn Ser Thr Ile Pro Ile Thr Ala Glu Val Phe Lys Lys His Gly Val
145                 150                 155                 160

Tyr Asn Pro Asn Lys Ile Phe Gly Val Thr Thr Leu Asp Ile Val Arg
                165                 170                 175

Ala Asn Thr Phe Val Ala Glu Leu Lys Gly Leu Asp Pro Ala Arg Val
            180                 185                 190

Asn Val Pro Val Ile Gly Gly His Ala Gly Lys Thr Ile Ile Pro Leu
        195                 200                 205

Ile Ser Gln Cys Thr Pro Lys Val Asp Phe Pro Gln Asp Gln Leu Thr
210                 215                 220

Ala Leu Thr Gly Arg Ile Gln Glu Ala Gly Thr Glu Val Val Lys Ala
225                 230                 235                 240

Lys Ala Gly Ala Gly Ser Ala Thr Leu Ser Met Ala Tyr Ala Gly Ala
                245                 250                 255

Arg Phe Val Phe Ser Leu Val Asp Ala Met Asn Gly Lys Glu Gly Val
            260                 265                 270

Val Glu Cys Ser Phe Val Lys Ser Gln Glu Thr Glu Cys Thr Tyr Phe
        275                 280                 285

Ser Thr Pro Leu Leu Leu Gly Lys Lys Gly Ile Glu Lys Asn Leu Gly
290                 295                 300

Ile Gly Lys Val Ser Ser Phe Glu Glu Lys Met Ile Ser Asp Ala Ile
305                 310                 315                 320

Pro Glu Leu Lys Ala Ser Ile Lys Lys Gly Glu Asp Phe Val Lys Thr
                325                 330                 335

Leu Lys

<210> SEQ ID NO 35
<211> LENGTH: 320
<212> TYPE: PRT
<213> ORGANISM: Homo sapiens

<400> SEQUENCE: 35

Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
                20                  25                  30

Thr Asp Glu Glu Ser Ile Leu Thr Leu Leu Thr Ser Arg Ser Asn Ala
            35                  40                  45

Gln Arg Gln Glu Ile Ser Ala Ala Phe Lys Thr Leu Phe Gly Arg Asp
        50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
        115                 120                 125

```
Tyr Glu Glu Tyr Gly Ser Ser Leu Glu Asp Val Val Gly Asp
    130             135                 140

Thr Ser Gly Tyr Tyr Gln Arg Met Leu Val Val Leu Gln Ala Asn
145             150                 155                 160

Arg Asp Pro Asp Ala Gly Ile Asp Glu Ala Gln Val Glu Gln Asp Ala
            165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
195                 200                 205

Val Phe Asp Lys Tyr Met Thr Ile Ser Gly Phe Gln Ile Glu Glu Thr
    210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
    275                 280                 285

Arg Lys Asn Phe Ala Thr Ser Leu Tyr Ser Met Ile Lys Gly Asp Thr
    290                 295                 300

Ser Gly Asp Tyr Lys Lys Ala Leu Leu Leu Leu Cys Gly Glu Asp Asp
305                 310                 315                 320

<210> SEQ ID NO 36
<211> LENGTH: 474
<212> TYPE: PRT
<213> ORGANISM: Homo sapiens

<400> SEQUENCE: 36

Met Ala Thr Asn Trp Gly Ser Leu Leu Gln Asp Lys Gln Gln Leu Glu
1               5                   10                  15

Glu Leu Ala Arg Gln Ala Val Asp Arg Ala Leu Ala Glu Gly Val Leu
            20                  25                  30

Leu Arg Thr Ser Gln Glu Pro Thr Ser Ser Glu Val Val Ser Tyr Ala
        35                  40                  45

Pro Phe Thr Leu Phe Pro Ser Leu Val Pro Ser Ala Leu Leu Glu Gln
    50                  55                  60

Ala Tyr Ala Val Gln Met Asp Phe Asn Leu Leu Val Asp Ala Val Ser
65                  70                  75                  80

Gln Asn Ala Ala Phe Leu Glu Gln Thr Leu Ser Ser Thr Ile Lys Gln
                85                  90                  95

Asp Asp Phe Thr Ala Arg Leu Phe Asp Ile His Lys Val Leu Lys
            100                 105                 110

Glu Gly Ile Ala Gln Thr Val Phe Leu Gly Leu Asn Arg Ser Asp Tyr
        115                 120                 125

Met Phe Gln Arg Ser Ala Asp Gly Ser Pro Ala Leu Lys Gln Ile Glu
    130                 135                 140

Ile Asn Thr Ile Ser Ala Ser Phe Gly Gly Leu Ala Ser Arg Thr Pro
145                 150                 155                 160

Ala Val His Arg His Val Leu Ser Val Leu Lys Thr Lys Glu Ala
                165                 170                 175

Gly Lys Ile Leu Ser Asn Asn Pro Ser Lys Gly Leu Ala Leu Gly Ile
            180                 185                 190
```

```
Ala Lys Ala Trp Glu Leu Tyr Gly Ser Pro Asn Ala Leu Val Leu Leu
            195                 200                 205

Ile Ala Gln Glu Lys Glu Arg Asn Ile Phe Asp Gln Arg Ala Ile Glu
        210                 215                 220

Asn Glu Leu Leu Ala Arg Asn Ile His Val Ile Arg Arg Thr Phe Glu
225                 230                 235                 240

Asp Ile Ser Glu Lys Gly Ser Leu Asp Gln Asp Arg Arg Leu Phe Val
                245                 250                 255

Asp Gly Gln Glu Ile Ala Val Val Tyr Phe Arg Asp Gly Tyr Met Pro
            260                 265                 270

Arg Gln Tyr Ser Leu Gln Asn Trp Glu Ala Arg Leu Leu Leu Glu Arg
        275                 280                 285

Ser His Ala Ala Lys Cys Pro Asp Ile Ala Thr Gln Leu Ala Gly Thr
    290                 295                 300

Lys Lys Val Gln Gln Glu Leu Ser Arg Pro Gly Met Leu Glu Met Leu
305                 310                 315                 320

Leu Pro Gly Gln Pro Glu Ala Val Ala Arg Leu Arg Ala Thr Phe Ala
                325                 330                 335

Gly Leu Tyr Ser Leu Asp Val Gly Glu Glu Gly Asp Gln Ala Ile Ala
            340                 345                 350

Glu Ala Leu Ala Ala Pro Ser Arg Phe Val Leu Lys Pro Gln Arg Glu
        355                 360                 365

Gly Gly Gly Asn Asn Leu Tyr Gly Glu Glu Met Val Gln Ala Leu Lys
    370                 375                 380

Gln Leu Lys Asp Ser Glu Arg Ala Ser Tyr Ile Leu Met Glu Lys
385                 390                 395                 400

Ile Glu Pro Glu Pro Phe Glu Asn Cys Leu Leu Arg Pro Gly Ser Pro
                405                 410                 415

Ala Arg Val Val Gln Cys Ile Ser Glu Leu Gly Ile Phe Gly Val Tyr
            420                 425                 430

Val Arg Gln Glu Lys Thr Leu Val Met Asn Lys His Val Gly His Leu
        435                 440                 445

Leu Arg Thr Lys Ala Ile Glu His Ala Asp Gly Gly Val Ala Ala Gly
    450                 455                 460

Val Ala Val Leu Asp Asn Pro Tyr Pro Val
465                 470

<210> SEQ ID NO 37
<211> LENGTH: 847
<212> TYPE: PRT
<213> ORGANISM: Homo sapiens

<400> SEQUENCE: 37

Met Ala Lys Pro Leu Thr Asp Gln Glu Lys Arg Arg Gln Ile Ser Ile
1               5                   10                  15

Arg Gly Ile Val Gly Val Glu Asn Val Ala Glu Leu Lys Lys Ser Phe
            20                  25                  30

Asn Arg His Leu His Phe Thr Leu Val Lys Asp Arg Asn Val Ala Thr
        35                  40                  45

Thr Arg Asp Tyr Tyr Phe Ala Leu Ala His Thr Val Arg Asp His Leu
    50                  55                  60

Val Gly Arg Trp Ile Arg Thr Gln Gln His Tyr Tyr Asp Lys Cys Pro
65                  70                  75                  80

Lys Arg Val Tyr Tyr Leu Ser Leu Glu Phe Tyr Met Gly Arg Thr Leu
```

-continued

```
                85                  90                  95
Gln Asn Thr Met Ile Asn Leu Gly Leu Gln Asn Ala Cys Asp Glu Ala
            100                 105                 110
Ile Tyr Gln Leu Gly Leu Asp Ile Glu Glu Leu Glu Glu Ile Glu Glu
            115                 120                 125
Asp Ala Gly Leu Gly Asn Gly Gly Leu Gly Arg Leu Ala Ala Cys Phe
            130                 135                 140
Leu Asp Ser Met Ala Thr Leu Gly Leu Ala Ala Tyr Gly Tyr Gly Ile
145                 150                 155                 160
Arg Tyr Glu Tyr Gly Ile Phe Asn Gln Lys Ile Arg Asp Gly Trp Gln
                165                 170                 175
Val Glu Glu Ala Asp Asp Trp Leu Arg Tyr Gly Asn Pro Trp Glu Lys
                180                 185                 190
Ser Arg Pro Glu Phe Met Leu Pro Val His Phe Tyr Gly Lys Val Glu
                195                 200                 205
His Thr Asn Thr Gly Thr Lys Trp Ile Asp Thr Gln Val Val Leu Ala
            210                 215                 220
Leu Pro Tyr Asp Thr Pro Val Pro Gly Tyr Met Asn Asn Thr Val Asn
225                 230                 235                 240
Thr Met Arg Leu Trp Ser Ala Arg Ala Pro Asn Asp Phe Asn Leu Arg
                245                 250                 255
Asp Phe Asn Val Gly Asp Tyr Ile Gln Ala Val Leu Asp Arg Asn Leu
            260                 265                 270
Ala Glu Asn Ile Ser Arg Val Leu Tyr Pro Asn Asp Asn Phe Phe Glu
            275                 280                 285
Gly Lys Glu Leu Arg Leu Lys Gln Glu Tyr Phe Val Val Ala Ala Thr
            290                 295                 300
Leu Gln Asp Ile Ile Arg Arg Phe Lys Ala Ser Lys Phe Gly Ser Thr
305                 310                 315                 320
Arg Gly Ala Gly Thr Val Phe Asp Ala Phe Pro Asp Gln Val Ala Ile
                325                 330                 335
Gln Leu Asn Asp Thr His Pro Ala Leu Ala Ile Pro Glu Leu Met Arg
            340                 345                 350
Ile Phe Val Asp Ile Glu Lys Leu Pro Trp Ser Lys Ala Trp Glu Leu
            355                 360                 365
Thr Gln Lys Thr Phe Ala Tyr Thr Asn His Thr Val Leu Pro Glu Ala
            370                 375                 380
Leu Glu Arg Trp Pro Val Asp Leu Val Glu Lys Leu Leu Pro Arg His
385                 390                 395                 400
Leu Glu Ile Ile Tyr Glu Ile Asn Gln Lys His Leu Asp Arg Ile Val
                405                 410                 415
Ala Leu Phe Pro Lys Asp Val Asp Arg Leu Arg Arg Met Ser Leu Ile
                420                 425                 430
Glu Glu Glu Gly Ser Lys Arg Ile Asn Met Ala His Leu Cys Ile Val
            435                 440                 445
Gly Ser His Ala Val Asn Gly Val Ala Lys Ile His Ser Asp Ile Val
            450                 455                 460
Lys Thr Lys Val Phe Lys Asp Phe Ser Glu Leu Glu Pro Asp Lys Phe
465                 470                 475                 480
Gln Asn Lys Thr Asn Gly Ile Thr Pro Arg Arg Trp Leu Leu Leu Cys
                485                 490                 495
Asn Pro Gly Leu Ala Glu Leu Ile Ala Glu Lys Ile Gly Glu Asp Tyr
            500                 505                 510
```

Val Lys Asp Leu Ser Gln Leu Thr Lys Leu His Ser Phe Leu Gly Asp
    515                 520                 525

Asp Val Phe Leu Arg Glu Leu Ala Lys Val Lys Gln Glu Asn Lys Leu
    530                 535                 540

Lys Phe Ser Gln Phe Leu Glu Thr Glu Tyr Lys Val Lys Ile Asn Pro
545                 550                 555                 560

Ser Ser Met Phe Asp Val Gln Val Lys Arg Ile His Glu Tyr Lys Arg
                565                 570                 575

Gln Leu Leu Asn Cys Leu His Val Ile Thr Met Tyr Asn Arg Ile Lys
                580                 585                 590

Lys Asp Pro Lys Lys Leu Phe Val Pro Arg Thr Val Ile Ile Gly Gly
        595                 600                 605

Lys Ala Ala Pro Gly Tyr His Met Ala Lys Met Ile Ile Lys Leu Ile
        610                 615                 620

Thr Ser Val Ala Asp Val Val Asn Asn Asp Pro Met Val Gly Ser Lys
625                 630                 635                 640

Leu Lys Val Ile Phe Leu Glu Asn Tyr Arg Val Ser Leu Ala Glu Lys
                645                 650                 655

Val Ile Pro Ala Thr Asp Leu Ser Glu Gln Ile Ser Thr Ala Gly Thr
            660                 665                 670

Glu Ala Ser Gly Thr Gly Asn Met Lys Phe Met Leu Asn Gly Ala Leu
        675                 680                 685

Thr Ile Gly Thr Met Asp Gly Ala Asn Val Glu Met Ala Glu Glu Ala
        690                 695                 700

Gly Glu Glu Asn Leu Phe Ile Phe Gly Met Arg Ile Asp Asp Val Ala
705                 710                 715                 720

Ala Leu Asp Lys Lys Gly Tyr Glu Ala Lys Glu Tyr Tyr Glu Ala Leu
                725                 730                 735

Pro Glu Leu Lys Leu Val Ile Asp Gln Ile Asp Asn Gly Phe Phe Ser
            740                 745                 750

Pro Lys Gln Pro Asp Leu Phe Lys Asp Ile Ile Asn Met Leu Phe Tyr
        755                 760                 765

His Asp Arg Phe Lys Val Phe Ala Asp Tyr Glu Ala Tyr Val Lys Cys
    770                 775                 780

Gln Asp Lys Val Ser Gln Leu Tyr Met Asn Pro Lys Ala Trp Asn Thr
785                 790                 795                 800

Met Val Leu Lys Asn Ile Ala Ala Ser Gly Lys Phe Ser Ser Asp Arg
                805                 810                 815

Thr Ile Lys Glu Tyr Ala Gln Asn Ile Trp Asn Val Glu Pro Ser Asp
            820                 825                 830

Leu Lys Ile Ser Leu Ser Asn Glu Ser Asn Lys Val Asn Gly Asn
        835                 840                 845

<210> SEQ ID NO 38
<211> LENGTH: 375
<212> TYPE: PRT
<213> ORGANISM: Homo sapiens

<400> SEQUENCE: 38

Met Ser Thr Ala Gly Lys Val Ile Lys Cys Lys Ala Ala Val Leu Trp
1               5                   10                  15

Glu Leu Lys Lys Pro Phe Ser Ile Glu Glu Val Glu Val Ala Pro Pro
            20                  25                  30

Lys Ala His Glu Val Arg Ile Lys Met Val Ala Ala Gly Ile Cys Arg

```
                35                  40                  45
Ser Asp Glu His Val Val Ser Gly Asn Leu Val Thr Pro Leu Pro Val
 50                  55                  60

Ile Leu Gly His Glu Ala Ala Gly Ile Val Glu Ser Val Gly Glu Gly
 65                  70                  75                  80

Val Thr Thr Val Lys Pro Gly Asp Lys Val Ile Pro Leu Phe Thr Pro
                 85                  90                  95

Gln Cys Gly Lys Cys Arg Ile Cys Lys Asn Pro Glu Ser Asn Tyr Cys
                100                 105                 110

Leu Lys Asn Asp Leu Gly Asn Pro Arg Gly Thr Leu Gln Asp Gly Thr
            115                 120                 125

Arg Arg Phe Thr Cys Ser Gly Lys Pro Ile His His Phe Val Gly Val
        130                 135                 140

Ser Thr Phe Ser Gln Tyr Thr Val Val Asp Glu Asn Ala Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Pro
            180                 185                 190

Gly Ser Thr Cys Ala Val Phe Gly Leu Gly Gly Val Gly Leu Ser Val
        195                 200                 205

Val Met Gly Cys Lys Ala Ala Gly Ala Ala Arg Ile Ile Ala Val Asp
210                 215                 220

Ile Asn Lys Asp Lys Phe Ala Lys Ala Lys Glu Leu Gly Ala Thr Glu
225                 230                 235                 240

Cys Ile Asn Pro Gln Asp Tyr Lys Lys Pro Ile Gln Glu Val Leu Lys
                245                 250                 255

Glu Met Thr Asp Gly Gly Val Asp Phe Ser Phe Glu Val Ile Gly Arg
            260                 265                 270

Leu Asp Thr Met Met Ala Ser Leu Leu Cys Cys His Glu Ala Cys Gly
        275                 280                 285

Thr Ser Val Ile Val Gly Val Pro Pro Asp Ser Gln Asn Leu Ser Ile
290                 295                 300

Asn Pro Met Leu Leu Leu Thr Gly Arg Thr Trp Lys Gly Ala Ile Phe
305                 310                 315                 320

Gly Gly Phe Lys Ser Lys Glu Ser Val Pro Lys Leu Val Ala Asp Phe
                325                 330                 335

Met Ala Lys Lys Phe Ser Leu Asp Ala Leu Ile Thr Asn Ile Leu Pro
            340                 345                 350

Phe Glu Lys Ile Asn Glu Gly Phe Asp Leu Leu Arg Ser Gly Lys Ser
        355                 360                 365

Ile Arg Thr Val Leu Thr Phe
370                 375

<210> SEQ ID NO 39
<211> LENGTH: 1311
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 39

Xaa Arg Glu Ile Val Thr Arg Asn Leu Ser Gln Pro Glu Ser Pro Val
 1               5                  10                  15
```

```
Leu Leu Pro Ala Thr Glu Met Ala Ser Leu Ser Leu Gln Glu Glu
            20                  25                  30

Asn Gln Leu Gln Gln Glu Leu Ser Arg Val Glu Asp Leu Leu Ala
        35                  40                  45

Gln Ser Arg Ala Glu Arg Asp Glu Leu Ala Ile Lys Tyr Asn Ala Val
50                  55                  60

Ser Glu Arg Asp Thr Glu His Ser Gln Asp Leu Glu Ser Ala Leu Ile
65                  70                  75                  80

Arg Leu Glu Glu Glu Gln Arg Ser Ala Ser Leu Ala Gln Val Asn
                85                  90                  95

Ala Met Leu Arg Glu Gln Leu Asp Gln Ala Gly Ser Ala Asn Gln Ala
                100                 105                 110

Leu Ser Glu Asp Ile Arg Lys Val Thr Asn Asp Trp Thr Arg Cys Arg
        115                 120                 125

Lys Glu Leu Glu His Arg Glu Ala Ala Trp Arg Arg Glu Glu Glu Ser
    130                 135                 140

Phe Asn Ala Tyr Phe Ser Asn Glu His Ser Arg Leu Leu Leu Leu Trp
145                 150                 155                 160

Arg Gln Val Val Gly Phe Arg Arg Leu Val Ser Glu Val Lys Met Phe
                165                 170                 175

Thr Glu Arg Asp Leu Leu Gln Leu Gly Gly Glu Leu Ala Arg Thr Ser
            180                 185                 190

Arg Ala Val Gln Glu Ala Gly Leu Gly Leu Ser Thr Gly Leu Arg Leu
        195                 200                 205

Ala Glu Ser Arg Ala Glu Ala Leu Glu Lys Gln Ala Leu Leu Gln
    210                 215                 220

Ala Gln Leu Glu Glu Gln Leu Arg Asp Lys Val Leu Arg Glu Lys Asp
225                 230                 235                 240

Leu Ala Gln Gln Gln Met Gln Ser Asp Leu Asp Lys Ala Asp Leu Ser
                245                 250                 255

Ala Arg Val Thr Glu Leu Gly Leu Ala Val Lys Arg Leu Glu Lys Gln
            260                 265                 270

Asn Leu Glu Lys Asp Gln Val Asn Lys Asp Leu Thr Glu Lys Leu Glu
        275                 280                 285

Ala Leu Glu Ser Leu Arg Leu Gln Glu Gln Ala Ala Leu Glu Thr Glu
    290                 295                 300

Asp Gly Glu Gly Leu Gln Gln Thr Leu Arg Asp Leu Ala Gln Ala Val
305                 310                 315                 320

Leu Ser Asp Ser Glu Ser Gly Val Gln Leu Ser Gly Ser Glu Arg Thr
                325                 330                 335

Ala Asp Ala Ser Asn Gly Ser Leu Arg Gly Leu Ser Gly Gln Arg Thr
            340                 345                 350

Pro Ser Pro Pro Arg Arg Ser Ser Pro Gly Arg Gly Arg Ser Pro Arg
        355                 360                 365

Arg Gly Pro Ser Pro Ala Cys Ser Asp Ser Ser Thr Leu Ala Leu Ile
    370                 375                 380

His Ser Ala Leu His Lys Arg Gln Leu Gln Val Gln Asp Met Arg Gly
385                 390                 395                 400

Arg Tyr Glu Ala Ser Gln Asp Leu Leu Gly Thr Leu Arg Lys Gln Leu
                405                 410                 415

Ser Asp Ser Glu Ser Glu Arg Arg Ala Leu Glu Glu Gln Leu Gln Arg
            420                 425                 430
```

```
Leu Arg Asp Lys Thr Asp Gly Ala Met Gln Ala His Glu Asp Ala Gln
        435                 440                 445

Arg Glu Val Gln Arg Leu Arg Ser Ala Asn Glu Leu Leu Ser Arg Glu
    450                 455                 460

Lys Ser Asn Leu Ala His Ser Leu Gln Val Ala Gln Gln Ala Glu
465                 470                 475                 480

Glu Leu Arg Gln Glu Arg Glu Lys Leu Gln Ala Ala Gln Glu Glu Leu
                485                 490                 495

Arg Arg Gln Arg Asp Arg Leu Glu Glu Gln Glu Asp Ala Val Gln
                500                 505                 510

Asp Gly Ala Arg Val Arg Arg Glu Leu Glu Arg Ser His Arg Gln Leu
            515                 520                 525

Glu Gln Leu Glu Gly Lys Arg Ser Val Leu Ala Lys Glu Leu Val Glu
        530                 535                 540

Val Arg Glu Ala Leu Ser Arg Ala Thr Leu Gln Arg Asp Met Leu Gln
545                 550                 555                 560

Ala Glu Lys Ala Glu Val Ala Glu Ala Leu Thr Lys Ala Glu Ala Gly
                565                 570                 575

Arg Val Glu Leu Glu Leu Ser Met Thr Lys Leu Arg Ala Glu Glu Ala
            580                 585                 590

Ser Leu Gln Asp Ser Leu Ser Lys Leu Ser Ala Leu Asn Glu Ser Leu
        595                 600                 605

Ala Gln Asp Lys Leu Asp Leu Asn Arg Leu Val Ala Gln Leu Glu Glu
    610                 615                 620

Glu Lys Ser Ala Leu Gln Gly Arg Gln Arg Ala Glu Gln Glu Ala
625                 630                 635                 640

Thr Val Ala Arg Glu Gln Glu Arg Leu Glu Glu Leu Arg Leu Glu
                645                 650                 655

Gln Glu Val Ala Arg Gln Gly Leu Glu Gly Ser Leu Arg Val Ala Glu
            660                 665                 670

Gln Ala Gln Glu Ala Leu Glu Gln Gln Leu Pro Thr Leu Arg His Glu
        675                 680                 685

Arg Ser Gln Leu Gln Glu Gln Leu Ala Gln Leu Ser Arg Gln Leu Ser
    690                 695                 700

Gly Arg Glu Gln Glu Leu Glu Gln Ala Arg Arg Glu Ala Gln Arg Gln
705                 710                 715                 720

Val Glu Ala Leu Glu Arg Ala Ala Arg Glu Lys Glu Ala Leu Ala Lys
                725                 730                 735

Glu His Ala Gly Leu Ala Val Gln Leu Val Ala Ala Glu Arg Glu Gly
            740                 745                 750

Arg Thr Leu Ser Glu Glu Ala Thr Arg Leu Arg Leu Glu Lys Glu Ala
        755                 760                 765

Leu Glu Gly Ser Leu Phe Glu Val Gln Arg Gln Leu Ala Gln Leu Glu
    770                 775                 780

Ala Arg Arg Glu Gln Leu Glu Ala Glu Gly Gln Ala Leu Leu Leu Ala
785                 790                 795                 800

Lys Glu Thr Leu Thr Gly Glu Leu Ala Gly Leu Arg Gln Gln Ile Ile
                805                 810                 815

Ala Thr Gln Glu Lys Ala Ser Leu Asp Lys Glu Leu Met Ala Gln Lys
            820                 825                 830

Leu Val Gln Ala Glu Arg Glu Ala Gln Ala Ser Leu Arg Glu Gln Arg
        835                 840                 845

Ala Ala His Glu Glu Asp Leu Gln Arg Leu Gln Arg Glu Lys Glu Ala
```

-continued

```
            850                 855                 860
Ala Trp Arg Glu Leu Glu Ala Glu Arg Ala Gln Leu Gln Ser Gln Leu
865                 870                 875                 880

Gln Arg Glu Gln Glu Glu Leu Leu Ala Arg Leu Glu Ala Glu Lys Glu
                    885                 890                 895

Glu Leu Ser Glu Glu Ile Ala Ala Leu Gln Gln Glu Arg Asp Glu Gly
                900                 905                 910

Leu Leu Leu Ala Glu Ser Glu Lys Gln Gln Ala Leu Ser Leu Lys Glu
            915                 920                 925

Ser Glu Lys Thr Ala Leu Ser Glu Lys Leu Met Gly Thr Arg His Ser
    930                 935                 940

Leu Ala Thr Ile Ser Leu Glu Met Glu Arg Gln Lys Arg Asp Ala Gln
945                 950                 955                 960

Ser Arg Gln Glu Gln Asp Arg Ser Thr Val Asn Ala Leu Thr Ser Glu
                965                 970                 975

Leu Arg Asp Leu Arg Ala Gln Arg Glu Glu Ala Ala Ala His Ala
                980                 985                 990

Gln Glu Val Arg Arg Leu Gln Glu  Gln Ala Arg Asp Leu Gly Lys Gln
            995                 1000                1005

Arg Asp  Ser Cys Leu Arg Glu  Ala Glu Glu Leu Arg  Thr Gln Leu
    1010                1015                1020

Arg Leu  Leu Glu Asp Ala Arg  Asp Gly Leu Arg Arg  Glu Leu Leu
    1025                1030                1035

Glu Ala  Gln Arg Lys Leu Arg  Glu Ser Gln Glu Gly  Arg Glu Val
    1040                1045                1050

Gln Arg  Gln Glu Ala Gly Glu  Leu Arg Arg Ser Leu  Gly Glu Gly
    1055                1060                1065

Ala Lys  Glu Arg Glu Ala Leu  Arg Arg Ser Asn Glu  Glu Leu Arg
    1070                1075                1080

Ser Ala  Val Lys Lys Ala Glu  Ser Glu Arg Ile Ser  Leu Lys Leu
    1085                1090                1095

Ala Asn  Glu Asp Lys Glu Gln  Lys Leu Ala Leu Leu  Glu Glu Ala
    1100                1105                1110

Arg Thr  Ala Val Gly Lys Glu  Ala Gly Glu Leu Arg  Thr Gly Leu
    1115                1120                1125

Gln Glu  Val Glu Arg Ser Arg  Leu Glu Ala Arg Arg  Glu Leu Gln
    1130                1135                1140

Glu Leu  Arg Arg Gln Met Lys  Met Leu Asp Ser Glu  Asn Thr Arg
    1145                1150                1155

Leu Gly  Arg Glu Leu Ala Glu  Leu Gln Gly Arg Leu  Ala Leu Gly
    1160                1165                1170

Glu Arg  Ala Glu Lys Glu Ser  Arg Arg Glu Thr Leu  Gly Leu Arg
    1175                1180                1185

Gln Arg  Leu Leu Lys Gly Glu  Ala Ser Leu Glu Val  Met Arg Gln
    1190                1195                1200

Glu Leu  Gln Val Ala Gln Arg  Lys Leu Gln Glu Gln  Glu Gly Glu
    1205                1210                1215

Phe Arg  Thr Arg Glu Arg Arg  Leu Leu Gly Ser Leu  Glu Glu Ala
    1220                1225                1230

Arg Gly  Thr Glu Lys Gln Gln  Leu Asp His Ala Arg  Gly Leu Glu
    1235                1240                1245

Leu Lys  Leu Glu Ala Ala Arg  Ala Glu Ala Ala Glu  Leu Gly Leu
    1250                1255                1260
```

```
Arg Leu Ser Ala Ala Glu Gly Arg Ala Gln Gly Leu Glu Ala Glu
    1265                1270                1275

Leu Ala Arg Val Glu Val Gln Arg Arg Ala Ala Glu Ala Gln Leu
    1280                1285                1290

Gly Gly Leu Arg Ser Ala Leu Arg Arg Gly Leu Gly Leu Gly Arg
    1295                1300                1305

Ala Pro Ser
    1310

<210> SEQ ID NO 40
<211> LENGTH: 154
<212> TYPE: PRT
<213> ORGANISM: Homo sapiens

<400> SEQUENCE: 40

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150

<210> SEQ ID NO 41
<211> LENGTH: 324
<212> TYPE: PRT
<213> ORGANISM: Homo sapiens

<400> SEQUENCE: 41

Met Asp Ser Lys Tyr Gln Cys Val Lys Leu Asn Asp Gly His Phe Met
1               5                   10                  15

Pro Val Leu Gly Phe Gly Thr Tyr Ala Pro Ala Glu Val Pro Lys Ser
            20                  25                  30

Lys Ala Leu Glu Ala Thr Lys Leu Ala Ile Glu Ala Gly Phe Arg His
        35                  40                  45

Ile Asp Ser Ala His Leu Tyr Asn Asn Glu Glu Gln Val Gly Leu Ala
    50                  55                  60

Ile Arg Ser Lys Ile Ala Asp Gly Ser Val Lys Arg Glu Asp Ile Phe
65                  70                  75                  80

Tyr Thr Ser Lys Leu Trp Cys Asn Ser His Arg Pro Glu Leu Val Arg
                85                  90                  95

Pro Ala Leu Glu Arg Ser Leu Lys Asn Leu Gln Leu Asp Tyr Val Asp
            100                 105                 110
```

```
Leu Tyr Leu Ile His Phe Pro Val Ser Val Lys Pro Gly Glu Glu Val
            115                 120                 125

Ile Pro Lys Asp Glu Asn Gly Lys Ile Leu Phe Asp Thr Val Asp Leu
    130                 135                 140

Cys Ala Thr Trp Glu Val Met Glu Lys Cys Lys Asp Ala Gly Leu Ala
145                 150                 155                 160

Lys Ser Ile Gly Val Ser Asn Phe Asn Arg Arg Gln Leu Glu Met Ile
                165                 170                 175

Leu Asn Lys Pro Gly Leu Lys Tyr Lys Pro Val Cys Asn Gln Val Glu
            180                 185                 190

Cys His Pro Tyr Phe Asn Gln Arg Lys Leu Leu Asp Phe Cys Lys Ser
        195                 200                 205

Lys Asp Ile Val Leu Val Ala Tyr Ser Ala Leu Gly Ser His Arg Glu
210                 215                 220

Glu Pro Trp Val Asp Pro Asn Ser Pro Val Leu Leu Glu Asp Pro Val
225                 230                 235                 240

Leu Cys Ala Leu Ala Lys Lys His Lys Arg Thr Pro Ala Leu Ile Ala
                245                 250                 255

Leu Arg Tyr Gln Leu Gln Arg Gly Val Val Val Leu Ala Lys Ser Tyr
            260                 265                 270

Asn Glu Gln Arg Ile Arg Gln Asn Val Gln Val Phe Glu Phe Gln Leu
        275                 280                 285

Thr Ser Glu Glu Met Lys Ala Ile Asp Gly Leu Asn Arg Asn Val Arg
290                 295                 300

Tyr Leu Thr Leu Asp Met Tyr Phe Ala Ser His Pro Asn Tyr Pro Tyr
305                 310                 315                 320

Ser Asp Glu Tyr

<210> SEQ ID NO 42
<211> LENGTH: 114
<212> TYPE: PRT
<213> ORGANISM: Homo sapiens

<400> SEQUENCE: 42

Met Ala Ser Val Ser Glu Leu Ala Cys Ile Tyr Ser Ala Leu Ile Leu
1               5                   10                  15

His Asp Asp Glu Val Thr Val Thr Glu Asp Lys Ile Asn Ala Leu Ile
            20                  25                  30

Lys Ala Ala Gly Val Asn Val Glu Pro Phe Trp Pro Gly Leu Phe Ala
        35                  40                  45

Lys Ala Leu Ala Asn Val Asn Ile Gly Ser Leu Ile Cys Asn Val Gly
    50                  55                  60

Ala Gly Gly Pro Ala Pro Ala Ala Gly Ala Ala Pro Ala Gly Gly Pro
65                  70                  75                  80

Ala Pro Ser Thr Ala Ala Ala Pro Ala Glu Glu Lys Lys Val Glu Ala
                85                  90                  95

Lys Lys Glu Glu Ser Glu Glu Ser Asp Asp Asp Met Gly Phe Gly Leu
            100                 105                 110

Phe Asp

<210> SEQ ID NO 43
<211> LENGTH: 945
<212> TYPE: PRT
<213> ORGANISM: Homo sapiens
```

```
<400> SEQUENCE: 43

Met Lys Arg Leu Thr Cys Phe Ile Cys Phe Phe Leu Ser Glu Val
1               5                   10                  15

Ser Gly Phe Glu Ile Pro Ile Asn Gly Leu Ser Glu Phe Val Asp Tyr
            20                  25                  30

Glu Asp Leu Val Glu Leu Ala Pro Gly Lys Phe Gln Leu Val Ala Glu
                35                  40                  45

Asn Arg Arg Tyr Gln Arg Ser Leu Pro Gly Glu Ser Glu Glu Met Met
50                  55                  60

Glu Glu Val Asp Gln Val Thr Leu Tyr Ser Tyr Lys Val Gln Ser Thr
65                  70                  75                  80

Ile Thr Ser Arg Met Ala Thr Thr Met Ile Gln Ser Lys Val Val Asn
                85                  90                  95

Asn Ser Pro Gln Pro Gln Asn Val Val Phe Asp Val Gln Ile Pro Lys
                100                 105                 110

Gly Ala Phe Ile Ser Asn Phe Ser Met Thr Val Asp Gly Lys Thr Phe
            115                 120                 125

Arg Ser Ser Ile Lys Glu Lys Thr Val Gly Arg Ala Leu Tyr Ala Gln
130                 135                 140

Ala Arg Ala Lys Gly Lys Thr Ala Gly Leu Val Arg Ser Ser Ala Leu
145                 150                 155                 160

Asp Met Glu Asn Phe Arg Thr Glu Val Asn Val Leu Pro Gly Ala Lys
                165                 170                 175

Val Gln Phe Glu Leu His Tyr Gln Glu Val Lys Trp Arg Lys Leu Gly
            180                 185                 190

Ser Tyr Glu His Arg Ile Tyr Leu Gln Pro Gly Arg Leu Ala Lys His
            195                 200                 205

Leu Glu Val Asp Val Trp Val Ile Glu Pro Gln Gly Leu Arg Phe Leu
210                 215                 220

His Val Pro Asp Thr Phe Glu Gly His Phe Asp Gly Val Pro Val Ile
225                 230                 235                 240

Ser Lys Gly Gln Gln Lys Ala His Val Ser Phe Lys Pro Thr Val Ala
                245                 250                 255

Gln Gln Arg Ile Cys Pro Asn Cys Arg Glu Thr Ala Val Asp Gly Glu
            260                 265                 270

Leu Val Val Leu Tyr Asp Val Lys Arg Glu Glu Lys Ala Gly Glu Leu
            275                 280                 285

Glu Val Phe Asn Gly Tyr Phe Val His Phe Phe Ala Pro Asp Asn Leu
290                 295                 300

Asp Pro Ile Pro Lys Asn Ile Leu Phe Val Ile Asp Val Ser Gly Ser
305                 310                 315                 320

Met Trp Gly Val Lys Met Lys Gln Thr Val Glu Ala Met Lys Thr Ile
                325                 330                 335

Leu Asp Asp Leu Arg Ala Glu Asp His Phe Ser Val Ile Asp Phe Asn
            340                 345                 350

Gln Asn Ile Arg Thr Trp Arg Asn Asp Leu Phe Gln Leu Gln Lys His
            355                 360                 365

Arg Leu Gln Met Pro Arg Tyr Ile Glu Lys Ile Gln Pro Ser Gly Gly
370                 375                 380

Thr Asn Ile Asn Glu Ala Leu Leu Arg Ala Ile Phe Ile Leu Asn Glu
385                 390                 395                 400

Ala Asn Asn Leu Gly Leu Leu Asp Pro Asn Ser Val Ser Leu Ile Ile
                405                 410                 415
```

```
Leu Val Ser Asp Gly Asp Pro Thr Val Gly Glu Leu Lys Leu Ser Lys
                420                 425                 430

Ile Gln Lys Asn Val Lys Glu Asn Ile Gln Asp Asn Ile Ser Leu Phe
                435                 440                 445

Ser Leu Gly Met Gly Phe Asp Val Asp Tyr Asp Phe Leu Lys Arg Leu
                450                 455                 460

Ser Asn Glu Asn His Gly Ile Ala Gln Arg Ile Tyr Gly Asn Gln Asp
465                 470                 475                 480

Thr Ser Ser Gln Leu Lys Lys Phe Tyr Asn Gln Val Ser Thr Pro Leu
                485                 490                 495

Leu Arg Asn Val Gln Phe Asn Tyr Pro His Thr Ser Val Thr Asp Val
                500                 505                 510

Thr Gln Asn Asn Phe His Asn Tyr Phe Gly Gly Ser Glu Ile Val Val
                515                 520                 525

Ala Gly Lys Phe Asp Pro Ala Lys Leu Asp Gln Ile Glu Ser Val Ile
                530                 535                 540

Thr Ala Thr Ser Ala Asn Thr Gln Leu Val Leu Glu Thr Leu Ala Gln
545                 550                 555                 560

Met Asp Asp Leu Gln Asp Phe Leu Ser Lys Asp Lys His Ala Asp Pro
                565                 570                 575

Asp Phe Thr Arg Lys Leu Trp Ala Tyr Leu Thr Ile Asn Gln Leu Leu
                580                 585                 590

Ala Glu Arg Ser Leu Ala Pro Thr Ala Ala Lys Arg Arg Ile Thr
                595                 600                 605

Arg Ser Ile Leu Gln Met Ser Leu Asp His His Ile Val Thr Pro Leu
                610                 615                 620

Thr Ser Leu Val Ile Glu Asn Glu Ala Gly Asp Glu Arg Met Leu Ala
625                 630                 635                 640

Asp Ala Pro Pro Gln Asp Pro Ser Cys Cys Ser Gly Ala Leu Tyr Tyr
                645                 650                 655

Gly Ser Lys Val Val Pro Asp Ser Thr Pro Ser Trp Ala Asn Pro Ser
                660                 665                 670

Pro Thr Pro Val Ile Ser Met Leu Ala Gln Gly Ser Gln Val Leu Glu
                675                 680                 685

Ser Thr Pro Pro His Val Met Arg Val Glu Asn Asp Pro His Phe
690                 695                 700

Ile Ile Tyr Leu Pro Lys Ser Gln Lys Asn Ile Cys Phe Asn Ile Asp
705                 710                 715                 720

Ser Glu Pro Gly Lys Ile Leu Asn Leu Val Ser Asp Pro Glu Ser Gly
                725                 730                 735

Ile Val Val Asn Gly Gln Leu Val Gly Ala Lys Lys Pro Asn Asn Gly
                740                 745                 750

Lys Leu Ser Thr Tyr Phe Gly Lys Leu Gly Phe Tyr Phe Gln Ser Glu
                755                 760                 765

Asp Ile Lys Ile Glu Ile Ser Thr Glu Thr Ile Thr Leu Ser His Gly
                770                 775                 780

Ser Ser Thr Phe Ser Leu Ser Trp Ser Asp Thr Ala Gln Val Thr Asn
785                 790                 795                 800

Gln Arg Val Gln Ile Ser Val Lys Lys Glu Lys Val Val Thr Ile Thr
                805                 810                 815

Leu Asp Lys Glu Met Ser Phe Ser Val Leu Leu His Arg Val Trp Lys
                820                 825                 830
```

Lys His Pro Val Asn Val Asp Phe Leu Gly Ile Tyr Ile Pro Pro Thr
         835                 840                 845

Asn Lys Phe Ser Pro Lys Ala His Gly Leu Ile Gly Gln Phe Met Gln
850                 855                 860

Glu Pro Lys Ile His Ile Phe Asn Glu Arg Pro Gly Lys Asp Pro Glu
865                 870                 875                 880

Lys Pro Glu Ala Ser Met Glu Val Lys Gly Gln Lys Leu Ile Ile Thr
                885                 890                 895

Arg Gly Leu Gln Lys Asp Tyr Arg Thr Asp Leu Val Phe Gly Thr Asp
            900                 905                 910

Val Thr Cys Trp Phe Val His Asn Ser Gly Lys Gly Phe Ile Asp Gly
        915                 920                 925

His Tyr Lys Asp Tyr Phe Val Pro Gln Leu Tyr Ser Phe Leu Lys Arg
    930                 935                 940

Pro
945

<210> SEQ ID NO 44
<211> LENGTH: 90
<212> TYPE: PRT
<213> ORGANISM: Homo sapiens

<400> SEQUENCE: 44

Met Lys Phe Leu Ala Val Leu Val Leu Leu Gly Val Ser Ile Phe Leu
1               5                   10                  15

Val Ser Ala Gln Asn Pro Thr Thr Ala Ala Pro Ala Asp Thr Tyr Pro
            20                  25                  30

Ala Thr Gly Pro Ala Asp Asp Glu Ala Pro Asp Ala Glu Thr Thr Ala
        35                  40                  45

Ala Ala Thr Thr Ala Thr Thr Ala Ala Pro Thr Thr Ala Thr Thr Ala
    50                  55                  60

Ala Ser Thr Thr Ala Arg Lys Asp Ile Pro Val Leu Pro Lys Trp Val
65                  70                  75                  80

Gly Asp Leu Pro Asn Gly Arg Val Cys Pro
                85                  90

<210> SEQ ID NO 45
<211> LENGTH: 90
<212> TYPE: PRT
<213> ORGANISM: Homo sapiens

<400> SEQUENCE: 45

Met Ala Cys Pro Leu Asp Gln Ala Ile Gly Leu Leu Val Ala Ile Phe
1               5                   10                  15

His Lys Tyr Ser Gly Arg Glu Gly Asp Lys His Thr Leu Ser Lys Lys
            20                  25                  30

Glu Leu Lys Glu Leu Ile Gln Lys Glu Leu Thr Ile Gly Ser Lys Leu
        35                  40                  45

Gln Asp Ala Glu Ile Ala Arg Leu Met Glu Asp Leu Asp Arg Asn Lys
    50                  55                  60

Asp Gln Glu Val Asn Phe Gln Glu Tyr Val Thr Phe Leu Gly Ala Leu
65                  70                  75                  80

Ala Leu Ile Tyr Asn Glu Ala Leu Lys Gly
                85                  90

<210> SEQ ID NO 46
<211> LENGTH: 358

<212> TYPE: PRT
<213> ORGANISM: Homo sapiens

<400> SEQUENCE: 46

```
Met Ser Ala Asp Ala Ala Gly Ala Pro Leu Pro Arg Leu Cys Cys
1               5                   10                  15

Leu Glu Lys Gly Pro Asn Gly Tyr Gly Phe His Leu His Gly Glu Lys
            20                  25                  30

Gly Lys Leu Gly Gln Tyr Ile Arg Leu Val Glu Pro Gly Ser Pro Ala
        35                  40                  45

Glu Lys Ala Gly Leu Leu Ala Gly Asp Arg Leu Val Glu Val Asn Gly
    50                  55                  60

Glu Asn Val Glu Lys Glu Thr His Gln Gln Val Val Ser Arg Ile Arg
65                  70                  75                  80

Ala Ala Leu Asn Ala Val Arg Leu Leu Val Val Asp Pro Glu Thr Asp
                85                  90                  95

Glu Gln Leu Gln Lys Leu Gly Val Gln Val Arg Glu Glu Leu Leu Arg
            100                 105                 110

Ala Gln Glu Ala Pro Gly Gln Ala Glu Pro Pro Ala Ala Ala Glu Val
        115                 120                 125

Gln Gly Ala Gly Asn Glu Asn Glu Pro Arg Glu Ala Asp Lys Ser His
    130                 135                 140

Pro Glu Gln Arg Glu Leu Arg Pro Arg Leu Cys Thr Met Lys Lys Gly
145                 150                 155                 160

Pro Ser Gly Tyr Gly Phe Asn Leu His Ser Asp Lys Ser Lys Pro Gly
                165                 170                 175

Gln Phe Ile Arg Ser Val Asp Pro Asp Ser Pro Ala Glu Ala Ser Gly
            180                 185                 190

Leu Arg Ala Gln Asp Arg Ile Val Glu Val Asn Gly Val Cys Met Glu
        195                 200                 205

Gly Lys Gln His Gly Asp Val Val Ser Ala Ile Arg Ala Gly Gly Asp
    210                 215                 220

Glu Thr Lys Leu Leu Val Val Asp Arg Glu Thr Asp Glu Phe Phe Lys
225                 230                 235                 240

Lys Cys Arg Val Ile Pro Ser Gln Glu His Leu Asn Gly Pro Leu Pro
                245                 250                 255

Val Pro Phe Thr Asn Gly Glu Ile Gln Lys Glu Asn Ser Arg Glu Ala
            260                 265                 270

Leu Ala Glu Ala Ala Leu Glu Ser Pro Arg Pro Ala Leu Val Arg Ser
        275                 280                 285

Ala Ser Ser Asp Thr Ser Glu Glu Leu Asn Ser Gln Asp Ser Pro Pro
    290                 295                 300

Lys Gln Asp Ser Thr Ala Pro Ser Ser Thr Ser Ser Ser Asp Pro Ile
305                 310                 315                 320

Leu Asp Phe Asn Ile Ser Leu Ala Met Ala Lys Glu Arg Ala His Gln
                325                 330                 335

Lys Arg Ser Ser Lys Arg Ala Pro Gln Met Asp Trp Ser Lys Lys Asn
            340                 345                 350

Glu Leu Phe Ser Asn Leu
        355
```

<210> SEQ ID NO 47
<211> LENGTH: 75
<212> TYPE: PRT
<213> ORGANISM: Homo sapiens

<400> SEQUENCE: 47

```
Met Ala Arg Tyr Glu Glu Val Ser Val Ser Gly Phe Glu Glu Phe His
1               5                   10                  15

Arg Ala Val Glu Gln His Asn Gly Lys Thr Ile Phe Ala Tyr Phe Thr
            20                  25                  30

Gly Ser Lys Asp Ala Gly Gly Lys Ser Trp Cys Pro Asp Cys Val Gln
        35                  40                  45

Ala Glu Pro Val Val Arg Gly Leu Lys His Ile Ser Glu Gly Cys
50                  55                  60

Val Phe Ile Tyr Cys Gln Val Gly Glu Lys Pro
65                  70                  75
```

<210> SEQ ID NO 48
<211> LENGTH: 339
<212> TYPE: PRT
<213> ORGANISM: Homo sapiens

<400> SEQUENCE: 48

```
Met Ala Glu Ala Ser Ser Asp Pro Gly Ala Glu Glu Arg Glu Glu Leu
1               5                   10                  15

Leu Gly Pro Thr Ala Gln Trp Ser Val Glu Asp Glu Glu Ala Val
            20                  25                  30

His Glu Gln Cys Gln His Glu Arg Asp Arg Gln Leu Gln Ala Gln Asp
        35                  40                  45

Glu Glu Gly Gly Gly His Val Pro Glu Arg Pro Lys Gln Glu Met Leu
    50                  55                  60

Leu Ser Leu Lys Pro Ser Glu Ala Pro Glu Leu Asp Glu Asp Glu Gly
65                  70                  75                  80

Phe Gly Asp Trp Ser Gln Arg Pro Glu Gln Arg Gln His Glu Gly
                85                  90                  95

Ala Gln Gly Ala Leu Asp Ser Gly Glu Pro Pro Gln Cys Arg Ser Pro
            100                 105                 110

Glu Gly Glu Gln Glu Asp Arg Pro Gly Leu His Ala Tyr Glu Lys Glu
        115                 120                 125

Asp Ser Asp Glu Val His Leu Glu Glu Leu Ser Leu Ser Lys Glu Gly
    130                 135                 140

Pro Gly Pro Glu Asp Thr Val Gln Asp Asn Leu Gly Ala Ala Gly Ala
145                 150                 155                 160

Glu Glu Glu Gln Glu Glu His Gln Lys Cys Gln Gln Pro Arg Thr Pro
                165                 170                 175

Ser Pro Leu Val Leu Glu Gly Thr Ile Glu Gln Ser Ser Pro Pro Leu
            180                 185                 190

Ser Pro Thr Thr Lys Leu Ile Asp Arg Thr Glu Ser Leu Asn Arg Ser
        195                 200                 205

Ile Glu Lys Ser Asn Ser Val Lys Lys Ser Gln Pro Asp Leu Pro Ile
    210                 215                 220

Ser Lys Ile Asp Gln Trp Leu Glu Gln Tyr Thr Gln Ala Ile Glu Thr
225                 230                 235                 240

Ala Gly Arg Thr Pro Lys Leu Ala Arg Gln Ala Ser Ile Glu Leu Pro
                245                 250                 255

Ser Met Ala Val Ala Ser Thr Lys Ser Arg Trp Glu Thr Gly Glu Val
            260                 265                 270

Gln Ala Gln Ser Ala Ala Lys Thr Pro Ser Cys Lys Asp Ile Val Ala
        275                 280                 285
```

-continued

```
Gly Asp Met Ser Lys Lys Ser Leu Trp Glu Gln Lys Gly Gly Ser Lys
            290                 295                 300
Thr Ser Ser Thr Ile Lys Ser Thr Pro Ser Gly Lys Arg Tyr Lys Phe
305                 310                 315                 320
Val Ala Thr Gly His Gly Lys Tyr Glu Lys Val Leu Val Glu Gly Gly
                325                 330                 335
Pro Ala Pro

<210> SEQ ID NO 49
<211> LENGTH: 177
<212> TYPE: PRT
<213> ORGANISM: Homo sapiens

<400> SEQUENCE: 49

Met Asp Leu Thr Thr Thr Met Ser Ser Lys Arg Thr Lys Thr Lys Thr
1               5                   10                  15
Lys Lys Arg Pro Gln Arg Ala Thr Ser Asn Val Phe Ala Met Phe Asp
            20                  25                  30
Gln Ser Gln Ile Gln Glu Phe Lys Glu Ala Phe Asn Met Ile Asp Gln
        35                  40                  45
Asn Arg Asp Gly Phe Ile Asp Lys Glu Asp Leu His Asp Met Leu Ala
    50                  55                  60
Ser Leu Gly Lys Asn Pro Thr Asp Glu Tyr Leu Asp Ala Met Met Asn
65                  70                  75                  80
Glu Ala Pro Gly Pro Ile Asn Phe Thr Met Phe Leu Thr Met Phe Gly
                85                  90                  95
Glu Lys Leu Asn Gly Thr Asp Pro Glu Asp Val Ile Arg Asn Ala Phe
            100                 105                 110
Ala Cys Phe Asp Glu Glu Ala Thr Gly Thr Ile Gln Glu Asp Tyr Leu
        115                 120                 125
Arg Glu Leu Leu Thr Thr Met Gly Asp Arg Phe Thr Asp Glu Glu Val
    130                 135                 140
Asp Glu Leu Tyr Arg Glu Ala Pro Ile Asp Lys Lys Gly Asn Phe Asn
145                 150                 155                 160
Tyr Ile Glu Phe Thr Arg Ile Leu Lys His Gly Ala Lys Asp Lys Asp
                165                 170                 175
Asp

<210> SEQ ID NO 50
<211> LENGTH: 461
<212> TYPE: PRT
<213> ORGANISM: Homo sapiens

<400> SEQUENCE: 50

Met Ser Leu Asp Ile Gln Ser Leu Asp Ile Gln Cys Glu Glu Leu Ser
1               5                   10                  15
Asp Ala Arg Trp Ala Glu Leu Leu Pro Leu Gln Gln Cys Gln Val
            20                  25                  30
Val Arg Leu Asp Asp Cys Gly Leu Thr Glu Ala Arg Cys Lys Asp Ile
        35                  40                  45
Ser Ser Ala Leu Arg Val Asn Pro Ala Leu Ala Glu Leu Asn Leu Arg
    50                  55                  60
Ser Asn Glu Leu Gly Asp Val Gly Val His Cys Val Leu Gln Gly Leu
65                  70                  75                  80
Gln Thr Pro Ser Cys Lys Ile Gln Lys Leu Ser Leu Gln Asn Cys Cys
```

|  |  |  |  |  | 85 |  |  |  | 90 |  |  |  | 95 |  |  |
|---|---|---|---|---|---|---|---|---|---|---|---|---|---|---|---|

Leu Thr Gly Ala Gly Cys Gly Val Leu Ser Ser Thr Leu Arg Thr Leu
              100                    105                  110

Pro Thr Leu Gln Glu Leu His Leu Ser Asp Asn Leu Leu Gly Asp Ala
     115                       120                  125

Gly Leu Gln Leu Leu Cys Glu Gly Leu Leu Asp Pro Gln Cys Arg Leu
130                    135                    140

Glu Lys Leu Gln Leu Glu Tyr Cys Ser Leu Ser Ala Ala Ser Cys Glu
145                  150                  155                  160

Pro Leu Ala Ser Val Leu Arg Ala Lys Pro Asp Phe Lys Glu Leu Thr
               165                  170                  175

Val Ser Asn Asn Asp Ile Asn Glu Ala Gly Val Arg Val Leu Cys Gln
         180                    185                  190

Gly Leu Lys Asp Ser Pro Cys Gln Leu Glu Ala Leu Lys Leu Glu Ser
             195                  200                  205

Cys Gly Val Thr Ser Asp Asn Cys Arg Asp Leu Cys Gly Ile Val Ala
210                    215                    220

Ser Lys Ala Ser Leu Arg Glu Leu Ala Leu Gly Ser Asn Lys Leu Gly
225                  230                  235                  240

Asp Val Gly Met Ala Glu Leu Cys Pro Gly Leu Leu His Pro Ser Ser
               245                  250                  255

Arg Leu Arg Thr Leu Trp Ile Trp Glu Cys Gly Ile Thr Ala Lys Gly
         260                    265                  270

Cys Gly Asp Leu Cys Arg Val Leu Arg Ala Lys Glu Ser Leu Lys Glu
             275                  280                  285

Leu Ser Leu Ala Gly Asn Glu Leu Gly Asp Glu Gly Ala Arg Leu Leu
290                    295                    300

Cys Glu Thr Leu Leu Glu Pro Gly Cys Gln Leu Glu Ser Leu Trp Val
305                  310                  315                  320

Lys Ser Cys Ser Phe Thr Ala Ala Cys Cys Ser His Phe Ser Ser Val
               325                  330                  335

Leu Ala Gln Asn Arg Phe Leu Leu Glu Leu Gln Ile Ser Asn Asn Arg
         340                    345                  350

Leu Glu Asp Ala Gly Val Arg Glu Leu Cys Gln Gly Leu Gly Gln Pro
             355                  360                  365

Gly Ser Val Leu Arg Val Leu Trp Leu Ala Asp Cys Asp Val Ser Asp
     370                      375                  380

Ser Ser Cys Ser Ser Leu Ala Ala Thr Leu Leu Ala Asn His Ser Leu
385                    390                  395                  400

Arg Glu Leu Asp Leu Ser Asn Asn Cys Leu Gly Asp Ala Gly Ile Leu
             405                  410                  415

Gln Leu Val Glu Ser Val Arg Gln Pro Gly Cys Leu Leu Glu Gln Leu
               420                  425                  430

Val Leu Tyr Asp Ile Tyr Trp Ser Glu Glu Met Glu Asp Arg Leu Gln
         435                    440                  445

Ala Leu Glu Lys Asp Lys Pro Ser Leu Arg Val Ile Ser
450                    455                  460

<210> SEQ ID NO 51
<211> LENGTH: 434
<212> TYPE: PRT
<213> ORGANISM: Homo sapiens

<400> SEQUENCE: 51

```
Met Ser Ile Leu Lys Ile His Ala Arg Glu Ile Phe Asp Ser Arg Gly
1               5                   10                  15

Asn Pro Thr Val Glu Val Asp Leu Phe Thr Ser Lys Gly Leu Phe Arg
                20                  25                  30

Ala Ala Val Pro Ser Gly Ala Ser Thr Gly Ile Tyr Glu Ala Leu Glu
            35                  40                  45

Leu Arg Asp Asn Asp Lys Thr Arg Tyr Met Gly Lys Gly Val Ser Lys
    50                  55                  60

Ala Val Glu His Ile Asn Lys Thr Ile Ala Pro Ala Leu Val Ser Lys
65                  70                  75                  80

Lys Leu Asn Val Thr Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
        115                 120                 125

Pro Leu Tyr Arg His Ile Ala Asp Leu Ala Gly Asn Ser Glu Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ala
                165                 170                 175

Asn Phe Arg Glu Ala Met Arg Ile Gly Ala Glu Val Tyr His Asn Leu
            180                 185                 190

Lys Asn Val Ile Lys Glu Lys Tyr Gly Lys Asp Ala Thr Asn Val Gly
        195                 200                 205

Asp Glu Gly Gly Phe Ala Pro Asn Ile Leu Glu Asn Lys Glu Gly Leu
    210                 215                 220

Glu Leu Leu Lys Thr Ala Ile Gly Lys Ala Gly Tyr Thr Asp Lys Val
225                 230                 235                 240

Val Ile Gly Met Asp Val Ala Ala Ser Glu Phe Phe Arg Ser Gly Lys
                245                 250                 255

Tyr Asp Leu Asp Phe Lys Ser Pro Asp Asp Pro Ser Arg Tyr Ile Ser
            260                 265                 270

Pro Asp Gln Leu Ala Asp Leu Tyr Lys Ser Phe Ile Lys Asp Tyr Pro
        275                 280                 285

Val Val Ser Ile Glu Asp Pro Phe Asp Gln Asp Asp Trp Gly Ala Trp
    290                 295                 300

Gln Lys Phe Thr Ala Ser Ala Gly Ile Gln Val Val Gly Asp Asp Leu
305                 310                 315                 320

Thr Val Thr Asn Pro Lys Arg Ile Ala Lys Ala Val Asn Glu Lys Ser
                325                 330                 335

Cys Asn Cys Leu Leu Leu Lys Val Asn Gln Ile Gly Ser Val Thr Glu
            340                 345                 350

Ser Leu Gln Ala Cys Lys Leu Ala Gln Ala Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Leu Arg Ile Glu Glu Glu
                405                 410                 415

Leu Gly Ser Lys Ala Lys Phe Ala Gly Arg Asn Phe Arg Asn Pro Leu
```

<210> SEQ ID NO 52
<211> LENGTH: 108
<212> TYPE: PRT
<213> ORGANISM: Homo sapiens

<400> SEQUENCE: 52

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Thr Trp
            20                  25                  30

Leu Ala Trp Tyr Gln Gln Lys Pro Gly Lys Ala Pro Lys Leu Leu Met
        35                  40                  45

Tyr Lys Ala Ser Ser Leu Glu Ser Gly Val Pro Ser Arg Phe Ile Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Asp Ser Lys
                85                  90                  95

Met Phe Gly Gln Gly Thr Lys Val Glu Val Lys Gly
            100                 105
```

<210> SEQ ID NO 53
<211> LENGTH: 386
<212> TYPE: PRT
<213> ORGANISM: Homo sapiens

<400> SEQUENCE: 53

```
Met Phe Ala Glu Ile Gln Ile Gln Asp Lys Asp Arg Met Gly Thr Ala
1               5                   10                  15

Gly Lys Val Ile Lys Cys Lys Ala Ala Val Leu Trp Glu Gln Lys Gln
            20                  25                  30

Pro Phe Ser Ile Glu Glu Ile Glu Val Ala Pro Pro Lys Thr Lys Glu
        35                  40                  45

Val Arg Ile Lys Ile Leu Ala Thr Gly Ile Cys Arg Thr Asp Asp His
50                  55                  60

Val Ile Lys Gly Thr Met Val Ser Lys Phe Pro Val Ile Val Gly His
65                  70                  75                  80

Glu Ala Thr Gly Ile Val Glu Ser Ile Gly Glu Gly Val Thr Thr Val
                85                  90                  95

Lys Pro Gly Asp Lys Val Ile Pro Leu Phe Leu Pro Gln Cys Arg Glu
            100                 105                 110

Cys Asn Ala Cys Arg Asn Pro Asp Gly Asn Leu Cys Ile Arg Ser Asp
        115                 120                 125

Ile Thr Gly Arg Gly Val Leu Ala Asp Gly Thr Thr Arg Phe Thr Cys
130                 135                 140

Lys Gly Lys Pro Val His His Phe Met Asn Thr Ser Thr Phe Thr Glu
145                 150                 155                 160

Tyr Thr Val Val Asp Glu Ser Ser Val Ala Lys Ile Asp Asp Ala Ala
                165                 170                 175

Pro Pro Glu Lys Val Cys Leu Ile Gly Cys Gly Phe Ser Thr Gly Tyr
            180                 185                 190

Gly Ala Ala Val Lys Thr Gly Lys Val Lys Pro Gly Ser Thr Cys Val
        195                 200                 205
```

Val Phe Gly Leu Gly Gly Val Gly Leu Ser Val Ile Met Gly Cys Lys
210                 215                 220

Ser Ala Gly Ala Ser Arg Ile Ile Gly Ile Asp Leu Asn Lys Asp Lys
225                 230                 235                 240

Phe Glu Lys Ala Met Ala Val Gly Ala Thr Glu Cys Ile Ser Pro Lys
                245                 250                 255

Asp Ser Thr Lys Pro Ile Ser Glu Val Leu Ser Glu Met Thr Gly Asn
                260                 265                 270

Asn Val Gly Tyr Thr Phe Glu Val Ile Gly His Leu Glu Thr Met Ile
            275                 280                 285

Asp Ala Leu Ala Ser Cys His Met Asn Tyr Gly Thr Ser Val Val Val
290                 295                 300

Gly Val Pro Pro Ser Ala Lys Met Leu Thr Tyr Asp Pro Met Leu Leu
305                 310                 315                 320

Phe Thr Gly Arg Thr Trp Lys Gly Cys Val Phe Gly Gly Leu Lys Ser
                325                 330                 335

Arg Asp Asp Val Pro Lys Leu Val Thr Glu Phe Leu Ala Lys Lys Phe
                340                 345                 350

Asp Leu Asp Gln Leu Ile Thr His Val Leu Pro Phe Lys Lys Ile Ser
            355                 360                 365

Glu Gly Phe Glu Leu Leu Asn Ser Gly Gln Ser Ile Arg Thr Val Leu
370                 375                 380

Thr Phe
385

<210> SEQ ID NO 54
<211> LENGTH: 352
<212> TYPE: PRT
<213> ORGANISM: Homo sapiens

<400> SEQUENCE: 54

Met Arg Ser Leu Gly Ala Leu Leu Leu Leu Leu Ser Ala Cys Leu Ala
1               5                   10                  15

Val Ser Ala Gly Pro Val Pro Thr Pro Pro Asp Asn Ile Gln Val Gln
            20                  25                  30

Glu Asn Phe Asn Ile Ser Arg Ile Tyr Gly Lys Trp Tyr Asn Leu Ala
        35                  40                  45

Ile Gly Ser Thr Cys Pro Trp Leu Lys Lys Ile Met Asp Arg Met Thr
50                  55                  60

Val Ser Thr Leu Val Leu Gly Glu Gly Ala Thr Glu Ala Glu Ile Ser
65                  70                  75                  80

Met Thr Ser Thr Arg Trp Arg Lys Gly Val Cys Glu Glu Thr Ser Gly
                85                  90                  95

Ala Tyr Glu Lys Thr Asp Thr Asp Gly Lys Phe Leu Tyr His Lys Ser
            100                 105                 110

Lys Trp Asn Ile Thr Met Glu Ser Tyr Val Val His Thr Asn Tyr Asp
        115                 120                 125

Glu Tyr Ala Ile Phe Leu Thr Lys Lys Phe Ser Arg His His Gly Pro
130                 135                 140

Thr Ile Thr Ala Lys Leu Tyr Gly Arg Ala Pro Gln Leu Arg Glu Thr
145                 150                 155                 160

Leu Leu Gln Asp Phe Arg Val Val Ala Gln Gly Val Gly Ile Pro Glu
                165                 170                 175

Asp Ser Ile Phe Thr Met Ala Asp Arg Gly Glu Cys Val Pro Gly Glu

```
            180             185             190
Gln Glu Pro Glu Pro Ile Leu Ile Pro Arg Val Arg Arg Ala Val Leu
            195                 200                 205

Pro Gln Glu Glu Glu Gly Ser Gly Gly Gly Gln Leu Val Thr Glu Val
        210                 215                 220

Thr Lys Lys Glu Asp Ser Cys Gln Leu Gly Tyr Ser Ala Gly Pro Cys
225                 230                 235                 240

Met Gly Met Thr Ser Arg Tyr Phe Tyr Asn Gly Thr Ser Met Ala Cys
                245                 250                 255

Glu Thr Phe Gln Tyr Gly Gly Cys Met Gly Asn Gly Asn Asn Phe Val
            260                 265                 270

Thr Glu Lys Glu Cys Leu Gln Thr Cys Arg Thr Val Ala Ala Cys Asn
        275                 280                 285

Leu Pro Ile Val Arg Gly Pro Cys Arg Ala Phe Ile Gln Leu Trp Ala
            290                 295                 300

Phe Asp Ala Val Lys Gly Lys Cys Val Leu Phe Pro Tyr Gly Gly Cys
305                 310                 315                 320

Gln Gly Asn Gly Asn Lys Phe Tyr Ser Glu Lys Glu Cys Arg Glu Tyr
                325                 330                 335

Cys Gly Val Pro Gly Asp Gly Asp Glu Glu Leu Arg Phe Ser Asn
            340                 345                 350

<210> SEQ ID NO 55
<211> LENGTH: 485
<212> TYPE: PRT
<213> ORGANISM: Homo sapiens

<400> SEQUENCE: 55

Met Arg Lys Arg Ala Pro Gln Ser Glu Met Ala Pro Ala Gly Val Ser
1               5                   10                  15

Leu Arg Ala Thr Ile Leu Cys Leu Leu Ala Trp Ala Gly Leu Ala Ala
            20                  25                  30

Gly Asp Arg Val Tyr Ile His Pro Phe His Leu Val Ile His Asn Glu
        35                  40                  45

Ser Thr Cys Glu Gln Leu Ala Lys Ala Asn Ala Gly Lys Pro Lys Asp
    50                  55                  60

Pro Thr Phe Ile Pro Ala Pro Ile Gln Ala Lys Thr Ser Pro Val Asp
65                  70                  75                  80

Glu Lys Ala Leu Gln Asp Gln Leu Val Leu Val Ala Ala Lys Leu Asp
                85                  90                  95

Thr Glu Asp Lys Leu Arg Ala Ala Met Val Gly Met Leu Ala Asn Phe
            100                 105                 110

Leu Gly Phe Arg Ile Tyr Gly Met His Ser Glu Leu Trp Gly Val Val
        115                 120                 125

His Gly Ala Thr Val Leu Ser Pro Thr Ala Val Phe Gly Thr Leu Ala
    130                 135                 140

Ser Leu Tyr Leu Gly Ala Leu Asp His Thr Ala Asp Arg Leu Gln Ala
145                 150                 155                 160

Ile Leu Gly Val Pro Trp Lys Asp Lys Asn Cys Thr Ser Arg Leu Asp
                165                 170                 175

Ala His Lys Val Leu Ser Ala Leu Gln Ala Val Gln Gly Leu Leu Val
            180                 185                 190

Ala Gln Gly Arg Ala Asp Ser Gln Ala Gln Leu Leu Leu Ser Thr Val
        195                 200                 205
```

-continued

Val Gly Val Phe Thr Ala Pro Gly Leu His Leu Lys Gln Pro Phe Val
    210                 215                 220

Gln Gly Leu Ala Leu Tyr Thr Pro Val Val Leu Pro Arg Ser Leu Asp
225                 230                 235                 240

Phe Thr Glu Leu Asp Val Ala Ala Glu Lys Ile Asp Arg Phe Met Gln
                245                 250                 255

Ala Val Thr Gly Trp Lys Thr Gly Cys Ser Leu Met Gly Ala Ser Val
            260                 265                 270

Asp Ser Thr Leu Ala Phe Asn Thr Tyr Val His Phe Gln Gly Lys Met
        275                 280                 285

Lys Gly Phe Ser Leu Leu Ala Glu Pro Gln Glu Phe Trp Val Asp Asn
    290                 295                 300

Ser Thr Ser Val Ser Val Pro Met Leu Ser Gly Met Gly Thr Phe Gln
305                 310                 315                 320

His Trp Ser Asp Ile Gln Asp Asn Phe Ser Val Thr Gln Val Pro Phe
                325                 330                 335

Thr Glu Ser Ala Cys Leu Leu Leu Ile Gln Pro His Tyr Ala Ser Asp
            340                 345                 350

Leu Asp Lys Val Glu Gly Leu Thr Phe Gln Gln Asn Ser Leu Asn Trp
        355                 360                 365

Met Lys Lys Leu Ser Pro Arg Thr Ile His Leu Thr Met Pro Gln Leu
    370                 375                 380

Val Leu Gln Gly Ser Tyr Asp Leu Gln Asp Leu Leu Ala Gln Ala Glu
385                 390                 395                 400

Leu Pro Ala Ile Leu His Thr Glu Leu Asn Leu Gln Lys Leu Ser Asn
                405                 410                 415

Asp Arg Ile Arg Val Gly Glu Val Leu Asn Ser Ile Phe Phe Glu Leu
            420                 425                 430

Glu Ala Asp Glu Arg Glu Pro Thr Glu Ser Thr Gln Gln Leu Asn Lys
        435                 440                 445

Pro Glu Val Leu Glu Val Thr Leu Asn Arg Pro Phe Leu Phe Ala Val
    450                 455                 460

Tyr Asp Gln Ser Ala Thr Ala Leu His Phe Leu Gly Arg Val Ala Asn
465                 470                 475                 480

Pro Leu Ser Thr Ala
                485

<210> SEQ ID NO 56
<211> LENGTH: 464
<212> TYPE: PRT
<213> ORGANISM: Homo sapiens

<400> SEQUENCE: 56

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
                100                 105                 110

Leu Ser Ile Ser Thr Ala Phe Ala Met Thr Lys Leu Gly Ala Cys Asn
            115                 120                 125

Asp Thr Leu Gln Gln Leu Met Glu Val Phe Lys Phe Asp Thr Ile Ser
        130                 135                 140

Glu Lys Thr Ser Asp Gln Ile His Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
            340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
    370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Arg Ser Leu Asn Pro Asn Arg Val
            420                 425                 430

Thr Phe Lys Ala Asn Arg Pro Phe Leu Val Phe Ile Arg Glu Val Pro
        435                 440                 445

Leu Asn Thr Ile Ile Phe Met Gly Arg Val Ala Asn Pro Cys Val Lys
    450                 455                 460

<210> SEQ ID NO 57
<211> LENGTH: 100
<212> TYPE: PRT
<213> ORGANISM: Homo sapiens

<400> SEQUENCE: 57

Met Lys Leu Leu Ala Ala Thr Val Leu Leu Leu Thr Ile Cys Ser Leu

```
  1               5                  10                 15
Glu Gly Ala Leu Val Arg Arg Gln Ala Lys Glu Pro Cys Val Glu Ser
                 20                 25                 30

Leu Val Ser Gln Tyr Phe Gln Thr Val Thr Asp Tyr Gly Lys Asp Leu
                 35                 40                 45

Met Glu Lys Val Lys Ser Pro Glu Leu Gln Ala Glu Ala Lys Ser Tyr
         50                 55                 60

Phe Glu Lys Ser Lys Glu Gln Leu Thr Pro Leu Ile Lys Lys Ala Gly
 65                 70                 75                 80

Thr Glu Leu Val Asn Phe Leu Ser Tyr Phe Val Glu Leu Gly Thr Gln
                 85                 90                 95

Pro Ala Thr Gln
            100
```

<210> SEQ ID NO 58
<211> LENGTH: 345
<212> TYPE: PRT
<213> ORGANISM: Homo sapiens

<400> SEQUENCE: 58

```
Met Ile Ser Pro Val Leu Ile Leu Phe Ser Ser Phe Leu Cys His Val
 1               5                  10                 15

Ala Ile Ala Gly Arg Thr Cys Pro Lys Pro Asp Asp Leu Pro Phe Ser
                 20                 25                 30

Thr Val Val Pro Leu Lys Thr Phe Tyr Glu Pro Gly Glu Glu Ile Thr
                 35                 40                 45

Tyr Ser Cys Lys Pro Gly Tyr Val Ser Arg Gly Gly Met Arg Lys Phe
         50                 55                 60

Ile Cys Pro Leu Thr Gly Leu Trp Pro Ile Asn Thr Leu Lys Cys Thr
 65                 70                 75                 80

Pro Arg Val Cys Pro Phe Ala Gly Ile Leu Glu Asn Gly Ala Val Arg
                 85                 90                 95

Tyr Thr Thr Phe Glu Tyr Pro Asn Thr Ile Ser Phe Ser Cys Asn Thr
                100                105                110

Gly Phe Tyr Leu Asn Gly Ala Asp Ser Ala Lys Cys Thr Glu Glu Gly
                115                120                125

Lys Trp Ser Pro Glu Leu Pro Val Cys Ala Pro Ile Ile Cys Pro Pro
        130                135                140

Pro Ser Ile Pro Thr Phe Ala Thr Leu Arg Val Tyr Lys Pro Ser Ala
145                150                155                160

Gly Asn Asn Ser Leu Tyr Arg Asp Thr Ala Val Phe Glu Cys Leu Pro
                165                170                175

Gln His Ala Met Phe Gly Asn Asp Thr Ile Thr Cys Thr Thr His Gly
                180                185                190

Asn Trp Thr Lys Leu Pro Glu Cys Arg Glu Val Lys Cys Pro Phe Pro
                195                200                205

Ser Arg Pro Asp Asn Gly Phe Val Asn Tyr Pro Ala Lys Pro Thr Leu
        210                215                220

Tyr Tyr Lys Asp Lys Ala Thr Phe Gly Cys His Asp Gly Tyr Ser Leu
225                230                235                240

Asp Gly Pro Glu Glu Ile Glu Cys Thr Lys Leu Gly Asn Trp Ser Ala
                245                250                255

Met Pro Ser Cys Lys Ala Ser Cys Lys Val Pro Val Lys Lys Ala Thr
                260                265                270
```

Val Val Tyr Gln Gly Glu Arg Val Lys Ile Gln Glu Lys Phe Lys Asn
        275                 280                 285

Gly Met Leu His Gly Asp Lys Val Ser Phe Phe Cys Lys Asn Lys Glu
        290                 295                 300

Lys Lys Cys Ser Tyr Thr Glu Asp Ala Gln Cys Ile Asp Gly Thr Ile
305                 310                 315                 320

Glu Val Pro Lys Cys Phe Lys Glu His Ser Ser Leu Ala Phe Trp Lys
            325                 330                 335

Thr Asp Ala Ser Asp Val Lys Pro Cys
            340                 345

<210> SEQ ID NO 59
<211> LENGTH: 694
<212> TYPE: PRT
<213> ORGANISM: Homo sapiens

<400> SEQUENCE: 59

Met Glu Gly Pro His Leu Pro Asn Lys Lys His Lys Lys Gln Ala
1               5                   10                  15

Val Lys Thr Glu Pro Glu Lys Lys Ser Gln Ser Thr Lys Leu Ser Val
            20                  25                  30

Val His Glu Lys Lys Ser Gln Glu Gly Lys Pro Lys Glu His Thr Glu
        35                  40                  45

Pro Lys Ser Leu Pro Lys Gln Ala Ser Asp Thr Gly Ser Asn Asp Ala
    50                  55                  60

His Asn Lys Lys Ala Val Ser Arg Ser Ala Glu Gln Gln Pro Ser Glu
65                  70                  75                  80

Lys Ser Thr Glu Pro Lys Thr Lys Pro Gln Asp Met Ile Ser Ala Gly
                85                  90                  95

Gly Glu Ser Val Ala Gly Ile Thr Ala Ile Ser Gly Lys Pro Gly Asp
            100                 105                 110

Lys Lys Lys Glu Lys Lys Ser Leu Thr Pro Ala Val Pro Val Glu Ser
        115                 120                 125

Lys Pro Asp Lys Pro Ser Gly Lys Ser Gly Met Asp Ala Ala Leu Asp
    130                 135                 140

Asp Leu Ile Asp Thr Leu Gly Gly Pro Glu Glu Thr Glu Glu Glu Asn
145                 150                 155                 160

Thr Thr Tyr Thr Gly Pro Glu Val Ser Asp Pro Met Ser Ser Thr Tyr
                165                 170                 175

Ile Glu Glu Leu Gly Lys Arg Glu Val Thr Ile Pro Pro Lys Tyr Arg
            180                 185                 190

Glu Leu Leu Ala Lys Lys Glu Gly Ile Thr Gly Pro Ala Asp Ser
        195                 200                 205

Ser Lys Pro Ile Gly Pro Asp Asp Ala Ile Asp Ala Leu Ser Ser Asp
    210                 215                 220

Phe Thr Cys Gly Ser Pro Thr Ala Ala Gly Lys Lys Thr Glu Lys Glu
225                 230                 235                 240

Glu Ser Thr Glu Val Leu Lys Ala Gln Ser Ala Gly Thr Val Arg Ser
                245                 250                 255

Ala Ala Pro Pro Gln Glu Lys Lys Arg Lys Val Glu Lys Asp Thr Met
            260                 265                 270

Ser Asp Gln Ala Leu Glu Ala Leu Ser Ala Ser Leu Gly Thr Arg Gln
        275                 280                 285

Ala Glu Pro Glu Leu Asp Leu Arg Ser Ile Lys Glu Val Asp Glu Ala
    290                 295                 300

Lys Ala Lys Glu Glu Lys Leu Glu Lys Cys Gly Asp Asp Glu Thr
305                 310                 315                 320

Ile Pro Ser Glu Tyr Arg Leu Lys Pro Ala Thr Asp Lys Asp Gly Lys
            325                 330                 335

Pro Leu Leu Pro Glu Pro Glu Leu Lys Pro Lys Pro Arg Ser Glu Ser
            340                 345                 350

Glu Leu Ile Asp Glu Leu Ser Glu Asp Phe Asp Arg Ser Glu Cys Lys
            355                 360                 365

Glu Lys Pro Ser Lys Pro Thr Glu Lys Thr Glu Ser Lys Ala Ala
370                 375                 380

Ala Pro Ala Pro Val Ser Glu Ala Val Cys Arg Thr Ser Met Cys Ser
385                 390                 395                 400

Ile Gln Ser Ala Pro Pro Glu Pro Ala Thr Leu Lys Gly Thr Val Pro
            405                 410                 415

Asp Asp Ala Val Glu Ala Leu Ala Asp Ser Leu Gly Lys Lys Glu Ala
            420                 425                 430

Asp Pro Glu Asp Gly Lys Pro Val Met Asp Lys Val Lys Glu Lys Ala
            435                 440                 445

Lys Glu Glu Asp Arg Glu Lys Leu Gly Glu Lys Glu Thr Ile Pro
450                 455                 460

Pro Asp Tyr Arg Leu Glu Glu Val Lys Asp Lys Asp Gly Lys Pro Leu
465                 470                 475                 480

Leu Pro Lys Glu Ser Lys Glu Gln Leu Pro Pro Met Ser Glu Asp Phe
            485                 490                 495

Leu Leu Asp Ala Leu Ser Glu Asp Phe Ser Gly Pro Gln Asn Ala Ser
            500                 505                 510

Ser Leu Lys Phe Glu Asp Ala Lys Leu Ala Ala Ala Ile Ser Glu Val
            515                 520                 525

Val Ser Gln Thr Pro Ala Ser Thr Thr Gln Ala Gly Ala Pro Pro Arg
530                 535                 540

Asp Thr Ser Gln Ser Asp Lys Asp Leu Asp Asp Ala Leu Asp Lys Leu
545                 550                 555                 560

Ser Asp Ser Leu Gly Gln Arg Gln Pro Asp Pro Asp Glu Asn Lys Pro
            565                 570                 575

Met Glu Asp Lys Val Lys Glu Lys Ala Lys Ala Glu His Arg Asp Lys
            580                 585                 590

Leu Gly Glu Arg Asp Asp Thr Ile Pro Pro Glu Tyr Arg His Leu Leu
            595                 600                 605

Asp Asp Asn Gly Gln Asp Lys Pro Val Lys Pro Thr Lys Lys Ser
610                 615                 620

Glu Asp Ser Lys Lys Pro Ala Asp Asp Gln Asp Pro Ile Asp Ala Leu
625                 630                 635                 640

Ser Gly Asp Leu Asp Ser Cys Pro Ser Thr Thr Glu Thr Ser Gln Asn
            645                 650                 655

Thr Ala Lys Asp Lys Cys Lys Lys Ala Ala Ser Ser Lys Ala Pro
            660                 665                 670

Lys Asn Gly Gly Lys Ala Lys Asp Ser Ala Lys Thr Thr Glu Glu Thr
            675                 680                 685

Ser Lys Pro Lys Asp Asp
    690

<210> SEQ ID NO 60
<211> LENGTH: 227

```
<212> TYPE: PRT
<213> ORGANISM: Homo sapiens

<400> SEQUENCE: 60

Met Gly Gly Lys Leu Ser Lys Lys Lys Gly Tyr Asn Val Asn Asp
1               5                   10                  15

Glu Lys Ala Lys Glu Lys Asp Lys Lys Ala Glu Gly Ala Ala Thr Glu
                20                  25                  30

Glu Glu Gly Thr Pro Lys Glu Ser Glu Pro Gln Ala Ala Ala Glu Pro
            35                  40                  45

Ala Glu Ala Lys Glu Gly Lys Glu Lys Pro Asp Gln Asp Ala Glu Gly
        50                  55                  60

Lys Ala Glu Glu Lys Glu Gly Glu Lys Asp Ala Ala Ala Lys Glu
65                  70                  75                  80

Glu Ala Pro Lys Ala Glu Pro Glu Lys Thr Glu Gly Ala Ala Glu Ala
                85                  90                  95

Lys Ala Glu Pro Pro Lys Ala Pro Glu Gln Glu Gln Ala Ala Pro Gly
                100                 105                 110

Pro Ala Ala Gly Gly Glu Ala Pro Lys Ala Ala Glu Ala Ala Ala Ala
            115                 120                 125

Pro Ala Glu Ser Ala Ala Pro Ala Ala Gly Glu Glu Pro Ser Lys Glu
        130                 135                 140

Glu Gly Glu Pro Lys Lys Thr Glu Ala Pro Ala Ala Pro Ala Ala Gln
145                 150                 155                 160

Glu Thr Lys Ser Asp Gly Ala Pro Ala Ser Asp Ser Lys Pro Gly Ser
                165                 170                 175

Ser Glu Ala Ala Pro Ser Ser Lys Glu Thr Pro Ala Ala Thr Glu Ala
                180                 185                 190

Pro Ser Ser Thr Pro Lys Ala Gln Gly Pro Ala Ala Ser Ala Glu Glu
            195                 200                 205

Pro Lys Pro Val Glu Ala Pro Ala Ala Asn Ser Asp Gln Thr Val Thr
        210                 215                 220

Val Lys Glu
225

<210> SEQ ID NO 61
<211> LENGTH: 368
<212> TYPE: PRT
<213> ORGANISM: Homo sapiens

<400> SEQUENCE: 61

Met Lys Ser Leu Val Leu Leu Leu Cys Leu Ala Gln Leu Trp Gly Cys
1               5                   10                  15

His Ser Ala Pro His Gly Pro Gly Leu Ile Tyr Arg Gln Pro Asn Cys
                20                  25                  30

Asp Asp Pro Glu Thr Glu Glu Ala Ala Leu Val Ala Ile Asp Tyr Ile
            35                  40                  45

Asn Gln Asn Leu Pro Trp Gly Tyr Lys His Thr Leu Asn Gln Ile Asp
        50                  55                  60

Glu Val Lys Val Trp Pro Gln Gln Pro Ser Gly Glu Leu Phe Glu Ile
65                  70                  75                  80

Glu Ile Asp Thr Leu Glu Thr Thr Cys His Val Leu Asp Pro Thr Pro
                85                  90                  95

Val Ala Arg Cys Ser Val Arg Gln Leu Lys Glu His Ala Val Glu Gly
                100                 105                 110
```

Asp Cys Asp Phe Gln Leu Leu Lys Leu Asp Gly Lys Phe Ser Val Val
            115                 120                 125

Tyr Ala Lys Cys Asp Ser Ser Pro Ala Asp Ser Ala Glu Asp Val Arg
130                 135                 140

Lys Val Cys Gln Asp Cys Pro Leu Leu Ala Pro Leu Asn Asp Thr Arg
145                 150                 155                 160

Val Val His Ala Ala Lys Ala Ala Leu Ala Ala Phe Asn Ala Gln Asn
                165                 170                 175

Asn Gly Ser Asn Phe Gln Leu Glu Glu Ile Ser Arg Ala Gln Leu Val
            180                 185                 190

Pro Leu Pro Pro Ser Thr Tyr Val Glu Phe Thr Val Ser Gly Thr Asp
        195                 200                 205

Cys Val Ala Lys Glu Ala Thr Glu Ala Ala Lys Cys Asn Leu Leu Ala
    210                 215                 220

Glu Lys Gln Tyr Gly Phe Cys Lys Ala Thr Leu Ser Glu Lys Leu Gly
225                 230                 235                 240

Gly Ala Glu Val Ala Val Thr Cys Met Val Phe Gln Thr Gln Pro Val
                245                 250                 255

Ser Ser Gln Pro Gln Pro Glu Gly Ala Asn Glu Ala Val Pro Thr Pro
            260                 265                 270

Val Val Asp Pro Asp Ala Pro Pro Ser Pro Pro Leu Gly Ala Pro Gly
        275                 280                 285

Leu Pro Pro Ala Gly Ser Pro Pro Asp Ser His Val Leu Leu Ala Ala
    290                 295                 300

Pro Pro Gly His Gln Leu His Arg Ala His Tyr Asp Leu Arg His Thr
305                 310                 315                 320

Phe Met Gly Val Val Ser Leu Gly Ser Pro Ser Gly Glu Val Ser His
                325                 330                 335

Pro Arg Lys Thr Arg Thr Val Val Gln Pro Ser Val Gly Ala Ala Ala
            340                 345                 350

Gly Pro Val Val Pro Pro Cys Pro Gly Arg Ile Arg His Phe Lys Val
        355                 360                 365

<210> SEQ ID NO 62
<211> LENGTH: 417
<212> TYPE: PRT
<213> ORGANISM: Homo sapiens

<400> SEQUENCE: 62

Met Leu Leu Ser Val Pro Leu Leu Leu Gly Leu Leu Gly Leu Ala Val
1               5                   10                  15

Ala Glu Pro Ala Val Tyr Phe Lys Glu Gln Phe Leu Asp Gly Asp Gly
            20                  25                  30

Trp Thr Ser Arg Trp Ile Glu Ser Lys His Lys Ser Asp Phe Gly Lys
        35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Asn Ser Leu Asp Gln Thr Asp Met His Gly Asp Ser Glu Tyr
        115                 120                 125

Asn Ile Met Phe Gly Pro Asp Ile Cys Gly Pro Gly Thr Lys Lys Val
            130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Glu Ala Glu Asp
370                 375                 380

Lys Glu Asp Asp Glu Asp Lys Asp Glu Asp Glu Glu Asp Glu Glu Asp
385                 390                 395                 400

Lys Glu Glu Asp Glu Glu Glu Asp Val Pro Gly Gln Ala Lys Asp Glu
                405                 410                 415

Leu

<210> SEQ ID NO 63
<211> LENGTH: 714
<212> TYPE: PRT
<213> ORGANISM: Homo sapiens

<400> SEQUENCE: 63

Met Ser Glu Glu Ile Ile Thr Pro Val Tyr Cys Thr Gly Val Ser Ala
1               5                   10                  15

Gln Val Gln Lys Gln Arg Ala Arg Glu Leu Gly Leu Gly Arg His Glu
            20                  25                  30

Asn Ala Ile Lys Tyr Leu Gly Gln Asp Tyr Glu Gln Leu Arg Val Arg
        35                  40                  45

Cys Leu Gln Ser Gly Thr Leu Phe Arg Asp Glu Ala Phe Pro Pro Val
    50                  55                  60

Pro Gln Ser Leu Gly Tyr Lys Asp Leu Gly Pro Asn Ser Ser Lys Thr
65                  70                  75                  80

```
Tyr Gly Ile Lys Trp Lys Arg Pro Thr Glu Leu Leu Ser Asn Pro Gln
            85                  90                  95

Phe Ile Val Asp Gly Ala Thr Arg Thr Asp Ile Cys Gln Gly Ala Leu
            100                 105                 110

Gly Asp Cys Trp Leu Leu Ala Ala Ile Ala Ser Leu Thr Leu Asn Asp
            115                 120                 125

Thr Leu Leu His Arg Val Val Pro His Gly Gln Ser Phe Gln Asn Gly
            130                 135                 140

Tyr Ala Gly Ile Phe His Phe Gln Leu Trp Gln Phe Gly Glu Trp Val
145                 150                 155                 160

Asp Val Val Val Asp Asp Leu Leu Pro Ile Lys Asp Gly Lys Leu Val
            165                 170                 175

Phe Val His Ser Ala Glu Gly Asn Glu Phe Trp Ser Ala Leu Leu Glu
            180                 185                 190

Lys Ala Tyr Ala Lys Val Asn Gly Ser Tyr Glu Ala Leu Ser Gly Gly
            195                 200                 205

Ser Thr Ser Glu Gly Phe Glu Asp Phe Thr Gly Gly Val Thr Glu Trp
    210                 215                 220

Tyr Glu Leu Arg Lys Ala Pro Ser Asp Leu Tyr Gln Ile Ile Leu Lys
225                 230                 235                 240

Ala Leu Glu Arg Gly Ser Leu Leu Gly Cys Ser Ile Asp Ile Ser Ser
            245                 250                 255

Val Leu Asp Met Glu Ala Ile Thr Phe Lys Lys Leu Val Lys Gly His
            260                 265                 270

Ala Tyr Ser Val Thr Gly Ala Lys Gln Val Asn Tyr Arg Gly Gln Val
    275                 280                 285

Val Ser Leu Ile Arg Met Arg Asn Pro Trp Gly Glu Val Glu Trp Thr
    290                 295                 300

Gly Ala Trp Ser Asp Ser Ser Glu Trp Asn Asn Val Asp Pro Tyr
305                 310                 315                 320

Glu Arg Asp Gln Leu Arg Val Lys Met Glu Asp Gly Glu Phe Trp Met
            325                 330                 335

Ser Phe Arg Asp Phe Met Arg Glu Phe Thr Arg Leu Glu Ile Cys Asn
            340                 345                 350

Leu Thr Pro Asp Ala Leu Lys Ser Arg Thr Ile Arg Lys Trp Asn Thr
            355                 360                 365

Thr Leu Tyr Glu Gly Thr Trp Arg Arg Gly Ser Thr Ala Gly Gly Cys
    370                 375                 380

Arg Asn Tyr Pro Ala Thr Phe Trp Val Asn Pro Gln Phe Lys Ile Arg
385                 390                 395                 400

Leu Asp Glu Thr Asp Asp Pro Asp Asp Tyr Gly Asp Arg Glu Ser Gly
            405                 410                 415

Cys Ser Phe Val Leu Ala Leu Met Gln Lys His Arg Arg Arg Glu Arg
            420                 425                 430

Arg Phe Gly Arg Asp Met Glu Thr Ile Gly Phe Ala Val Tyr Glu Val
    435                 440                 445

Pro Pro Glu Leu Val Gly Gln Pro Ala Val His Leu Lys Arg Asp Phe
450                 455                 460

Phe Leu Ala Asn Ala Ser Arg Ala Arg Ser Glu Gln Phe Ile Asn Leu
465                 470                 475                 480

Arg Glu Val Ser Thr Arg Phe Arg Leu Pro Pro Gly Glu Tyr Val Val
            485                 490                 495
```

```
Val Pro Ser Thr Phe Glu Pro Asn Lys Gly Asp Phe Val Leu Arg
                500                 505                 510

Phe Phe Ser Glu Lys Ser Ala Gly Thr Val Glu Leu Asp Asp Gln Ile
            515                 520                 525

Gln Ala Asn Leu Pro Asp Glu Gln Val Leu Ser Glu Glu Ile Asp
        530                 535                 540

Glu Asn Phe Lys Ala Leu Phe Arg Gln Leu Ala Gly Glu Asp Met Glu
545                 550                 555                 560

Ile Ser Val Lys Glu Leu Arg Thr Ile Leu Asn Arg Ile Ile Ser Lys
                565                 570                 575

His Lys Asp Leu Arg Thr Lys Gly Phe Ser Leu Glu Ser Cys Arg Ser
            580                 585                 590

Met Val Asn Leu Met Asp Arg Asp Gly Asn Gly Lys Leu Gly Leu Val
        595                 600                 605

Glu Phe Asn Ile Leu Trp Asn Arg Ile Arg Asn Tyr Leu Ser Ile Phe
        610                 615                 620

Arg Lys Phe Asp Leu Asp Lys Ser Gly Ser Met Ser Ala Tyr Glu Met
625                 630                 635                 640

Arg Met Ala Ile Glu Ser Ala Gly Phe Lys Leu Asn Lys Lys Leu Tyr
                645                 650                 655

Glu Leu Ile Ile Thr Arg Tyr Ser Glu Pro Asp Leu Ala Val Asp Phe
            660                 665                 670

Asp Asn Phe Val Cys Cys Leu Val Arg Leu Glu Thr Met Phe Arg Phe
        675                 680                 685

Phe Lys Thr Leu Asp Thr Asp Leu Asp Gly Val Val Thr Phe Asp Leu
        690                 695                 700

Phe Lys Trp Leu Gln Leu Thr Met Phe Ala
705                 710

<210> SEQ ID NO 64
<211> LENGTH: 191
<212> TYPE: PRT
<213> ORGANISM: Homo sapiens

<400> SEQUENCE: 64

Met Gln Thr Ile Lys Cys Val Val Val Gly Asp Gly Ala Val Gly Lys
1               5                   10                  15

Thr Cys Leu Leu Ile Ser Tyr Thr Thr Asn Lys Phe Pro Ser Glu Tyr
            20                  25                  30

Val Pro Thr Val Phe Asp Asn Tyr Ala Val Thr Val Met Ile Gly Gly
        35                  40                  45

Glu Pro Tyr Thr Leu Gly Leu Phe Asp Thr Ala Gly Gln Glu Asp Tyr
    50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
                85                  90                  95

Trp Val Pro Glu Ile Thr His His Cys Pro Lys Thr Pro Phe Leu Leu
            100                 105                 110

Val Gly Thr Gln Ile Asp Leu Arg Asp Asp Pro Ser Thr Ile Glu Lys
        115                 120                 125

Leu Ala Lys Asn Lys Gln Lys Pro Ile Thr Pro Glu Thr Ala Glu Lys
    130                 135                 140

Leu Ala Arg Asp Leu Lys Ala Val Lys Tyr Val Glu Cys Ser Ala Leu
145                 150                 155                 160
```

-continued

Thr Gln Lys Gly Leu Lys Asn Val Phe Asp Glu Ala Ile Leu Ala Ala
                165                 170                 175

Leu Glu Pro Pro Glu Pro Lys Lys Ser Arg Arg Cys Val Leu Leu
            180                 185                 190

<210> SEQ ID NO 65
<211> LENGTH: 1663
<212> TYPE: PRT
<213> ORGANISM: Homo sapiens

<400> SEQUENCE: 65

Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
            20                  25                  30

Ile Leu Arg Leu Glu Ser Glu Glu Thr Met Val Leu Glu Ala His Asp
        35                  40                  45

Ala Gln Gly Asp Val Pro Val Thr Val Thr Val His Asp Phe Pro Gly
    50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
            100                 105                 110

Gly Thr Gln Val Val Glu Lys Val Val Leu Val Ser Leu Gln Ser Gly
        115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
        195                 200                 205

Tyr Tyr Glu Asn Ser Pro Gln Gln Val Phe Ser Thr Glu Phe Glu Val
    210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
            260                 265                 270

Phe Gly Ile Gln Asp Gly Glu Gln Arg Ile Ser Leu Pro Glu Ser Leu
        275                 280                 285

Lys Arg Ile Pro Ile Glu Asp Gly Ser Gly Glu Val Val Leu Ser Arg
    290                 295                 300

Lys Val Leu Leu Asp Gly Val Gln Asn Pro Arg Ala Glu Asp Leu Val
305                 310                 315                 320

Gly Lys Ser Leu Tyr Val Ser Ala Thr Val Ile Leu His Ser Gly Ser
                325                 330                 335

Asp Met Val Gln Ala Glu Arg Ser Gly Ile Pro Ile Val Thr Ser Pro

```
            340                 345                 350
Tyr Gln Ile His Phe Thr Lys Thr Pro Lys Tyr Phe Lys Pro Gly Met
            355                 360                 365
Pro Phe Asp Leu Met Val Phe Val Thr Asn Pro Asp Gly Ser Pro Ala
            370                 375                 380
Tyr Arg Val Pro Val Ala Val Gln Gly Glu Asp Thr Val Gln Ser Leu
385                 390                 395                 400
Thr Gln Gly Asp Gly Val Ala Lys Leu Ser Ile Asn Thr His Pro Ser
                    405                 410                 415
Gln Lys Pro Leu Ser Ile Thr Val Arg Thr Lys Lys Gln Glu Leu Ser
                420                 425                 430
Glu Ala Glu Gln Ala Thr Arg Thr Met Gln Ala Leu Pro Tyr Ser Thr
            435                 440                 445
Val Gly Asn Ser Asn Asn Tyr Leu His Leu Ser Val Leu Arg Thr Glu
            450                 455                 460
Leu Arg Pro Gly Glu Thr Leu Asn Val Asn Phe Leu Leu Arg Met Asp
465                 470                 475                 480
Arg Ala His Glu Ala Lys Ile Arg Tyr Tyr Thr Tyr Leu Ile Met Asn
                    485                 490                 495
Lys Gly Arg Leu Leu Lys Ala Gly Arg Gln Val Arg Glu Pro Gly Gln
                500                 505                 510
Asp Leu Val Val Leu Pro Leu Ser Ile Thr Thr Asp Phe Ile Pro Ser
            515                 520                 525
Phe Arg Leu Val Ala Tyr Tyr Thr Leu Ile Gly Ala Ser Gly Gln Arg
            530                 535                 540
Glu Val Val Ala Asp Ser Val Trp Val Asp Val Lys Asp Ser Cys Val
545                 550                 555                 560
Gly Ser Leu Val Val Lys Ser Gly Gln Ser Glu Asp Arg Gln Pro Val
                565                 570                 575
Pro Gly Gln Gln Met Thr Leu Lys Ile Glu Gly Asp His Gly Ala Arg
                580                 585                 590
Val Val Leu Val Ala Val Asp Lys Gly Val Phe Val Leu Asn Lys Lys
            595                 600                 605
Asn Lys Leu Thr Gln Ser Lys Ile Trp Asp Val Val Glu Lys Ala Asp
            610                 615                 620
Ile Gly Cys Thr Pro Gly Ser Gly Lys Asp Tyr Ala Gly Val Phe Ser
625                 630                 635                 640
Asp Ala Gly Leu Thr Phe Thr Ser Ser Ser Gly Gln Gln Thr Ala Gln
                    645                 650                 655
Arg Ala Glu Leu Gln Cys Pro Gln Pro Ala Ala Arg Arg Arg Arg Ser
                660                 665                 670
Val Gln Leu Thr Glu Lys Arg Met Asp Lys Val Gly Lys Tyr Pro Lys
            675                 680                 685
Glu Leu Arg Lys Cys Cys Glu Asp Gly Met Arg Glu Asn Pro Met Arg
            690                 695                 700
Phe Ser Cys Gln Arg Arg Thr Arg Phe Ile Ser Leu Gly Glu Ala Cys
705                 710                 715                 720
Lys Lys Val Phe Leu Asp Cys Cys Asn Tyr Ile Thr Glu Leu Arg Arg
                    725                 730                 735
Gln His Ala Arg Ala Ser His Leu Gly Leu Ala Arg Ser Asn Leu Asp
                740                 745                 750
Glu Asp Ile Ile Ala Glu Glu Asn Ile Val Ser Arg Ser Glu Phe Pro
            755                 760                 765
```

-continued

```
Glu Ser Trp Leu Trp Asn Val Glu Asp Leu Lys Glu Pro Pro Lys Asn
        770             775             780

Gly Ile Ser Thr Lys Leu Met Asn Ile Phe Leu Lys Asp Ser Ile Thr
785             790             795             800

Thr Trp Glu Ile Leu Ala Val Ser Met Ser Asp Lys Lys Gly Ile Cys
            805             810             815

Val Ala Asp Pro Phe Glu Val Thr Val Met Gln Asp Phe Phe Ile Asp
            820             825             830

Leu Arg Leu Pro Tyr Ser Val Arg Asn Glu Gln Val Glu Ile Arg
            835             840             845

Ala Val Leu Tyr Asn Tyr Arg Gln Asn Gln Glu Leu Lys Val Arg Val
        850             855             860

Glu Leu Leu His Asn Pro Ala Phe Cys Ser Leu Ala Thr Thr Lys Arg
865             870             875             880

Arg His Gln Gln Thr Val Thr Ile Pro Pro Lys Ser Ser Leu Ser Val
            885             890             895

Pro Tyr Val Ile Val Pro Leu Lys Thr Gly Leu Gln Glu Val Glu Val
            900             905             910

Lys Ala Ala Val Tyr His His Phe Ile Ser Asp Gly Val Arg Lys Ser
        915             920             925

Leu Lys Val Val Pro Glu Gly Ile Arg Met Asn Lys Thr Val Ala Val
        930             935             940

Arg Thr Leu Asp Pro Glu Arg Leu Gly Arg Glu Gly Val Gln Lys Glu
945             950             955             960

Asp Ile Pro Pro Ala Asp Leu Ser Asp Gln Val Pro Asp Thr Glu Ser
            965             970             975

Glu Thr Arg Ile Leu Leu Gln Gly Thr Pro Val Ala Gln Met Thr Glu
            980             985             990

Asp Ala Val Asp Ala Glu Arg Leu  Lys His Leu Ile Val  Thr Pro Ser
            995             1000            1005

Gly Cys  Gly Glu Gln Asn Met  Ile Gly Met Thr Pro  Thr Val Ile
    1010            1015            1020

Ala Val  His Tyr Leu Asp Glu  Thr Glu Gln Trp Glu  Lys Phe Gly
    1025            1030            1035

Leu Glu  Lys Arg Gln Gly Ala  Leu Glu Leu Ile Lys  Lys Gly Tyr
    1040            1045            1050

Thr Gln  Gln Leu Ala Phe Arg  Gln Pro Ser Ser Ala  Phe Ala Ala
    1055            1060            1065

Phe Val  Lys Arg Ala Pro Ser  Thr Trp Leu Thr Ala  Tyr Val Val
    1070            1075            1080

Lys Val  Phe Ser Leu Ala Val  Asn Leu Ile Ala Ile  Asp Ser Gln
    1085            1090            1095

Val Leu  Cys Gly Ala Val Lys  Trp Leu Ile Leu Glu  Lys Gln Lys
    1100            1105            1110

Pro Asp  Gly Val Phe Gln Glu  Asp Ala Pro Val Ile  His Gln Glu
    1115            1120            1125

Met Ile  Gly Gly Leu Arg Asn  Asn Asn Glu Lys Asp  Met Ala Leu
    1130            1135            1140

Thr Ala  Phe Val Leu Ile Ser  Leu Gln Glu Ala Lys  Asp Ile Cys
    1145            1150            1155

Glu Glu  Gln Val Asn Ser Leu  Pro Gly Ser Ile Thr  Lys Ala Gly
    1160            1165            1170
```

```
Asp Phe Leu Glu Ala Asn Tyr Met Asn Leu Gln Arg Ser Tyr Thr
1175                1180                1185

Val Ala Ile Ala Gly Tyr Ala Leu Ala Gln Met Gly Arg Leu Lys
1190                1195                1200

Gly Pro Leu Leu Asn Lys Phe Leu Thr Thr Ala Lys Asp Lys Asn
1205                1210                1215

Arg Trp Glu Asp Pro Gly Lys Gln Leu Tyr Asn Val Glu Ala Thr
1220                1225                1230

Ser Tyr Ala Leu Leu Ala Leu Leu Gln Leu Lys Asp Phe Asp Phe
1235                1240                1245

Val Pro Pro Val Val Arg Trp Leu Asn Glu Gln Arg Tyr Tyr Gly
1250                1255                1260

Gly Gly Tyr Gly Ser Thr Gln Ala Thr Phe Met Val Phe Gln Ala
1265                1270                1275

Leu Ala Gln Tyr Gln Lys Asp Ala Pro Asp His Gln Glu Leu Asn
1280                1285                1290

Leu Asp Val Ser Leu Gln Leu Pro Ser Arg Ser Ser Lys Ile Thr
1295                1300                1305

His Arg Ile His Trp Glu Ser Ala Ser Leu Leu Arg Ser Glu Glu
1310                1315                1320

Thr Lys Glu Asn Glu Gly Phe Thr Val Thr Ala Glu Gly Lys Gly
1325                1330                1335

Gln Gly Thr Leu Ser Val Val Thr Met Tyr His Ala Lys Ala Lys
1340                1345                1350

Asp Gln Leu Thr Cys Asn Lys Phe Asp Leu Lys Val Thr Ile Lys
1355                1360                1365

Pro Ala Pro Glu Thr Glu Lys Arg Pro Gln Asp Ala Lys Asn Thr
1370                1375                1380

Met Ile Leu Glu Ile Cys Thr Arg Tyr Arg Gly Asp Gln Asp Ala
1385                1390                1395

Thr Met Ser Ile Leu Asp Ile Ser Met Met Thr Gly Phe Ala Pro
1400                1405                1410

Asp Thr Asp Asp Leu Lys Gln Leu Ala Asn Gly Val Asp Arg Tyr
1415                1420                1425

Ile Ser Lys Tyr Glu Leu Asp Lys Ala Phe Ser Asp Arg Asn Thr
1430                1435                1440

Leu Ile Ile Tyr Leu Asp Lys Val Ser His Ser Glu Asp Asp Cys
1445                1450                1455

Leu Ala Phe Lys Val His Gln Tyr Phe Asn Val Glu Leu Ile Gln
1460                1465                1470

Pro Gly Ala Val Lys Val Tyr Ala Tyr Tyr Asn Leu Glu Glu Ser
1475                1480                1485

Cys Thr Arg Phe Tyr His Pro Glu Lys Glu Asp Gly Lys Leu Asn
1490                1495                1500

Lys Leu Cys Arg Asp Glu Leu Cys Arg Cys Ala Glu Glu Asn Cys
1505                1510                1515

Phe Ile Gln Lys Ser Asp Asp Lys Val Thr Leu Glu Glu Arg Leu
1520                1525                1530

Asp Lys Ala Cys Glu Pro Gly Val Asp Tyr Val Tyr Lys Thr Arg
1535                1540                1545

Leu Val Lys Val Gln Leu Ser Asn Asp Phe Asp Glu Tyr Ile Met
1550                1555                1560

Ala Ile Glu Gln Thr Ile Lys Ser Gly Ser Asp Glu Val Gln Val
```

```
                   1565                1570                1575

Gly Gln Gln Arg Thr Phe Ile Ser Pro Ile Lys Cys Arg Glu Ala
           1580                1585                1590

Leu Lys Leu Glu Glu Lys Lys His Tyr Leu Met Trp Gly Leu Ser
   1595                1600                1605

Ser Asp Phe Trp Gly Glu Lys Pro Asn Leu Ser Tyr Ile Ile Gly
   1610                1615                1620

Lys Asp Thr Trp Val Glu His Trp Pro Glu Glu Asp Glu Cys Gln
   1625                1630                1635

Asp Glu Glu Asn Gln Lys Gln Cys Gln Asp Leu Gly Ala Phe Thr
   1640                1645                1650

Glu Ser Met Val Val Phe Gly Cys Pro Asn
   1655                1660

<210> SEQ ID NO 66
<211> LENGTH: 461
<212> TYPE: PRT
<213> ORGANISM: Homo sapiens

<400> SEQUENCE: 66

Met Ser Arg Gln Val Val Arg Ser Ser Lys Phe Arg His Val Phe Gly
1               5                   10                  15

Gln Pro Ala Lys Ala Asp Gln Cys Tyr Glu Asp Val Arg Val Ser Gln
            20                  25                  30

Thr Thr Trp Asp Ser Gly Phe Cys Ala Val Asn Pro Lys Phe Val Ala
        35                  40                  45

Leu Ile Cys Glu Ala Ser Gly Gly Gly Ala Phe Leu Val Leu Pro Leu
    50                  55                  60

Gly Lys Thr Gly Arg Val Asp Lys Asn Ala Pro Thr Val Cys Gly His
65                  70                  75                  80

Thr Ala Pro Val Leu Asp Ile Ala Trp Cys Pro His Asn Asp Asn Val
                85                  90                  95

Ile Ala Ser Gly Ser Glu Asp Cys Thr Val Met Val Trp Glu Ile Pro
            100                 105                 110

Asp Gly Gly Leu Met Leu Pro Leu Arg Glu Pro Val Val Thr Leu Glu
        115                 120                 125

Gly His Thr Lys Arg Val Gly Ile Val Ala Trp His Thr Thr Ala Gln
    130                 135                 140

Asn Val Leu Leu Ser Ala Gly Cys Asp Asn Val Ile Met Val Trp Asp
145                 150                 155                 160

Val Gly Thr Gly Ala Ala Met Leu Thr Leu Gly Pro Glu Val His Pro
                165                 170                 175

Asp Thr Ile Tyr Ser Val Asp Trp Ser Arg Asp Gly Gly Leu Ile Cys
            180                 185                 190

Thr Ser Cys Arg Asp Lys Arg Val Arg Ile Ile Glu Pro Arg Lys Gly
        195                 200                 205

Thr Val Val Ala Glu Lys Asp Arg Pro His Glu Gly Thr Arg Pro Val
    210                 215                 220

Arg Ala Val Phe Val Ser Glu Gly Lys Ile Leu Thr Thr Gly Phe Ser
225                 230                 235                 240

Arg Met Ser Glu Arg Gln Val Ala Leu Trp Asp Thr Lys His Leu Glu
                245                 250                 255

Glu Pro Leu Ser Leu Gln Glu Leu Asp Thr Ser Ser Gly Val Leu Leu
            260                 265                 270
```

Pro Phe Phe Asp Pro Asp Thr Asn Ile Val Tyr Leu Cys Gly Lys Gly
            275                 280                 285

Asp Ser Ser Ile Arg Tyr Phe Glu Ile Thr Ser Glu Ala Pro Phe Leu
        290                 295                 300

His Tyr Leu Ser Met Phe Ser Ser Lys Glu Ser Gln Arg Gly Met Gly
305                 310                 315                 320

Tyr Met Pro Lys Arg Gly Leu Glu Val Asn Lys Cys Glu Ile Ala Arg
                325                 330                 335

Phe Tyr Lys Leu His Glu Arg Arg Cys Glu Pro Ile Ala Met Thr Val
            340                 345                 350

Pro Arg Lys Ser Asp Leu Phe Gln Glu Asp Leu Tyr Pro Pro Thr Ala
        355                 360                 365

Gly Pro Asp Pro Ala Leu Thr Ala Glu Glu Trp Leu Gly Gly Arg Asp
370                 375                 380

Ala Gly Pro Leu Leu Ile Ser Leu Lys Asp Gly Tyr Val Pro Pro Lys
385                 390                 395                 400

Ser Arg Glu Leu Arg Val Asn Arg Gly Leu Asp Thr Gly Arg Arg Arg
                405                 410                 415

Ala Ala Pro Glu Ala Ser Gly Thr Pro Ser Ser Asp Ala Val Ser Arg
            420                 425                 430

Leu Glu Glu Glu Met Arg Lys Leu Gln Ala Thr Val Gln Glu Leu Gln
        435                 440                 445

Lys Arg Leu Asp Arg Leu Glu Glu Thr Val Gln Ala Lys
450                 455                 460

<210> SEQ ID NO 67
<211> LENGTH: 868
<212> TYPE: PRT
<213> ORGANISM: Homo sapiens

<400> SEQUENCE: 67

Met Ala Thr Phe Ile Ser Val Gln Leu Lys Lys Thr Ser Glu Val Asp
1               5                   10                  15

Leu Ala Lys Pro Leu Val Lys Phe Ile Gln Gln Thr Tyr Pro Ser Gly
            20                  25                  30

Gly Glu Glu Gln Ala Gln Tyr Cys Arg Ala Ala Glu Leu Ser Lys
        35                  40                  45

Leu Arg Arg Ala Ala Val Gly Arg Pro Leu Asp Lys His Glu Gly Ala
50                  55                  60

Leu Glu Thr Leu Leu Arg Tyr Tyr Asp Gln Ile Cys Ser Ile Glu Pro
65                  70                  75                  80

Lys Phe Pro Phe Ser Glu Asn Gln Ile Cys Leu Thr Phe Thr Trp Lys
                85                  90                  95

Asp Ala Phe Asp Lys Gly Ser Leu Phe Gly Gly Ser Val Lys Leu Ala
            100                 105                 110

Leu Ala Ser Leu Gly Tyr Glu Lys Ser Cys Val Leu Phe Asn Cys Ala
        115                 120                 125

Ala Leu Ala Ser Gln Ile Ala Ala Glu Gln Asn Leu Asp Asn Asp Glu
    130                 135                 140

Gly Leu Lys Ile Ala Ala Lys His Tyr Gln Phe Ala Ser Gly Ala Phe
145                 150                 155                 160

Leu His Ile Lys Glu Thr Val Leu Ser Ala Leu Ser Arg Glu Pro Thr
                165                 170                 175

Val Asp Ile Ser Pro Asp Thr Val Gly Thr Leu Ser Leu Ile Met Leu
            180                 185                 190

```
Ala Gln Ala Gln Glu Val Phe Phe Leu Lys Ala Thr Arg Asp Lys Met
            195                 200                 205

Lys Asp Ala Ile Ile Ala Lys Leu Ala Asn Gln Ala Ala Asp Tyr Phe
        210                 215                 220

Gly Asp Ala Phe Lys Gln Cys Gln Tyr Lys Asp Thr Leu Pro Lys Glu
225                 230                 235                 240

Val Phe Pro Val Leu Ala Ala Lys His Cys Ile Met Gln Ala Asn Ala
                245                 250                 255

Glu Tyr His Gln Ser Ile Leu Ala Lys Gln Gln Lys Lys Phe Gly Glu
            260                 265                 270

Glu Ile Ala Arg Leu Gln His Ala Ala Glu Leu Ile Lys Thr Val Ala
        275                 280                 285

Ser Arg Tyr Asp Glu Tyr Val Asn Val Lys Asp Phe Ser Asp Lys Ile
        290                 295                 300

Asn Arg Ala Leu Ala Ala Lys Lys Asp Asn Asp Phe Ile Tyr His
305                 310                 315                 320

Asp Arg Val Pro Asp Leu Lys Asp Leu Asp Pro Ile Gly Lys Ala Thr
                325                 330                 335

Leu Val Lys Ser Thr Pro Val Asn Val Pro Ile Ser Gln Lys Phe Thr
            340                 345                 350

Asp Leu Phe Glu Lys Met Val Pro Val Ser Val Gln Gln Ser Leu Ala
        355                 360                 365

Ala Tyr Asn Gln Arg Lys Ala Asp Leu Val Asn Arg Ser Ile Ala Gln
        370                 375                 380

Met Arg Glu Ala Thr Thr Leu Ala Asn Gly Val Leu Ala Ser Leu Asn
385                 390                 395                 400

Leu Pro Ala Ala Ile Glu Asp Val Ser Gly Asp Thr Val Pro Gln Ser
                405                 410                 415

Ile Leu Thr Lys Ser Arg Ser Val Ile Glu Gln Gly Gly Ile Gln Thr
            420                 425                 430

Val Asp Gln Leu Ile Lys Glu Leu Pro Glu Leu Leu Gln Arg Asn Arg
        435                 440                 445

Glu Ile Leu Asp Glu Ser Leu Arg Leu Leu Asp Glu Glu Ala Thr
450                 455                 460

Asp Asn Asp Leu Arg Ala Lys Phe Lys Glu Arg Trp Gln Arg Thr Pro
465                 470                 475                 480

Ser Asn Glu Leu Tyr Lys Pro Leu Arg Ala Glu Gly Thr Asn Phe Arg
                485                 490                 495

Thr Val Leu Asp Lys Ala Val Gln Ala Asp Gly Gln Val Lys Glu Cys
            500                 505                 510

Tyr Gln Ser His Arg Asp Thr Ile Val Leu Leu Cys Lys Pro Glu Pro
        515                 520                 525

Glu Leu Asn Ala Ala Ile Pro Ser Ala Asn Pro Ala Lys Thr Met Gln
        530                 535                 540

Gly Ser Glu Val Val Asn Val Leu Lys Ser Leu Leu Ser Asn Leu Asp
545                 550                 555                 560

Glu Val Lys Lys Glu Arg Glu Gly Leu Glu Asn Asp Leu Lys Ser Val
                565                 570                 575

Asn Phe Asp Met Thr Ser Lys Phe Leu Thr Ala Leu Ala Gln Asp Gly
            580                 585                 590

Val Ile Asn Glu Glu Ala Leu Ser Val Thr Glu Leu Asp Arg Val Tyr
        595                 600                 605
```

Gly Gly Leu Thr Thr Lys Val Gln Glu Ser Leu Lys Lys Gln Glu Gly
610                615                620

Leu Leu Lys Asn Ile Gln Val Ser His Gln Glu Phe Ser Lys Met Lys
625                630                635                640

Gln Ser Asn Asn Glu Ala Asn Leu Arg Glu Val Leu Lys Asn Leu
            645                650                655

Ala Thr Ala Tyr Asp Asn Phe Val Glu Leu Val Ala Asn Leu Lys Glu
            660                665                670

Gly Thr Lys Phe Tyr Asn Glu Leu Thr Glu Ile Leu Val Arg Phe Gln
            675                680                685

Asn Lys Cys Ser Asp Ile Val Phe Ala Arg Lys Thr Glu Arg Asp Glu
            690                695                700

Leu Leu Lys Asp Leu Gln Gln Ser Ile Ala Arg Glu Pro Ser Ala Pro
705                710                715                720

Ser Ile Pro Thr Pro Ala Tyr Gln Ser Ser Pro Ala Gly Gly His Ala
            725                730                735

Pro Thr Pro Pro Thr Pro Ala Pro Arg Thr Met Pro Pro Thr Lys Pro
            740                745                750

Gln Pro Pro Ala Arg Pro Pro Pro Val Leu Pro Ala Asn Arg Ala
            755                760                765

Pro Ser Ala Thr Ala Pro Ser Pro Val Gly Ala Gly Thr Ala Ala Pro
770                775                780

Ala Pro Ser Gln Thr Pro Gly Ser Ala Pro Pro Gln Ala Gln Gly
785                790                795                800

Pro Pro Tyr Pro Thr Tyr Pro Gly Tyr Pro Gly Tyr Cys Gln Met Pro
            805                810                815

Met Pro Met Gly Tyr Asn Pro Tyr Ala Tyr Gly Gln Tyr Asn Met Pro
            820                825                830

Tyr Pro Pro Val Tyr His Gln Ser Pro Gly Gln Ala Pro Tyr Pro Gly
            835                840                845

Pro Gln Gln Pro Ser Tyr Pro Phe Pro Gln Pro Gln Gln Ser Tyr
            850                855                860

Tyr Pro Gln Gln
865

<210> SEQ ID NO 68
<211> LENGTH: 94
<212> TYPE: PRT
<213> ORGANISM: Homo sapiens

<400> SEQUENCE: 68

Met Arg Thr Leu Ala Ile Leu Ala Ala Ile Leu Leu Val Ala Leu Gln
1                5                10                15

Ala Gln Ala Glu Pro Leu Gln Ala Arg Ala Asp Glu Val Ala Ala Ala
            20                25                30

Pro Glu Gln Ile Ala Ala Asp Ile Pro Glu Val Val Val Ser Leu Ala
            35                40                45

Trp Asp Glu Ser Leu Ala Pro Lys His Pro Gly Ser Arg Lys Asn Met
            50                55                60

Ala Cys Tyr Cys Arg Ile Pro Ala Cys Ile Ala Gly Glu Arg Arg Tyr
65                70                75                80

Gly Thr Cys Ile Tyr Gln Gly Arg Leu Trp Ala Phe Cys Cys
            85                90

<210> SEQ ID NO 69

```
<211> LENGTH: 275
<212> TYPE: PRT
<213> ORGANISM: Homo sapiens

<400> SEQUENCE: 69

Met Glu Glu Val Arg Glu Gly His Ala Leu Gly Gly Met Glu Ala
1               5                   10                  15

Asp Gly Pro Ala Ser Leu Gln Glu Leu Pro Pro Ser Pro Arg Ser Pro
            20                  25                  30

Ser Pro Pro Ser Pro Pro Leu Pro Ser Pro Ser Leu Pro
        35                  40                  45

Ser Pro Ala Ala Pro Glu Ala Pro Glu Leu Pro Glu Pro Ala Gln Pro
    50                  55                  60

Ser Glu Ala His Ala Arg Gln Leu Leu Leu Glu Glu Trp Gly Pro Leu
65                  70                  75                  80

Ser Gly Gly Leu Glu Leu Pro Gln Arg Leu Thr Trp Lys Leu Leu Leu
                85                  90                  95

Leu Arg Arg Pro Leu Tyr Arg Asn Leu Leu Arg Ser Pro Asn Pro Glu
            100                 105                 110

Gly Ile Asn Ile Tyr Glu Pro Ala Pro Pro Thr Gly Pro Thr Gln Arg
        115                 120                 125

Pro Leu Glu Thr Leu Gly Asn Phe Arg Gly Trp Tyr Ile Arg Thr Glu
130                 135                 140

Lys Leu Gln Gln Asn Gln Ser Trp Thr Val Lys Gln Gln Cys Val Asp
145                 150                 155                 160

Leu Leu Ala Glu Gly Leu Trp Glu Glu Leu Leu Asp Asp Glu Gln Pro
                165                 170                 175

Ala Ile Thr Val Met Asp Trp Phe Glu Asp Ser Arg Leu Asp Ala Cys
            180                 185                 190

Val Tyr Glu Leu His Val Trp Leu Leu Ala Ala Asp Arg Arg Thr Val
        195                 200                 205

Ile Ala Gln His His Val Ala Pro Arg Thr Ser Gly Arg Gly Pro Pro
    210                 215                 220

Gly Arg Trp Val Gln Val Ser His Val Phe Arg His Tyr Gly Pro Gly
225                 230                 235                 240

Val Arg Phe Ile His Phe Leu His Lys Ala Lys Asn Arg Met Glu Pro
                245                 250                 255

Gly Gly Leu Arg Arg Thr Arg Val Thr Asp Ser Ser Val Ser Val Gln
            260                 265                 270

Leu Arg Glu
    275

<210> SEQ ID NO 70
<211> LENGTH: 188
<212> TYPE: PRT
<213> ORGANISM: Homo sapiens

<400> SEQUENCE: 70

Met Ala Asn Ser Gly Cys Lys Asp Val Thr Gly Pro Asp Glu Glu Ser
1               5                   10                  15

Phe Leu Tyr Phe Ala Tyr Gly Ser Asn Leu Leu Thr Glu Arg Ile His
            20                  25                  30

Leu Arg Asn Pro Ser Ala Ala Phe Phe Cys Val Ala Arg Leu Gln Asp
        35                  40                  45

Phe Lys Leu Asp Phe Gly Asn Ser Gln Gly Lys Thr Ser Gln Thr Trp
    50                  55                  60
```

```
His Gly Gly Ile Ala Thr Ile Phe Gln Ser Pro Gly Asp Glu Val Trp
 65                  70                  75                  80

Gly Val Val Trp Lys Met Asn Lys Ser Asn Leu Asn Ser Leu Asp Glu
                 85                  90                  95

Gln Glu Gly Val Lys Ser Gly Met Tyr Val Val Ile Glu Val Lys Val
            100                 105                 110

Ala Thr Gln Glu Gly Lys Glu Ile Thr Cys Arg Ser Tyr Leu Met Thr
            115                 120                 125

Asn Tyr Glu Ser Ala Pro Pro Ser Pro Gln Tyr Lys Lys Ile Ile Cys
130                 135                 140

Met Gly Ala Lys Glu Asn Gly Leu Pro Leu Glu Tyr Gln Glu Lys Leu
145                 150                 155                 160

Lys Ala Ile Glu Pro Asn Asp Tyr Thr Gly Lys Val Ser Glu Glu Ile
                165                 170                 175

Glu Asp Ile Ile Lys Lys Gly Glu Thr Gln Thr Leu
            180                 185

<210> SEQ ID NO 71
<211> LENGTH: 522
<212> TYPE: PRT
<213> ORGANISM: Homo sapiens

<400> SEQUENCE: 71

Met Ala Leu Leu Pro Arg Ala Leu Ser Ala Gly Ala Gly Pro Ser Trp
  1               5                  10                  15

Arg Arg Ala Ala Arg Ala Phe Arg Gly Phe Leu Leu Leu Leu Pro Glu
                 20                  25                  30

Pro Ala Ala Leu Thr Arg Ala Leu Ser Arg Ala Met Ala Cys Arg Gln
             35                  40                  45

Glu Pro Gln Pro Gln Gly Pro Pro Ala Ala Gly Ala Val Ala Ser
 50                  55                  60

Tyr Asp Tyr Leu Val Ile Gly Gly Gly Ser Gly Gly Leu Ala Ser Ala
 65                  70                  75                  80

Arg Arg Ala Ala Glu Leu Gly Ala Arg Ala Ala Val Val Glu Ser His
                 85                  90                  95

Lys Leu Gly Gly Thr Cys Val Asn Val Gly Cys Val Pro Lys Lys Val
            100                 105                 110

Met Trp Asn Thr Ala Val His Ser Glu Phe Met His Asp His Ala Asp
            115                 120                 125

Tyr Gly Phe Pro Ser Cys Glu Gly Lys Phe Asn Trp Arg Val Ile Lys
            130                 135                 140

Glu Lys Arg Asp Ala Tyr Val Ser Arg Leu Asn Ala Ile Tyr Gln Asn
145                 150                 155                 160

Asn Leu Thr Lys Ser His Ile Glu Ile Ile Arg Gly His Ala Ala Phe
                165                 170                 175

Thr Ser Asp Pro Lys Pro Thr Ile Glu Val Ser Gly Lys Lys Tyr Thr
            180                 185                 190

Ala Pro His Ile Leu Ile Ala Thr Gly Gly Met Pro Ser Thr Pro His
            195                 200                 205

Glu Ser Gln Ile Pro Gly Ala Ser Leu Gly Ile Thr Ser Asp Gly Phe
            210                 215                 220

Phe Gln Leu Glu Glu Leu Pro Gly Arg Ser Val Ile Val Gly Ala Gly
225                 230                 235                 240

Tyr Ile Ala Val Glu Met Ala Gly Ile Leu Ser Ala Leu Gly Ser Lys
```

```
                        245                 250                 255
Thr Ser Leu Met Ile Arg His Asp Lys Val Leu Arg Ser Phe Asp Ser
            260                 265                 270

Met Ile Ser Thr Asn Cys Thr Glu Glu Leu Glu Asn Ala Gly Val Glu
            275                 280                 285

Val Leu Lys Phe Ser Gln Val Lys Glu Val Lys Lys Thr Leu Ser Gly
            290                 295                 300

Leu Glu Val Ser Met Val Thr Ala Val Pro Gly Arg Leu Pro Val Met
305                 310                 315                 320

Thr Met Ile Pro Asp Val Asp Cys Leu Leu Trp Ala Ile Gly Arg Val
            325                 330                 335

Pro Asn Thr Lys Asp Leu Ser Leu Asn Lys Leu Gly Ile Gln Thr Asp
            340                 345                 350

Asp Lys Gly His Ile Ile Val Asp Glu Phe Gln Asn Thr Asn Val Lys
            355                 360                 365

Gly Ile Tyr Ala Val Gly Asp Val Cys Gly Lys Ala Leu Leu Thr Pro
            370                 375                 380

Val Ala Ile Ala Ala Gly Arg Lys Leu Ala His Arg Leu Phe Glu Tyr
385                 390                 395                 400

Lys Glu Asp Ser Lys Leu Asp Tyr Asn Asn Ile Pro Thr Val Val Phe
            405                 410                 415

Ser His Pro Pro Ile Gly Thr Val Gly Leu Thr Glu Asp Glu Ala Ile
            420                 425                 430

His Lys Tyr Gly Ile Glu Asn Val Lys Thr Tyr Ser Thr Ser Phe Thr
            435                 440                 445

Pro Met Tyr His Ala Val Thr Lys Arg Lys Thr Lys Cys Val Met Lys
            450                 455                 460

Met Val Cys Ala Asn Lys Glu Glu Lys Val Val Gly Ile His Met Gln
465                 470                 475                 480

Gly Leu Gly Cys Asp Glu Met Leu Gln Gly Phe Ala Val Ala Val Lys
            485                 490                 495

Met Gly Ala Thr Lys Ala Asp Phe Asp Asn Thr Val Ala Ile His Pro
            500                 505                 510

Thr Ser Ser Glu Glu Leu Val Thr Leu Arg
            515                 520

<210> SEQ ID NO 72
<211> LENGTH: 644
<212> TYPE: PRT
<213> ORGANISM: Homo sapiens

<400> SEQUENCE: 72

Met Ser Arg Gln Phe Ser Ser Arg Ser Gly Tyr Arg Ser Gly Gly Gly
1               5                   10                  15

Phe Ser Ser Gly Ser Ala Gly Ile Ile Asn Tyr Gln Arg Arg Thr Thr
            20                  25                  30

Ser Ser Ser Thr Arg Arg Ser Gly Gly Gly Gly Arg Phe Ser Ser
            35                  40                  45

Cys Gly Gly Gly Gly Ser Phe Gly Ala Gly Gly Phe Gly Ser
            50                  55                  60

Arg Ser Leu Val Asn Leu Gly Ser Lys Ser Ile Ser Ile Ser Val
65                  70                  75                  80

Ala Arg Gly Gly Gly Arg Gly Ser Gly Phe Gly Gly Tyr Gly Gly
            85                  90                  95
```

```
Gly Gly Phe Gly Gly Gly Phe Gly Gly Gly Phe Gly Gly
            100                 105                 110
Gly Ile Gly Gly Gly Phe Gly Phe Gly Ser Gly Gly Gly
        115                 120                 125
Phe Gly Gly Gly Phe Gly Gly Gly Tyr Gly Gly Tyr Gly
    130                 135                 140
Pro Val Cys Pro Pro Gly Gly Ile Gln Glu Val Thr Ile Asn Gln Ser
145                 150                 155                 160
Leu Leu Gln Pro Leu Asn Val Glu Ile Asp Pro Glu Ile Gln Lys Val
                165                 170                 175
Lys Ser Arg Glu Arg Glu Gln Ile Lys Ser Leu Asn Asn Gln Phe Ala
            180                 185                 190
Ser Phe Ile Asp Lys Val Arg Phe Leu Glu Gln Gln Asn Gln Val Leu
        195                 200                 205
Gln Thr Lys Trp Glu Leu Leu Gln Gln Val Asp Thr Ser Thr Arg Thr
    210                 215                 220
His Asn Leu Glu Pro Tyr Phe Glu Ser Phe Ile Asn Asn Leu Arg Arg
225                 230                 235                 240
Arg Val Asp Gln Leu Lys Ser Asp Gln Ser Arg Leu Asp Ser Glu Leu
                245                 250                 255
Lys Asn Met Gln Asp Met Val Glu Asp Tyr Arg Asn Lys Tyr Glu Asp
            260                 265                 270
Glu Ile Asn Lys Arg Thr Asn Ala Glu Asn Glu Phe Val Thr Ile Lys
        275                 280                 285
Lys Asp Val Asp Gly Ala Tyr Met Thr Lys Val Asp Leu Gln Ala Lys
    290                 295                 300
Leu Asp Asn Leu Gln Gln Glu Ile Asp Phe Leu Thr Ala Leu Tyr Gln
305                 310                 315                 320
Ala Glu Leu Ser Gln Met Gln Thr Gln Ile Ser Glu Thr Asn Val Ile
                325                 330                 335
Leu Ser Met Asp Asn Asn Arg Ser Leu Asp Leu Asp Ser Ile Ile Ala
            340                 345                 350
Glu Val Lys Ala Gln Tyr Glu Asp Ile Ala Gln Lys Ser Lys Ala Glu
        355                 360                 365
Ala Glu Ser Leu Tyr Gln Ser Lys Tyr Glu Glu Leu Gln Ile Thr Ala
    370                 375                 380
Gly Arg His Gly Asp Ser Val Arg Asn Ser Lys Ile Glu Ile Ser Glu
385                 390                 395                 400
Leu Asn Arg Val Ile Gln Arg Leu Arg Ser Glu Ile Asp Asn Val Lys
                405                 410                 415
Lys Gln Ile Ser Asn Leu Gln Gln Ser Ile Ser Asp Ala Glu Gln Arg
            420                 425                 430
Gly Glu Asn Ala Leu Lys Asp Ala Lys Asn Lys Leu Asn Asp Leu Glu
        435                 440                 445
Asp Ala Leu Gln Gln Ala Lys Glu Asp Leu Ala Arg Leu Leu Arg Asp
    450                 455                 460
Tyr Gln Glu Leu Met Asn Thr Lys Leu Ala Leu Asp Leu Glu Ile Ala
465                 470                 475                 480
Thr Tyr Arg Thr Leu Leu Glu Gly Glu Glu Ser Arg Met Ser Gly Glu
                485                 490                 495
Cys Ala Pro Asn Val Ser Val Ser Val Ser Thr Ser His Thr Thr Ile
            500                 505                 510
Ser Gly Gly Gly Ser Arg Gly Gly Gly Gly Gly Tyr Gly Ser Gly
```

```
                515                 520                 525
Gly Ser Ser Tyr Gly Ser Gly Gly Ser Tyr Gly Ser Gly Gly
    530                 535                 540
Gly Gly Gly Gly Arg Gly Ser Tyr Gly Ser Gly Ser Ser Tyr Gly
545                 550                 555                 560
Ser Gly Gly Gly Ser Tyr Gly Ser Gly Gly Gly Gly His Gly
                565                 570                 575
Ser Tyr Gly Ser Gly Ser Ser Gly Gly Tyr Arg Gly Gly Ser Gly
            580                 585                 590
Gly Gly Gly Gly Ser Ser Gly Gly Arg Gly Ser Gly Gly Ser
            595                 600                 605
Ser Gly Gly Ser Ile Gly Gly Arg Gly Ser Ser Gly Gly Val Lys
        610                 615                 620
Ser Ser Gly Gly Ser Ser Ser Val Lys Phe Val Ser Thr Thr Tyr Ser
625                 630                 635                 640
Gly Val Thr Arg

<210> SEQ ID NO 73
<211> LENGTH: 196
<212> TYPE: PRT
<213> ORGANISM: Homo sapiens

<400> SEQUENCE: 73

Met Lys Pro Leu Val Val Phe Val Leu Gly Gly Pro Gly Ala Gly Lys
1               5                   10                  15
Gly Thr Gln Cys Ala Arg Ile Val Glu Lys Tyr Gly Tyr Thr His Leu
            20                  25                  30
Ser Ala Gly Glu Leu Leu Arg Asp Glu Arg Lys Asn Pro Asp Ser Gln
        35                  40                  45
Tyr Gly Glu Leu Ile Glu Lys Tyr Ile Lys Glu Gly Lys Ile Val Pro
    50                  55                  60
Val Glu Ile Thr Ile Ser Leu Leu Lys Arg Glu Met Asp Gln Thr Met
65                  70                  75                  80
Ala Ala Asn Ala Gln Lys Asn Lys Phe Leu Ile Asp Gly Phe Pro Arg
                85                  90                  95
Asn Gln Asp Asn Leu Gln Gly Trp Asn Lys Thr Met Asp Gly Lys Ala
            100                 105                 110
Asp Val Ser Phe Val Leu Phe Phe Asp Cys Asn Asn Glu Ile Cys Ile
        115                 120                 125
Glu Arg Cys Leu Glu Arg Gly Lys Ser Ser Gly Arg Ser Asp Asp Asn
    130                 135                 140
Arg Glu Ser Leu Glu Lys Arg Ile Gln Thr Tyr Leu Gln Ser Thr Lys
145                 150                 155                 160
Pro Ile Ile Asp Leu Tyr Glu Glu Met Gly Lys Val Lys Lys Ile Asp
                165                 170                 175
Ala Ser Lys Ser Val Asp Glu Val Phe Asp Glu Val Val Gln Ile Phe
            180                 185                 190
Asp Lys Glu Gly
        195

<210> SEQ ID NO 74
<211> LENGTH: 630
<212> TYPE: PRT
<213> ORGANISM: Homo sapiens

<400> SEQUENCE: 74
```

```
Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
            245                 250                 255

Gln Pro Ile Ile Arg Ser Ile Pro Gln Gly Ile Val Ala Ala Trp Arg
        260                 265                 270

Gln Arg Ser Ser Arg Asp Pro Ser Trp Arg Gln Pro Glu Arg Thr Ile
    275                 280                 285

Leu Arg Pro Arg Phe Arg Arg Glu Val Glu Lys Thr Ala Cys Pro Ser
290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
            325                 330                 335

Asp Arg Val Asn Ala Ile Pro Phe Thr Tyr Glu Gln Leu Asp Val Leu
        340                 345                 350

Lys His Lys Leu Asp Glu Leu Tyr Pro Gln Gly Tyr Pro Glu Ser Val
    355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415
```

```
Pro Gln Val Ala Thr Leu Ile Asp Arg Phe Val Lys Gly Arg Gly Gln
                420                 425                 430

Leu Asp Lys Asp Thr Leu Asp Thr Leu Thr Ala Phe Tyr Pro Gly Tyr
            435                 440                 445

Leu Cys Ser Leu Ser Pro Glu Glu Leu Ser Ser Val Pro Pro Ser Ser
        450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
            500                 505                 510

Thr Glu Asp Leu Lys Ala Leu Ser Gln Gln Asn Val Ser Met Asp Leu
        515                 520                 525

Ala Thr Phe Met Lys Leu Arg Thr Asp Ala Val Leu Pro Leu Thr Val
530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
        595                 600                 605

Pro Cys Leu Leu Gly Pro Gly Pro Val Leu Thr Val Leu Ala Leu Leu
610                 615                 620

Leu Ala Ser Thr Leu Ala
625                 630

<210> SEQ ID NO 75
<211> LENGTH: 576
<212> TYPE: PRT
<213> ORGANISM: Homo sapiens

<400> SEQUENCE: 75

Met Ala Gln Gly Val Leu Trp Ile Leu Leu Gly Leu Leu Leu Trp Ser
1               5                   10                  15

Asp Pro Gly Thr Ala Ser Leu Pro Leu Leu Met Asp Ser Val Ile Gln
            20                  25                  30

Ala Leu Ala Glu Leu Glu Gln Lys Val Pro Ala Ala Lys Thr Arg His
        35                  40                  45

Thr Ala Ser Ala Trp Leu Met Ser Ala Pro Asn Ser Gly Pro His Asn
    50                  55                  60

Arg Leu Tyr His Phe Leu Leu Gly Ala Trp Ser Leu Asn Ala Thr Glu
65                  70                  75                  80

Leu Asp Pro Cys Pro Leu Ser Pro Glu Leu Leu Gly Leu Thr Lys Glu
                85                  90                  95

Val Ala Arg His Asp Val Arg Glu Gly Lys Glu Tyr Gly Val Val Leu
            100                 105                 110

Ala Pro Asp Gly Ser Thr Val Ala Val Glu Pro Leu Leu Ala Gly Leu
        115                 120                 125

Glu Ala Gly Leu Gln Gly Arg Arg Val Ile Asn Leu Pro Leu Asp Ser
    130                 135                 140

Met Ala Ala Pro Trp Glu Thr Gly Asp Thr Phe Pro Asp Val Val Ala
145                 150                 155                 160
```

```
Ile Ala Pro Asp Val Arg Ala Thr Ser Ser Pro Gly Leu Arg Asp Gly
                165                 170                 175

Ser Pro Asp Val Thr Thr Ala Asp Ile Gly Ala Asn Thr Pro Asp Ala
            180                 185                 190

Thr Lys Gly Cys Pro Asp Val Gln Ala Ser Leu Pro Ala Lys Ala
        195                 200                 205

Lys Ser Pro Pro Thr Met Val Asp Ser Leu Leu Ala Val Thr Leu Ala
210                 215                 220

Gly Asn Leu Gly Leu Thr Phe Leu Arg Gly Ser Gln Thr Gln Ser His
225                 230                 235                 240

Pro Asp Leu Gly Thr Glu Gly Cys Trp Asp Gln Leu Ser Ala Pro Arg
                245                 250                 255

Thr Phe Thr Leu Leu Asp Pro Lys Ala Ser Leu Leu Thr Met Ala Phe
            260                 265                 270

Leu Asn Gly Ala Leu Asp Gly Val Ile Leu Gly Asp Tyr Leu Ser Arg
        275                 280                 285

Thr Pro Glu Pro Arg Pro Ser Leu Ser His Leu Leu Ser Gln Tyr Tyr
    290                 295                 300

Gly Ala Gly Val Ala Arg Asp Pro Gly Phe Arg Ser Asn Phe Arg Arg
305                 310                 315                 320

Gln Asn Gly Ala Ala Leu Thr Ser Ala Ser Ile Leu Ala Gln Gln Val
                325                 330                 335

Trp Gly Thr Leu Val Leu Leu Gln Arg Leu Glu Pro Val His Leu Gln
            340                 345                 350

Leu Gln Cys Met Ser Gln Glu Gln Leu Ala Gln Val Ala Ala Asn Ala
        355                 360                 365

Thr Lys Glu Phe Thr Glu Ala Phe Leu Gly Cys Pro Ala Ile His Pro
    370                 375                 380

Arg Cys Arg Trp Gly Ala Ala Pro Tyr Arg Gly Arg Pro Lys Leu Leu
385                 390                 395                 400

Gln Leu Pro Leu Gly Phe Leu Tyr Val His His Thr Tyr Val Pro Ala
                405                 410                 415

Pro Pro Cys Thr Asp Phe Thr Arg Cys Ala Ala Asn Met Arg Ser Met
            420                 425                 430

Gln Arg Tyr His Gln Asp Thr Gln Gly Trp Gly Asp Ile Gly Tyr Ser
        435                 440                 445

Phe Val Val Gly Ser Asp Gly Tyr Val Tyr Glu Gly Arg Gly Trp His
    450                 455                 460

Trp Val Gly Ala His Thr Leu Gly His Asn Ser Arg Gly Phe Gly Val
465                 470                 475                 480

Ala Ile Val Gly Asn Tyr Thr Ala Ala Leu Pro Thr Glu Ala Ala Leu
                485                 490                 495

Arg Thr Val Arg Asp Thr Leu Pro Ser Cys Ala Val Arg Ala Gly Leu
            500                 505                 510

Leu Arg Pro Asp Tyr Ala Leu Leu Gly His Arg Gln Leu Val Arg Thr
        515                 520                 525

Asp Cys Pro Gly Asp Ala Leu Phe Asp Leu Leu Arg Thr Trp Pro His
    530                 535                 540

Phe Thr Ala Thr Val Lys Pro Arg Pro Ala Arg Ser Val Ser Lys Arg
545                 550                 555                 560

Ser Arg Arg Glu Pro Pro Arg Thr Leu Pro Ala Thr Asp Leu Gln
                565                 570                 575
```

<210> SEQ ID NO 76
<211> LENGTH: 538
<212> TYPE: PRT
<213> ORGANISM: Homo sapiens

<400> SEQUENCE: 76

```
Met Ala Ala Glu Gln Asp Pro Glu Ala Arg Ala Ala Arg Pro Leu
1               5                   10                  15

Leu Thr Asp Leu Tyr Gln Ala Thr Met Ala Leu Gly Tyr Trp Arg Ala
                20                  25                  30

Gly Arg Ala Arg Asp Ala Ala Glu Phe Glu Leu Phe Arg Arg Cys
            35                  40                  45

Pro Phe Gly Gly Ala Phe Ala Leu Ala Ala Gly Leu Arg Asp Cys Val
50                  55                  60

Arg Phe Leu Arg Ala Phe Arg Leu Arg Asp Ala Asp Val Gln Phe Leu
65                  70                  75                  80

Ala Ser Val Leu Pro Pro Asp Thr Asp Pro Ala Phe Phe Glu His Leu
                85                  90                  95

Arg Ala Leu Asp Cys Ser Glu Val Thr Val Arg Ala Leu Pro Glu Gly
                100                 105                 110

Ser Leu Ala Phe Pro Gly Val Pro Leu Leu Gln Val Ser Gly Pro Leu
            115                 120                 125

Leu Val Val Gln Leu Leu Glu Thr Pro Leu Leu Cys Leu Val Ser Tyr
        130                 135                 140

Ala Ser Leu Val Ala Thr Asn Ala Ala Arg Leu Arg Leu Ile Ala Gly
145                 150                 155                 160

Pro Glu Lys Arg Leu Leu Glu Met Gly Leu Arg Arg Ala Gln Gly Pro
                165                 170                 175

Asp Gly Gly Leu Thr Ala Ser Thr Tyr Ser Tyr Leu Gly Gly Phe Asp
            180                 185                 190

Ser Ser Ser Asn Val Leu Ala Gly Gln Leu Arg Gly Val Pro Val Ala
        195                 200                 205

Gly Thr Leu Ala His Ser Phe Val Thr Ser Phe Ser Gly Ser Glu Val
    210                 215                 220

Pro Pro Asp Pro Met Leu Ala Pro Ala Gly Glu Gly Pro Gly Val
225                 230                 235                 240

Asp Leu Ala Ala Lys Ala Gln Val Trp Leu Glu Gln Val Cys Ala His
                245                 250                 255

Leu Gly Leu Gly Val Gln Glu Pro His Pro Gly Glu Arg Ala Ala Phe
            260                 265                 270

Val Ala Tyr Ala Leu Ala Phe Pro Arg Ala Phe Gln Gly Leu Leu Asp
        275                 280                 285

Thr Tyr Ser Val Trp Arg Ser Gly Leu Pro Asn Phe Leu Ala Val Ala
    290                 295                 300

Leu Ala Leu Gly Glu Leu Gly Tyr Arg Ala Val Gly Val Arg Leu Asp
305                 310                 315                 320

Ser Gly Asp Leu Leu Gln Gln Ala Gln Glu Ile Arg Lys Val Phe Arg
                325                 330                 335

Ala Ala Ala Ala Gln Phe Gln Val Pro Trp Leu Glu Ser Val Leu Ile
            340                 345                 350

Val Val Ser Asn Asn Ile Asp Glu Glu Ala Leu Ala Arg Leu Ala Gln
        355                 360                 365

Glu Gly Ser Glu Val Asn Val Ile Gly Ile Gly Thr Ser Val Val Thr
    370                 375                 380
```

```
Cys Pro Gln Pro Ser Leu Gly Gly Val Tyr Lys Leu Val Ala Val
385                 390                 395                 400

Gly Gly Gln Pro Arg Met Lys Leu Thr Glu Asp Pro Glu Lys Gln Thr
            405                 410                 415

Leu Pro Gly Ser Lys Ala Ala Phe Arg Leu Leu Gly Ser Asp Gly Ser
                420                 425                 430

Pro Leu Met Asp Met Leu Gln Leu Ala Glu Glu Pro Val Pro Gln Ala
        435                 440                 445

Gly Gln Glu Leu Arg Val Trp Pro Pro Gly Ala Gln Glu Pro Cys Thr
    450                 455                 460

Val Arg Pro Ala Gln Val Glu Pro Leu Leu Arg Leu Cys Leu Gln Gln
465                 470                 475                 480

Gly Gln Leu Cys Glu Pro Leu Pro Ser Leu Ala Glu Ser Arg Ala Leu
            485                 490                 495

Ala Gln Leu Ser Leu Ser Arg Leu Ser Pro Glu His Arg Arg Leu Arg
                500                 505                 510

Ser Pro Ala Gln Tyr Gln Val Val Leu Ser Glu Arg Leu Gln Ala Leu
        515                 520                 525

Val Asn Ser Leu Cys Ala Gly Gln Ser Pro
    530                 535

<210> SEQ ID NO 77
<211> LENGTH: 911
<212> TYPE: PRT
<213> ORGANISM: Homo sapiens

<400> SEQUENCE: 77

Met Asp Gly Ala Met Gly Pro Arg Gly Leu Leu Leu Cys Met Tyr Leu
1               5                   10                  15

Val Ser Leu Leu Ile Leu Gln Ala Met Pro Ala Leu Gly Ser Ala Thr
                20                  25                  30

Gly Arg Ser Lys Ser Ser Glu Lys Arg Gln Ala Val Asp Thr Ala Val
            35                  40                  45

Asp Gly Val Phe Ile Arg Ser Leu Lys Val Asn Cys Lys Val Thr Ser
    50                  55                  60

Arg Phe Ala His Tyr Val Val Thr Ser Gln Val Val Asn Thr Ala Asn
65                  70                  75                  80

Glu Ala Arg Glu Val Ala Phe Asp Leu Glu Ile Pro Lys Thr Ala Phe
                85                  90                  95

Ile Ser Asp Phe Ala Val Thr Asp Gly Asn Ala Phe Ile Gly Asp
            100                 105                 110

Ile Lys Asp Lys Val Thr Ala Trp Lys Gln Tyr Arg Lys Ala Ala Ile
    115                 120                 125

Ser Gly Glu Asn Ala Gly Leu Val Arg Ala Ser Gly Arg Thr Met Glu
130                 135                 140

Gln Phe Thr Ile His Leu Thr Val Asn Pro Gln Ser Lys Val Thr Phe
145                 150                 155                 160

Gln Leu Thr Tyr Glu Glu Val Leu Lys Arg Asn His Met Gln Tyr Glu
                165                 170                 175

Ile Val Ile Lys Val Lys Pro Lys Gln Leu Val His His Phe Glu Ile
            180                 185                 190

Asp Val Asp Ile Phe Glu Pro Gln Gly Ile Ser Lys Leu Asp Ala Gln
    195                 200                 205

Ala Ser Phe Leu Pro Lys Glu Leu Ala Ala Gln Thr Ile Lys Lys Ser
```

```
            210                 215                 220
Phe Ser Gly Lys Lys Gly His Val Leu Phe Arg Pro Thr Val Ser Gln
225                 230                 235                 240

Gln Gln Ser Cys Pro Thr Cys Ser Thr Ser Leu Leu Asn Gly His Phe
                245                 250                 255

Lys Val Thr Tyr Asp Val Ser Arg Asp Lys Ile Cys Asp Leu Leu Val
                260                 265                 270

Ala Asn Asn His Phe Ala His Phe Phe Ala Pro Gln Asn Leu Thr Asn
            275                 280                 285

Met Asn Lys Asn Val Val Phe Val Ile Asp Ile Ser Gly Ser Met Arg
        290                 295                 300

Gly Gln Lys Val Lys Gln Thr Lys Glu Ala Leu Leu Lys Ile Leu Gly
305                 310                 315                 320

Asp Met Gln Pro Gly Asp Tyr Phe Asp Leu Val Leu Phe Gly Thr Arg
                325                 330                 335

Val Gln Ser Trp Lys Gly Ser Leu Val Gln Ala Ser Glu Ala Asn Leu
                340                 345                 350

Gln Ala Ala Gln Asp Phe Val Arg Gly Phe Ser Leu Asp Glu Ala Thr
            355                 360                 365

Asn Leu Asn Gly Gly Leu Leu Arg Gly Ile Glu Ile Leu Asn Gln Val
        370                 375                 380

Gln Glu Ser Leu Pro Glu Leu Ser Asn His Ala Ser Ile Leu Ile Met
385                 390                 395                 400

Leu Thr Asp Gly Asp Pro Thr Glu Gly Val Thr Asp Arg Ser Gln Ile
                405                 410                 415

Leu Lys Asn Val Arg Asn Ala Ile Arg Gly Arg Phe Pro Leu Tyr Asn
                420                 425                 430

Leu Gly Phe Gly His Asn Val Asp Phe Asn Phe Leu Glu Val Met Ser
            435                 440                 445

Met Glu Asn Asn Gly Arg Ala Gln Arg Ile Tyr Glu Asp His Asp Ala
        450                 455                 460

Thr Gln Gln Leu Gln Gly Phe Tyr Ser Gln Val Ala Lys Pro Leu Leu
465                 470                 475                 480

Val Asp Val Asp Leu Gln Tyr Pro Gln Asp Ala Val Leu Ala Leu Thr
                485                 490                 495

Gln Asn His His Lys Gln Tyr Tyr Glu Gly Ser Glu Ile Val Val Ala
            500                 505                 510

Gly Arg Ile Ala Asp Asn Lys Gln Ser Ser Phe Lys Ala Asp Val Gln
        515                 520                 525

Ala His Gly Glu Gly Gln Glu Phe Ser Ile Thr Cys Leu Val Asp Glu
530                 535                 540

Glu Glu Met Lys Lys Leu Leu Arg Glu Arg Gly His Met Leu Glu Asn
545                 550                 555                 560

His Val Glu Arg Leu Trp Ala Tyr Leu Thr Ile Gln Glu Leu Leu Ala
                565                 570                 575

Lys Arg Met Lys Val Asp Arg Glu Glu Arg Ala Asn Leu Ser Ser Gln
                580                 585                 590

Ala Leu Gln Met Ser Leu Asp Tyr Gly Phe Val Thr Pro Leu Thr Ser
            595                 600                 605

Met Ser Ile Arg Gly Met Ala Asp Gln Asp Gly Leu Lys Pro Thr Ile
        610                 615                 620

Asp Lys Pro Ser Glu Asp Ser Pro Pro Leu Glu Met Leu Gly Pro Arg
625                 630                 635                 640
```

```
Arg Thr Phe Val Leu Ser Ala Leu Gln Pro Ser Pro Thr His Ser Ser
                645                 650                 655

Ser Asn Thr Gln Arg Leu Pro Asp Arg Val Thr Gly Val Asp Thr Asp
            660                 665                 670

Pro His Phe Ile Ile His Val Pro Gln Lys Glu Asp Thr Leu Cys Phe
        675                 680                 685

Asn Ile Asn Glu Glu Pro Gly Val Ile Leu Ser Leu Val Gln Asp Pro
    690                 695                 700

Asn Thr Gly Phe Ser Val Asn Gly Gln Leu Ile Gly Asn Lys Ala Arg
705                 710                 715                 720

Ser Pro Gly Gln His Asp Gly Thr Tyr Phe Gly Arg Leu Gly Ile Ala
                725                 730                 735

Asn Pro Ala Thr Asp Phe Gln Leu Glu Val Thr Pro Gln Asn Ile Thr
            740                 745                 750

Leu Asn Pro Gly Phe Gly Gly Pro Val Phe Ser Trp Arg Asp Gln Ala
        755                 760                 765

Val Leu Arg Gln Asp Gly Val Val Thr Ile Asn Lys Lys Arg Asn
    770                 775                 780

Leu Val Val Ser Val Asp Asp Gly Gly Thr Phe Glu Val Val Leu His
785                 790                 795                 800

Arg Val Trp Lys Gly Ser Ser Val His Gln Asp Phe Leu Gly Phe Tyr
                805                 810                 815

Val Leu Asp Ser His Arg Met Ser Ala Arg Thr His Gly Leu Leu Gly
            820                 825                 830

Gln Phe Phe His Pro Ile Gly Phe Glu Val Ser Asp Ile His Pro Gly
        835                 840                 845

Ser Asp Pro Thr Lys Pro Asp Ala Thr Met Val Arg Asn Arg Arg
    850                 855                 860

Leu Thr Val Thr Arg Gly Leu Gln Lys Asp Tyr Ser Lys Asp Pro Trp
865                 870                 875                 880

His Gly Ala Glu Val Ser Cys Trp Phe Ile His Asn Asn Gly Ala Gly
                885                 890                 895

Leu Ile Asp Gly Ala Tyr Thr Asp Tyr Ile Val Pro Asp Ile Phe
            900                 905                 910

<210> SEQ ID NO 78
<211> LENGTH: 306
<212> TYPE: PRT
<213> ORGANISM: Homo sapiens

<400> SEQUENCE: 78

Met Arg Pro Ala Ala Leu Arg Gly Ala Leu Leu Gly Cys Leu Cys Leu
1               5                   10                  15

Ala Leu Leu Cys Leu Gly Gly Ala Asp Lys Arg Leu Arg Asp Asn His
                20                  25                  30

Glu Trp Lys Lys Leu Ile Met Val Gln His Trp Pro Glu Thr Val Cys
            35                  40                  45

Glu Lys Ile Gln Asn Asp Cys Arg Asp Pro Pro Asp Tyr Trp Thr Ile
        50                  55                  60

His Gly Leu Trp Pro Asp Lys Ser Glu Gly Cys Asn Arg Ser Trp Pro
65                  70                  75                  80

Phe Asn Leu Glu Glu Ile Lys Val Leu Thr Phe Asn Tyr Ile Ser Thr
                85                  90                  95

Ala Glu Cys Ser Ser His Arg Leu Ser Ser Ser Pro Pro Gly Leu Thr
```

```
                100             105             110
Ala Gly Asn Gly Phe Trp Gly Gly Ser Glu Glu Arg Cys Gly Arg Gly
            115                 120                 125
Trp Pro Met Phe Leu Glu Gln Ile Lys Asp Leu Leu Pro Glu Met Arg
        130                 135                 140
Ala Tyr Trp Pro Asp Val Ile His Ser Phe Pro Asn Arg Ser Arg Phe
145                 150                 155                 160
Trp Lys His Glu Trp Glu Lys His Gly Thr Cys Ala Ala Gln Val Asp
                165                 170                 175
Ala Leu Asn Ser Gln Lys Lys Tyr Phe Gly Arg Ser Leu Glu Leu Tyr
            180                 185                 190
Arg Glu Leu Asp Leu Asn Ser Val Leu Leu Lys Leu Gly Ile Lys Pro
        195                 200                 205
Ser Ile Asn Tyr Tyr Gln Val Ala Asp Phe Lys Asp Ala Leu Ala Arg
210                 215                 220
Val Tyr Gly Val Ile Pro Lys Ile Gln Cys Leu Pro Pro Ser Gln Asp
225                 230                 235                 240
Glu Glu Val Gln Thr Ile Gly Gln Ile Glu Leu Cys Leu Thr Lys Gln
                245                 250                 255
Asp Gln Gln Leu Gln Asn Cys Thr Glu Pro Gly Glu Gln Pro Ser Pro
            260                 265                 270
Lys Gln Glu Val Trp Leu Ala Asn Gly Ala Ala Glu Ser Arg Gly Leu
        275                 280                 285
Arg Val Cys Glu Asp Gly Pro Val Phe Tyr Pro Pro Lys Lys Thr
    290                 295                 300
Lys His
305

<210> SEQ ID NO 79
<211> LENGTH: 222
<212> TYPE: PRT
<213> ORGANISM: Homo sapiens

<400> SEQUENCE: 79

Met Leu Ser Arg Ala Val Cys Gly Thr Ser Arg Gln Leu Ala Pro Ala
1               5                   10                  15
Leu Gly Tyr Leu Gly Ser Arg Gln Lys His Ser Leu Pro Asp Leu Pro
            20                  25                  30
Tyr Asp Tyr Gly Ala Leu Glu Pro His Ile Asn Ala Gln Ile Met Gln
        35                  40                  45
Leu His His Ser Lys His His Ala Ala Tyr Val Asn Asn Leu Asn Val
50                  55                  60
Thr Glu Glu Lys Tyr Gln Glu Ala Leu Ala Lys Gly Asp Val Thr Ala
65                  70                  75                  80
Gln Ile Ala Leu Gln Pro Ala Leu Lys Phe Asn Gly Gly Gly His Ile
                85                  90                  95
Asn His Ser Ile Phe Trp Thr Asn Leu Ser Pro Asn Gly Gly Gly Glu
            100                 105                 110
Pro Lys Gly Glu Leu Leu Glu Ala Ile Lys Arg Asp Phe Gly Ser Phe
        115                 120                 125
Asp Lys Phe Lys Glu Lys Leu Thr Ala Ala Ser Val Gly Val Gln Gly
    130                 135                 140
Ser Gly Trp Gly Trp Leu Gly Phe Asn Lys Glu Arg Gly His Leu Gln
145                 150                 155                 160
```

```
Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Lys
    210                 215                 220
```

<210> SEQ ID NO 80
<211> LENGTH: 169
<212> TYPE: PRT
<213> ORGANISM: Homo sapiens

<400> SEQUENCE: 80

```
Met Ser Ser Tyr Gln Gln Lys Gln Thr Phe Thr Pro Pro Pro Gln Leu
1               5                   10                  15

Gln Gln Gln Gln Val Lys Gln Pro Ser Gln Pro Pro Gln Glu Ile
            20                  25                  30

Phe Val Pro Thr Thr Lys Glu Pro Cys His Ser Lys Val Pro Gln Pro
            35                  40                  45

Gly Asn Thr Lys Ile Pro Glu Pro Gly Cys Thr Lys Val Pro Glu Pro
    50                  55                  60

Gly Cys Thr Lys Val Pro Glu Pro Gly Cys Thr Lys Val Pro Glu Pro
65                  70                  75                  80

Gly Cys Thr Lys Val Pro Glu Pro Gly Cys Thr Lys Val Pro Glu Pro
                85                  90                  95

Gly Cys Thr Lys Val Pro Glu Pro Gly Tyr Thr Lys Val Pro Glu Pro
            100                 105                 110

Gly Ser Ile Lys Val Pro Asp Gln Gly Phe Ile Lys Phe Pro Glu Pro
            115                 120                 125

Gly Ala Ile Lys Val Pro Glu Gln Gly Tyr Thr Lys Val Pro Val Pro
            130                 135                 140

Gly Tyr Thr Lys Leu Pro Glu Pro Cys Pro Ser Thr Val Thr Pro Gly
145                 150                 155                 160

Pro Ala Gln Gln Lys Thr Lys Gln Lys
                165
```

<210> SEQ ID NO 81
<211> LENGTH: 550
<212> TYPE: PRT
<213> ORGANISM: Homo sapiens

<400> SEQUENCE: 81

```
Met Trp Lys Ala Ser Ala Gly His Ala Val Ser Ile Ala Gln Asp Asp
1               5                   10                  15

Ala Gly Ala Asp Asp Trp Glu Thr Asp Pro Asp Phe Val Asn Asp Val
            20                  25                  30

Ser Glu Lys Glu Gln Arg Trp Gly Ala Lys Thr Val Gln Gly Ser Gly
            35                  40                  45

His Gln Glu His Ile Asn Ile His Lys Leu Arg Glu Asn Val Phe Gln
        50                  55                  60

Glu His Gln Thr Leu Lys Glu Lys Glu Leu Glu Thr Gly Pro Lys Ala
65                  70                  75                  80

Ser His Gly Tyr Gly Gly Lys Phe Gly Val Glu Gln Asp Arg Met Asp
                85                  90                  95
```

```
Lys Ser Ala Val Gly His Glu Tyr Gln Ser Lys Leu Ser Lys His Cys
                100                 105                 110

Ser Gln Val Asp Ser Val Arg Gly Phe Gly Gly Lys Phe Gly Val Gln
                115                 120                 125

Met Asp Arg Val Asp Gln Ser Ala Val Gly Phe Glu Tyr Gln Gly Lys
            130                 135                 140

Thr Glu Lys His Ala Ser Gln Lys Asp Tyr Ser Ser Gly Phe Gly Gly
145                 150                 155                 160

Lys Tyr Gly Val Gln Ala Asp Arg Val Asp Lys Ser Ala Val Gly Phe
                165                 170                 175

Asp Tyr Gln Gly Lys Thr Glu Lys His Glu Ser Gln Arg Asp Tyr Ser
            180                 185                 190

Lys Gly Phe Gly Gly Lys Tyr Gly Ile Asp Lys Asp Lys Val Asp Lys
            195                 200                 205

Ser Ala Val Gly Phe Glu Tyr Gln Gly Lys Thr Glu Lys His Glu Ser
210                 215                 220

Gln Lys Asp Tyr Val Lys Gly Phe Gly Gly Lys Phe Gly Val Gln Thr
225                 230                 235                 240

Asp Arg Gln Asp Lys Cys Ala Leu Gly Trp Asp His Gln Glu Lys Leu
                245                 250                 255

Gln Leu His Glu Ser Gln Lys Asp Tyr Lys Thr Gly Phe Gly Gly Lys
            260                 265                 270

Phe Gly Val Gln Ser Glu Arg Gln Asp Ser Ala Ala Val Gly Phe Asp
            275                 280                 285

Tyr Lys Glu Lys Leu Ala Lys His Glu Ser Gln Asp Tyr Ser Lys
            290                 295                 300

Gly Phe Gly Gly Lys Tyr Gly Val Gln Lys Asp Arg Met Asp Lys Asn
305                 310                 315                 320

Ala Ser Thr Phe Glu Asp Val Thr Gln Val Ser Ser Ala Tyr Gln Lys
                325                 330                 335

Thr Val Pro Val Glu Ala Val Thr Ser Lys Thr Ser Asn Ile Arg Ala
            340                 345                 350

Asn Phe Glu Asn Leu Ala Lys Glu Lys Glu Gln Glu Asp Arg Arg Lys
            355                 360                 365

Ala Glu Ala Glu Arg Ala Gln Arg Met Ala Lys Glu Arg Gln Glu Gln
            370                 375                 380

Glu Glu Ala Arg Arg Lys Leu Glu Glu Gln Ala Arg Ala Lys Thr Gln
385                 390                 395                 400

Thr Pro Pro Val Ser Pro Ala Pro Gln Pro Thr Glu Glu Arg Leu Pro
                405                 410                 415

Ser Ser Pro Val Tyr Glu Asp Ala Ala Ser Phe Lys Ala Glu Leu Ser
                420                 425                 430

Tyr Arg Gly Pro Val Ser Gly Thr Glu Pro Glu Pro Val Tyr Ser Met
            435                 440                 445

Glu Ala Ala Asp Tyr Arg Glu Ala Ser Ser Gln Gln Gly Leu Ala Tyr
450                 455                 460

Ala Thr Glu Ala Val Tyr Glu Ser Ala Glu Ala Pro Gly His Tyr Pro
465                 470                 475                 480

Ala Glu Asp Ser Thr Tyr Asp Glu Tyr Glu Asn Asp Leu Gly Ile Thr
                485                 490                 495

Ala Val Ala Leu Tyr Asp Tyr Gln Ala Ala Gly Asp Asp Glu Ile Ser
            500                 505                 510

Phe Asp Pro Asp Asp Ile Ile Thr Asn Ile Glu Met Ile Asp Asp Gly
```

```
                515                 520                 525
Trp Trp Arg Gly Val Cys Lys Gly Arg Tyr Gly Leu Phe Pro Ala Asn
    530                 535                 540
Tyr Val Glu Leu Arg Gln
545             550

<210> SEQ ID NO 82
<211> LENGTH: 445
<212> TYPE: PRT
<213> ORGANISM: Homo sapiens

<400> SEQUENCE: 82

Met Arg Glu Ile Val His Leu Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Glu Arg Ile Asn
        35                  40                  45

Val Tyr Tyr Asn Glu Ala Thr Gly Gly Lys Tyr Val Pro Arg Ala Val
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Arg Lys Glu Ala Glu Ser Cys Asp
        115                 120                 125

Cys Leu Gln Gly Phe Gln Leu Thr His Ser Leu Gly Gly Gly Thr Gly
        130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Met Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335
```

-continued

```
Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ser Ala Thr Phe Ile
355                 360                 365

Gly Asn Ser Thr Ala Ile Gln Glu Leu Phe Lys Arg Ile Ser Glu Gln
        370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Gly Glu Phe Glu Glu Glu Ala Glu Glu Val Ala
        435                 440                 445

<210> SEQ ID NO 83
<211> LENGTH: 227
<212> TYPE: PRT
<213> ORGANISM: Homo sapiens

<400> SEQUENCE: 83

Met Ala Gly Ile Thr Thr Ile Glu Ala Val Lys Arg Lys Ile Gln Val
1               5                   10                  15

Leu Gln Gln Gln Ala Asp Asp Ala Glu Glu Arg Ala Glu Arg Leu Gln
            20                  25                  30

Arg Glu Val Glu Gly Glu Arg Arg Ala Arg Glu Gln Ala Glu Ala Glu
        35                  40                  45

Val Ala Ser Leu Asn Arg Arg Ile Gln Leu Val Glu Glu Glu Leu Asp
50                  55                  60

Arg Ala Gln Glu Arg Leu Ala Thr Ala Leu Gln Lys Leu Glu Glu Ala
65                  70                  75                  80

Glu Lys Ala Ala Asp Glu Ser Glu Arg Gly Met Lys Val Ile Glu Asn
                85                  90                  95

Arg Ala Leu Lys Asp Glu Glu Lys Met Glu Leu Gln Glu Ile Gln Leu
            100                 105                 110

Lys Glu Ala Lys His Ile Ala Glu Glu Ala Asp Arg Lys Tyr Glu Glu
        115                 120                 125

Val Ala Arg Lys Leu Val Ile Ile Glu Gly Asp Leu Glu Arg Thr Glu
130                 135                 140

Glu Arg Ala Glu Leu Ala Glu Ser Arg Cys Arg Glu Met Asp Glu Gln
145                 150                 155                 160

Ile Arg Leu Met Asp Gln Asn Leu Lys Cys Leu Ser Ala Ala Glu Glu
                165                 170                 175

Lys Ala Glu Thr Arg Ala Glu Phe Ala Glu Arg Ser Val Ala Lys Leu
            180                 185                 190

Glu Lys Thr Ile Asp Asp Leu Glu Asp Lys Leu Lys Cys Thr Lys Glu
        195                 200                 205

Glu His Leu Cys Thr Gln Arg Met Leu Asp Gln Thr Leu Leu Asp Leu
210                 215                 220

Asn Glu Met
225

<210> SEQ ID NO 84
<211> LENGTH: 698
<212> TYPE: PRT
<213> ORGANISM: Homo sapiens
```

<400> SEQUENCE: 84

```
Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
            165                 170                 175

Cys Ala Pro Cys Ala Asp Gly Thr Asp Phe Pro Gln Leu Cys Gln Leu
        180                 185                 190

Cys Pro Gly Cys Gly Cys Ser Thr Leu Asn Gln Tyr Phe Gly Tyr Ser
    195                 200                 205

Gly Ala Phe Lys Cys Leu Lys Asp Gly Ala Gly Asp Val Ala Phe Val
    210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
            245                 250                 255

Tyr Lys Asp Cys His Leu Ala Gln Val Pro Ser His Thr Val Val Ala
        260                 265                 270

Arg Ser Met Gly Gly Lys Glu Asp Leu Ile Trp Glu Leu Leu Asn Gln
    275                 280                 285

Ala Gln Glu His Phe Gly Lys Asp Lys Ser Lys Glu Phe Gln Leu Phe
290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
            325                 330                 335

Glu Tyr Val Thr Ala Ile Arg Asn Leu Arg Glu Gly Thr Cys Pro Glu
        340                 345                 350

Ala Pro Thr Asp Glu Cys Lys Pro Val Lys Trp Cys Ala Leu Ser His
    355                 360                 365

His Glu Arg Leu Lys Cys Asp Glu Trp Ser Val Asn Ser Val Gly Lys
    370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
```

```
            405                 410                 415
Ile Ala Gly Lys Cys Gly Leu Val Pro Val Leu Ala Glu Asn Tyr Asn
            420                 425                 430

Lys Ser Asp Asn Cys Glu Asp Thr Pro Glu Ala Gly Tyr Phe Ala Ile
            435                 440                 445

Ala Val Val Lys Lys Ser Ala Ser Asp Leu Thr Trp Asp Asn Leu Lys
        450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
            485                 490                 495

Glu Phe Phe Ser Glu Gly Cys Ala Pro Gly Ser Lys Lys Asp Ser Ser
            500                 505                 510

Leu Cys Lys Leu Cys Met Gly Ser Gly Leu Asn Leu Cys Glu Pro Asn
            515                 520                 525

Asn Lys Glu Gly Tyr Tyr Gly Tyr Thr Gly Ala Phe Arg Cys Leu Val
            530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
            580                 585                 590

Tyr Ala Asn Cys His Leu Ala Arg Ala Pro Asn His Ala Val Val Thr
            595                 600                 605

Arg Lys Asp Lys Glu Ala Cys Val His Lys Ile Leu Arg Gln Gln Gln
610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
            645                 650                 655

Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
            675                 680                 685

Leu Leu Glu Ala Cys Thr Phe Arg Arg Pro
            690                 695

<210> SEQ ID NO 85
<211> LENGTH: 210
<212> TYPE: PRT
<213> ORGANISM: Homo sapiens

<400> SEQUENCE: 85

Met Pro Pro Tyr Thr Val Val Tyr Phe Pro Val Arg Gly Arg Cys Ala
1               5                   10                  15

Ala Leu Arg Met Leu Leu Ala Asp Gln Gly Gln Ser Trp Lys Glu Glu
            20                  25                  30

Val Val Thr Val Glu Thr Trp Gln Glu Gly Ser Leu Lys Ala Ser Cys
        35                  40                  45

Leu Tyr Gly Gln Leu Pro Lys Phe Gln Asp Gly Asp Leu Thr Leu Tyr
    50                  55                  60

Gln Ser Asn Thr Ile Leu Arg His Leu Gly Arg Thr Leu Gly Leu Tyr
65                  70                  75                  80
```

```
Gly Lys Asp Gln Gln Glu Ala Ala Leu Val Asp Met Val Asn Asp Gly
             85                  90                  95

Val Glu Asp Leu Arg Cys Lys Tyr Ile Ser Leu Ile Tyr Thr Asn Tyr
            100                 105                 110

Glu Ala Gly Lys Asp Asp Tyr Val Lys Ala Leu Pro Gly Gln Leu Lys
            115                 120                 125

Pro Phe Glu Thr Leu Leu Ser Gln Asn Gln Gly Gly Lys Thr Phe Ile
            130                 135                 140

Val Gly Asp Gln Ile Ser Phe Ala Asp Tyr Asn Leu Leu Asp Leu Leu
145                 150                 155                 160

Leu Ile His Glu Val Leu Ala Pro Gly Cys Leu Asp Ala Phe Pro Leu
                165                 170                 175

Leu Ser Ala Tyr Val Gly Arg Leu Ser Ala Arg Pro Lys Leu Lys Ala
            180                 185                 190

Phe Leu Ala Ser Pro Glu Tyr Val Asn Leu Pro Ile Asn Gly Asn Gly
            195                 200                 205

Lys Gln
    210

<210> SEQ ID NO 86
<211> LENGTH: 478
<212> TYPE: PRT
<213> ORGANISM: Homo sapiens

<400> SEQUENCE: 86

Met Ala Pro Leu Arg Pro Leu Leu Ile Leu Ala Leu Leu Ala Trp Val
1               5                  10                  15

Ala Leu Ala Asp Gln Glu Ser Cys Lys Gly Arg Cys Thr Glu Gly Phe
            20                  25                  30

Asn Val Asp Lys Lys Cys Gln Cys Asp Glu Leu Cys Ser Tyr Tyr Gln
            35                  40                  45

Ser Cys Cys Thr Asp Tyr Thr Ala Glu Cys Lys Pro Gln Val Thr Arg
        50                  55                  60

Gly Asp Val Phe Thr Met Pro Glu Asp Glu Tyr Thr Val Tyr Asp Asp
65                  70                  75                  80

Gly Glu Glu Lys Asn Asn Ala Thr Val His Glu Gln Val Gly Gly Pro
                85                  90                  95

Ser Leu Thr Ser Asp Leu Gln Ala Gln Ser Lys Gly Asn Pro Glu Gln
            100                 105                 110

Thr Pro Val Leu Lys Pro Glu Glu Ala Pro Ala Pro Glu Val Gly
            115                 120                 125

Ala Ser Lys Pro Glu Gly Ile Asp Ser Arg Pro Glu Thr Leu His Pro
130                 135                 140

Gly Arg Pro Gln Pro Pro Ala Glu Glu Glu Leu Cys Ser Gly Lys Pro
145                 150                 155                 160

Phe Asp Ala Phe Thr Asp Leu Lys Asn Gly Ser Leu Phe Ala Phe Arg
            165                 170                 175

Gly Gln Tyr Cys Tyr Glu Leu Asp Glu Lys Ala Val Arg Pro Gly Tyr
            180                 185                 190

Pro Lys Leu Ile Arg Asp Val Trp Gly Ile Glu Gly Pro Ile Asp Ala
            195                 200                 205

Ala Phe Thr Arg Ile Asn Cys Gln Gly Lys Thr Tyr Leu Phe Lys Gly
            210                 215                 220

Ser Gln Tyr Trp Arg Phe Glu Asp Gly Val Leu Asp Pro Asp Tyr Pro
225                 230                 235                 240
```

```
Arg Asn Ile Ser Asp Gly Phe Asp Gly Ile Pro Asp Asn Val Asp Ala
                245                 250                 255

Ala Leu Ala Leu Pro Ala His Ser Tyr Ser Gly Arg Glu Arg Val Tyr
            260                 265                 270

Phe Phe Lys Gly Lys Gln Tyr Trp Glu Tyr Gln Phe Gln His Gln Pro
            275                 280                 285

Ser Gln Glu Glu Cys Glu Gly Ser Ser Leu Ser Ala Val Phe Glu His
        290                 295                 300

Phe Ala Met Met Gln Arg Asp Ser Trp Glu Asp Ile Phe Glu Leu Leu
305                 310                 315                 320

Phe Trp Gly Arg Thr Ser Ala Gly Thr Arg Gln Pro Gln Phe Ile Ser
                325                 330                 335

Arg Asp Trp His Gly Val Pro Gly Gln Val Asp Ala Ala Met Ala Gly
            340                 345                 350

Arg Ile Tyr Ile Ser Gly Met Ala Pro Arg Pro Ser Leu Ala Lys Lys
            355                 360                 365

Gln Arg Phe Arg His Arg Asn Arg Lys Gly Tyr Arg Ser Gln Arg Gly
        370                 375                 380

His Ser Arg Gly Arg Asn Gln Asn Ser Arg Arg Pro Ser Arg Ala Thr
385                 390                 395                 400

Trp Leu Ser Leu Phe Ser Ser Glu Glu Ser Asn Leu Gly Ala Asn Asn
                405                 410                 415

Tyr Asp Asp Tyr Arg Met Asp Trp Leu Val Pro Ala Thr Cys Glu Pro
            420                 425                 430

Ile Gln Ser Val Phe Phe Phe Ser Gly Asp Lys Tyr Tyr Arg Val Asn
            435                 440                 445

Leu Arg Thr Arg Arg Val Asp Thr Val Asp Pro Pro Tyr Pro Arg Ser
        450                 455                 460

Ile Ala Gln Tyr Trp Leu Gly Cys Pro Ala Pro Gly His Leu
465                 470                 475

<210> SEQ ID NO 87
<211> LENGTH: 114
<212> TYPE: PRT
<213> ORGANISM: Homo sapiens

<400> SEQUENCE: 87

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
                20                  25                  30

Asn Gln Gly Glu Phe Lys Glu Leu Val Arg Lys Asp Leu Gln Asn Phe
            35                  40                  45

Leu Lys Lys Glu Asn Lys Asn Glu Lys Val Ile Glu His Ile Met Glu
        50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro

<210> SEQ ID NO 88
```

```
<211> LENGTH: 15
<212> TYPE: PRT
<213> ORGANISM: Homo sapiens

<400> SEQUENCE: 88

Ser Cys Cys Glu Glu Gln Asn Lys Val Asn Cys Leu Gln Thr Arg
1               5                   10                  15

<210> SEQ ID NO 89
<211> LENGTH: 14
<212> TYPE: PRT
<213> ORGANISM: Homo sapiens

<400> SEQUENCE: 89

Ala Glu Ser Pro Glu Val Cys Phe Asn Glu Glu Ser Pro Lys
1               5                   10

<210> SEQ ID NO 90
<211> LENGTH: 14
<212> TYPE: PRT
<213> ORGANISM: Homo sapiens

<400> SEQUENCE: 90

Glu Gly Lys Phe Thr Asp Ser Glu Asn Val Cys Gln Glu Arg
1               5                   10

<210> SEQ ID NO 91
<211> LENGTH: 13
<212> TYPE: PRT
<213> ORGANISM: Homo sapiens

<400> SEQUENCE: 91

Glu Ser Leu Leu Asn His Phe Leu Tyr Glu Val Ala Arg
1               5                   10

<210> SEQ ID NO 92
<211> LENGTH: 11
<212> TYPE: PRT
<213> ORGANISM: Homo sapiens

<400> SEQUENCE: 92

Phe Thr Asp Ser Glu Asn Val Cys Gln Glu Arg
1               5                   10

<210> SEQ ID NO 93
<211> LENGTH: 12
<212> TYPE: PRT
<213> ORGANISM: Homo sapiens

<400> SEQUENCE: 93

Arg His Pro Asp Leu Ser Ile Pro Glu Leu Leu Arg
1               5                   10

<210> SEQ ID NO 94
<211> LENGTH: 17
<212> TYPE: PRT
<213> ORGANISM: Homo sapiens

<400> SEQUENCE: 94

Ser Asp Val Gly Phe Leu Pro Pro Phe Pro Thr Leu Asp Pro Glu Glu
1               5                   10                  15

Lys

<210> SEQ ID NO 95
```

```
<211> LENGTH: 28
<212> TYPE: PRT
<213> ORGANISM: Homo sapiens

<400> SEQUENCE: 95

Cys Ser Pro His Leu Val Leu Ser Ala Leu Thr Ser Asp Asn His Gly
 1               5                  10                  15

Ala Thr Tyr Ala Phe Ser Gly Thr His Tyr Trp Arg
             20                  25

<210> SEQ ID NO 96
<211> LENGTH: 9
<212> TYPE: PRT
<213> ORGANISM: Homo sapiens

<400> SEQUENCE: 96

Asp Tyr Phe Met Pro Cys Pro Gly Arg
 1               5

<210> SEQ ID NO 97
<211> LENGTH: 24
<212> TYPE: PRT
<213> ORGANISM: Homo sapiens

<400> SEQUENCE: 97

Glu Val Gly Thr Pro His Gly Ile Ile Leu Asp Ser Val Asp Ala Ala
 1               5                  10                  15

Phe Ile Cys Pro Gly Ser Ser Arg
             20

<210> SEQ ID NO 98
<211> LENGTH: 14
<212> TYPE: PRT
<213> ORGANISM: Homo sapiens

<400> SEQUENCE: 98

Glu Trp Phe Trp Asp Leu Ala Thr Gly Thr Met Lys Glu Arg
 1               5                  10

<210> SEQ ID NO 99
<211> LENGTH: 12
<212> TYPE: PRT
<213> ORGANISM: Homo sapiens

<400> SEQUENCE: 99

Gly Asp Lys Val Trp Val Tyr Pro Pro Glu Lys Lys
 1               5                  10

<210> SEQ ID NO 100
<211> LENGTH: 15
<212> TYPE: PRT
<213> ORGANISM: Homo sapiens

<400> SEQUENCE: 100

Gly Glu Cys Gln Ala Glu Gly Val Leu Phe Phe Gln Gly Asp Arg
 1               5                  10                  15

<210> SEQ ID NO 101
<211> LENGTH: 11
<212> TYPE: PRT
<213> ORGANISM: Homo sapiens

<400> SEQUENCE: 101

Gly Gly Tyr Thr Leu Val Ser Gly Tyr Pro Lys
```

```
<210> SEQ ID NO 102
<211> LENGTH: 21
<212> TYPE: PRT
<213> ORGANISM: Homo sapiens

<400> SEQUENCE: 102

Leu Leu Gln Asp Glu Phe Pro Gly Ile Pro Ser Pro Leu Asp Ala Ala
1               5                   10                  15

Val Glu Cys His Arg
            20

<210> SEQ ID NO 103
<211> LENGTH: 11
<212> TYPE: PRT
<213> ORGANISM: Homo sapiens

<400> SEQUENCE: 103

Asn Phe Pro Ser Pro Val Asp Ala Ala Phe Arg
1               5                   10

<210> SEQ ID NO 104
<211> LENGTH: 10
<212> TYPE: PRT
<213> ORGANISM: Homo sapiens

<400> SEQUENCE: 104

Gln Gly His Asn Ser Val Phe Leu Ile Lys
1               5                   10

<210> SEQ ID NO 105
<211> LENGTH: 8
<212> TYPE: PRT
<213> ORGANISM: Homo sapiens

<400> SEQUENCE: 105

Arg Leu Trp Trp Leu Asp Leu Lys
1               5

<210> SEQ ID NO 106
<211> LENGTH: 16
<212> TYPE: PRT
<213> ORGANISM: Homo sapiens

<400> SEQUENCE: 106

Ser Gly Ala Gln Ala Thr Trp Thr Glu Leu Pro Trp Pro His Glu Lys
1               5                   10                  15

<210> SEQ ID NO 107
<211> LENGTH: 30
<212> TYPE: PRT
<213> ORGANISM: Homo sapiens

<400> SEQUENCE: 107

Ser Leu Gly Pro Asn Ser Cys Ser Ala Asn Gly Pro Gly Leu Tyr Leu
1               5                   10                  15

Ile His Gly Pro Asn Leu Tyr Cys Tyr Ser Asp Val Glu Lys
            20                  25                  30

<210> SEQ ID NO 108
<211> LENGTH: 35
<212> TYPE: PRT
<213> ORGANISM: Homo sapiens
```

-continued

```
<400> SEQUENCE: 108

Ser Leu Gly Pro Asn Ser Cys Ser Ala Asn Gly Pro Gly Leu Tyr Leu
1               5                   10                  15

Ile His Gly Pro Asn Leu Tyr Cys Tyr Ser Asp Val Glu Lys Leu Asn
                20                  25                  30

Ala Ala Lys
        35

<210> SEQ ID NO 109
<211> LENGTH: 9
<212> TYPE: PRT
<213> ORGANISM: Homo sapiens

<400> SEQUENCE: 109

Val Trp Val Tyr Pro Pro Glu Lys Lys
1               5

<210> SEQ ID NO 110
<211> LENGTH: 13
<212> TYPE: PRT
<213> ORGANISM: Homo sapiens

<400> SEQUENCE: 110

Trp Lys Asn Phe Pro Ser Pro Val Asp Ala Ala Phe Arg
1               5                   10

<210> SEQ ID NO 111
<211> LENGTH: 15
<212> TYPE: PRT
<213> ORGANISM: Homo sapiens

<400> SEQUENCE: 111

Trp Leu Gly Arg Tyr Tyr Cys Phe Gln Gly Asn Gln Phe Leu Arg
1               5                   10                  15

<210> SEQ ID NO 112
<211> LENGTH: 11
<212> TYPE: PRT
<213> ORGANISM: Homo sapiens

<400> SEQUENCE: 112

Tyr Tyr Cys Phe Gln Gly Asn Gln Phe Leu Arg
1               5                   10

<210> SEQ ID NO 113
<211> LENGTH: 20
<212> TYPE: PRT
<213> ORGANISM: Homo sapiens

<400> SEQUENCE: 113

Ala Asp Glu Ile Ala Lys Ala Gln Val Ala Arg Pro Gly Gly Asp Thr
1               5                   10                  15

Ile Phe Gly Lys
            20

<210> SEQ ID NO 114
<211> LENGTH: 20
<212> TYPE: PRT
<213> ORGANISM: Homo sapiens

<400> SEQUENCE: 114

Cys Leu Ala Phe His Asp Ile Ser Pro Gln Ala Pro Thr His Phe Leu
```

```
1               5                   10                  15

Val Ile Pro Lys
            20

<210> SEQ ID NO 115
<211> LENGTH: 26
<212> TYPE: PRT
<213> ORGANISM: Homo sapiens

<400> SEQUENCE: 115

Cys Cys Val Glu Cys Pro Pro Cys Pro Ala Pro Val Ala Gly Pro
1               5                   10                  15

Ser Val Phe Leu Phe Pro Pro Lys Pro Lys
            20                  25

<210> SEQ ID NO 116
<211> LENGTH: 14
<212> TYPE: PRT
<213> ORGANISM: Homo sapiens

<400> SEQUENCE: 116

Cys Lys Val Ser Asn Lys Gly Leu Pro Ala Pro Ile Glu Lys
1               5                   10

<210> SEQ ID NO 117
<211> LENGTH: 7
<212> TYPE: PRT
<213> ORGANISM: Homo sapiens

<400> SEQUENCE: 117

Asp Thr Leu Met Ile Ser Arg
1               5

<210> SEQ ID NO 118
<211> LENGTH: 12
<212> TYPE: PRT
<213> ORGANISM: Homo sapiens

<400> SEQUENCE: 118

Gly Pro Ser Val Phe Pro Leu Ala Pro Cys Ser Arg
1               5                   10

<210> SEQ ID NO 119
<211> LENGTH: 27
<212> TYPE: PRT
<213> ORGANISM: Homo sapiens

<400> SEQUENCE: 119

Lys Cys Cys Val Glu Cys Pro Pro Cys Pro Ala Pro Val Ala Gly
1               5                   10                  15

Pro Ser Val Phe Leu Phe Pro Pro Lys Pro Lys
            20                  25

<210> SEQ ID NO 120
<211> LENGTH: 10
<212> TYPE: PRT
<213> ORGANISM: Homo sapiens

<400> SEQUENCE: 120

Asn Gln Val Ser Leu Thr Cys Leu Val Lys
1               5                   10

<210> SEQ ID NO 121
```

```
<211> LENGTH: 14
<212> TYPE: PRT
<213> ORGANISM: Homo sapiens

<400> SEQUENCE: 121

Ser Thr Ser Glu Ser Thr Ala Ala Leu Gly Cys Leu Val Lys
1               5                   10

<210> SEQ ID NO 122
<211> LENGTH: 17
<212> TYPE: PRT
<213> ORGANISM: Homo sapiens

<400> SEQUENCE: 122

Thr Lys Gly Gln Pro Arg Glu Pro Gln Val Tyr Thr Leu Pro Pro Ser
1               5                   10                  15

Arg

<210> SEQ ID NO 123
<211> LENGTH: 17
<212> TYPE: PRT
<213> ORGANISM: Homo sapiens

<400> SEQUENCE: 123

Thr Thr Pro Pro Met Leu Asp Ser Asp Gly Ser Phe Phe Leu Tyr Ser
1               5                   10                  15

Lys

<210> SEQ ID NO 124
<211> LENGTH: 12
<212> TYPE: PRT
<213> ORGANISM: Homo sapiens

<400> SEQUENCE: 124

Val Ser Asn Lys Gly Leu Pro Ala Pro Ile Glu Lys
1               5                   10

<210> SEQ ID NO 125
<211> LENGTH: 16
<212> TYPE: PRT
<213> ORGANISM: Homo sapiens

<400> SEQUENCE: 125

Val Val Ser Val Leu Thr Val Val His Gln Asp Trp Leu Asn Gly Lys
1               5                   10                  15

<210> SEQ ID NO 126
<211> LENGTH: 19
<212> TYPE: PRT
<213> ORGANISM: Homo sapiens

<400> SEQUENCE: 126

Val Val Ser Val Leu Thr Val Val His Gln Asp Trp Leu Asn Gly Lys
1               5                   10                  15

Glu Tyr Lys

<210> SEQ ID NO 127
<211> LENGTH: 11
<212> TYPE: PRT
<213> ORGANISM: Homo sapiens

<400> SEQUENCE: 127

Ala Glu Asp Thr Ala Val Tyr Tyr Cys Ala Lys
```

<210> SEQ ID NO 128
<211> LENGTH: 19
<212> TYPE: PRT
<213> ORGANISM: Homo sapiens

<400> SEQUENCE: 128

Glu Val Gln Leu Leu Glu Ser Gly Gly Gly Leu Val Gln Pro Gly Gly
1               5                   10                  15

Ser Leu Arg

<210> SEQ ID NO 129
<211> LENGTH: 19
<212> TYPE: PRT
<213> ORGANISM: Homo sapiens

<400> SEQUENCE: 129

Ala Ala Pro Ser Val Thr Leu Phe Pro Pro Ser Ser Glu Glu Leu Gln
1               5                   10                  15

Ala Asn Lys

<210> SEQ ID NO 130
<211> LENGTH: 17
<212> TYPE: PRT
<213> ORGANISM: Homo sapiens

<400> SEQUENCE: 130

Ala Asp Ser Ser Pro Val Lys Ala Gly Val Glu Thr Thr Thr Pro Ser
1               5                   10                  15

Lys

<210> SEQ ID NO 131
<211> LENGTH: 22
<212> TYPE: PRT
<213> ORGANISM: Homo sapiens

<400> SEQUENCE: 131

Ala Asp Ser Ser Pro Val Lys Ala Gly Val Glu Thr Thr Thr Pro Ser
1               5                   10                  15

Lys Gln Ser Asn Asn Lys
            20

<210> SEQ ID NO 132
<211> LENGTH: 10
<212> TYPE: PRT
<213> ORGANISM: Homo sapiens

<400> SEQUENCE: 132

Ala Gly Val Glu Thr Thr Thr Pro Ser Lys
1               5                   10

<210> SEQ ID NO 133
<211> LENGTH: 30
<212> TYPE: PRT
<213> ORGANISM: Homo sapiens

<400> SEQUENCE: 133

Ala Gly Val Glu Thr Thr Thr Pro Ser Lys Gln Ser Asn Asn Lys Tyr
1               5                   10                  15

Ala Ala Ser Ser Tyr Leu Ser Leu Thr Pro Glu Gln Trp Lys
            20                  25                  30

<210> SEQ ID NO 134
<211> LENGTH: 20
<212> TYPE: PRT
<213> ORGANISM: Homo sapiens

<400> SEQUENCE: 134

Gln Ser Asn Asn Lys Tyr Ala Ala Ser Ser Tyr Leu Ser Leu Thr Pro
1               5                   10                  15

Glu Gln Trp Lys
            20

<210> SEQ ID NO 135
<211> LENGTH: 18
<212> TYPE: PRT
<213> ORGANISM: Homo sapiens

<400> SEQUENCE: 135

Ser His Lys Ser Tyr Ser Cys Gln Val Thr His Glu Gly Ser Thr Val
1               5                   10                  15

Glu Lys

<210> SEQ ID NO 136
<211> LENGTH: 15
<212> TYPE: PRT
<213> ORGANISM: Homo sapiens

<400> SEQUENCE: 136

Ser Tyr Ser Cys Gln Val Thr His Glu Gly Ser Thr Val Glu Lys
1               5                   10                  15

<210> SEQ ID NO 137
<211> LENGTH: 23
<212> TYPE: PRT
<213> ORGANISM: Homo sapiens

<400> SEQUENCE: 137

Ser Tyr Ser Cys Gln Val Thr His Glu Gly Ser Thr Val Glu Lys Thr
1               5                   10                  15

Val Ala Pro Thr Glu Cys Ser
            20

<210> SEQ ID NO 138
<211> LENGTH: 8
<212> TYPE: PRT
<213> ORGANISM: Homo sapiens

<400> SEQUENCE: 138

Thr Val Ala Pro Thr Glu Cys Ser
1               5

<210> SEQ ID NO 139
<211> LENGTH: 15
<212> TYPE: PRT
<213> ORGANISM: Homo sapiens

<400> SEQUENCE: 139

Tyr Ala Ala Ser Ser Tyr Leu Ser Leu Thr Pro Glu Gln Trp Lys
1               5                   10                  15

<210> SEQ ID NO 140
<211> LENGTH: 11
<212> TYPE: PRT

```
<213> ORGANISM: Homo sapiens

<400> SEQUENCE: 140

Ala Ile Ser Gly Glu Asn Ala Gly Leu Val Arg
1               5                   10

<210> SEQ ID NO 141
<211> LENGTH: 10
<212> TYPE: PRT
<213> ORGANISM: Homo sapiens

<400> SEQUENCE: 141

Glu Val Ala Phe Asp Leu Glu Ile Pro Lys
1               5                   10

<210> SEQ ID NO 142
<211> LENGTH: 18
<212> TYPE: PRT
<213> ORGANISM: Homo sapiens

<400> SEQUENCE: 142

Phe Ala His Tyr Val Val Thr Ser Gln Val Val Asn Thr Ala Asn Glu
1               5                   10                  15

Ala Arg

<210> SEQ ID NO 143
<211> LENGTH: 13
<212> TYPE: PRT
<213> ORGANISM: Homo sapiens

<400> SEQUENCE: 143

Gln Tyr Tyr Glu Gly Ser Glu Ile Val Val Ala Gly Arg
1               5                   10

<210> SEQ ID NO 144
<211> LENGTH: 15
<212> TYPE: PRT
<213> ORGANISM: Homo sapiens

<400> SEQUENCE: 144

Ala Glu Asp His Phe Ser Val Ile Asp Phe Asn Gln Asn Ile Arg
1               5                   10                  15

<210> SEQ ID NO 145
<211> LENGTH: 13
<212> TYPE: PRT
<213> ORGANISM: Homo sapiens

<400> SEQUENCE: 145

Ala His Val Ser Phe Lys Pro Thr Val Ala Gln Gln Arg
1               5                   10

<210> SEQ ID NO 146
<211> LENGTH: 20
<212> TYPE: PRT
<213> ORGANISM: Homo sapiens

<400> SEQUENCE: 146

Phe Leu His Val Pro Asp Thr Phe Glu Gly His Phe Asp Gly Val Pro
1               5                   10                  15

Val Ile Ser Lys
            20
```

```
<210> SEQ ID NO 147
<211> LENGTH: 11
<212> TYPE: PRT
<213> ORGANISM: Homo sapiens

<400> SEQUENCE: 147

Phe Tyr Asn Gln Val Ser Thr Pro Leu Leu Arg
1               5                   10

<210> SEQ ID NO 148
<211> LENGTH: 15
<212> TYPE: PRT
<213> ORGANISM: Homo sapiens

<400> SEQUENCE: 148

Ile Gln Pro Ser Gly Gly Thr Asn Ile Asn Glu Ala Leu Leu Arg
1               5                   10                  15

<210> SEQ ID NO 149
<211> LENGTH: 10
<212> TYPE: PRT
<213> ORGANISM: Homo sapiens

<400> SEQUENCE: 149

Thr Glu Val Asn Val Leu Pro Gly Ala Lys
1               5                   10

<210> SEQ ID NO 150
<211> LENGTH: 11
<212> TYPE: PRT
<213> ORGANISM: Homo sapiens

<400> SEQUENCE: 150

Val Gln Phe Glu Leu His Tyr Gln Glu Val Lys
1               5                   10

<210> SEQ ID NO 151
<211> LENGTH: 19
<212> TYPE: PRT
<213> ORGANISM: Homo sapiens

<400> SEQUENCE: 151

Val Val Asn Asn Ser Pro Gln Pro Gln Asn Val Val Phe Asp Val Gln
1               5                   10                  15

Ile Pro Lys

<210> SEQ ID NO 152
<211> LENGTH: 24
<212> TYPE: PRT
<213> ORGANISM: Homo sapiens

<400> SEQUENCE: 152

His Arg Gln Gly Pro Val Asn Leu Leu Ser Asp Pro Glu Gln Gly Val
1               5                   10                  15

Glu Val Thr Gly Gln Tyr Glu Arg
            20

<210> SEQ ID NO 153
<211> LENGTH: 9
<212> TYPE: PRT
<213> ORGANISM: Homo sapiens

<400> SEQUENCE: 153

Leu Gly Val Tyr Glu Leu Leu Leu Lys
```

```
<210> SEQ ID NO 154
<211> LENGTH: 10
<212> TYPE: PRT
<213> ORGANISM: Homo sapiens

<400> SEQUENCE: 154

Ala Glu Ala Glu Ser Leu Tyr Gln Ser Lys
1               5                   10

<210> SEQ ID NO 155
<211> LENGTH: 9
<212> TYPE: PRT
<213> ORGANISM: Homo sapiens

<400> SEQUENCE: 155

Ala Gln Tyr Glu Asp Ile Ala Gln Lys
1               5

<210> SEQ ID NO 156
<211> LENGTH: 18
<212> TYPE: PRT
<213> ORGANISM: Homo sapiens

<400> SEQUENCE: 156

Glu Gln Ile Lys Ser Leu Asn Asn Gln Phe Ala Ser Phe Ile Asp Lys
1               5                   10                  15

Val Arg

<210> SEQ ID NO 157
<211> LENGTH: 12
<212> TYPE: PRT
<213> ORGANISM: Homo sapiens

<400> SEQUENCE: 157

Phe Leu Glu Gln Gln Asn Gln Val Leu Gln Thr Lys
1               5                   10

<210> SEQ ID NO 158
<211> LENGTH: 24
<212> TYPE: PRT
<213> ORGANISM: Homo sapiens

<400> SEQUENCE: 158

Phe Leu Glu Gln Gln Asn Gln Val Leu Gln Thr Lys Trp Glu Leu Leu
1               5                   10                  15

Gln Gln Val Asp Thr Ser Thr Arg
            20

<210> SEQ ID NO 159
<211> LENGTH: 20
<212> TYPE: PRT
<213> ORGANISM: Homo sapiens

<400> SEQUENCE: 159

Phe Ser Ser Cys Gly Gly Gly Gly Ser Phe Gly Ala Gly Gly Gly
1               5                   10                  15

Phe Gly Ser Arg
            20

<210> SEQ ID NO 160
<211> LENGTH: 31
```

```
<212> TYPE: PRT
<213> ORGANISM: Homo sapiens

<400> SEQUENCE: 160

Gly Gly Gly Gly Gly Tyr Gly Ser Gly Gly Ser Ser Tyr Gly Ser
1               5                   10                  15
Gly Gly Gly Ser Tyr Gly Ser Gly Gly Gly Gly Gly Arg
            20                  25                  30

<210> SEQ ID NO 161
<211> LENGTH: 14
<212> TYPE: PRT
<213> ORGANISM: Homo sapiens

<400> SEQUENCE: 161

Gly Ser Gly Gly Ser Ser Gly Gly Ser Ile Gly Gly Arg
1               5                   10

<210> SEQ ID NO 162
<211> LENGTH: 8
<212> TYPE: PRT
<213> ORGANISM: Homo sapiens

<400> SEQUENCE: 162

Ile Glu Ile Ser Glu Leu Asn Arg
1               5

<210> SEQ ID NO 163
<211> LENGTH: 11
<212> TYPE: PRT
<213> ORGANISM: Homo sapiens

<400> SEQUENCE: 163

Leu Ala Leu Asp Leu Glu Ile Ala Thr Tyr Arg
1               5                   10

<210> SEQ ID NO 164
<211> LENGTH: 16
<212> TYPE: PRT
<213> ORGANISM: Homo sapiens

<400> SEQUENCE: 164

Leu Asp Ser Glu Leu Lys Asn Met Gln Asp Met Val Glu Asp Tyr Arg
1               5                   10                  15

<210> SEQ ID NO 165
<211> LENGTH: 12
<212> TYPE: PRT
<213> ORGANISM: Homo sapiens

<400> SEQUENCE: 165

Leu Leu Arg Asp Tyr Gln Glu Leu Met Asn Thr Lys
1               5                   10

<210> SEQ ID NO 166
<211> LENGTH: 12
<212> TYPE: PRT
<213> ORGANISM: Homo sapiens

<400> SEQUENCE: 166

Leu Asn Asp Leu Glu Asp Ala Leu Gln Gln Ala Lys
1               5                   10

<210> SEQ ID NO 167
```

```
<211> LENGTH: 10
<212> TYPE: PRT
<213> ORGANISM: Homo sapiens

<400> SEQUENCE: 167

Leu Arg Ser Glu Ile Asp Asn Val Lys Lys
1               5                   10

<210> SEQ ID NO 168
<211> LENGTH: 14
<212> TYPE: PRT
<213> ORGANISM: Homo sapiens

<400> SEQUENCE: 168

Asn Lys Leu Asn Asp Leu Glu Asp Ala Leu Gln Gln Ala Lys
1               5                   10

<210> SEQ ID NO 169
<211> LENGTH: 19
<212> TYPE: PRT
<213> ORGANISM: Homo sapiens

<400> SEQUENCE: 169

Asn Lys Leu Asn Asp Leu Glu Asp Ala Leu Gln Gln Ala Lys Glu Asp
1               5                   10                  15

Leu Ala Arg

<210> SEQ ID NO 170
<211> LENGTH: 10
<212> TYPE: PRT
<213> ORGANISM: Homo sapiens

<400> SEQUENCE: 170

Asn Lys Tyr Glu Asp Glu Ile Asn Lys Arg
1               5                   10

<210> SEQ ID NO 171
<211> LENGTH: 15
<212> TYPE: PRT
<213> ORGANISM: Homo sapiens

<400> SEQUENCE: 171

Asn Ser Lys Ile Glu Ile Ser Glu Leu Asn Arg Val Ile Gln Arg
1               5                   10                  15

<210> SEQ ID NO 172
<211> LENGTH: 15
<212> TYPE: PRT
<213> ORGANISM: Homo sapiens

<400> SEQUENCE: 172

Gln Ile Ser Asn Leu Gln Gln Ser Ile Ser Asp Ala Glu Gln Arg
1               5                   10                  15

<210> SEQ ID NO 173
<211> LENGTH: 23
<212> TYPE: PRT
<213> ORGANISM: Homo sapiens

<400> SEQUENCE: 173

Ser Glu Ile Asp Asn Val Lys Lys Gln Ile Ser Asn Leu Gln Gln Ser
1               5                   10                  15

Ile Ser Asp Ala Glu Gln Arg
            20
```

<210> SEQ ID NO 174
<211> LENGTH: 17
<212> TYPE: PRT
<213> ORGANISM: Homo sapiens

<400> SEQUENCE: 174

Ser Gly Gly Gly Phe Ser Ser Gly Ser Ala Gly Ile Ile Asn Tyr Gln
1               5                   10                  15

Arg

<210> SEQ ID NO 175
<211> LENGTH: 18
<212> TYPE: PRT
<213> ORGANISM: Homo sapiens

<400> SEQUENCE: 175

Ser Gly Gly Gly Phe Ser Ser Gly Ser Ala Gly Ile Ile Asn Tyr Gln
1               5                   10                  15

Arg Arg

<210> SEQ ID NO 176
<211> LENGTH: 27
<212> TYPE: PRT
<213> ORGANISM: Homo sapiens

<400> SEQUENCE: 176

Ser Gly Gly Gly Gly Gly Arg Phe Ser Ser Cys Gly Gly Gly Gly
1               5                   10                  15

Ser Phe Gly Ala Gly Gly Gly Phe Gly Ser Arg
            20                  25

<210> SEQ ID NO 177
<211> LENGTH: 21
<212> TYPE: PRT
<213> ORGANISM: Homo sapiens

<400> SEQUENCE: 177

Ser Gly Tyr Arg Ser Gly Gly Gly Phe Ser Ser Gly Ser Ala Gly Ile
1               5                   10                  15

Ile Asn Tyr Gln Arg
            20

<210> SEQ ID NO 178
<211> LENGTH: 8
<212> TYPE: PRT
<213> ORGANISM: Homo sapiens

<400> SEQUENCE: 178

Ser Ile Ser Ile Ser Val Ala Arg
1               5

<210> SEQ ID NO 179
<211> LENGTH: 12
<212> TYPE: PRT
<213> ORGANISM: Homo sapiens

<400> SEQUENCE: 179

Ser Lys Ala Glu Ala Glu Ser Leu Tyr Gln Ser Lys
1               5                   10

<210> SEQ ID NO 180

```
<211> LENGTH: 22
<212> TYPE: PRT
<213> ORGANISM: Homo sapiens

<400> SEQUENCE: 180

Ser Lys Ala Glu Ala Glu Ser Leu Tyr Gln Ser Lys Tyr Glu Glu Leu
1               5                   10                  15

Gln Ile Thr Ala Gly Arg
            20

<210> SEQ ID NO 181
<211> LENGTH: 12
<212> TYPE: PRT
<213> ORGANISM: Homo sapiens

<400> SEQUENCE: 181

Ser Leu Asp Leu Asp Ser Ile Ile Ala Glu Val Lys
1               5                   10

<210> SEQ ID NO 182
<211> LENGTH: 12
<212> TYPE: PRT
<213> ORGANISM: Homo sapiens

<400> SEQUENCE: 182

Ser Leu Asn Asn Gln Phe Ala Ser Phe Ile Asp Lys
1               5                   10

<210> SEQ ID NO 183
<211> LENGTH: 14
<212> TYPE: PRT
<213> ORGANISM: Homo sapiens

<400> SEQUENCE: 183

Ser Leu Asn Asn Gln Phe Ala Ser Phe Ile Asp Lys Val Arg
1               5                   10

<210> SEQ ID NO 184
<211> LENGTH: 8
<212> TYPE: PRT
<213> ORGANISM: Homo sapiens

<400> SEQUENCE: 184

Leu Val Asn Leu Gly Gly Ser Lys
1               5

<210> SEQ ID NO 185
<211> LENGTH: 17
<212> TYPE: PRT
<213> ORGANISM: Homo sapiens

<400> SEQUENCE: 185

Ser Leu Val Asn Leu Gly Gly Ser Lys Ser Ile Ser Ile Ser Val Ala
1               5                   10                  15

Arg

<210> SEQ ID NO 186
<211> LENGTH: 16
<212> TYPE: PRT
<213> ORGANISM: Homo sapiens

<400> SEQUENCE: 186

Thr His Asn Leu Glu Pro Tyr Phe Glu Ser Phe Ile Asn Asn Leu Arg
1               5                   10                  15
```

<210> SEQ ID NO 187
<211> LENGTH: 17
<212> TYPE: PRT
<213> ORGANISM: Homo sapiens

<400> SEQUENCE: 187

Thr His Asn Leu Glu Pro Tyr Phe Glu Ser Phe Ile Asn Asn Leu Arg
1               5                   10                  15

Arg

<210> SEQ ID NO 188
<211> LENGTH: 9
<212> TYPE: PRT
<213> ORGANISM: Homo sapiens

<400> SEQUENCE: 188

Thr Leu Leu Glu Gly Glu Glu Ser Arg
1               5

<210> SEQ ID NO 189
<211> LENGTH: 11
<212> TYPE: PRT
<213> ORGANISM: Homo sapiens

<400> SEQUENCE: 189

Thr Asn Ala Glu Asn Glu Phe Val Thr Ile Lys
1               5                   10

<210> SEQ ID NO 190
<211> LENGTH: 12
<212> TYPE: PRT
<213> ORGANISM: Homo sapiens

<400> SEQUENCE: 190

Thr Asn Ala Glu Asn Glu Phe Val Thr Ile Lys Lys
1               5                   10

<210> SEQ ID NO 191
<211> LENGTH: 12
<212> TYPE: PRT
<213> ORGANISM: Homo sapiens

<400> SEQUENCE: 191

Trp Glu Leu Leu Gln Gln Val Asp Thr Ser Thr Arg
1               5                   10

<210> SEQ ID NO 192
<211> LENGTH: 10
<212> TYPE: PRT
<213> ORGANISM: Homo sapiens

<400> SEQUENCE: 192

Tyr Glu Glu Leu Gln Ile Thr Ala Gly Arg
1               5                   10

<210> SEQ ID NO 193
<211> LENGTH: 16
<212> TYPE: PRT
<213> ORGANISM: Homo sapiens

<400> SEQUENCE: 193

Tyr Glu Glu Leu Gln Ile Thr Ala Gly Arg His Gly Asp Ser Val Arg
1               5                   10                  15

<210> SEQ ID NO 194
<211> LENGTH: 20
<212> TYPE: PRT
<213> ORGANISM: Homo sapiens

<400> SEQUENCE: 194

Ala Glu Ala Glu Ser Leu Tyr Gln Ser Lys Tyr Glu Glu Leu Gln Ile
1               5                   10                  15

Thr Ala Gly Arg
            20

<210> SEQ ID NO 195
<211> LENGTH: 13
<212> TYPE: PRT
<213> ORGANISM: Homo sapiens

<400> SEQUENCE: 195

Ala Gly Lys Gly Met His Gly Gly Val Pro Gly Gly Lys
1               5                   10

<210> SEQ ID NO 196
<211> LENGTH: 10
<212> TYPE: PRT
<213> ORGANISM: Homo sapiens

<400> SEQUENCE: 196

Gly Met His Gly Gly Val Pro Gly Gly Lys
1               5                   10

<210> SEQ ID NO 197
<211> LENGTH: 7
<212> TYPE: PRT
<213> ORGANISM: Homo sapiens

<400> SEQUENCE: 197

Gln Glu Leu Asn Pro Leu Lys
1               5

<210> SEQ ID NO 198
<211> LENGTH: 10
<212> TYPE: PRT
<213> ORGANISM: Homo sapiens

<400> SEQUENCE: 198

Gln Phe Ile Glu Ser Glu Cys Ile Pro Arg
1               5                   10

<210> SEQ ID NO 199
<211> LENGTH: 13
<212> TYPE: PRT
<213> ORGANISM: Homo sapiens

<400> SEQUENCE: 199

Ala Gly Lys Gly Met His Gly Gly Val Pro Gly Gly Lys
1               5                   10

<210> SEQ ID NO 200
<211> LENGTH: 25
<212> TYPE: PRT
<213> ORGANISM: Homo sapiens

<400> SEQUENCE: 200

Ala Gly Lys Gly Met His Gly Gly Val Pro Gly Gly Lys Gln Phe Ile

```
            1               5                  10                  15
Glu Asn Gly Ser Glu Phe Ala Gln Lys
            20                  25

<210> SEQ ID NO 201
<211> LENGTH: 8
<212> TYPE: PRT
<213> ORGANISM: Homo sapiens

<400> SEQUENCE: 201

Phe Ser Leu Leu Lys Pro Trp Ala
1               5

<210> SEQ ID NO 202
<211> LENGTH: 10
<212> TYPE: PRT
<213> ORGANISM: Homo sapiens

<400> SEQUENCE: 202

Gly Met His Gly Gly Val Pro Gly Gly Lys
1               5                  10

<210> SEQ ID NO 203
<211> LENGTH: 22
<212> TYPE: PRT
<213> ORGANISM: Homo sapiens

<400> SEQUENCE: 203

Gly Met His Gly Gly Val Pro Gly Gly Lys Gln Phe Ile Glu Asn Gly
1               5                  10                  15

Ser Glu Phe Ala Gln Lys
            20

<210> SEQ ID NO 204
<211> LENGTH: 25
<212> TYPE: PRT
<213> ORGANISM: Homo sapiens

<400> SEQUENCE: 204

Gly Met His Gly Gly Val Pro Gly Gly Lys Gln Phe Ile Glu Asn Gly
1               5                  10                  15

Ser Glu Phe Ala Gln Lys Leu Leu Lys
            20                  25

<210> SEQ ID NO 205
<211> LENGTH: 9
<212> TYPE: PRT
<213> ORGANISM: Homo sapiens

<400> SEQUENCE: 205

Lys Phe Ser Leu Leu Lys Pro Trp Ala
1               5

<210> SEQ ID NO 206
<211> LENGTH: 7
<212> TYPE: PRT
<213> ORGANISM: Homo sapiens

<400> SEQUENCE: 206

Gln Glu Leu Asn Pro Leu Lys
1               5

<210> SEQ ID NO 207
```

```
<211> LENGTH: 12
<212> TYPE: PRT
<213> ORGANISM: Homo sapiens

<400> SEQUENCE: 207

Gln Glu Leu Asn Pro Leu Lys Ser Ile Val Glu Lys
1               5                   10

<210> SEQ ID NO 208
<211> LENGTH: 12
<212> TYPE: PRT
<213> ORGANISM: Homo sapiens

<400> SEQUENCE: 208

Gln Phe Ile Glu Asn Gly Ser Glu Phe Ala Gln Lys
1               5                   10

<210> SEQ ID NO 209
<211> LENGTH: 15
<212> TYPE: PRT
<213> ORGANISM: Homo sapiens

<400> SEQUENCE: 209

Gln Phe Ile Glu Asn Gly Ser Glu Phe Ala Gln Lys Leu Leu Lys
1               5                   10                  15

<210> SEQ ID NO 210
<211> LENGTH: 16
<212> TYPE: PRT
<213> ORGANISM: Homo sapiens

<400> SEQUENCE: 210

Gln Phe Ile Glu Asn Gly Ser Glu Phe Ala Gln Lys Leu Leu Lys Lys
1               5                   10                  15

<210> SEQ ID NO 211
<211> LENGTH: 11
<212> TYPE: PRT
<213> ORGANISM: Homo sapiens

<400> SEQUENCE: 211

Ser Ile Leu Leu Thr Glu Gln Ala Leu Ala Lys
1               5                   10

<210> SEQ ID NO 212
<211> LENGTH: 14
<212> TYPE: PRT
<213> ORGANISM: Homo sapiens

<400> SEQUENCE: 212

Ser Ile Leu Leu Thr Glu Gln Ala Leu Ala Lys Ala Gly Lys
1               5                   10

<210> SEQ ID NO 213
<211> LENGTH: 16
<212> TYPE: PRT
<213> ORGANISM: Homo sapiens

<400> SEQUENCE: 213

Ser Ile Val Glu Lys Ser Ile Leu Leu Thr Glu Gln Ala Leu Ala Lys
1               5                   10                  15

<210> SEQ ID NO 214
<211> LENGTH: 19
<212> TYPE: PRT
```

<213> ORGANISM: Homo sapiens

<400> SEQUENCE: 214

Ser Ile Val Glu Lys Ser Ile Leu Leu Thr Glu Gln Ala Leu Ala Lys
1               5                   10                  15

Ala Gly Lys

<210> SEQ ID NO 215
<211> LENGTH: 29
<212> TYPE: PRT
<213> ORGANISM: Homo sapiens

<400> SEQUENCE: 215

Asp Ile Glu Asn Gln Tyr Glu Thr Gln Ile Thr Gln Ile Glu His Glu
1               5                   10                  15

Val Ser Ser Ser Gly Gln Glu Val Gln Ser Ser Ala Lys
            20                  25

<210> SEQ ID NO 216
<211> LENGTH: 23
<212> TYPE: PRT
<213> ORGANISM: Homo sapiens

<400> SEQUENCE: 216

Glu Ile Glu Thr Tyr His Asn Leu Leu Glu Gly Gly Gln Glu Asp Phe
1               5                   10                  15

Glu Ser Ser Gly Ala Gly Lys
            20

<210> SEQ ID NO 217
<211> LENGTH: 25
<212> TYPE: PRT
<213> ORGANISM: Homo sapiens

<400> SEQUENCE: 217

Phe Ser Ser Ser Gly Gly Gly Gly Gly Gly Arg Phe Ser Ser Ser
1               5                   10                  15

Ser Gly Tyr Gly Gly Gly Ser Ser Arg
            20                  25

<210> SEQ ID NO 218
<211> LENGTH: 13
<212> TYPE: PRT
<213> ORGANISM: Homo sapiens

<400> SEQUENCE: 218

Phe Ser Ser Ser Ser Gly Tyr Gly Gly Gly Ser Ser Arg
1               5                   10

<210> SEQ ID NO 219
<211> LENGTH: 32
<212> TYPE: PRT
<213> ORGANISM: Homo sapiens

<400> SEQUENCE: 219

Gly Gly Gly Gly Ser Phe Gly Tyr Ser Tyr Gly Gly Gly Ser Gly Gly
1               5                   10                  15

Gly Phe Ser Ala Ser Ser Leu Gly Gly Gly Phe Gly Gly Gly Ser Arg
            20                  25                  30

<210> SEQ ID NO 220
<211> LENGTH: 23

```
<212> TYPE: PRT
<213> ORGANISM: Homo sapiens

<400> SEQUENCE: 220

Gly Gly Ser Gly Gly Ser Tyr Gly Gly Gly Ser Gly Gly Gly Tyr
1               5                   10                  15

Gly Gly Gly Ser Gly Ser Arg
            20

<210> SEQ ID NO 221
<211> LENGTH: 16
<212> TYPE: PRT
<213> ORGANISM: Homo sapiens

<400> SEQUENCE: 221

His Gly Val Gln Glu Leu Glu Ile Glu Leu Gln Ser Gln Leu Ser Lys
1               5                   10                  15

<210> SEQ ID NO 222
<211> LENGTH: 17
<212> TYPE: PRT
<213> ORGANISM: Homo sapiens

<400> SEQUENCE: 222

His Gly Val Gln Glu Leu Glu Ile Glu Leu Gln Ser Gln Leu Ser Lys
1               5                   10                  15

Lys

<210> SEQ ID NO 223
<211> LENGTH: 7
<212> TYPE: PRT
<213> ORGANISM: Homo sapiens

<400> SEQUENCE: 223

Leu Ala Ser Tyr Leu Asp Lys
1               5

<210> SEQ ID NO 224
<211> LENGTH: 21
<212> TYPE: PRT
<213> ORGANISM: Homo sapiens

<400> SEQUENCE: 224

Leu Ala Ser Tyr Leu Asp Lys Val Gln Ala Leu Glu Glu Ala Asn Asn
1               5                   10                  15

Asp Leu Glu Asn Lys
            20

<210> SEQ ID NO 225
<211> LENGTH: 26
<212> TYPE: PRT
<213> ORGANISM: Homo sapiens

<400> SEQUENCE: 225

Leu Glu Lys Glu Ile Glu Thr Tyr His Asn Leu Leu Glu Gly Gly Gln
1               5                   10                  15

Glu Asp Phe Glu Ser Ser Gly Ala Gly Lys
            20                  25

<210> SEQ ID NO 226
<211> LENGTH: 32
<212> TYPE: PRT
<213> ORGANISM: Homo sapiens
```

<400> SEQUENCE: 226

Asn Arg Lys Asp Ile Glu Asn Gln Tyr Glu Thr Gln Ile Thr Gln Ile
1               5                   10                  15

Glu His Glu Val Ser Ser Ser Gly Gln Glu Val Gln Ser Ser Ala Lys
            20                  25                  30

<210> SEQ ID NO 227
<211> LENGTH: 9
<212> TYPE: PRT
<213> ORGANISM: Homo sapiens

<400> SEQUENCE: 227

Gln Glu Tyr Glu Gln Leu Ile Ala Lys
1               5

<210> SEQ ID NO 228
<211> LENGTH: 11
<212> TYPE: PRT
<213> ORGANISM: Homo sapiens

<400> SEQUENCE: 228

Gln Gly Val Asp Ala Asp Ile Asn Gly Leu Arg
1               5                   10

<210> SEQ ID NO 229
<211> LENGTH: 10
<212> TYPE: PRT
<213> ORGANISM: Homo sapiens

<400> SEQUENCE: 229

Gln Val Leu Asp Asn Leu Thr Met Glu Lys
1               5                   10

<210> SEQ ID NO 230
<211> LENGTH: 12
<212> TYPE: PRT
<213> ORGANISM: Homo sapiens

<400> SEQUENCE: 230

Ser Cys Arg Gln Phe Ser Ser Tyr Leu Ser Arg
1               5                   10

<210> SEQ ID NO 231
<211> LENGTH: 16
<212> TYPE: PRT
<213> ORGANISM: Homo sapiens

<400> SEQUENCE: 231

Ser Gly Gly Gly Gly Gly Gly Leu Gly Ser Gly Gly Ser Ile Arg
1               5                   10                  15

<210> SEQ ID NO 232
<211> LENGTH: 9
<212> TYPE: PRT
<213> ORGANISM: Homo sapiens

<400> SEQUENCE: 232

Ser Thr Met Gln Glu Leu Asn Ser Arg
1               5

<210> SEQ ID NO 233
<211> LENGTH: 9
<212> TYPE: PRT

```
<213> ORGANISM: Homo sapiens

<400> SEQUENCE: 233

Thr Leu Leu Asp Ile Asp Asn Thr Arg
1               5

<210> SEQ ID NO 234
<211> LENGTH: 15
<212> TYPE: PRT
<213> ORGANISM: Homo sapiens

<400> SEQUENCE: 234

Thr Leu Asn Asp Met Arg Gln Glu Tyr Glu Gln Leu Ile Ala Lys
1               5                   10                  15

<210> SEQ ID NO 235
<211> LENGTH: 14
<212> TYPE: PRT
<213> ORGANISM: Homo sapiens

<400> SEQUENCE: 235

Val Gln Ala Leu Glu Glu Ala Asn Asn Asp Leu Glu Asn Lys
1               5                   10

<210> SEQ ID NO 236
<211> LENGTH: 10
<212> TYPE: PRT
<213> ORGANISM: Homo sapiens

<400> SEQUENCE: 236

Asp Leu Leu Leu Pro Gln Pro Asp Leu Arg
1               5                   10

<210> SEQ ID NO 237
<211> LENGTH: 7
<212> TYPE: PRT
<213> ORGANISM: Homo sapiens

<400> SEQUENCE: 237

Gly Pro Leu Gln Leu Glu Arg
1               5

<210> SEQ ID NO 238
<211> LENGTH: 10
<212> TYPE: PRT
<213> ORGANISM: Homo sapiens

<400> SEQUENCE: 238

Val Ala Ala Gly Ala Phe Gln Gly Leu Arg
1               5                   10

<210> SEQ ID NO 239
<211> LENGTH: 13
<212> TYPE: PRT
<213> ORGANISM: Homo sapiens

<400> SEQUENCE: 239

Ala Thr Leu Lys Asp Gln Leu Ile Tyr Asn Leu Leu Lys
1               5                   10

<210> SEQ ID NO 240
<211> LENGTH: 21
<212> TYPE: PRT
<213> ORGANISM: Homo sapiens
```

<400> SEQUENCE: 240

Ala Thr Leu Lys Asp Gln Leu Ile Tyr Asn Leu Leu Lys Glu Glu Gln
1               5                   10                  15

Thr Pro Gln Asn Lys
            20

<210> SEQ ID NO 241
<211> LENGTH: 15
<212> TYPE: PRT
<213> ORGANISM: Homo sapiens

<400> SEQUENCE: 241

Asp Leu Ala Asp Glu Leu Ala Leu Val Asp Val Ile Glu Asp Lys
1               5                   10                  15

<210> SEQ ID NO 242
<211> LENGTH: 9
<212> TYPE: PRT
<213> ORGANISM: Homo sapiens

<400> SEQUENCE: 242

Asp Gln Leu Ile Tyr Asn Leu Leu Lys
1               5

<210> SEQ ID NO 243
<211> LENGTH: 17
<212> TYPE: PRT
<213> ORGANISM: Homo sapiens

<400> SEQUENCE: 243

Asp Gln Leu Ile Tyr Asn Leu Leu Lys Glu Glu Gln Thr Pro Gln Asn
1               5                   10                  15

Lys

<210> SEQ ID NO 244
<211> LENGTH: 9
<212> TYPE: PRT
<213> ORGANISM: Homo sapiens

<400> SEQUENCE: 244

Leu Val Ile Ile Thr Ala Gly Ala Arg
1               5

<210> SEQ ID NO 245
<211> LENGTH: 14
<212> TYPE: PRT
<213> ORGANISM: Homo sapiens

<400> SEQUENCE: 245

Asn Arg Val Ile Gly Ser Gly Cys Asn Leu Asp Ser Ala Arg
1               5                   10

<210> SEQ ID NO 246
<211> LENGTH: 14
<212> TYPE: PRT
<213> ORGANISM: Homo sapiens

<400> SEQUENCE: 246

Asn Val Asn Ile Phe Lys Phe Ile Ile Pro Asn Val Val Lys
1               5                   10

<210> SEQ ID NO 247
<211> LENGTH: 11

<212> TYPE: PRT
<213> ORGANISM: Homo sapiens

<400> SEQUENCE: 247

Gln Val Val Glu Ser Ala Tyr Glu Val Ile Lys
1               5                   10

<210> SEQ ID NO 248
<211> LENGTH: 10
<212> TYPE: PRT
<213> ORGANISM: Homo sapiens

<400> SEQUENCE: 248

Ser Ala Asp Thr Leu Trp Gly Ile Gln Lys
1               5                   10

<210> SEQ ID NO 249
<211> LENGTH: 16
<212> TYPE: PRT
<213> ORGANISM: Homo sapiens

<400> SEQUENCE: 249

Thr Leu His Pro Asp Leu Gly Thr Asp Lys Asp Lys Glu Gln Trp Lys
1               5                   10                  15

<210> SEQ ID NO 250
<211> LENGTH: 12
<212> TYPE: PRT
<213> ORGANISM: Homo sapiens

<400> SEQUENCE: 250

Val Ile Gly Ser Gly Cys Asn Leu Asp Ser Ala Arg
1               5                   10

<210> SEQ ID NO 251
<211> LENGTH: 10
<212> TYPE: PRT
<213> ORGANISM: Homo sapiens

<400> SEQUENCE: 251

Val Thr Leu Thr Ser Glu Glu Glu Ala Arg
1               5                   10

<210> SEQ ID NO 252
<211> LENGTH: 14
<212> TYPE: PRT
<213> ORGANISM: Homo sapiens

<400> SEQUENCE: 252

Ile Val Ala Asp Lys Asp Tyr Ser Val Thr Ala Asn Ser Lys
1               5                   10

<210> SEQ ID NO 253
<211> LENGTH: 16
<212> TYPE: PRT
<213> ORGANISM: Homo sapiens

<400> SEQUENCE: 253

Leu Ile Ala Pro Val Ala Glu Glu Glu Ala Thr Val Pro Asn Asn Lys
1               5                   10                  15

<210> SEQ ID NO 254
<211> LENGTH: 10
<212> TYPE: PRT
<213> ORGANISM: Homo sapiens

```
<400> SEQUENCE: 254

Ser Ala Asp Thr Leu Trp Asp Ile Gln Lys
1               5                   10

<210> SEQ ID NO 255
<211> LENGTH: 15
<212> TYPE: PRT
<213> ORGANISM: Homo sapiens

<400> SEQUENCE: 255

Ser Leu Ala Asp Glu Leu Ala Leu Val Asp Val Leu Glu Asp Lys
1               5                   10                  15

<210> SEQ ID NO 256
<211> LENGTH: 12
<212> TYPE: PRT
<213> ORGANISM: Homo sapiens

<400> SEQUENCE: 256

Val Ile Gly Ser Gly Cys Asn Leu Asp Ser Ala Arg
1               5                   10

<210> SEQ ID NO 257
<211> LENGTH: 12
<212> TYPE: PRT
<213> ORGANISM: Homo sapiens

<400> SEQUENCE: 257

Ala Glu Ala Ser Ser Asp Pro Gly Ala Glu Glu Arg
1               5                   10

<210> SEQ ID NO 258
<211> LENGTH: 20
<212> TYPE: PRT
<213> ORGANISM: Homo sapiens

<400> SEQUENCE: 258

Asp Arg Gln Leu Gln Ala Gln Asp Glu Glu Gly Gly His Val Pro
1               5                   10                  15

Glu Arg Pro Lys
            20

<210> SEQ ID NO 259
<211> LENGTH: 27
<212> TYPE: PRT
<213> ORGANISM: Homo sapiens

<400> SEQUENCE: 259

Glu Gly Pro Gly Pro Glu Asp Thr Val Gln Asp Asn Leu Gly Ala Ala
1               5                   10                  15

Gly Ala Glu Glu Glu Gln Glu Glu His Gln Lys
            20                  25

<210> SEQ ID NO 260
<211> LENGTH: 13
<212> TYPE: PRT
<213> ORGANISM: Homo sapiens

<400> SEQUENCE: 260

Trp Glu Thr Gly Glu Val Gln Ala Gln Ser Ala Ala Lys
1               5                   10
```

```
<210> SEQ ID NO 261
<211> LENGTH: 17
<212> TYPE: PRT
<213> ORGANISM: Homo sapiens

<400> SEQUENCE: 261

Ser Gln Glu Thr Glu Cys Thr Tyr Phe Ser Thr Pro Leu Leu Leu Gly
1               5                   10                  15

Lys

<210> SEQ ID NO 262
<211> LENGTH: 19
<212> TYPE: PRT
<213> ORGANISM: Homo sapiens

<400> SEQUENCE: 262

Val Ala Val Leu Gly Ala Ser Gly Gly Ile Gly Gln Pro Leu Ser Leu
1               5                   10                  15

Leu Leu Lys

<210> SEQ ID NO 263
<211> LENGTH: 12
<212> TYPE: PRT
<213> ORGANISM: Homo sapiens

<400> SEQUENCE: 263

Ala Leu Gly Gly Leu Ala Cys Asp Leu Pro Gly Arg
1               5                   10

<210> SEQ ID NO 264
<211> LENGTH: 24
<212> TYPE: PRT
<213> ORGANISM: Homo sapiens

<400> SEQUENCE: 264

Ala Leu Gly Gly Leu Ala Cys Asp Leu Pro Gly Arg Phe Val Ala Glu
1               5                   10                  15

Ser Ala Glu Val Leu Leu Pro Arg
            20

<210> SEQ ID NO 265
<211> LENGTH: 10
<212> TYPE: PRT
<213> ORGANISM: Homo sapiens

<400> SEQUENCE: 265

Glu Ile Asp Glu Ser Leu Ile Phe Tyr Lys
1               5                   10

<210> SEQ ID NO 266
<211> LENGTH: 12
<212> TYPE: PRT
<213> ORGANISM: Homo sapiens

<400> SEQUENCE: 266

Phe Val Ala Glu Ser Ala Glu Val Leu Leu Pro Arg
1               5                   10

<210> SEQ ID NO 267
<211> LENGTH: 12
<212> TYPE: PRT
<213> ORGANISM: Homo sapiens

<400> SEQUENCE: 267
```

Gly Leu Leu Pro Val Leu Gly Gln Pro Ile Ile Arg
1               5                   10

<210> SEQ ID NO 268
<211> LENGTH: 10
<212> TYPE: PRT
<213> ORGANISM: Homo sapiens

<400> SEQUENCE: 268

Gly Ser Leu Leu Ser Glu Ala Asp Val Arg
1               5                   10

<210> SEQ ID NO 269
<211> LENGTH: 14
<212> TYPE: PRT
<213> ORGANISM: Homo sapiens

<400> SEQUENCE: 269

Ile Gln Ser Phe Leu Gly Gly Ala Pro Thr Glu Asp Leu Lys
1               5                   10

<210> SEQ ID NO 270
<211> LENGTH: 11
<212> TYPE: PRT
<213> ORGANISM: Homo sapiens

<400> SEQUENCE: 270

Ile Thr Lys Ala Asn Val Asp Leu Leu Pro Arg
1               5                   10

<210> SEQ ID NO 271
<211> LENGTH: 10
<212> TYPE: PRT
<213> ORGANISM: Homo sapiens

<400> SEQUENCE: 271

Leu Leu Gly Pro His Val Glu Gly Leu Lys
1               5                   10

<210> SEQ ID NO 272
<211> LENGTH: 14
<212> TYPE: PRT
<213> ORGANISM: Homo sapiens

<400> SEQUENCE: 272

Leu Leu Gly Pro His Val Glu Gly Leu Lys Ala Glu Glu Arg
1               5                   10

<210> SEQ ID NO 273
<211> LENGTH: 12
<212> TYPE: PRT
<213> ORGANISM: Homo sapiens

<400> SEQUENCE: 273

Leu Leu Pro Ala Ala Leu Ala Cys Trp Gly Val Arg
1               5                   10

<210> SEQ ID NO 274
<211> LENGTH: 16
<212> TYPE: PRT
<213> ORGANISM: Homo sapiens

<400> SEQUENCE: 274

Leu Arg Thr Asp Ala Val Leu Pro Leu Thr Val Ala Glu Val Gln Lys

-continued

```
1               5                   10                  15
```

<210> SEQ ID NO 275
<211> LENGTH: 17
<212> TYPE: PRT
<213> ORGANISM: Homo sapiens

<400> SEQUENCE: 275

```
Leu Val Ser Cys Pro Gly Pro Leu Asp Gln Asp Gln Gln Glu Ala Ala
1               5                   10                  15

Arg
```

<210> SEQ ID NO 276
<211> LENGTH: 8
<212> TYPE: PRT
<213> ORGANISM: Homo sapiens

<400> SEQUENCE: 276

```
Gln Leu Asp Val Leu Tyr Pro Lys
1               5
```

<210> SEQ ID NO 277
<211> LENGTH: 17
<212> TYPE: PRT
<213> ORGANISM: Homo sapiens

<400> SEQUENCE: 277

```
Gln Leu Leu Gly Phe Pro Cys Ala Glu Val Ser Gly Leu Ser Thr Glu
1               5                   10                  15

Arg
```

<210> SEQ ID NO 278
<211> LENGTH: 14
<212> TYPE: PRT
<213> ORGANISM: Homo sapiens

<400> SEQUENCE: 278

```
Thr Asp Ala Val Leu Pro Leu Thr Val Ala Glu Val Gln Lys
1               5                   10
```

<210> SEQ ID NO 279
<211> LENGTH: 15
<212> TYPE: PRT
<213> ORGANISM: Homo sapiens

<400> SEQUENCE: 279

```
Val Asn Ala Ile Pro Phe Thr Tyr Glu Gln Leu Asp Val Leu Lys
1               5                   10                  15
```

<210> SEQ ID NO 280
<211> LENGTH: 18
<212> TYPE: PRT
<213> ORGANISM: Homo sapiens

<400> SEQUENCE: 280

```
His Leu Ala Cys Leu Pro Arg Glu Pro Gly Leu Cys Thr Trp Gln Ser
1               5                   10                  15

Leu Arg
```

<210> SEQ ID NO 281
<211> LENGTH: 25
<212> TYPE: PRT
<213> ORGANISM: Homo sapiens

<400> SEQUENCE: 281

Leu Gln Asp Gly Leu Leu His Ile Thr Thr Cys Ser Phe Val Ala Pro
1               5                   10                  15

Trp Asn Ser Leu Ser Leu Ala Gln Arg
            20                  25

<210> SEQ ID NO 282
<211> LENGTH: 19
<212> TYPE: PRT
<213> ORGANISM: Homo sapiens

<400> SEQUENCE: 282

Leu Gln Ser Gly Thr His Cys Leu Trp Thr Asp Gln Leu Leu Gln Gly
1               5                   10                  15

Ser Glu Lys

<210> SEQ ID NO 283
<211> LENGTH: 20
<212> TYPE: PRT
<213> ORGANISM: Homo sapiens

<400> SEQUENCE: 283

Thr Tyr Thr Val Gly Cys Glu Glu Cys Thr Val Phe Pro Cys Leu Ser
1               5                   10                  15

Ile Pro Cys Lys
            20

<210> SEQ ID NO 284
<211> LENGTH: 9
<212> TYPE: PRT
<213> ORGANISM: Homo sapiens

<400> SEQUENCE: 284

Trp Val Gly Asp Leu Pro Asn Gly Arg
1               5

<210> SEQ ID NO 285
<211> LENGTH: 12
<212> TYPE: PRT
<213> ORGANISM: Homo sapiens

<400> SEQUENCE: 285

Trp Val Gly Asp Leu Pro Asn Gly Arg Val Cys Pro
1               5                   10

<210> SEQ ID NO 286
<211> LENGTH: 11
<212> TYPE: PRT
<213> ORGANISM: Homo sapiens

<400> SEQUENCE: 286

Phe Thr Asp Glu Glu Val Asp Glu Leu Tyr Arg
1               5                   10

<210> SEQ ID NO 287
<211> LENGTH: 10
<212> TYPE: PRT
<213> ORGANISM: Homo sapiens

<400> SEQUENCE: 287

Gly Asn Phe Asn Tyr Ile Glu Phe Thr Arg
1               5                   10

<210> SEQ ID NO 288
<211> LENGTH: 11
<212> TYPE: PRT
<213> ORGANISM: Homo sapiens

<400> SEQUENCE: 288

Leu Asn Gly Thr Asp Pro Glu Asp Val Ile Arg
1               5                   10

<210> SEQ ID NO 289
<211> LENGTH: 17
<212> TYPE: PRT
<213> ORGANISM: Homo sapiens

<400> SEQUENCE: 289

Glu Ala Leu Ala Glu Ala Ala Leu Glu Ser Pro Arg Pro Ala Leu Val
1               5                   10                  15

Arg

<210> SEQ ID NO 290
<211> LENGTH: 31
<212> TYPE: PRT
<213> ORGANISM: Homo sapiens

<400> SEQUENCE: 290

Glu Glu Leu Leu Arg Ala Gln Glu Ala Pro Gly Gln Ala Glu Pro Pro
1               5                   10                  15

Ala Ala Ala Glu Val Gln Gly Ala Gly Asn Glu Asn Glu Pro Arg
            20                  25                  30

<210> SEQ ID NO 291
<211> LENGTH: 14
<212> TYPE: PRT
<213> ORGANISM: Homo sapiens

<400> SEQUENCE: 291

Leu Leu Val Val Asp Pro Glu Thr Asp Glu Gln Leu Gln Lys
1               5                   10

<210> SEQ ID NO 292
<211> LENGTH: 10
<212> TYPE: PRT
<213> ORGANISM: Homo sapiens

<400> SEQUENCE: 292

Leu Val Glu Pro Gly Ser Pro Ala Glu Lys
1               5                   10

<210> SEQ ID NO 293
<211> LENGTH: 14
<212> TYPE: PRT
<213> ORGANISM: Homo sapiens

<400> SEQUENCE: 293

Ser Val Asp Pro Asp Ser Pro Ala Glu Ala Ser Gly Leu Arg
1               5                   10

<210> SEQ ID NO 294
<211> LENGTH: 23
<212> TYPE: PRT
<213> ORGANISM: Homo sapiens

<400> SEQUENCE: 294

Gly Ser Gln Thr Gln Ser His Pro Asp Leu Gly Thr Glu Gly Cys Trp
1               5                   10                  15

Asp Gln Leu Ser Ala Pro Arg
            20

<210> SEQ ID NO 295
<211> LENGTH: 13
<212> TYPE: PRT
<213> ORGANISM: Homo sapiens

<400> SEQUENCE: 295

Thr Asp Cys Pro Gly Asp Ala Leu Phe Asp Leu Leu Arg
1               5                   10

<210> SEQ ID NO 296
<211> LENGTH: 9
<212> TYPE: PRT
<213> ORGANISM: Homo sapiens

<400> SEQUENCE: 296

Ala Ala Glu Gln Asp Pro Glu Ala Arg
1               5

<210> SEQ ID NO 297
<211> LENGTH: 14
<212> TYPE: PRT
<213> ORGANISM: Homo sapiens

<400> SEQUENCE: 297

Leu Gln Ala Leu Val Asn Ser Leu Cys Ala Gly Gln Ser Pro
1               5                   10

<210> SEQ ID NO 298
<211> LENGTH: 14
<212> TYPE: PRT
<213> ORGANISM: Homo sapiens

<400> SEQUENCE: 298

Leu Arg Ser Pro Ala Gln Tyr Gln Val Val Leu Ser Glu Arg
1               5                   10

<210> SEQ ID NO 299
<211> LENGTH: 12
<212> TYPE: PRT
<213> ORGANISM: Homo sapiens

<400> SEQUENCE: 299

Asp Ser Pro Ser Val Trp Ala Ala Val Pro Gly Lys
1               5                   10

<210> SEQ ID NO 300
<211> LENGTH: 11
<212> TYPE: PRT
<213> ORGANISM: Homo sapiens

<400> SEQUENCE: 300

Glu Gly Val His Gly Gly Leu Ile Asn Lys Lys
1               5                   10

<210> SEQ ID NO 301
<211> LENGTH: 14
<212> TYPE: PRT
<213> ORGANISM: Homo sapiens

```
<400> SEQUENCE: 301

Ser Ser Phe Tyr Val Asn Gly Leu Thr Leu Gly Gly Gln Lys
1               5                   10

<210> SEQ ID NO 302
<211> LENGTH: 19
<212> TYPE: PRT
<213> ORGANISM: Homo sapiens

<400> SEQUENCE: 302

Ser Ser Phe Tyr Val Asn Gly Leu Thr Leu Gly Gly Gln Lys Cys Ser
1               5                   10                  15

Val Ile Arg

<210> SEQ ID NO 303
<211> LENGTH: 14
<212> TYPE: PRT
<213> ORGANISM: Homo sapiens

<400> SEQUENCE: 303

Ser Thr Gly Gly Ala Pro Thr Phe Asn Val Thr Val Thr Lys
1               5                   10

<210> SEQ ID NO 304
<211> LENGTH: 17
<212> TYPE: PRT
<213> ORGANISM: Homo sapiens

<400> SEQUENCE: 304

Ser Thr Gly Gly Ala Pro Thr Phe Asn Val Thr Val Thr Lys Thr Asp
1               5                   10                  15

Lys

<210> SEQ ID NO 305
<211> LENGTH: 16
<212> TYPE: PRT
<213> ORGANISM: Homo sapiens

<400> SEQUENCE: 305

Thr Phe Val Asn Ile Thr Pro Ala Glu Val Gly Val Leu Val Gly Lys
1               5                   10                  15

<210> SEQ ID NO 306
<211> LENGTH: 18
<212> TYPE: PRT
<213> ORGANISM: Homo sapiens

<400> SEQUENCE: 306

Thr Phe Val Asn Ile Thr Pro Ala Glu Val Gly Val Leu Val Gly Lys
1               5                   10                  15

Asp Arg

<210> SEQ ID NO 307
<211> LENGTH: 16
<212> TYPE: PRT
<213> ORGANISM: Homo sapiens

<400> SEQUENCE: 307

Thr Lys Ser Thr Gly Gly Ala Pro Thr Phe Asn Val Thr Val Thr Lys
1               5                   10                  15

<210> SEQ ID NO 308
```

<211> LENGTH: 19
<212> TYPE: PRT
<213> ORGANISM: Homo sapiens

<400> SEQUENCE: 308

Thr Lys Ser Thr Gly Gly Ala Pro Thr Phe Asn Val Thr Val Thr Lys
1               5                   10                  15

Thr Asp Lys

<210> SEQ ID NO 309
<211> LENGTH: 10
<212> TYPE: PRT
<213> ORGANISM: Homo sapiens

<400> SEQUENCE: 309

Ala Thr Phe Ile Ser Val Gln Leu Lys Lys
1               5                   10

<210> SEQ ID NO 310
<211> LENGTH: 11
<212> TYPE: PRT
<213> ORGANISM: Homo sapiens

<400> SEQUENCE: 310

Phe Tyr Asn Glu Leu Thr Glu Ile Leu Val Arg
1               5                   10

<210> SEQ ID NO 311
<211> LENGTH: 14
<212> TYPE: PRT
<213> ORGANISM: Homo sapiens

<400> SEQUENCE: 311

Leu Ala Asn Gln Ala Ala Asp Tyr Phe Gly Asp Ala Phe Lys
1               5                   10

<210> SEQ ID NO 312
<211> LENGTH: 13
<212> TYPE: PRT
<213> ORGANISM: Homo sapiens

<400> SEQUENCE: 312

Leu Leu Asp Glu Glu Glu Ala Thr Asp Asn Asp Leu Arg
1               5                   10

<210> SEQ ID NO 313
<211> LENGTH: 16
<212> TYPE: PRT
<213> ORGANISM: Homo sapiens

<400> SEQUENCE: 313

Ser Val Ile Glu Gln Gly Gly Ile Gln Thr Val Asp Gln Leu Ile Lys
1               5                   10                  15

<210> SEQ ID NO 314
<211> LENGTH: 26
<212> TYPE: PRT
<213> ORGANISM: Homo sapiens

<400> SEQUENCE: 314

Cys Ile Trp Gly Pro Ser Tyr Trp Cys Gln Asn Thr Glu Thr Ala Ala
1               5                   10                  15

Gln Cys Asn Ala Val Glu His Cys Lys Arg
            20                  25

```
<210> SEQ ID NO 315
<211> LENGTH: 15
<212> TYPE: PRT
<213> ORGANISM: Homo sapiens

<400> SEQUENCE: 315

Glu Ile Val Asp Ser Tyr Leu Pro Val Ile Leu Asp Ile Ile Lys
1               5                   10                  15

<210> SEQ ID NO 316
<211> LENGTH: 10
<212> TYPE: PRT
<213> ORGANISM: Homo sapiens

<400> SEQUENCE: 316

Gly Ser Ala Val Trp Cys Gln Asn Val Lys
1               5                   10

<210> SEQ ID NO 317
<211> LENGTH: 13
<212> TYPE: PRT
<213> ORGANISM: Homo sapiens

<400> SEQUENCE: 317

His Cys Leu Gln Thr Val Trp Asn Lys Pro Thr Val Lys
1               5                   10

<210> SEQ ID NO 318
<211> LENGTH: 9
<212> TYPE: PRT
<213> ORGANISM: Homo sapiens

<400> SEQUENCE: 318

His Leu Ala Glu Leu Asn His Gln Lys
1               5

<210> SEQ ID NO 319
<211> LENGTH: 12
<212> TYPE: PRT
<213> ORGANISM: Homo sapiens

<400> SEQUENCE: 319

Ala Phe Ile Gln Leu Trp Ala Phe Asp Ala Val Lys
1               5                   10

<210> SEQ ID NO 320
<211> LENGTH: 14
<212> TYPE: PRT
<213> ORGANISM: Homo sapiens

<400> SEQUENCE: 320

Ala Phe Ile Gln Leu Trp Ala Phe Asp Ala Val Lys Gly Lys
1               5                   10

<210> SEQ ID NO 321
<211> LENGTH: 15
<212> TYPE: PRT
<213> ORGANISM: Homo sapiens

<400> SEQUENCE: 321

Cys Val Leu Phe Pro Tyr Gly Gly Cys Gln Gly Asn Gly Asn Lys
1               5                   10                  15
```

```
<210> SEQ ID NO 322
<211> LENGTH: 15
<212> TYPE: PRT
<213> ORGANISM: Homo sapiens

<400> SEQUENCE: 322

Thr Val Ala Ala Cys Asn Leu Pro Ile Val Arg Gly Pro Cys Arg
1               5                   10                  15

<210> SEQ ID NO 323
<211> LENGTH: 8
<212> TYPE: PRT
<213> ORGANISM: Homo sapiens

<400> SEQUENCE: 323

Glu Thr Leu Leu Gln Asp Phe Arg
1               5

<210> SEQ ID NO 324
<211> LENGTH: 15
<212> TYPE: PRT
<213> ORGANISM: Homo sapiens

<400> SEQUENCE: 324

Glu Tyr Cys Gly Val Pro Gly Asp Gly Asp Glu Glu Leu Leu Arg
1               5                   10                  15

<210> SEQ ID NO 325
<211> LENGTH: 11
<212> TYPE: PRT
<213> ORGANISM: Homo sapiens

<400> SEQUENCE: 325

Thr Val Ala Ala Cys Asn Leu Pro Ile Val Arg
1               5                   10

<210> SEQ ID NO 326
<211> LENGTH: 20
<212> TYPE: PRT
<213> ORGANISM: Homo sapiens

<400> SEQUENCE: 326

Asp Lys Leu Ala Ala Cys Leu Glu Gly Asn Cys Ala Glu Gly Leu Gly
1               5                   10                  15

Thr Asn Tyr Arg
            20

<210> SEQ ID NO 327
<211> LENGTH: 10
<212> TYPE: PRT
<213> ORGANISM: Homo sapiens

<400> SEQUENCE: 327

Glu Leu Leu Glu Ser Tyr Ile Asp Gly Arg
1               5                   10

<210> SEQ ID NO 328
<211> LENGTH: 16
<212> TYPE: PRT
<213> ORGANISM: Homo sapiens

<400> SEQUENCE: 328

Lys Ser Pro Gln Glu Leu Leu Cys Gly Ala Ser Leu Ile Ser Asp Arg
1               5                   10                  15
```

<210> SEQ ID NO 329
<211> LENGTH: 19
<212> TYPE: PRT
<213> ORGANISM: Homo sapiens

<400> SEQUENCE: 329

Leu Ala Val Thr Thr His Gly Leu Pro Cys Leu Ala Trp Ala Ser Ala
1               5                   10                  15

Gln Ala Lys

<210> SEQ ID NO 330
<211> LENGTH: 9
<212> TYPE: PRT
<213> ORGANISM: Homo sapiens

<400> SEQUENCE: 330

Ser Gly Ile Glu Cys Gln Leu Trp Arg
1               5

<210> SEQ ID NO 331
<211> LENGTH: 13
<212> TYPE: PRT
<213> ORGANISM: Homo sapiens

<400> SEQUENCE: 331

Thr Ala Thr Ser Glu Tyr Gln Thr Phe Phe Asn Pro Arg
1               5                   10

<210> SEQ ID NO 332
<211> LENGTH: 26
<212> TYPE: PRT
<213> ORGANISM: Homo sapiens

<400> SEQUENCE: 332

Ser Glu Gly Ser Ser Val Asn Leu Ser Pro Pro Leu Glu Gln Cys Val
1               5                   10                  15

Pro Asp Arg Gly Gln Gln Tyr Gln Gly Arg
            20                  25

<210> SEQ ID NO 333
<211> LENGTH: 15
<212> TYPE: PRT
<213> ORGANISM: Homo sapiens

<400> SEQUENCE: 333

Ala Asn Asn Thr Phe Tyr Gly Leu Ser Ala Gly Val Phe Thr Lys
1               5                   10                  15

<210> SEQ ID NO 334
<211> LENGTH: 14
<212> TYPE: PRT
<213> ORGANISM: Homo sapiens

<400> SEQUENCE: 334

Glu Leu Gly Glu Tyr Gly Phe His Glu Tyr Thr Glu Val Lys
1               5                   10

<210> SEQ ID NO 335
<211> LENGTH: 10
<212> TYPE: PRT
<213> ORGANISM: Homo sapiens

<400> SEQUENCE: 335

Phe Lys Ser Leu Asp Asp Val Ile Lys Arg
1               5                   10

<210> SEQ ID NO 336
<211> LENGTH: 17
<212> TYPE: PRT
<213> ORGANISM: Homo sapiens

<400> SEQUENCE: 336

Gly Tyr Phe Val Gln Pro Thr Val Phe Ser Asn Val Thr Asp Glu Met
1               5                   10                  15

Arg

<210> SEQ ID NO 337
<211> LENGTH: 14
<212> TYPE: PRT
<213> ORGANISM: Homo sapiens

<400> SEQUENCE: 337

Ile Phe Ile Asn Asn Glu Trp His Asp Ser Val Ser Gly Lys
1               5                   10

<210> SEQ ID NO 338
<211> LENGTH: 13
<212> TYPE: PRT
<213> ORGANISM: Homo sapiens

<400> SEQUENCE: 338

Ile Phe Val Glu Glu Ser Ile Tyr Asp Glu Phe Val Arg
1               5                   10

<210> SEQ ID NO 339
<211> LENGTH: 14
<212> TYPE: PRT
<213> ORGANISM: Homo sapiens

<400> SEQUENCE: 339

Ile Phe Val Glu Glu Ser Ile Tyr Asp Glu Phe Val Arg Arg
1               5                   10

<210> SEQ ID NO 340
<211> LENGTH: 31
<212> TYPE: PRT
<213> ORGANISM: Homo sapiens

<400> SEQUENCE: 340

Ile Gly Pro Ala Leu Ser Cys Gly Asn Thr Val Val Lys Pro Ala
1               5                   10                  15

Glu Gln Thr Pro Leu Thr Ala Leu His Val Ala Ser Leu Ile Lys
            20                  25                  30

<210> SEQ ID NO 341
<211> LENGTH: 10
<212> TYPE: PRT
<213> ORGANISM: Homo sapiens

<400> SEQUENCE: 341

Ile Leu Asp Leu Ile Glu Ser Gly Lys Lys
1               5                   10

<210> SEQ ID NO 342
<211> LENGTH: 26
<212> TYPE: PRT
<213> ORGANISM: Homo sapiens

<400> SEQUENCE: 342

Lys Phe Pro Val Phe Asn Pro Ala Thr Glu Glu Leu Cys Gln Val
1               5                   10                  15

Glu Glu Gly Asp Lys Glu Asp Val Asp Lys
            20                  25

<210> SEQ ID NO 343
<211> LENGTH: 25
<212> TYPE: PRT
<213> ORGANISM: Homo sapiens

<400> SEQUENCE: 343

Lys Tyr Ile Leu Gly Asn Pro Leu Thr Pro Gly Val Thr Gln Gly Pro
1               5                   10                  15

Gln Ile Asp Lys Glu Gln Tyr Asp Lys
            20                  25

<210> SEQ ID NO 344
<211> LENGTH: 7
<212> TYPE: PRT
<213> ORGANISM: Homo sapiens

<400> SEQUENCE: 344

Leu Ala Asp Leu Ile Glu Arg
1               5

<210> SEQ ID NO 345
<211> LENGTH: 11
<212> TYPE: PRT
<213> ORGANISM: Homo sapiens

<400> SEQUENCE: 345

Leu Glu Cys Gly Gly Gly Pro Trp Gly Asn Lys
1               5                   10

<210> SEQ ID NO 346
<211> LENGTH: 11
<212> TYPE: PRT
<213> ORGANISM: Homo sapiens

<400> SEQUENCE: 346

Leu Leu Tyr Lys Leu Ala Asp Leu Ile Glu Arg
1               5                   10

<210> SEQ ID NO 347
<211> LENGTH: 15
<212> TYPE: PRT
<213> ORGANISM: Homo sapiens

<400> SEQUENCE: 347

Leu Tyr Ser Asn Ala Tyr Leu Asn Asp Leu Ala Gly Cys Ile Lys
1               5                   10                  15

<210> SEQ ID NO 348
<211> LENGTH: 16
<212> TYPE: PRT
<213> ORGANISM: Homo sapiens

<400> SEQUENCE: 348

Arg Ala Asn Asn Thr Phe Tyr Gly Leu Ser Ala Gly Val Phe Thr Lys
1               5                   10                  15

```
<210> SEQ ID NO 349
<211> LENGTH: 23
<212> TYPE: PRT
<213> ORGANISM: Homo sapiens

<400> SEQUENCE: 349

Ser Leu Asp Asp Val Ile Lys Arg Ala Asn Asn Thr Phe Tyr Gly Leu
1               5                   10                  15

Ser Ala Gly Val Phe Thr Lys
            20

<210> SEQ ID NO 350
<211> LENGTH: 16
<212> TYPE: PRT
<213> ORGANISM: Homo sapiens

<400> SEQUENCE: 350

Ser Ser Ser Gly Thr Pro Asp Leu Pro Val Leu Leu Thr Asp Leu Lys
1               5                   10                  15

<210> SEQ ID NO 351
<211> LENGTH: 13
<212> TYPE: PRT
<213> ORGANISM: Homo sapiens

<400> SEQUENCE: 351

Thr Ile Pro Ile Asp Gly Asn Phe Phe Thr Tyr Thr Arg
1               5                   10

<210> SEQ ID NO 352
<211> LENGTH: 12
<212> TYPE: PRT
<213> ORGANISM: Homo sapiens

<400> SEQUENCE: 352

Tyr Cys Ala Gly Trp Ala Asp Lys Ile Gln Gly Arg
1               5                   10

<210> SEQ ID NO 353
<211> LENGTH: 24
<212> TYPE: PRT
<213> ORGANISM: Homo sapiens

<400> SEQUENCE: 353

Tyr Ile Leu Gly Asn Pro Leu Thr Pro Gly Val Thr Gln Gly Pro Gln
1               5                   10                  15

Ile Asp Lys Glu Gln Tyr Asp Lys
            20

<210> SEQ ID NO 354
<211> LENGTH: 11
<212> TYPE: PRT
<213> ORGANISM: Homo sapiens

<400> SEQUENCE: 354

Val Ala Phe Thr Gly Ser Thr Glu Val Gly Lys
1               5                   10

<210> SEQ ID NO 355
<211> LENGTH: 9
<212> TYPE: PRT
<213> ORGANISM: Homo sapiens

<400> SEQUENCE: 355
```

-continued

Asp Leu Cys Gly Ile Val Ala Ser Lys
1               5

<210> SEQ ID NO 356
<211> LENGTH: 14
<212> TYPE: PRT
<213> ORGANISM: Homo sapiens

<400> SEQUENCE: 356

Glu Leu Cys Gln Gly Leu Gly Gln Pro Gly Ser Val Leu Arg
1               5                   10

<210> SEQ ID NO 357
<211> LENGTH: 15
<212> TYPE: PRT
<213> ORGANISM: Homo sapiens

<400> SEQUENCE: 357

Glu Leu Ser Leu Ala Gly Asn Glu Leu Gly Asp Glu Gly Ala Arg
1               5                   10                  15

<210> SEQ ID NO 358
<211> LENGTH: 10
<212> TYPE: PRT
<213> ORGANISM: Homo sapiens

<400> SEQUENCE: 358

Leu Asp Asp Cys Gly Leu Thr Glu Ala Arg
1               5                   10

<210> SEQ ID NO 359
<211> LENGTH: 22
<212> TYPE: PRT
<213> ORGANISM: Homo sapiens

<400> SEQUENCE: 359

Ser Asn Glu Leu Gly Asp Val Gly Val His Cys Val Leu Gln Gly Leu
1               5                   10                  15

Gln Thr Pro Ser Cys Lys
            20

<210> SEQ ID NO 360
<211> LENGTH: 12
<212> TYPE: PRT
<213> ORGANISM: Homo sapiens

<400> SEQUENCE: 360

Thr Leu Trp Ile Trp Glu Cys Gly Ile Thr Ala Lys
1               5                   10

<210> SEQ ID NO 361
<211> LENGTH: 11
<212> TYPE: PRT
<213> ORGANISM: Homo sapiens

<400> SEQUENCE: 361

Val Asn Pro Ala Leu Ala Glu Leu Asn Leu Arg
1               5                   10

<210> SEQ ID NO 362
<211> LENGTH: 15
<212> TYPE: PRT
<213> ORGANISM: Homo sapiens

<400> SEQUENCE: 362

```
Trp Ala Glu Leu Leu Pro Leu Leu Gln Gln Cys Gln Val Val Arg
1               5                   10                  15
```

<210> SEQ ID NO 363
<211> LENGTH: 12
<212> TYPE: PRT
<213> ORGANISM: Homo sapiens

<400> SEQUENCE: 363

```
Leu Glu Ser Cys Gly Val Thr Ser Asp Asn Cys Arg
1               5                   10
```

<210> SEQ ID NO 364
<211> LENGTH: 10
<212> TYPE: PRT
<213> ORGANISM: Homo sapiens

<400> SEQUENCE: 364

```
Glu Leu Asp Leu Asn Ser Val Leu Leu Lys
1               5                   10
```

<210> SEQ ID NO 365
<211> LENGTH: 13
<212> TYPE: PRT
<213> ORGANISM: Homo sapiens

<400> SEQUENCE: 365

```
Gln Glu Val Trp Leu Ala Asn Gly Ala Ala Glu Ser Arg
1               5                   10
```

<210> SEQ ID NO 366
<211> LENGTH: 21
<212> TYPE: PRT
<213> ORGANISM: Homo sapiens

<400> SEQUENCE: 366

```
Leu Gly Ile Lys Pro Ser Ile Asn Tyr Tyr Gln Val Ala Asp Phe Lys
1               5                   10                  15

Asp Ala Leu Ala Arg
            20
```

<210> SEQ ID NO 367
<211> LENGTH: 16
<212> TYPE: PRT
<213> ORGANISM: Homo sapiens

<400> SEQUENCE: 367

```
His Gly Thr Cys Ala Ala Gln Val Asp Ala Leu Asn Ser Gln Lys Lys
1               5                   10                  15
```

<210> SEQ ID NO 368
<211> LENGTH: 15
<212> TYPE: PRT
<213> ORGANISM: Homo sapiens

<400> SEQUENCE: 368

```
His Gly Thr Cys Ala Ala Gln Val Asp Ala Leu Asn Ser Gln Lys
1               5                   10                  15
```

<210> SEQ ID NO 369
<211> LENGTH: 8
<212> TYPE: PRT
<213> ORGANISM: Homo sapiens -continued

```
<400> SEQUENCE: 369

Leu Ala Leu Leu Glu Glu Ala Arg
1               5

<210> SEQ ID NO 370
<211> LENGTH: 11
<212> TYPE: PRT
<213> ORGANISM: Homo sapiens

<400> SEQUENCE: 370

Ala Leu Asn Ser Ile Ile Asp Val Tyr His Lys
1               5                   10

<210> SEQ ID NO 371
<211> LENGTH: 16
<212> TYPE: PRT
<213> ORGANISM: Homo sapiens

<400> SEQUENCE: 371

Ala Leu Asn Ser Ile Ile Asp Val Tyr His Lys Tyr Ser Leu Ile Lys
1               5                   10                  15

<210> SEQ ID NO 372
<211> LENGTH: 16
<212> TYPE: PRT
<213> ORGANISM: Homo sapiens

<400> SEQUENCE: 372

Asp Asp Leu Lys Lys Leu Leu Glu Thr Glu Cys Pro Gln Tyr Ile Arg
1               5                   10                  15

<210> SEQ ID NO 373
<211> LENGTH: 21
<212> TYPE: PRT
<213> ORGANISM: Homo sapiens

<400> SEQUENCE: 373

Glu Leu Asp Ile Asn Thr Asp Gly Ala Val Asn Phe Gln Glu Phe Leu
1               5                   10                  15

Ile Leu Val Ile Lys
            20

<210> SEQ ID NO 374
<211> LENGTH: 7
<212> TYPE: PRT
<213> ORGANISM: Homo sapiens

<400> SEQUENCE: 374

Gly Ala Asp Val Trp Phe Lys
1               5

<210> SEQ ID NO 375
<211> LENGTH: 8
<212> TYPE: PRT
<213> ORGANISM: Homo sapiens

<400> SEQUENCE: 375

Gly Asn Phe His Ala Val Tyr Arg
1               5

<210> SEQ ID NO 376
<211> LENGTH: 12
<212> TYPE: PRT
<213> ORGANISM: Homo sapiens
```

<400> SEQUENCE: 376

Gly Asn Phe His Ala Val Tyr Arg Asp Asp Leu Lys
1               5                   10

<210> SEQ ID NO 377
<211> LENGTH: 13
<212> TYPE: PRT
<213> ORGANISM: Homo sapiens

<400> SEQUENCE: 377

Gly Asn Phe His Ala Val Tyr Arg Asp Asp Leu Lys Lys
1               5                   10

<210> SEQ ID NO 378
<211> LENGTH: 12
<212> TYPE: PRT
<213> ORGANISM: Homo sapiens

<400> SEQUENCE: 378

Lys Leu Leu Glu Thr Glu Cys Pro Gln Tyr Ile Arg
1               5                   10

<210> SEQ ID NO 379
<211> LENGTH: 11
<212> TYPE: PRT
<213> ORGANISM: Homo sapiens

<400> SEQUENCE: 379

Leu Leu Glu Thr Glu Cys Pro Gln Tyr Ile Arg
1               5                   10

<210> SEQ ID NO 380
<211> LENGTH: 8
<212> TYPE: PRT
<213> ORGANISM: Homo sapiens

<400> SEQUENCE: 380

Met Gly Val Ala Ala His Lys Lys
1               5

<210> SEQ ID NO 381
<211> LENGTH: 7
<212> TYPE: PRT
<213> ORGANISM: Homo sapiens

<400> SEQUENCE: 381

Met Leu Thr Glu Leu Glu Lys
1               5

<210> SEQ ID NO 382
<211> LENGTH: 7
<212> TYPE: PRT
<213> ORGANISM: Homo sapiens

<400> SEQUENCE: 382

Asp Leu Gln Asn Phe Leu Lys
1               5

<210> SEQ ID NO 383
<211> LENGTH: 8
<212> TYPE: PRT
<213> ORGANISM: Homo sapiens

<400> SEQUENCE: 383

```
Asp Leu Gln Asn Phe Leu Lys Lys
1               5

<210> SEQ ID NO 384
<211> LENGTH: 11
<212> TYPE: PRT
<213> ORGANISM: Homo sapiens

<400> SEQUENCE: 384

Asp Leu Gln Asn Phe Leu Lys Lys Glu Asn Lys
1               5                   10

<210> SEQ ID NO 385
<211> LENGTH: 12
<212> TYPE: PRT
<213> ORGANISM: Homo sapiens

<400> SEQUENCE: 385

Glu Leu Val Arg Lys Asp Leu Gln Asn Phe Leu Lys
1               5                   10

<210> SEQ ID NO 386
<211> LENGTH: 8
<212> TYPE: PRT
<213> ORGANISM: Homo sapiens

<400> SEQUENCE: 386

Lys Asp Leu Gln Asn Phe Leu Lys
1               5

<210> SEQ ID NO 387
<211> LENGTH: 9
<212> TYPE: PRT
<213> ORGANISM: Homo sapiens

<400> SEQUENCE: 387

Lys Asp Leu Gln Asn Phe Leu Lys Lys
1               5

<210> SEQ ID NO 388
<211> LENGTH: 13
<212> TYPE: PRT
<213> ORGANISM: Homo sapiens

<400> SEQUENCE: 388

Leu Gly His Pro Asp Thr Leu Asn Gln Gly Glu Phe Lys
1               5                   10

<210> SEQ ID NO 389
<211> LENGTH: 17
<212> TYPE: PRT
<213> ORGANISM: Homo sapiens

<400> SEQUENCE: 389

Leu Gly His Pro Asp Thr Leu Asn Gln Gly Glu Phe Lys Glu Leu Val
1               5                   10                  15

Arg

<210> SEQ ID NO 390
<211> LENGTH: 8
<212> TYPE: PRT
<213> ORGANISM: Homo sapiens

<400> SEQUENCE: 390
```

```
Leu Thr Trp Ala Ser His Glu Lys
1               5
```

<210> SEQ ID NO 391
<211> LENGTH: 21
<212> TYPE: PRT
<213> ORGANISM: Homo sapiens

<400> SEQUENCE: 391

```
Met His Glu Gly Asp Glu Gly Pro Gly His His His Lys Pro Gly Leu
1               5                   10                  15

Gly Glu Gly Thr Pro
            20
```

<210> SEQ ID NO 392
<211> LENGTH: 15
<212> TYPE: PRT
<213> ORGANISM: Homo sapiens

<400> SEQUENCE: 392

```
Asn Ile Glu Thr Ile Ile Asn Thr Phe His Gln Tyr Ser Val Lys
1               5                   10                  15
```

<210> SEQ ID NO 393
<211> LENGTH: 28
<212> TYPE: PRT
<213> ORGANISM: Homo sapiens

<400> SEQUENCE: 393

```
Asn Ile Glu Thr Ile Ile Asn Thr Phe His Gln Tyr Ser Val Lys Leu
1               5                   10                  15

Gly His Pro Asp Thr Leu Asn Gln Gly Glu Phe Lys
            20                  25
```

<210> SEQ ID NO 394
<211> LENGTH: 9
<212> TYPE: PRT
<213> ORGANISM: Homo sapiens

<400> SEQUENCE: 394

```
Thr Cys Lys Met Ser Gln Leu Glu Arg
1               5
```

<210> SEQ ID NO 395
<211> LENGTH: 15
<212> TYPE: PRT
<213> ORGANISM: Homo sapiens

<400> SEQUENCE: 395

```
Val Ile Glu His Ile Met Glu Asp Leu Asp Thr Asn Ala Asp Lys
1               5                   10                  15
```

<210> SEQ ID NO 396
<211> LENGTH: 17
<212> TYPE: PRT
<213> ORGANISM: Homo sapiens

<400> SEQUENCE: 396

```
Ala Cys Pro Leu Asp Gln Ala Ile Gly Leu Leu Val Ala Ile Phe His
1               5                   10                  15

Lys
```

```
<210> SEQ ID NO 397
<211> LENGTH: 12
<212> TYPE: PRT
<213> ORGANISM: Homo sapiens

<400> SEQUENCE: 397

Glu Leu Ile Gln Lys Glu Leu Thr Ile Gly Ser Lys
1               5                   10

<210> SEQ ID NO 398
<211> LENGTH: 20
<212> TYPE: PRT
<213> ORGANISM: Homo sapiens

<400> SEQUENCE: 398

Glu Leu Ile Gln Lys Glu Leu Thr Ile Gly Ser Lys Leu Gln Asp Ala
1               5                   10                  15

Glu Ile Ala Arg
            20

<210> SEQ ID NO 399
<211> LENGTH: 15
<212> TYPE: PRT
<213> ORGANISM: Homo sapiens

<400> SEQUENCE: 399

Glu Leu Lys Glu Leu Ile Gln Lys Glu Leu Thr Ile Gly Ser Lys
1               5                   10                  15

<210> SEQ ID NO 400
<211> LENGTH: 15
<212> TYPE: PRT
<213> ORGANISM: Homo sapiens

<400> SEQUENCE: 400

Glu Leu Thr Ile Gly Ser Lys Leu Gln Asp Ala Glu Ile Ala Arg
1               5                   10                  15

<210> SEQ ID NO 401
<211> LENGTH: 9
<212> TYPE: PRT
<213> ORGANISM: Homo sapiens

<400> SEQUENCE: 401

Lys Glu Leu Lys Glu Leu Ile Gln Lys
1               5

<210> SEQ ID NO 402
<211> LENGTH: 8
<212> TYPE: PRT
<213> ORGANISM: Homo sapiens

<400> SEQUENCE: 402

Leu Gln Asp Ala Glu Ile Ala Arg
1               5

<210> SEQ ID NO 403
<211> LENGTH: 28
<212> TYPE: PRT
<213> ORGANISM: Homo sapiens

<400> SEQUENCE: 403

Asn Lys Asp Gln Glu Val Asn Phe Gln Glu Tyr Val Thr Phe Leu Gly
1               5                   10                  15
```

Ala Leu Ala Leu Ile Tyr Asn Glu Ala Leu Lys Gly
            20                  25

<210> SEQ ID NO 404
<211> LENGTH: 13
<212> TYPE: PRT
<213> ORGANISM: Homo sapiens

<400> SEQUENCE: 404

Tyr Ser Gly Arg Glu Gly Asp Lys His Thr Leu Ser Lys
1               5                   10

<210> SEQ ID NO 405
<211> LENGTH: 16
<212> TYPE: PRT
<213> ORGANISM: Homo sapiens

<400> SEQUENCE: 405

Phe Pro Glu Pro Gly Ala Ile Lys Val Pro Glu Gln Gly Tyr Thr Lys
1               5                   10                  15

<210> SEQ ID NO 406
<211> LENGTH: 17
<212> TYPE: PRT
<213> ORGANISM: Homo sapiens

<400> SEQUENCE: 406

Leu Pro Glu Pro Cys Pro Ser Thr Val Thr Pro Gly Pro Ala Gln Gln
1               5                   10                  15

Lys

<210> SEQ ID NO 407
<211> LENGTH: 16
<212> TYPE: PRT
<213> ORGANISM: Homo sapiens

<400> SEQUENCE: 407

Gln Pro Ser Gln Pro Pro Pro Gln Glu Ile Phe Val Pro Thr Thr Lys
1               5                   10                  15

<210> SEQ ID NO 408
<211> LENGTH: 22
<212> TYPE: PRT
<213> ORGANISM: Homo sapiens

<400> SEQUENCE: 408

Gln Pro Ser Gln Pro Pro Pro Gln Glu Ile Phe Val Pro Thr Thr Lys
1               5                   10                  15

Glu Pro Cys His Ser Lys
            20

<210> SEQ ID NO 409
<211> LENGTH: 15
<212> TYPE: PRT
<213> ORGANISM: Homo sapiens

<400> SEQUENCE: 409

Gln Thr Phe Thr Pro Pro Pro Gln Leu Gln Gln Gln Gln Val Lys
1               5                   10                  15

<210> SEQ ID NO 410
<211> LENGTH: 16
<212> TYPE: PRT
<213> ORGANISM: Homo sapiens

```
<400> SEQUENCE: 410

Val Pro Asp Gln Gly Phe Ile Lys Phe Pro Glu Pro Gly Ala Ile Lys
1               5                   10                  15

<210> SEQ ID NO 411
<211> LENGTH: 16
<212> TYPE: PRT
<213> ORGANISM: Homo sapiens

<400> SEQUENCE: 411

Val Pro Glu Pro Gly Cys Thr Lys Val Pro Glu Pro Gly Cys Thr Lys
1               5                   10                  15

<210> SEQ ID NO 412
<211> LENGTH: 16
<212> TYPE: PRT
<213> ORGANISM: Homo sapiens

<400> SEQUENCE: 412

Val Pro Gln Pro Gly Asn Thr Lys Ile Pro Glu Pro Gly Cys Thr Lys
1               5                   10                  15

<210> SEQ ID NO 413
<211> LENGTH: 12
<212> TYPE: PRT
<213> ORGANISM: Homo sapiens

<400> SEQUENCE: 413

Val Ala Gly Gln Asp Gly Ser Val Val Gln Phe Lys
1               5                   10

<210> SEQ ID NO 414
<211> LENGTH: 10
<212> TYPE: PRT
<213> ORGANISM: Homo sapiens

<400> SEQUENCE: 414

Glu Glu Asp Ile Asp Glu Asn Leu Leu Phe
1               5                   10

<210> SEQ ID NO 415
<211> LENGTH: 29
<212> TYPE: PRT
<213> ORGANISM: Homo sapiens

<400> SEQUENCE: 415

Glu His Ala Asn Ser Lys Gln Glu Glu Asp Asn Thr Gln Ser Asp Asp
1               5                   10                  15

Ile Leu Glu Glu Ser Asp Gln Pro Thr Gln Val Ser Lys
            20                  25

<210> SEQ ID NO 416
<211> LENGTH: 15
<212> TYPE: PRT
<213> ORGANISM: Homo sapiens

<400> SEQUENCE: 416

Thr Gly Leu Glu Ala Ile Ser Asn His Lys Glu Thr Glu Glu Lys
1               5                   10                  15

<210> SEQ ID NO 417
<211> LENGTH: 13
<212> TYPE: PRT
```

-continued

<213> ORGANISM: Homo sapiens

<400> SEQUENCE: 417

Gly His Gln Leu Gln Leu Asp Tyr Phe Gly Ala Cys Lys
1               5                   10

<210> SEQ ID NO 418
<211> LENGTH: 19
<212> TYPE: PRT
<213> ORGANISM: Homo sapiens

<400> SEQUENCE: 418

His Ser Ala Ser Asp Asp Tyr Phe Ile Pro Ser Gln Ala Phe Leu Glu
1               5                   10                  15

Ala Glu Arg

<210> SEQ ID NO 419
<211> LENGTH: 21
<212> TYPE: PRT
<213> ORGANISM: Homo sapiens

<400> SEQUENCE: 419

Asn His Gly Val Asp Asp Asp Gly Asp Asp Gly Asp Asp Gly Gly
1               5                   10                  15

Thr Asp Gly Pro Arg
            20

<210> SEQ ID NO 420
<211> LENGTH: 16
<212> TYPE: PRT
<213> ORGANISM: Homo sapiens

<400> SEQUENCE: 420

Ser Ile Pro Thr Cys Thr Asp Phe Glu Val Ile Gln Phe Pro Leu Arg
1               5                   10                  15

<210> SEQ ID NO 421
<211> LENGTH: 8
<212> TYPE: PRT
<213> ORGANISM: Homo sapiens

<400> SEQUENCE: 421

Ala Asn Phe Glu Asn Leu Ala Lys
1               5

<210> SEQ ID NO 422
<211> LENGTH: 13
<212> TYPE: PRT
<213> ORGANISM: Homo sapiens

<400> SEQUENCE: 422

Tyr Gly Leu Phe Pro Ala Asn Tyr Val Glu Leu Arg Gln
1               5                   10

<210> SEQ ID NO 423
<211> LENGTH: 10
<212> TYPE: PRT
<213> ORGANISM: Homo sapiens

<400> SEQUENCE: 423

Tyr Gly Val Gln Ala Asp Arg Val Asp Lys
1               5                   10

```
<210> SEQ ID NO 424
<211> LENGTH: 14
<212> TYPE: PRT
<213> ORGANISM: Homo sapiens

<400> SEQUENCE: 424

Ala Asp Asp Leu Gly Lys Gly Gly Asn Glu Glu Ser Thr Lys
1               5                   10

<210> SEQ ID NO 425
<211> LENGTH: 21
<212> TYPE: PRT
<213> ORGANISM: Homo sapiens

<400> SEQUENCE: 425

Ala Asp Asp Leu Gly Lys Gly Gly Asn Glu Glu Ser Thr Lys Thr Gly
1               5                   10                  15

Asn Ala Gly Ser Arg
            20

<210> SEQ ID NO 426
<211> LENGTH: 23
<212> TYPE: PRT
<213> ORGANISM: Homo sapiens

<400> SEQUENCE: 426

Ala Thr Lys Ala Val Cys Val Leu Lys Gly Asp Gly Pro Val Gln Gly
1               5                   10                  15

Ile Ile Asn Phe Glu Gln Lys
            20

<210> SEQ ID NO 427
<211> LENGTH: 20
<212> TYPE: PRT
<213> ORGANISM: Homo sapiens

<400> SEQUENCE: 427

Ala Val Cys Val Leu Lys Gly Asp Gly Pro Val Gln Gly Ile Ile Asn
1               5                   10                  15

Phe Glu Gln Lys
            20

<210> SEQ ID NO 428
<211> LENGTH: 13
<212> TYPE: PRT
<213> ORGANISM: Homo sapiens

<400> SEQUENCE: 428

Glu Ser Asn Gly Pro Val Lys Val Trp Gly Ser Ile Lys
1               5                   10

<210> SEQ ID NO 429
<211> LENGTH: 14
<212> TYPE: PRT
<213> ORGANISM: Homo sapiens

<400> SEQUENCE: 429

Gly Asp Gly Pro Val Gln Gly Ile Ile Asn Phe Glu Gln Lys
1               5                   10

<210> SEQ ID NO 430
<211> LENGTH: 36
<212> TYPE: PRT
<213> ORGANISM: Homo sapiens
```

<400> SEQUENCE: 430

His Val Gly Asp Leu Gly Asn Val Thr Ala Asp Lys Asp Gly Val Ala
1               5                   10                  15

Asp Val Ser Ile Glu Asp Ser Val Ile Ser Leu Ser Gly Asp His Cys
            20                  25                  30

Ile Ile Gly Arg
        35

<210> SEQ ID NO 431
<211> LENGTH: 14
<212> TYPE: PRT
<213> ORGANISM: Homo sapiens

<400> SEQUENCE: 431

Ala Ile Trp Asn Val Ile Asn Trp Glu Asn Val Thr Glu Arg
1               5                   10

<210> SEQ ID NO 432
<211> LENGTH: 14
<212> TYPE: PRT
<213> ORGANISM: Homo sapiens

<400> SEQUENCE: 432

Gly Asp Val Thr Ala Gln Ile Ala Leu Gln Pro Ala Leu Lys
1               5                   10

<210> SEQ ID NO 433
<211> LENGTH: 19
<212> TYPE: PRT
<213> ORGANISM: Homo sapiens

<400> SEQUENCE: 433

Asp Ala Gly Gly Lys Ser Trp Cys Pro Asp Cys Val Gln Ala Glu Pro
1               5                   10                  15

Val Val Arg

<210> SEQ ID NO 434
<211> LENGTH: 14
<212> TYPE: PRT
<213> ORGANISM: Homo sapiens

<400> SEQUENCE: 434

Ser Trp Cys Pro Asp Cys Val Gln Ala Glu Pro Val Val Arg
1               5                   10

<210> SEQ ID NO 435
<211> LENGTH: 10
<212> TYPE: PRT
<213> ORGANISM: Homo sapiens

<400> SEQUENCE: 435

Thr Ile Phe Ala Tyr Phe Thr Gly Ser Lys
1               5                   10

<210> SEQ ID NO 436
<211> LENGTH: 13
<212> TYPE: PRT
<213> ORGANISM: Homo sapiens

<400> SEQUENCE: 436

Ala Ala Asp Asp Thr Trp Glu Pro Phe Ala Ser Gly Lys
1               5                   10

```
<210> SEQ ID NO 437
<211> LENGTH: 13
<212> TYPE: PRT
<213> ORGANISM: Homo sapiens

<400> SEQUENCE: 437

Gly Ser Pro Ala Ile Asn Val Ala Val His Val Phe Arg
1               5                   10

<210> SEQ ID NO 438
<211> LENGTH: 14
<212> TYPE: PRT
<213> ORGANISM: Homo sapiens

<400> SEQUENCE: 438

Lys Ala Ala Asp Asp Thr Trp Glu Pro Phe Ala Ser Gly Lys
1               5                   10

<210> SEQ ID NO 439
<211> LENGTH: 24
<212> TYPE: PRT
<213> ORGANISM: Homo sapiens

<400> SEQUENCE: 439

Arg Tyr Thr Ile Ala Ala Leu Leu Ser Pro Tyr Ser Tyr Ser Thr Thr
1               5                   10                  15

Ala Val Val Thr Asn Pro Lys Glu
            20

<210> SEQ ID NO 440
<211> LENGTH: 22
<212> TYPE: PRT
<213> ORGANISM: Homo sapiens

<400> SEQUENCE: 440

Thr Ser Glu Ser Gly Glu Leu His Gly Leu Thr Thr Glu Glu Glu Phe
1               5                   10                  15

Val Glu Gly Ile Tyr Lys
            20

<210> SEQ ID NO 441
<211> LENGTH: 19
<212> TYPE: PRT
<213> ORGANISM: Homo sapiens

<400> SEQUENCE: 441

Val Leu Asp Ala Val Arg Gly Ser Pro Ala Ile Asn Val Ala Val His
1               5                   10                  15

Val Phe Arg

<210> SEQ ID NO 442
<211> LENGTH: 23
<212> TYPE: PRT
<213> ORGANISM: Homo sapiens

<400> SEQUENCE: 442

Tyr Thr Ile Ala Ala Leu Leu Ser Pro Tyr Ser Tyr Ser Thr Thr Ala
1               5                   10                  15

Val Val Thr Asn Pro Lys Glu
            20
```

<210> SEQ ID NO 443
<211> LENGTH: 11
<212> TYPE: PRT
<213> ORGANISM: Homo sapiens

<400> SEQUENCE: 443

Ala Gly Ile Thr Thr Ile Glu Ala Val Lys Arg
1               5                   10

<210> SEQ ID NO 444
<211> LENGTH: 15
<212> TYPE: PRT
<213> ORGANISM: Homo sapiens

<400> SEQUENCE: 444

His Ile Ala Glu Glu Ala Asp Arg Lys Tyr Glu Glu Val Ala Arg
1               5                   10                  15

<210> SEQ ID NO 445
<211> LENGTH: 10
<212> TYPE: PRT
<213> ORGANISM: Homo sapiens

<400> SEQUENCE: 445

Ile Gln Leu Val Glu Glu Glu Leu Asp Arg
1               5                   10

<210> SEQ ID NO 446
<211> LENGTH: 14
<212> TYPE: PRT
<213> ORGANISM: Homo sapiens

<400> SEQUENCE: 446

Ile Gln Leu Val Glu Glu Glu Leu Asp Arg Ala Gln Glu Arg
1               5                   10

<210> SEQ ID NO 447
<211> LENGTH: 14
<212> TYPE: PRT
<213> ORGANISM: Homo sapiens

<400> SEQUENCE: 447

Ile Gln Val Leu Gln Gln Gln Ala Asp Asp Ala Glu Glu Arg
1               5                   10

<210> SEQ ID NO 448
<211> LENGTH: 17
<212> TYPE: PRT
<213> ORGANISM: Homo sapiens

<400> SEQUENCE: 448

Ile Gln Val Leu Gln Gln Gln Ala Asp Asp Ala Glu Glu Arg Ala Glu
1               5                   10                  15

Arg

<210> SEQ ID NO 449
<211> LENGTH: 15
<212> TYPE: PRT
<213> ORGANISM: Homo sapiens

<400> SEQUENCE: 449

Lys Ile Gln Val Leu Gln Gln Gln Ala Asp Asp Ala Glu Glu Arg
1               5                   10                  15

```
<210> SEQ ID NO 450
<211> LENGTH: 15
<212> TYPE: PRT
<213> ORGANISM: Homo sapiens

<400> SEQUENCE: 450

Arg Ile Gln Leu Val Glu Glu Leu Asp Arg Ala Gln Glu Arg
1               5                   10                  15

<210> SEQ ID NO 451
<211> LENGTH: 10
<212> TYPE: PRT
<213> ORGANISM: Homo sapiens

<400> SEQUENCE: 451

Thr Ile Asp Asp Leu Glu Asp Lys Leu Lys
1               5                   10

<210> SEQ ID NO 452
<211> LENGTH: 16
<212> TYPE: PRT
<213> ORGANISM: Homo sapiens

<400> SEQUENCE: 452

Thr Ile Thr Leu Glu Val Glu Pro Ser Asp Thr Ile Glu Asn Val Lys
1               5                   10                  15

<210> SEQ ID NO 453
<211> LENGTH: 16
<212> TYPE: PRT
<213> ORGANISM: Homo sapiens

<400> SEQUENCE: 453

Asp Glu Arg Lys Asn Pro Asp Ser Gln Tyr Gly Glu Leu Ile Glu Lys
1               5                   10                  15

<210> SEQ ID NO 454
<211> LENGTH: 17
<212> TYPE: PRT
<213> ORGANISM: Homo sapiens

<400> SEQUENCE: 454

Ile Val Glu Lys Tyr Gly Tyr Thr His Leu Ser Ala Gly Glu Leu Leu
1               5                   10                  15

Arg

<210> SEQ ID NO 455
<211> LENGTH: 13
<212> TYPE: PRT
<213> ORGANISM: Homo sapiens

<400> SEQUENCE: 455

Lys Asn Pro Asp Ser Gln Tyr Gly Glu Leu Ile Glu Lys
1               5                   10

<210> SEQ ID NO 456
<211> LENGTH: 10
<212> TYPE: PRT
<213> ORGANISM: Homo sapiens

<400> SEQUENCE: 456

Asn Lys Phe Leu Ile Asp Gly Phe Pro Arg
1               5                   10
```

```
<210> SEQ ID NO 457
<211> LENGTH: 10
<212> TYPE: PRT
<213> ORGANISM: Homo sapiens

<400> SEQUENCE: 457

Asn Gln Asp Asn Leu Gln Gly Trp Asn Lys
1               5                   10

<210> SEQ ID NO 458
<211> LENGTH: 11
<212> TYPE: PRT
<213> ORGANISM: Homo sapiens

<400> SEQUENCE: 458

Ser Asp Asp Asn Arg Glu Ser Leu Glu Lys Arg
1               5                   10

<210> SEQ ID NO 459
<211> LENGTH: 13
<212> TYPE: PRT
<213> ORGANISM: Homo sapiens

<400> SEQUENCE: 459

Tyr Gly Tyr Thr His Leu Ser Ala Gly Glu Leu Leu Arg
1               5                   10

<210> SEQ ID NO 460
<211> LENGTH: 7
<212> TYPE: PRT
<213> ORGANISM: Homo sapiens

<400> SEQUENCE: 460

Ala Cys Gln Gln Phe Leu Lys
1               5

<210> SEQ ID NO 461
<211> LENGTH: 9
<212> TYPE: PRT
<213> ORGANISM: Homo sapiens

<400> SEQUENCE: 461

Lys Gln Cys Pro Cys Asp His Phe Lys
1               5

<210> SEQ ID NO 462
<211> LENGTH: 17
<212> TYPE: PRT
<213> ORGANISM: Homo sapiens

<400> SEQUENCE: 462

Trp Leu Gln Glu Gly Gly Gln Glu Cys Glu Cys Lys Asp Trp Phe Leu
1               5                   10                  15

Arg

<210> SEQ ID NO 463
<211> LENGTH: 22
<212> TYPE: PRT
<213> ORGANISM: Homo sapiens

<400> SEQUENCE: 463

Glu Val Val Ser Leu Thr Glu Ala Cys Cys Ala Glu Gly Ala Asp Pro
1               5                   10                  15

Asp Cys Tyr Asp Thr Arg
```

```
<210> SEQ ID NO 464
<211> LENGTH: 8
<212> TYPE: PRT
<213> ORGANISM: Homo sapiens

<400> SEQUENCE: 464

Phe Glu Asp Cys Cys Gln Glu Lys
1               5

<210> SEQ ID NO 465
<211> LENGTH: 22
<212> TYPE: PRT
<213> ORGANISM: Homo sapiens

<400> SEQUENCE: 465

His Gln Pro Gln Glu Phe Pro Thr Tyr Val Glu Pro Thr Asn Asp Glu
1               5                   10                  15

Ile Cys Glu Ala Phe Arg
            20

<210> SEQ ID NO 466
<211> LENGTH: 26
<212> TYPE: PRT
<213> ORGANISM: Homo sapiens

<400> SEQUENCE: 466

His Gln Pro Gln Glu Phe Pro Thr Tyr Val Glu Pro Thr Asn Asp Glu
1               5                   10                  15

Ile Cys Glu Ala Phe Arg Lys Asp Pro Lys
            20                  25

<210> SEQ ID NO 467
<211> LENGTH: 15
<212> TYPE: PRT
<213> ORGANISM: Homo sapiens

<400> SEQUENCE: 467

Lys Phe Pro Ser Gly Thr Phe Glu Gln Val Ser Gln Leu Val Lys
1               5                   10                  15

<210> SEQ ID NO 468
<211> LENGTH: 11
<212> TYPE: PRT
<213> ORGANISM: Homo sapiens

<400> SEQUENCE: 468

Leu Lys Ala Lys Leu Pro Asp Ala Thr Pro Lys
1               5                   10

<210> SEQ ID NO 469
<211> LENGTH: 11
<212> TYPE: PRT
<213> ORGANISM: Homo sapiens

<400> SEQUENCE: 469

Asn Ser Lys Phe Glu Asp Cys Cys Gln Glu Lys
1               5                   10

<210> SEQ ID NO 470
<211> LENGTH: 11
<212> TYPE: PRT
<213> ORGANISM: Homo sapiens
```

<400> SEQUENCE: 470

Arg Thr His Leu Pro Glu Val Phe Leu Ser Lys
1               5                   10

<210> SEQ ID NO 471
<211> LENGTH: 20
<212> TYPE: PRT
<213> ORGANISM: Homo sapiens

<400> SEQUENCE: 471

Ser Cys Glu Ser Asn Ser Pro Phe Pro Val His Pro Gly Thr Ala Glu
1               5                   10                  15

Cys Cys Thr Lys
            20

<210> SEQ ID NO 472
<211> LENGTH: 18
<212> TYPE: PRT
<213> ORGANISM: Homo sapiens

<400> SEQUENCE: 472

Ser Leu Gly Glu Cys Cys Asp Val Glu Asp Ser Thr Thr Cys Phe Asn
1               5                   10                  15

Ala Lys

<210> SEQ ID NO 473
<211> LENGTH: 24
<212> TYPE: PRT
<213> ORGANISM: Homo sapiens

<400> SEQUENCE: 473

Ser Leu Gly Glu Cys Cys Asp Val Glu Asp Ser Thr Thr Cys Phe Asn
1               5                   10                  15

Ala Lys Gly Pro Leu Leu Lys Lys
            20

<210> SEQ ID NO 474
<211> LENGTH: 10
<212> TYPE: PRT
<213> ORGANISM: Homo sapiens

<400> SEQUENCE: 474

Thr His Leu Pro Glu Val Phe Leu Ser Lys
1               5                   10

<210> SEQ ID NO 475
<211> LENGTH: 14
<212> TYPE: PRT
<213> ORGANISM: Homo sapiens

<400> SEQUENCE: 475

Val Cys Ser Gln Tyr Ala Ala Tyr Gly Glu Lys Lys Ser Arg
1               5                   10

<210> SEQ ID NO 476
<211> LENGTH: 11
<212> TYPE: PRT
<213> ORGANISM: Homo sapiens

<400> SEQUENCE: 476

Val Met Asp Lys Tyr Thr Phe Glu Leu Ser Arg
1               5                   10

<210> SEQ ID NO 477
<211> LENGTH: 27
<212> TYPE: PRT
<213> ORGANISM: Homo sapiens

<400> SEQUENCE: 477

Cys Gln Cys Asp Glu Leu Cys Ser Tyr Tyr Gln Ser Cys Cys Thr Asp
1               5                   10                  15

Tyr Thr Ala Glu Cys Lys Pro Gln Val Thr Arg
            20                  25

<210> SEQ ID NO 478
<211> LENGTH: 15
<212> TYPE: PRT
<213> ORGANISM: Homo sapiens

<400> SEQUENCE: 478

Asp Val Trp Gly Ile Glu Gly Pro Ile Asp Ala Ala Phe Thr Arg
1               5                   10                  15

<210> SEQ ID NO 479
<211> LENGTH: 10
<212> TYPE: PRT
<213> ORGANISM: Homo sapiens

<400> SEQUENCE: 479

Gly Gln Tyr Cys Tyr Glu Leu Asp Glu Lys
1               5                   10

<210> SEQ ID NO 480
<211> LENGTH: 15
<212> TYPE: PRT
<213> ORGANISM: Homo sapiens

<400> SEQUENCE: 480

Ser Ile Ala Gln Tyr Trp Leu Gly Cys Pro Ala Pro Gly His Leu
1               5                   10                  15

<210> SEQ ID NO 481
<211> LENGTH: 9
<212> TYPE: PRT
<213> ORGANISM: Homo sapiens

<400> SEQUENCE: 481

Ala Leu Phe Val Ser Glu Glu Glu Lys
1               5

<210> SEQ ID NO 482
<211> LENGTH: 10
<212> TYPE: PRT
<213> ORGANISM: Homo sapiens

<400> SEQUENCE: 482

Ala Leu Phe Val Ser Glu Glu Glu Lys Lys
1               5                   10

<210> SEQ ID NO 483
<211> LENGTH: 8
<212> TYPE: PRT
<213> ORGANISM: Homo sapiens

<400> SEQUENCE: 483

Cys Leu Val Asn Leu Ile Glu Lys

```
1               5
```

<210> SEQ ID NO 484
<211> LENGTH: 10
<212> TYPE: PRT
<213> ORGANISM: Homo sapiens

<400> SEQUENCE: 484

```
Asp Ala Gln Tyr Ala Pro Gly Tyr Asp Lys
1               5                   10
```

<210> SEQ ID NO 485
<211> LENGTH: 12
<212> TYPE: PRT
<213> ORGANISM: Homo sapiens

<400> SEQUENCE: 485

```
Asp Ala Gln Tyr Ala Pro Gly Tyr Asp Lys Val Lys
1               5                   10
```

<210> SEQ ID NO 486
<211> LENGTH: 21
<212> TYPE: PRT
<213> ORGANISM: Homo sapiens

<400> SEQUENCE: 486

```
Asp Ala Gln Tyr Ala Pro Gly Tyr Asp Lys Val Lys Asp Ile Ser Glu
1               5                   10                  15

Val Val Thr Pro Arg
            20
```

<210> SEQ ID NO 487
<211> LENGTH: 9
<212> TYPE: PRT
<213> ORGANISM: Homo sapiens

<400> SEQUENCE: 487

```
Asp Ile Ser Glu Val Val Thr Pro Arg
1               5
```

<210> SEQ ID NO 488
<211> LENGTH: 16
<212> TYPE: PRT
<213> ORGANISM: Homo sapiens

<400> SEQUENCE: 488

```
Glu Ala Gly Ile Pro Glu Phe Tyr Asp Tyr Asp Val Ala Leu Ile Lys
1               5                   10                  15
```

<210> SEQ ID NO 489
<211> LENGTH: 10
<212> TYPE: PRT
<213> ORGANISM: Homo sapiens

<400> SEQUENCE: 489

```
Glu Glu Leu Leu Pro Ala Gln Asp Ile Lys
1               5                   10
```

<210> SEQ ID NO 490
<211> LENGTH: 11
<212> TYPE: PRT
<213> ORGANISM: Homo sapiens

<400> SEQUENCE: 490

```
Glu Lys Leu Gln Asp Glu Asp Leu Gly Phe Leu
1               5                  10
```

<210> SEQ ID NO 491
<211> LENGTH: 17
<212> TYPE: PRT
<213> ORGANISM: Homo sapiens

<400> SEQUENCE: 491

```
Phe Leu Cys Thr Gly Gly Val Ser Pro Tyr Ala Asp Pro Asn Thr Cys
1               5                  10                  15

Arg
```

<210> SEQ ID NO 492
<211> LENGTH: 28
<212> TYPE: PRT
<213> ORGANISM: Homo sapiens

<400> SEQUENCE: 492

```
Phe Leu Cys Thr Gly Gly Val Ser Pro Tyr Ala Asp Pro Asn Thr Cys
1               5                  10                  15

Arg Gly Asp Ser Gly Gly Pro Leu Ile Val His Lys
            20                  25
```

<210> SEQ ID NO 493
<211> LENGTH: 29
<212> TYPE: PRT
<213> ORGANISM: Homo sapiens

<400> SEQUENCE: 493

```
Phe Leu Cys Thr Gly Gly Val Ser Pro Tyr Ala Asp Pro Asn Thr Cys
1               5                  10                  15

Arg Gly Asp Ser Gly Gly Pro Leu Ile Val His Lys Arg
            20                  25
```

<210> SEQ ID NO 494
<211> LENGTH: 9
<212> TYPE: PRT
<213> ORGANISM: Homo sapiens

<400> SEQUENCE: 494

```
Lys Asp Asn Glu Gln His Val Phe Lys
1               5
```

<210> SEQ ID NO 495
<211> LENGTH: 11
<212> TYPE: PRT
<213> ORGANISM: Homo sapiens

<400> SEQUENCE: 495

```
Leu Glu Asp Ser Val Thr Tyr His Cys Ser Arg
1               5                  10
```

<210> SEQ ID NO 496
<211> LENGTH: 24
<212> TYPE: PRT
<213> ORGANISM: Homo sapiens

<400> SEQUENCE: 496

```
Leu Leu Gln Glu Gly Gln Ala Leu Glu Tyr Val Cys Pro Ser Gly Phe
1               5                  10                  15

Tyr Pro Tyr Pro Val Gln Thr Arg
            20
```

<210> SEQ ID NO 497
<211> LENGTH: 11
<212> TYPE: PRT
<213> ORGANISM: Homo sapiens

<400> SEQUENCE: 497

Leu Pro Pro Thr Thr Thr Cys Gln Gln Gln Lys
1               5                   10

<210> SEQ ID NO 498
<211> LENGTH: 21
<212> TYPE: PRT
<213> ORGANISM: Homo sapiens

<400> SEQUENCE: 498

Leu Pro Pro Thr Thr Thr Cys Gln Gln Gln Lys Glu Glu Leu Leu Pro
1               5                   10                  15

Ala Gln Asp Ile Lys
            20

<210> SEQ ID NO 499
<211> LENGTH: 9
<212> TYPE: PRT
<213> ORGANISM: Homo sapiens

<400> SEQUENCE: 499

Leu Gln Asp Glu Asp Leu Gly Phe Leu
1               5

<210> SEQ ID NO 500
<211> LENGTH: 9
<212> TYPE: PRT
<213> ORGANISM: Homo sapiens

<400> SEQUENCE: 500

Ser Thr Gly Ser Trp Ser Thr Leu Lys
1               5

<210> SEQ ID NO 501
<211> LENGTH: 17
<212> TYPE: PRT
<213> ORGANISM: Homo sapiens

<400> SEQUENCE: 501

Ser Thr Gly Ser Trp Ser Thr Leu Lys Thr Gln Asp Gln Lys Thr Val
1               5                   10                  15

Arg

<210> SEQ ID NO 502
<211> LENGTH: 9
<212> TYPE: PRT
<213> ORGANISM: Homo sapiens

<400> SEQUENCE: 502

Val Ala Ser Tyr Gly Val Lys Pro Arg
1               5

<210> SEQ ID NO 503
<211> LENGTH: 14
<212> TYPE: PRT
<213> ORGANISM: Homo sapiens

<400> SEQUENCE: 503

Val Ser Glu Ala Asp Ser Ser Asn Ala Asp Trp Val Thr Lys
1               5                   10

<210> SEQ ID NO 504
<211> LENGTH: 25
<212> TYPE: PRT
<213> ORGANISM: Homo sapiens

<400> SEQUENCE: 504

Trp Ser Gly Gln Thr Ala Ile Cys Asp Asn Gly Ala Gly Tyr Cys Ser
1               5                   10                  15

Asn Pro Gly Ile Pro Ile Gly Thr Arg
            20                  25

<210> SEQ ID NO 505
<211> LENGTH: 26
<212> TYPE: PRT
<213> ORGANISM: Homo sapiens

<400> SEQUENCE: 505

Trp Ser Gly Gln Thr Ala Ile Cys Asp Asn Gly Ala Gly Tyr Cys Ser
1               5                   10                  15

Asn Pro Gly Ile Pro Ile Gly Thr Arg Lys
            20                  25

<210> SEQ ID NO 506
<211> LENGTH: 11
<212> TYPE: PRT
<213> ORGANISM: Homo sapiens

<400> SEQUENCE: 506

Tyr Gly Leu Val Thr Tyr Ala Thr Tyr Pro Lys
1               5                   10

<210> SEQ ID NO 507
<211> LENGTH: 15
<212> TYPE: PRT
<213> ORGANISM: Homo sapiens

<400> SEQUENCE: 507

Tyr Gly Leu Val Thr Tyr Ala Thr Tyr Pro Lys Ile Trp Val Lys
1               5                   10                  15

<210> SEQ ID NO 508
<211> LENGTH: 18
<212> TYPE: PRT
<213> ORGANISM: Homo sapiens

<400> SEQUENCE: 508

Tyr Gly Gln Thr Ile Arg Pro Ile Cys Leu Pro Cys Thr Glu Gly Thr
1               5                   10                  15

Thr Arg

<210> SEQ ID NO 509
<211> LENGTH: 15
<212> TYPE: PRT
<213> ORGANISM: Homo sapiens

<400> SEQUENCE: 509

Glu Tyr Ala Gln Asn Ile Trp Asn Val Glu Pro Ser Asp Leu Lys
1               5                   10                  15

```
<210> SEQ ID NO 510
<211> LENGTH: 10
<212> TYPE: PRT
<213> ORGANISM: Homo sapiens

<400> SEQUENCE: 510

Phe Ser Gln Phe Leu Glu Thr Glu Tyr Lys
1               5                   10

<210> SEQ ID NO 511
<211> LENGTH: 12
<212> TYPE: PRT
<213> ORGANISM: Homo sapiens

<400> SEQUENCE: 511

Ile Phe Val Asp Ile Glu Lys Leu Pro Trp Ser Lys
1               5                   10

<210> SEQ ID NO 512
<211> LENGTH: 14
<212> TYPE: PRT
<213> ORGANISM: Homo sapiens

<400> SEQUENCE: 512

Ile Gly Glu Asp Tyr Val Lys Asp Leu Ser Gln Leu Thr Lys
1               5                   10

<210> SEQ ID NO 513
<211> LENGTH: 17
<212> TYPE: PRT
<213> ORGANISM: Homo sapiens

<400> SEQUENCE: 513

Leu Lys Gln Glu Tyr Phe Val Val Ala Ala Thr Leu Gln Asp Ile Ile
1               5                   10                  15

Arg

<210> SEQ ID NO 514
<211> LENGTH: 14
<212> TYPE: PRT
<213> ORGANISM: Homo sapiens

<400> SEQUENCE: 514

Leu Val Ile Asp Gln Ile Asp Asn Gly Phe Phe Ser Pro Lys
1               5                   10

<210> SEQ ID NO 515
<211> LENGTH: 14
<212> TYPE: PRT
<213> ORGANISM: Homo sapiens

<400> SEQUENCE: 515

Val Pro Thr Ala Asn Val Ser Val Val Asp Leu Thr Cys Arg
1               5                   10

<210> SEQ ID NO 516
<211> LENGTH: 24
<212> TYPE: PRT
<213> ORGANISM: Homo sapiens

<400> SEQUENCE: 516

Val Ile His Asp Asn Phe Gly Ile Val Glu Gly Leu Met Thr Thr Val
1               5                   10                  15

His Ala Ile Thr Ala Thr Gln Lys
```

```
<210> SEQ ID NO 517
<211> LENGTH: 8
<212> TYPE: PRT
<213> ORGANISM: Homo sapiens

<400> SEQUENCE: 517

Val Gly Val Asn Gly Phe Gly Arg
1               5

<210> SEQ ID NO 518
<211> LENGTH: 18
<212> TYPE: PRT
<213> ORGANISM: Homo sapiens

<400> SEQUENCE: 518

Leu Val Ile Asn Gly Asn Pro Ile Thr Ile Phe Gln Glu Arg Asp Pro
1               5                  10                  15

Ser Lys

<210> SEQ ID NO 519
<211> LENGTH: 14
<212> TYPE: PRT
<213> ORGANISM: Homo sapiens

<400> SEQUENCE: 519

Leu Val Ile Asn Gly Asn Pro Ile Thr Ile Phe Gln Glu Arg
1               5                  10

<210> SEQ ID NO 520
<211> LENGTH: 14
<212> TYPE: PRT
<213> ORGANISM: Homo sapiens

<400> SEQUENCE: 520

Leu Ile Ser Trp Tyr Asp Asn Glu Phe Gly Tyr Ser Asn Arg
1               5                  10

<210> SEQ ID NO 521
<211> LENGTH: 17
<212> TYPE: PRT
<213> ORGANISM: Homo sapiens

<400> SEQUENCE: 521

Ile Ile Ser Asn Ala Ser Cys Thr Thr Asn Cys Leu Ala Pro Leu Ala
1               5                  10                  15

Lys

<210> SEQ ID NO 522
<211> LENGTH: 12
<212> TYPE: PRT
<213> ORGANISM: Homo sapiens

<400> SEQUENCE: 522

Gly Lys Val Lys Val Gly Val Asn Gly Phe Gly Arg
1               5                  10

<210> SEQ ID NO 523
<211> LENGTH: 15
<212> TYPE: PRT
<213> ORGANISM: Homo sapiens

<400> SEQUENCE: 523
```

```
Gly Ala Leu Gln Asn Ile Ile Pro Ala Ser Thr Gly Ala Ala Lys
1               5                   10                  15

<210> SEQ ID NO 524
<211> LENGTH: 18
<212> TYPE: PRT
<213> ORGANISM: Homo sapiens

<400> SEQUENCE: 524

Asp Gly Arg Gly Ala Leu Gln Asn Ile Ile Pro Ala Ser Thr Gly Ala
1               5                   10                  15

Ala Lys

<210> SEQ ID NO 525
<211> LENGTH: 23
<212> TYPE: PRT
<213> ORGANISM: Homo sapiens

<400> SEQUENCE: 525

Ala Glu Asn Gly Lys Leu Val Ile Asn Gly Asn Pro Ile Thr Ile Phe
1               5                   10                  15

Gln Glu Arg Asp Pro Ser Lys
            20

<210> SEQ ID NO 526
<211> LENGTH: 19
<212> TYPE: PRT
<213> ORGANISM: Homo sapiens

<400> SEQUENCE: 526

Ala Glu Asn Gly Lys Leu Val Ile Asn Gly Asn Pro Ile Thr Ile Phe
1               5                   10                  15

Gln Glu Arg

<210> SEQ ID NO 527
<211> LENGTH: 9
<212> TYPE: PRT
<213> ORGANISM: Homo sapiens

<400> SEQUENCE: 527

Ala Ile Glu Asn Glu Leu Leu Ala Arg
1               5

<210> SEQ ID NO 528
<211> LENGTH: 11
<212> TYPE: PRT
<213> ORGANISM: Homo sapiens

<400> SEQUENCE: 528

Ala Thr Asn Trp Gly Ser Leu Leu Gln Asp Lys
1               5                   10

<210> SEQ ID NO 529
<211> LENGTH: 18
<212> TYPE: PRT
<213> ORGANISM: Homo sapiens

<400> SEQUENCE: 529

Tyr Ile Ser Leu Ile Tyr Thr Asn Tyr Glu Ala Gly Lys Asp Asp Tyr
1               5                   10                  15

Val Lys
```

<210> SEQ ID NO 530
<211> LENGTH: 13
<212> TYPE: PRT
<213> ORGANISM: Homo sapiens

<400> SEQUENCE: 530

Tyr Ile Ser Leu Ile Tyr Thr Asn Tyr Glu Ala Gly Lys
1               5                   10

<210> SEQ ID NO 531
<211> LENGTH: 13
<212> TYPE: PRT
<213> ORGANISM: Homo sapiens

<400> SEQUENCE: 531

Pro Pro Tyr Thr Val Val Tyr Phe Pro Val Arg Gly Arg
1               5                   10

<210> SEQ ID NO 532
<211> LENGTH: 11
<212> TYPE: PRT
<213> ORGANISM: Homo sapiens

<400> SEQUENCE: 532

Pro Pro Tyr Thr Val Val Tyr Phe Pro Val Arg
1               5                   10

<210> SEQ ID NO 533
<211> LENGTH: 11
<212> TYPE: PRT
<213> ORGANISM: Homo sapiens

<400> SEQUENCE: 533

Met Leu Leu Ala Asp Gln Gly Gln Ser Trp Lys
1               5                   10

<210> SEQ ID NO 534
<211> LENGTH: 21
<212> TYPE: PRT
<213> ORGANISM: Homo sapiens

<400> SEQUENCE: 534

Leu Lys Ala Phe Leu Ala Ser Pro Glu Tyr Val Asn Leu Pro Ile Asn
1               5                   10                  15

Gly Asn Gly Lys Gln
            20

<210> SEQ ID NO 535
<211> LENGTH: 20
<212> TYPE: PRT
<213> ORGANISM: Homo sapiens

<400> SEQUENCE: 535

Leu Lys Ala Phe Leu Ala Ser Pro Glu Tyr Val Asn Leu Pro Ile Asn
1               5                   10                  15

Gly Asn Gly Lys
            20

<210> SEQ ID NO 536
<211> LENGTH: 20
<212> TYPE: PRT
<213> ORGANISM: Homo sapiens

<400> SEQUENCE: 536

Phe Gln Asp Gly Asp Leu Thr Leu Tyr Gln Ser Asn Thr Ile Leu Arg
1               5                   10                  15

His Leu Gly Arg
            20

<210> SEQ ID NO 537
<211> LENGTH: 16
<212> TYPE: PRT
<213> ORGANISM: Homo sapiens

<400> SEQUENCE: 537

Phe Gln Asp Gly Asp Leu Thr Leu Tyr Gln Ser Asn Thr Ile Leu Arg
1               5                   10                  15

<210> SEQ ID NO 538
<211> LENGTH: 15
<212> TYPE: PRT
<213> ORGANISM: Homo sapiens

<400> SEQUENCE: 538

Glu Glu Val Val Thr Val Glu Thr Trp Gln Glu Gly Ser Leu Lys
1               5                   10                  15

<210> SEQ ID NO 539
<211> LENGTH: 20
<212> TYPE: PRT
<213> ORGANISM: Homo sapiens

<400> SEQUENCE: 539

Cys Lys Tyr Ile Ser Leu Ile Tyr Thr Asn Tyr Glu Ala Gly Lys Asp
1               5                   10                  15

Asp Tyr Val Lys
            20

<210> SEQ ID NO 540
<211> LENGTH: 10
<212> TYPE: PRT
<213> ORGANISM: Homo sapiens

<400> SEQUENCE: 540

Ala Ser Cys Leu Tyr Gly Gln Leu Pro Lys
1               5                   10

<210> SEQ ID NO 541
<211> LENGTH: 20
<212> TYPE: PRT
<213> ORGANISM: Homo sapiens

<400> SEQUENCE: 541

Ala Leu Pro Gly Gln Leu Lys Pro Phe Glu Thr Leu Leu Ser Gln Asn
1               5                   10                  15

Gln Gly Gly Lys
            20

<210> SEQ ID NO 542
<211> LENGTH: 19
<212> TYPE: PRT
<213> ORGANISM: Homo sapiens

<400> SEQUENCE: 542

Ala Phe Leu Ala Ser Pro Glu Tyr Val Asn Leu Pro Ile Asn Gly Asn
1               5                   10                  15

Gly Lys Gln

<210> SEQ ID NO 543
<211> LENGTH: 18
<212> TYPE: PRT
<213> ORGANISM: Homo sapiens

<400> SEQUENCE: 543

Ala Phe Leu Ala Ser Pro Glu Tyr Val Asn Leu Pro Ile Asn Gly Asn
1               5                   10                  15

Gly Lys

<210> SEQ ID NO 544
<211> LENGTH: 14
<212> TYPE: PRT
<213> ORGANISM: Homo sapiens

<400> SEQUENCE: 544

Ser Asn Glu Glu Gly Ser Glu Glu Lys Gly Pro Glu Val Arg
1               5                   10

<210> SEQ ID NO 545
<211> LENGTH: 15
<212> TYPE: PRT
<213> ORGANISM: Homo sapiens

<400> SEQUENCE: 545

Asn Leu Leu Ser Val Ala Tyr Lys Asn Val Val Gly Gly Gln Arg
1               5                   10                  15

<210> SEQ ID NO 546
<211> LENGTH: 8
<212> TYPE: PRT
<213> ORGANISM: Homo sapiens

<400> SEQUENCE: 546

Asn Leu Leu Ser Val Ala Tyr Lys
1               5

<210> SEQ ID NO 547
<211> LENGTH: 7
<212> TYPE: PRT
<213> ORGANISM: Homo sapiens

<400> SEQUENCE: 547

Leu Ala Glu Gln Ala Glu Arg
1               5

<210> SEQ ID NO 548
<211> LENGTH: 9
<212> TYPE: PRT
<213> ORGANISM: Homo sapiens

<400> SEQUENCE: 548

Gly Glu Glu Leu Ser Cys Glu Glu Arg
1               5

<210> SEQ ID NO 549
<211> LENGTH: 14
<212> TYPE: PRT
<213> ORGANISM: Homo sapiens

<400> SEQUENCE: 549

Gly Ala Val Glu Lys Gly Glu Glu Leu Ser Cys Glu Glu Arg

-continued

```
<210> SEQ ID NO 550
<211> LENGTH: 10
<212> TYPE: PRT
<213> ORGANISM: Homo sapiens

<400> SEQUENCE: 550

Asp Ser Thr Leu Ile Met Gln Leu Leu Arg
1               5                   10

<210> SEQ ID NO 551
<211> LENGTH: 24
<212> TYPE: PRT
<213> ORGANISM: Homo sapiens

<400> SEQUENCE: 551

Asp Asn Leu Thr Leu Trp Thr Ala Asp Asn Ala Gly Glu Glu Gly Gly
1               5                   10                  15

Glu Ala Pro Gln Glu Pro Gln Ser
            20

<210> SEQ ID NO 552
<211> LENGTH: 13
<212> TYPE: PRT
<213> ORGANISM: Homo sapiens

<400> SEQUENCE: 552

Tyr Leu Ala Glu Val Ala Thr Gly Asp Asp Lys Lys Arg
1               5                   10

<210> SEQ ID NO 553
<211> LENGTH: 16
<212> TYPE: PRT
<213> ORGANISM: Homo sapiens

<400> SEQUENCE: 553

Ala Ala Gly Val Asn Val Glu Pro Phe Trp Pro Gly Leu Phe Ala Lys
1               5                   10                  15

<210> SEQ ID NO 554
<211> LENGTH: 17
<212> TYPE: PRT
<213> ORGANISM: Homo sapiens

<400> SEQUENCE: 554

Val Cys Leu Ile Gly Cys Gly Phe Ser Thr Gly Tyr Gly Ser Ala Val
1               5                   10                  15

Lys

<210> SEQ ID NO 555
<211> LENGTH: 9
<212> TYPE: PRT
<213> ORGANISM: Homo sapiens

<400> SEQUENCE: 555

Asn Pro Glu Ser Asn Tyr Cys Leu Lys
1               5

<210> SEQ ID NO 556
<211> LENGTH: 14
<212> TYPE: PRT
<213> ORGANISM: Homo sapiens
```

```
<400> SEQUENCE: 556

Lys Pro Phe Ser Ile Glu Glu Val Glu Val Ala Pro Pro Lys
1               5                   10

<210> SEQ ID NO 557
<211> LENGTH: 9
<212> TYPE: PRT
<213> ORGANISM: Homo sapiens

<400> SEQUENCE: 557

Ile Asn Glu Gly Phe Asp Leu Leu Arg
1               5

<210> SEQ ID NO 558
<211> LENGTH: 12
<212> TYPE: PRT
<213> ORGANISM: Homo sapiens

<400> SEQUENCE: 558

Ile Cys Lys Asn Pro Glu Ser Asn Tyr Cys Leu Lys
1               5                   10

<210> SEQ ID NO 559
<211> LENGTH: 14
<212> TYPE: PRT
<213> ORGANISM: Homo sapiens

<400> SEQUENCE: 559

Glu Leu Gly Ala Thr Glu Cys Ile Asn Pro Gln Asp Tyr Lys
1               5                   10

<210> SEQ ID NO 560
<211> LENGTH: 8
<212> TYPE: PRT
<213> ORGANISM: Homo sapiens

<400> SEQUENCE: 560

Ala Ala Val Leu Trp Glu Leu Lys
1               5

<210> SEQ ID NO 561
<211> LENGTH: 15
<212> TYPE: PRT
<213> ORGANISM: Homo sapiens

<400> SEQUENCE: 561

Glu Cys Asn Ala Cys Arg Asn Pro Asp Gly Asn Leu Cys Ile Arg
1               5                   10                  15

<210> SEQ ID NO 562
<211> LENGTH: 28
<212> TYPE: PRT
<213> ORGANISM: Homo sapiens

<400> SEQUENCE: 562

Phe Pro Val Ile Val Gly His Glu Ala Thr Gly Ile Val Glu Ser Ile
1               5                   10                  15

Gly Glu Gly Val Thr Thr Val Lys Pro Gly Asp Lys
            20                  25

<210> SEQ ID NO 563
<211> LENGTH: 10
<212> TYPE: PRT
<213> ORGANISM: Homo sapiens
```

```
<400> SEQUENCE: 563

Ile Lys Ile Leu Ala Thr Gly Ile Cys Arg
1               5                   10

<210> SEQ ID NO 564
<211> LENGTH: 8
<212> TYPE: PRT
<213> ORGANISM: Homo sapiens

<400> SEQUENCE: 564

Ile Leu Ala Thr Gly Ile Cys Arg
1               5

<210> SEQ ID NO 565
<211> LENGTH: 15
<212> TYPE: PRT
<213> ORGANISM: Homo sapiens

<400> SEQUENCE: 565

Ile Ser Glu Gly Phe Glu Leu Leu Asn Ser Gly Gln Ser Ile Arg
1               5                   10                  15

<210> SEQ ID NO 566
<211> LENGTH: 15
<212> TYPE: PRT
<213> ORGANISM: Homo sapiens

<400> SEQUENCE: 566

Lys Phe Asp Leu Asp Gln Leu Ile Thr His Val Leu Pro Phe Lys
1               5                   10                  15

<210> SEQ ID NO 567
<211> LENGTH: 9
<212> TYPE: PRT
<213> ORGANISM: Homo sapiens

<400> SEQUENCE: 567

Asn Pro Asp Gly Asn Leu Cys Ile Arg
1               5

<210> SEQ ID NO 568
<211> LENGTH: 17
<212> TYPE: PRT
<213> ORGANISM: Homo sapiens

<400> SEQUENCE: 568

Val Cys Leu Ile Gly Cys Gly Phe Ser Thr Gly Tyr Gly Ala Ala Val
1               5                   10                  15

Lys

<210> SEQ ID NO 569
<211> LENGTH: 10
<212> TYPE: PRT
<213> ORGANISM: Homo sapiens

<400> SEQUENCE: 569

Val Ile Pro Leu Phe Leu Pro Gln Cys Arg
1               5                   10

<210> SEQ ID NO 570
<211> LENGTH: 26
<212> TYPE: PRT
<213> ORGANISM: Homo sapiens
```

```
<400> SEQUENCE: 570

Ile Asp Asp Ala Ala Pro Pro Glu Lys Val Cys Leu Ile Gly Cys Gly
1               5                   10                  15

Phe Ser Thr Gly Tyr Gly Ala Ala Val Lys
            20                  25

<210> SEQ ID NO 571
<211> LENGTH: 17
<212> TYPE: PRT
<213> ORGANISM: Homo sapiens

<400> SEQUENCE: 571

Tyr Lys Pro Val Cys Asn Gln Val Glu Cys His Pro Tyr Phe Asn Gln
1               5                   10                  15

Arg

<210> SEQ ID NO 572
<211> LENGTH: 19
<212> TYPE: PRT
<213> ORGANISM: Homo sapiens

<400> SEQUENCE: 572

His Ile Asp Ser Ala His Leu Tyr Asn Asn Glu Glu Gln Val Gly Leu
1               5                   10                  15

Ala Ile Arg

<210> SEQ ID NO 573
<211> LENGTH: 8
<212> TYPE: PRT
<213> ORGANISM: Homo sapiens

<400> SEQUENCE: 573

Leu Ala Ile Glu Ala Gly Phe Arg
1               5

<210> SEQ ID NO 574
<211> LENGTH: 22
<212> TYPE: PRT
<213> ORGANISM: Homo sapiens

<400> SEQUENCE: 574

Leu Asn Asp Gly His Phe Met Pro Val Leu Gly Phe Gly Thr Tyr Ala
1               5                   10                  15

Pro Ala Glu Val Pro Lys
            20

<210> SEQ ID NO 575
<211> LENGTH: 9
<212> TYPE: PRT
<213> ORGANISM: Homo sapiens

<400> SEQUENCE: 575

Arg Glu Asp Ile Phe Tyr Thr Ser Lys
1               5

<210> SEQ ID NO 576
<211> LENGTH: 16
<212> TYPE: PRT
<213> ORGANISM: Homo sapiens

<400> SEQUENCE: 576
```

```
Ser Lys Asp Ile Val Leu Val Ala Tyr Ser Ala Leu Gly Ser His Arg
1               5                   10                  15
```

<210> SEQ ID NO 577
<211> LENGTH: 8
<212> TYPE: PRT
<213> ORGANISM: Homo sapiens

<400> SEQUENCE: 577

```
Thr Pro Ala Leu Ile Ala Leu Arg
1               5
```

<210> SEQ ID NO 578
<211> LENGTH: 11
<212> TYPE: PRT
<213> ORGANISM: Homo sapiens

<400> SEQUENCE: 578

```
Ile Thr Leu Leu Ser Ala Leu Val Glu Thr Arg
1               5                   10
```

<210> SEQ ID NO 579
<211> LENGTH: 10
<212> TYPE: PRT
<213> ORGANISM: Homo sapiens

<400> SEQUENCE: 579

```
Asn Leu Ala Val Ser Gln Val Val His Lys
1               5                   10
```

<210> SEQ ID NO 580
<211> LENGTH: 18
<212> TYPE: PRT
<213> ORGANISM: Homo sapiens

<400> SEQUENCE: 580

```
Leu Tyr Gly Ser Glu Ala Phe Ala Thr Asp Phe Gln Asp Ser Ala Ala
1               5                   10                  15

Ala Lys
```

<210> SEQ ID NO 581
<211> LENGTH: 9
<212> TYPE: PRT
<213> ORGANISM: Homo sapiens

<400> SEQUENCE: 581

```
Glu Ile Gly Glu Leu Tyr Leu Pro Lys
1               5
```

<210> SEQ ID NO 582
<211> LENGTH: 12
<212> TYPE: PRT
<213> ORGANISM: Homo sapiens

<400> SEQUENCE: 582

```
Asp Glu Glu Leu Ser Cys Thr Val Val Glu Leu Lys
1               5                   10
```

<210> SEQ ID NO 583
<211> LENGTH: 10
<212> TYPE: PRT
<213> ORGANISM: Homo sapiens

<400> SEQUENCE: 583

```
Ala Asp Leu Ser Gly Ile Thr Gly Ala Arg
1               5                   10
```

<210> SEQ ID NO 584
<211> LENGTH: 11
<212> TYPE: PRT
<213> ORGANISM: Homo sapiens

<400> SEQUENCE: 584

```
Ile Thr Leu Leu Ser Ala Leu Val Glu Thr Arg
1               5                   10
```

<210> SEQ ID NO 585
<211> LENGTH: 12
<212> TYPE: PRT
<213> ORGANISM: Homo sapiens

<400> SEQUENCE: 585

```
Ala Val His Lys Ala Val Leu Thr Ile Asp Glu Lys
1               5                   10
```

<210> SEQ ID NO 586
<211> LENGTH: 16
<212> TYPE: PRT
<213> ORGANISM: Homo sapiens

<400> SEQUENCE: 586

```
Asp Thr Glu Glu Glu Asp Phe His Val Asp Gln Val Thr Thr Val Lys
1               5                   10                  15
```

<210> SEQ ID NO 587
<211> LENGTH: 15
<212> TYPE: PRT
<213> ORGANISM: Homo sapiens

<400> SEQUENCE: 587

```
Phe Asn Lys Pro Phe Val Phe Leu Met Ile Glu Gln Asn Thr Lys
1               5                   10                  15
```

<210> SEQ ID NO 588
<211> LENGTH: 8
<212> TYPE: PRT
<213> ORGANISM: Homo sapiens

<400> SEQUENCE: 588

```
Phe Leu Glu Asn Glu Asp Arg Arg
1               5
```

<210> SEQ ID NO 589
<211> LENGTH: 14
<212> TYPE: PRT
<213> ORGANISM: Homo sapiens

<400> SEQUENCE: 589

```
Ile Thr Pro Asn Leu Ala Glu Phe Ala Phe Ser Leu Tyr Arg
1               5                   10
```

<210> SEQ ID NO 590
<211> LENGTH: 14
<212> TYPE: PRT
<213> ORGANISM: Homo sapiens

<400> SEQUENCE: 590

```
Lys Gln Ile Asn Asp Tyr Val Glu Lys Gly Thr Gln Gly Lys
1               5                   10
```

<210> SEQ ID NO 591
<211> LENGTH: 10
<212> TYPE: PRT
<213> ORGANISM: Homo sapiens

<400> SEQUENCE: 591

Leu Ser Ile Thr Gly Thr Tyr Asp Leu Lys
1               5                   10

<210> SEQ ID NO 592
<211> LENGTH: 15
<212> TYPE: PRT
<213> ORGANISM: Homo sapiens

<400> SEQUENCE: 592

Leu Gln His Leu Glu Asn Glu Leu Thr His Asp Ile Ile Thr Lys
1               5                   10                  15

<210> SEQ ID NO 593
<211> LENGTH: 9
<212> TYPE: PRT
<213> ORGANISM: Homo sapiens

<400> SEQUENCE: 593

Leu Ser Ser Trp Val Leu Leu Met Lys
1               5

<210> SEQ ID NO 594
<211> LENGTH: 19
<212> TYPE: PRT
<213> ORGANISM: Homo sapiens

<400> SEQUENCE: 594

Leu Tyr His Ser Glu Ala Phe Thr Val Asn Phe Gly Asp Thr Glu Glu
1               5                   10                  15

Ala Lys Lys

<210> SEQ ID NO 595
<211> LENGTH: 8
<212> TYPE: PRT
<213> ORGANISM: Homo sapiens

<400> SEQUENCE: 595

Gln Ile Asn Asp Tyr Val Glu Lys
1               5

<210> SEQ ID NO 596
<211> LENGTH: 13
<212> TYPE: PRT
<213> ORGANISM: Homo sapiens

<400> SEQUENCE: 596

Gln Ile Asn Asp Tyr Val Glu Lys Gly Thr Gln Gly Lys
1               5                   10

<210> SEQ ID NO 597
<211> LENGTH: 8
<212> TYPE: PRT
<213> ORGANISM: Homo sapiens

<400> SEQUENCE: 597

Ser Ala Ser Leu His Leu Pro Lys
1               5

```
<210> SEQ ID NO 598
<211> LENGTH: 24
<212> TYPE: PRT
<213> ORGANISM: Homo sapiens

<400> SEQUENCE: 598

Thr Leu Asn Gln Pro Asp Ser Gln Leu Gln Leu Thr Thr Gly Asn Gly
1               5                   10                  15

Leu Phe Leu Ser Glu Gly Leu Lys
            20

<210> SEQ ID NO 599
<211> LENGTH: 10
<212> TYPE: PRT
<213> ORGANISM: Homo sapiens

<400> SEQUENCE: 599

Ser Val Leu Gly Gln Leu Gly Ile Thr Lys
1               5                   10

<210> SEQ ID NO 600
<211> LENGTH: 18
<212> TYPE: PRT
<213> ORGANISM: Homo sapiens

<400> SEQUENCE: 600

Val Phe Ser Asn Gly Ala Asp Leu Ser Gly Val Thr Glu Glu Ala Pro
1               5                   10                  15

Leu Lys

<210> SEQ ID NO 601
<211> LENGTH: 18
<212> TYPE: PRT
<213> ORGANISM: Homo sapiens

<400> SEQUENCE: 601

Val Phe Ser Asn Gly Ala Asp Leu Ser Gly Val Thr Glu Glu Ala Pro
1               5                   10                  15

Leu Lys

<210> SEQ ID NO 602
<211> LENGTH: 17
<212> TYPE: PRT
<213> ORGANISM: Homo sapiens

<400> SEQUENCE: 602

Val Thr Leu Thr Cys Val Ala Pro Leu Ser Gly Val Asp Phe Gln Leu
1               5                   10                  15

Arg

<210> SEQ ID NO 603
<211> LENGTH: 20
<212> TYPE: PRT
<213> ORGANISM: Homo sapiens

<400> SEQUENCE: 603

Ser Gly Leu Ser Thr Gly Trp Thr Gln Leu Ser Lys Leu Leu Glu Leu
1               5                   10                  15

Thr Gly Pro Lys
            20
```

<210> SEQ ID NO 604
<211> LENGTH: 12
<212> TYPE: PRT
<213> ORGANISM: Homo sapiens

<400> SEQUENCE: 604

Ser Gly Leu Ser Thr Gly Trp Thr Gln Leu Ser Lys
1               5                   10

<210> SEQ ID NO 605
<211> LENGTH: 10
<212> TYPE: PRT
<213> ORGANISM: Homo sapiens

<400> SEQUENCE: 605

Arg Gly Glu Lys Glu Leu Leu Val Pro Arg
1               5                   10

<210> SEQ ID NO 606
<211> LENGTH: 14
<212> TYPE: PRT
<213> ORGANISM: Homo sapiens

<400> SEQUENCE: 606

Cys Glu Gly Pro Ile Pro Asp Val Thr Phe Glu Leu Leu Arg
1               5                   10

<210> SEQ ID NO 607
<211> LENGTH: 11
<212> TYPE: PRT
<213> ORGANISM: Homo sapiens

<400> SEQUENCE: 607

Ala Thr Trp Ser Gly Ala Val Leu Ala Gly Arg
1               5                   10

<210> SEQ ID NO 608
<211> LENGTH: 22
<212> TYPE: PRT
<213> ORGANISM: Homo sapiens

<400> SEQUENCE: 608

Thr Pro Gly Ala Ala Ala Asn Leu Glu Leu Ile Phe Val Gly Pro Gln
1               5                   10                  15

His Ala Gly Asn Tyr Arg
            20

<210> SEQ ID NO 609
<211> LENGTH: 9
<212> TYPE: PRT
<213> ORGANISM: Homo sapiens

<400> SEQUENCE: 609

Cys Leu Ala Pro Leu Glu Gly Ala Arg
1               5

<210> SEQ ID NO 610
<211> LENGTH: 21
<212> TYPE: PRT
<213> ORGANISM: Homo sapiens

<400> SEQUENCE: 610

Thr Val Val Gln Pro Ser Val Gly Ala Ala Ala Gly Pro Val Val Pro
1               5                   10                  15

Pro Cys Pro Gly Arg
            20

<210> SEQ ID NO 611
<211> LENGTH: 14
<212> TYPE: PRT
<213> ORGANISM: Homo sapiens

<400> SEQUENCE: 611

Glu His Ala Val Glu Gly Asp Cys Asp Phe Gln Leu Leu Lys
1               5                   10

<210> SEQ ID NO 612
<211> LENGTH: 7
<212> TYPE: PRT
<213> ORGANISM: Homo sapiens

<400> SEQUENCE: 612

Phe Ser Val Val Tyr Ala Lys
1               5

<210> SEQ ID NO 613
<211> LENGTH: 10
<212> TYPE: PRT
<213> ORGANISM: Homo sapiens

<400> SEQUENCE: 613

His Thr Leu Asn Gln Ile Asp Glu Val Lys
1               5                   10

<210> SEQ ID NO 614
<211> LENGTH: 11
<212> TYPE: PRT
<213> ORGANISM: Homo sapiens

<400> SEQUENCE: 614

Leu Asp Gly Lys Phe Ser Val Val Tyr Ala Lys
1               5                   10

<210> SEQ ID NO 615
<211> LENGTH: 27
<212> TYPE: PRT
<213> ORGANISM: Homo sapiens

<400> SEQUENCE: 615

Tyr Asn Ile Leu Pro Glu Lys Glu Glu Phe Pro Phe Ala Leu Gly Val
1               5                   10                  15

Gln Thr Leu Pro Gln Thr Cys Asp Glu Pro Lys
            20                  25

<210> SEQ ID NO 616
<211> LENGTH: 14
<212> TYPE: PRT
<213> ORGANISM: Homo sapiens

<400> SEQUENCE: 616

Val Thr Gly Glu Gly Cys Val Tyr Leu Gln Thr Ser Leu Lys
1               5                   10

<210> SEQ ID NO 617
<211> LENGTH: 12
<212> TYPE: PRT
<213> ORGANISM: Homo sapiens

```
<400> SEQUENCE: 617

Val Thr Ala Ala Pro Gln Ser Val Cys Ala Leu Arg
1               5                   10

<210> SEQ ID NO 618
<211> LENGTH: 18
<212> TYPE: PRT
<213> ORGANISM: Homo sapiens

<400> SEQUENCE: 618

Val Ser Val Gln Leu Glu Ala Ser Pro Ala Phe Leu Ala Val Pro Val
1               5                   10                  15

Glu Lys

<210> SEQ ID NO 619
<211> LENGTH: 11
<212> TYPE: PRT
<213> ORGANISM: Homo sapiens

<400> SEQUENCE: 619

Val Gly Phe Tyr Glu Ser Asp Val Met Gly Arg
1               5                   10

<210> SEQ ID NO 620
<211> LENGTH: 16
<212> TYPE: PRT
<213> ORGANISM: Homo sapiens

<400> SEQUENCE: 620

Val Asp Ser His Phe Arg Gln Gly Ile Pro Phe Gly Gln Val Arg
1               5                   10                  15

<210> SEQ ID NO 621
<211> LENGTH: 19
<212> TYPE: PRT
<213> ORGANISM: Homo sapiens

<400> SEQUENCE: 621

Val Asp Leu Ser Phe Ser Pro Ser Gln Ser Leu Pro Ala Ser His Ala
1               5                   10                  15

His Leu Arg

<210> SEQ ID NO 622
<211> LENGTH: 14
<212> TYPE: PRT
<213> ORGANISM: Homo sapiens

<400> SEQUENCE: 622

Thr Glu Val Ser Ser Asn His Val Leu Ile Tyr Leu Asp Lys
1               5                   10

<210> SEQ ID NO 623
<211> LENGTH: 22
<212> TYPE: PRT
<213> ORGANISM: Homo sapiens

<400> SEQUENCE: 623

Ser Leu Phe Thr Asp Leu Glu Ala Glu Asn Asp Val Leu His Cys Val
1               5                   10                  15

Ala Phe Ala Val Pro Lys
                20
```

```
<210> SEQ ID NO 624
<211> LENGTH: 13
<212> TYPE: PRT
<213> ORGANISM: Homo sapiens

<400> SEQUENCE: 624

Ser Lys Ala Ile Gly Tyr Leu Asn Thr Gly Tyr Gln Arg
1               5                   10

<210> SEQ ID NO 625
<211> LENGTH: 23
<212> TYPE: PRT
<213> ORGANISM: Homo sapiens

<400> SEQUENCE: 625

Gln Gln Asn Ala Gln Gly Gly Phe Ser Thr Gln Asp Thr Val Val
1               5                   10                  15

Ala Leu His Ala Leu Ser Lys
            20

<210> SEQ ID NO 626
<211> LENGTH: 17
<212> TYPE: PRT
<213> ORGANISM: Homo sapiens

<400> SEQUENCE: 626

Gln Leu Asn Tyr Lys His Tyr Asp Gly Ser Tyr Ser Thr Phe Gly Glu
1               5                   10                  15

Arg

<210> SEQ ID NO 627
<211> LENGTH: 10
<212> TYPE: PRT
<213> ORGANISM: Homo sapiens

<400> SEQUENCE: 627

Gln Gly Ile Pro Phe Phe Gly Gln Val Arg
1               5                   10

<210> SEQ ID NO 628
<211> LENGTH: 16
<212> TYPE: PRT
<213> ORGANISM: Homo sapiens

<400> SEQUENCE: 628

Gln Phe Ser Phe Pro Leu Ser Ser Glu Pro Phe Gln Gly Ser Tyr Lys
1               5                   10                  15

<210> SEQ ID NO 629
<211> LENGTH: 13
<212> TYPE: PRT
<213> ORGANISM: Homo sapiens

<400> SEQUENCE: 629

Asn Gln Gly Asn Thr Trp Leu Thr Ala Phe Val Leu Lys
1               5                   10

<210> SEQ ID NO 630
<211> LENGTH: 12
<212> TYPE: PRT
<213> ORGANISM: Homo sapiens

<400> SEQUENCE: 630

Asn Glu Asp Ser Leu Val Phe Val Gln Thr Asp Lys
```

```
<210> SEQ ID NO 631
<211> LENGTH: 18
<212> TYPE: PRT
<213> ORGANISM: Homo sapiens

<400> SEQUENCE: 631

Leu Leu Ile Tyr Ala Val Leu Pro Thr Gly Asp Val Ile Gly Asp Ser
1               5                   10                  15

Ala Lys

<210> SEQ ID NO 632
<211> LENGTH: 19
<212> TYPE: PRT
<213> ORGANISM: Homo sapiens

<400> SEQUENCE: 632

Leu His Thr Glu Ala Gln Ile Gln Glu Glu Gly Thr Val Val Glu Leu
1               5                   10                  15

Thr Gly Arg

<210> SEQ ID NO 633
<211> LENGTH: 19
<212> TYPE: PRT
<213> ORGANISM: Homo sapiens

<400> SEQUENCE: 633

Lys Tyr Ser Asp Ala Ser Asp Cys His Gly Glu Asp Ser Gln Ala Phe
1               5                   10                  15

Cys Glu Lys

<210> SEQ ID NO 634
<211> LENGTH: 14
<212> TYPE: PRT
<213> ORGANISM: Homo sapiens

<400> SEQUENCE: 634

Ile Ala Gln Trp Gln Ser Phe Gln Leu Glu Gly Gly Leu Lys
1               5                   10

<210> SEQ ID NO 635
<211> LENGTH: 16
<212> TYPE: PRT
<213> ORGANISM: Homo sapiens

<400> SEQUENCE: 635

Phe Ser Gly Gln Leu Asn Ser His Gly Cys Phe Tyr Gln Gln Val Lys
1               5                   10                  15

<210> SEQ ID NO 636
<211> LENGTH: 9
<212> TYPE: PRT
<213> ORGANISM: Homo sapiens

<400> SEQUENCE: 636

Phe Glu Val Gln Val Thr Val Pro Lys
1               5

<210> SEQ ID NO 637
<211> LENGTH: 16
<212> TYPE: PRT
<213> ORGANISM: Homo sapiens
```

<400> SEQUENCE: 637

Asp Thr Val Ile Lys Pro Leu Leu Val Glu Pro Glu Gly Leu Glu Lys
1               5                   10                  15

<210> SEQ ID NO 638
<211> LENGTH: 15
<212> TYPE: PRT
<213> ORGANISM: Homo sapiens

<400> SEQUENCE: 638

Ala Leu Leu Ala Tyr Ala Phe Ala Leu Ala Gly Asn Gln Asp Lys
1               5                   10                  15

<210> SEQ ID NO 639
<211> LENGTH: 11
<212> TYPE: PRT
<213> ORGANISM: Homo sapiens

<400> SEQUENCE: 639

Ala Ile Gly Tyr Leu Asn Thr Gly Tyr Gln Arg
1               5                   10

<210> SEQ ID NO 640
<211> LENGTH: 15
<212> TYPE: PRT
<213> ORGANISM: Homo sapiens

<400> SEQUENCE: 640

Ala Ala Gln Val Thr Ile Gln Ser Ser Gly Thr Phe Ser Ser Lys
1               5                   10                  15

<210> SEQ ID NO 641
<211> LENGTH: 12
<212> TYPE: PRT
<213> ORGANISM: Homo sapiens

<400> SEQUENCE: 641

Val Gly Trp Glu Gln Leu Leu Thr Thr Ile Ala Arg
1               5                   10

<210> SEQ ID NO 642
<211> LENGTH: 12
<212> TYPE: PRT
<213> ORGANISM: Homo sapiens

<400> SEQUENCE: 642

Thr Ile Asn Glu Val Glu Asn Gln Ile Leu Thr Arg
1               5                   10

<210> SEQ ID NO 643
<211> LENGTH: 13
<212> TYPE: PRT
<213> ORGANISM: Homo sapiens

<400> SEQUENCE: 643

Cys Gln Leu Glu Ile Asn Phe Asn Thr Leu Gln Thr Lys
1               5                   10

<210> SEQ ID NO 644
<211> LENGTH: 16
<212> TYPE: PRT
<213> ORGANISM: Homo sapiens

<400> SEQUENCE: 644

Glu Thr Thr Asp Thr Asp Thr Ala Asp Gln Val Ile Ala Ser Phe Lys
1               5                   10                  15

<210> SEQ ID NO 645
<211> LENGTH: 11
<212> TYPE: PRT
<213> ORGANISM: Homo sapiens

<400> SEQUENCE: 645

Asp Tyr Glu Thr Ala Thr Leu Ser Asp Ile Lys
1               5                   10

<210> SEQ ID NO 646
<211> LENGTH: 13
<212> TYPE: PRT
<213> ORGANISM: Homo sapiens

<400> SEQUENCE: 646

His Arg Asp Tyr Glu Thr Ala Thr Leu Ser Asp Ile Lys
1               5                   10

<210> SEQ ID NO 647
<211> LENGTH: 26
<212> TYPE: PRT
<213> ORGANISM: Homo sapiens

<400> SEQUENCE: 647

Ile Ala Glu Ser Asn His Ile Lys Leu Ser Gly Ser Asn Pro Tyr Thr
1               5                   10                  15

Thr Val Thr Pro Gln Ile Ile Asn Ser Lys
            20                  25

<210> SEQ ID NO 648
<211> LENGTH: 15
<212> TYPE: PRT
<213> ORGANISM: Homo sapiens

<400> SEQUENCE: 648

Ile Cys Asp Gln Trp Asp Ala Leu Gly Ser Leu Thr His Ser Arg
1               5                   10                  15

<210> SEQ ID NO 649
<211> LENGTH: 17
<212> TYPE: PRT
<213> ORGANISM: Homo sapiens

<400> SEQUENCE: 649

Lys Asp Asp Pro Val Thr Asn Leu Asn Asn Ala Phe Glu Val Ala Glu
1               5                   10                  15

Lys

<210> SEQ ID NO 650
<211> LENGTH: 10
<212> TYPE: PRT
<213> ORGANISM: Homo sapiens

<400> SEQUENCE: 650

Leu Ala Ser Asp Leu Leu Glu Trp Ile Arg
1               5                   10

<210> SEQ ID NO 651
<211> LENGTH: 18
<212> TYPE: PRT

<213> ORGANISM: Homo sapiens

<400> SEQUENCE: 651

Leu Ser Gly Ser Asn Pro Tyr Thr Thr Val Thr Pro Gln Ile Ile Asn
1               5                   10                  15

Ser Lys

<210> SEQ ID NO 652
<211> LENGTH: 21
<212> TYPE: PRT
<213> ORGANISM: Homo sapiens

<400> SEQUENCE: 652

Leu Ser Gly Ser Asn Pro Tyr Thr Thr Val Thr Pro Gln Ile Ile Asn
1               5                   10                  15

Ser Lys Trp Glu Lys
            20

<210> SEQ ID NO 653
<211> LENGTH: 16
<212> TYPE: PRT
<213> ORGANISM: Homo sapiens

<400> SEQUENCE: 653

Gln Phe Ala Ser Gln Ala Asn Val Val Gly Pro Trp Ile Gln Thr Lys
1               5                   10                  15

<210> SEQ ID NO 654
<211> LENGTH: 10
<212> TYPE: PRT
<213> ORGANISM: Homo sapiens

<400> SEQUENCE: 654

Ser Thr Leu Pro Asp Ala Asp Arg Glu Arg
1               5                   10

<210> SEQ ID NO 655
<211> LENGTH: 15
<212> TYPE: PRT
<213> ORGANISM: Homo sapiens

<400> SEQUENCE: 655

Val Leu Ala Gly Asp Lys Asn Phe Ile Thr Ala Glu Glu Leu Arg
1               5                   10                  15

<210> SEQ ID NO 656
<211> LENGTH: 13
<212> TYPE: PRT
<213> ORGANISM: Homo sapiens

<400> SEQUENCE: 656

Gly Asn Pro Thr Val Glu Val Asp Leu Phe Thr Ser Lys
1               5                   10

<210> SEQ ID NO 657
<211> LENGTH: 8
<212> TYPE: PRT
<213> ORGANISM: Homo sapiens

<400> SEQUENCE: 657

Ser Cys Asn Cys Leu Leu Leu Lys
1               5

```
<210> SEQ ID NO 658
<211> LENGTH: 15
<212> TYPE: PRT
<213> ORGANISM: Homo sapiens

<400> SEQUENCE: 658

Val Asn Gln Ile Gly Ser Val Thr Glu Ser Leu Gln Ala Cys Lys
1               5                   10                  15

<210> SEQ ID NO 659
<211> LENGTH: 18
<212> TYPE: PRT
<213> ORGANISM: Homo sapiens

<400> SEQUENCE: 659

Ala Ala Val Pro Ser Gly Ala Ser Thr Gly Ile Tyr Glu Ala Leu Glu
1               5                   10                  15

Leu Arg

<210> SEQ ID NO 660
<211> LENGTH: 12
<212> TYPE: PRT
<213> ORGANISM: Homo sapiens

<400> SEQUENCE: 660

Ala Gly Ala Val Glu Lys Gly Val Pro Leu Tyr Arg
1               5                   10

<210> SEQ ID NO 661
<211> LENGTH: 7
<212> TYPE: PRT
<213> ORGANISM: Homo sapiens

<400> SEQUENCE: 661

Ala Val Glu His Ile Asn Lys
1               5

<210> SEQ ID NO 662
<211> LENGTH: 16
<212> TYPE: PRT
<213> ORGANISM: Homo sapiens

<400> SEQUENCE: 662

Ala Val Glu His Ile Asn Lys Thr Ile Ala Pro Ala Leu Val Ser Lys
1               5                   10                  15

<210> SEQ ID NO 663
<211> LENGTH: 19
<212> TYPE: PRT
<213> ORGANISM: Homo sapiens

<400> SEQUENCE: 663

Asp Ala Thr Asn Val Gly Asp Glu Gly Gly Phe Ala Pro Asn Ile Leu
1               5                   10                  15

Glu Asn Lys

<210> SEQ ID NO 664
<211> LENGTH: 26
<212> TYPE: PRT
<213> ORGANISM: Homo sapiens

<400> SEQUENCE: 664

Asp Ala Thr Asn Val Gly Asp Glu Gly Gly Phe Ala Pro Asn Ile Leu
1               5                   10                  15
```

Glu Asn Lys Glu Gly Leu Glu Leu Leu Lys
            20                  25

<210> SEQ ID NO 665
<211> LENGTH: 19
<212> TYPE: PRT
<213> ORGANISM: Homo sapiens

<400> SEQUENCE: 665

Glu Ile Phe Asp Ser Arg Gly Asn Pro Thr Val Glu Val Asp Leu Phe
1               5                   10                  15

Thr Ser Lys

<210> SEQ ID NO 666
<211> LENGTH: 23
<212> TYPE: PRT
<213> ORGANISM: Homo sapiens

<400> SEQUENCE: 666

Glu Ile Phe Asp Ser Arg Gly Asn Pro Thr Val Glu Val Asp Leu Phe
1               5                   10                  15

Thr Ser Lys Gly Leu Phe Arg
            20

<210> SEQ ID NO 667
<211> LENGTH: 24
<212> TYPE: PRT
<213> ORGANISM: Homo sapiens

<400> SEQUENCE: 667

Glu Lys Tyr Gly Lys Asp Ala Thr Asn Val Gly Asp Glu Gly Gly Phe
1               5                   10                  15

Ala Pro Asn Ile Leu Glu Asn Lys
            20

<210> SEQ ID NO 668
<211> LENGTH: 21
<212> TYPE: PRT
<213> ORGANISM: Homo sapiens

<400> SEQUENCE: 668

Phe Thr Ala Ser Ala Gly Ile Gln Val Val Gly Asp Asp Leu Thr Val
1               5                   10                  15

Thr Asn Pro Lys Arg
            20

<210> SEQ ID NO 669
<211> LENGTH: 30
<212> TYPE: PRT
<213> ORGANISM: Homo sapiens

<400> SEQUENCE: 669

His Ile Ala Asp Leu Ala Gly Asn Ser Glu Val Ile Leu Pro Val Pro
1               5                   10                  15

Ala Phe Asn Val Ile Asn Gly Gly Ser His Ala Gly Asn Lys
            20                  25                  30

<210> SEQ ID NO 670
<211> LENGTH: 8
<212> TYPE: PRT
<213> ORGANISM: Homo sapiens

<400> SEQUENCE: 670

Ile Glu Glu Glu Leu Gly Ser Lys
1               5

<210> SEQ ID NO 671
<211> LENGTH: 10
<212> TYPE: PRT
<213> ORGANISM: Homo sapiens

<400> SEQUENCE: 671

Ile Glu Glu Glu Leu Gly Ser Lys Ala Lys
1               5                   10

<210> SEQ ID NO 672
<211> LENGTH: 14
<212> TYPE: PRT
<213> ORGANISM: Homo sapiens

<400> SEQUENCE: 672

Ile Glu Glu Glu Leu Gly Ser Lys Ala Lys Phe Ala Gly Arg
1               5                   10

<210> SEQ ID NO 673
<211> LENGTH: 10
<212> TYPE: PRT
<213> ORGANISM: Homo sapiens

<400> SEQUENCE: 673

Ile Gly Ala Glu Val Tyr His Asn Leu Lys
1               5                   10

<210> SEQ ID NO 674
<211> LENGTH: 14
<212> TYPE: PRT
<213> ORGANISM: Homo sapiens

<400> SEQUENCE: 674

Ile Gly Ala Glu Val Tyr His Asn Leu Lys Asn Val Ile Lys
1               5                   10

<210> SEQ ID NO 675
<211> LENGTH: 9
<212> TYPE: PRT
<213> ORGANISM: Homo sapiens

<400> SEQUENCE: 675

Lys Leu Asn Val Thr Glu Gln Glu Lys
1               5

<210> SEQ ID NO 676
<211> LENGTH: 12
<212> TYPE: PRT
<213> ORGANISM: Homo sapiens

<400> SEQUENCE: 676

Lys Leu Asn Val Thr Glu Gln Glu Lys Ile Asp Lys
1               5                   10

<210> SEQ ID NO 677
<211> LENGTH: 14
<212> TYPE: PRT
<213> ORGANISM: Homo sapiens

<400> SEQUENCE: 677

Leu Ala Gln Ala Asn Gly Trp Gly Val Met Val Ser His Arg
1               5                   10

<210> SEQ ID NO 678
<211> LENGTH: 8
<212> TYPE: PRT
<213> ORGANISM: Homo sapiens

<400> SEQUENCE: 678

Asn Phe Arg Asn Pro Leu Ala Lys
1               5

<210> SEQ ID NO 679
<211> LENGTH: 22
<212> TYPE: PRT
<213> ORGANISM: Homo sapiens

<400> SEQUENCE: 679

Ser Gly Glu Thr Glu Asp Thr Phe Ile Ala Asp Leu Val Val Gly Leu
1               5                   10                  15

Cys Thr Gly Gln Ile Lys
            20

<210> SEQ ID NO 680
<211> LENGTH: 16
<212> TYPE: PRT
<213> ORGANISM: Homo sapiens

<400> SEQUENCE: 680

Ser Gly Lys Tyr Asp Leu Asp Phe Lys Ser Pro Asp Asp Pro Ser Arg
1               5                   10                  15

<210> SEQ ID NO 681
<211> LENGTH: 8
<212> TYPE: PRT
<213> ORGANISM: Homo sapiens

<400> SEQUENCE: 681

Ser Ile Leu Lys Ile His Ala Arg
1               5

<210> SEQ ID NO 682
<211> LENGTH: 19
<212> TYPE: PRT
<213> ORGANISM: Homo sapiens

<400> SEQUENCE: 682

Ser Pro Asp Asp Pro Ser Arg Tyr Ile Ser Pro Asp Gln Leu Ala Asp
1               5                   10                  15

Leu Tyr Lys

<210> SEQ ID NO 683
<211> LENGTH: 9
<212> TYPE: PRT
<213> ORGANISM: Homo sapiens

<400> SEQUENCE: 683

Thr Ile Ala Pro Ala Leu Val Ser Lys
1               5

<210> SEQ ID NO 684
<211> LENGTH: 22
<212> TYPE: PRT
<213> ORGANISM: Homo sapiens

<400> SEQUENCE: 684

Tyr Gly Lys Asp Ala Thr Asn Val Gly Asp Glu Gly Gly Phe Ala Pro
1               5                   10                  15

Asn Ile Leu Glu Asn Lys
            20

<210> SEQ ID NO 685
<211> LENGTH: 29
<212> TYPE: PRT
<213> ORGANISM: Homo sapiens

<400> SEQUENCE: 685

Tyr Gly Lys Asp Ala Thr Asn Val Gly Asp Glu Gly Gly Phe Ala Pro
1               5                   10                  15

Asn Ile Leu Glu Asn Lys Glu Gly Leu Glu Leu Leu Lys
            20                  25

<210> SEQ ID NO 686
<211> LENGTH: 12
<212> TYPE: PRT
<213> ORGANISM: Homo sapiens

<400> SEQUENCE: 686

Tyr Ile Ser Pro Asp Gln Leu Ala Asp Leu Tyr Lys
1               5                   10

<210> SEQ ID NO 687
<211> LENGTH: 6
<212> TYPE: PRT
<213> ORGANISM: Homo sapiens

<400> SEQUENCE: 687

Tyr Asn Gln Leu Leu Arg
1               5

<210> SEQ ID NO 688
<211> LENGTH: 14
<212> TYPE: PRT
<213> ORGANISM: Homo sapiens

<400> SEQUENCE: 688

Tyr Asn Gln Leu Leu Arg Ile Glu Glu Glu Leu Gly Ser Lys
1               5                   10

<210> SEQ ID NO 689
<211> LENGTH: 16
<212> TYPE: PRT
<213> ORGANISM: Homo sapiens

<400> SEQUENCE: 689

Tyr Asn Gln Leu Leu Arg Ile Glu Glu Glu Leu Gly Ser Lys Ala Lys
1               5                   10                  15

<210> SEQ ID NO 690
<211> LENGTH: 13
<212> TYPE: PRT
<213> ORGANISM: Homo sapiens

<400> SEQUENCE: 690

Tyr Asp Leu Asp Phe Lys Ser Pro Asp Asp Pro Ser Arg
1               5                   10

<210> SEQ ID NO 691
<211> LENGTH: 17
<212> TYPE: PRT
<213> ORGANISM: Homo sapiens

<400> SEQUENCE: 691

Val Leu Ser Ala Leu Gln Ala Val Gln Gly Leu Leu Val Ala Gln Gly
1               5                   10                  15

Arg

<210> SEQ ID NO 692
<211> LENGTH: 13
<212> TYPE: PRT
<213> ORGANISM: Homo sapiens

<400> SEQUENCE: 692

Ser Leu Asp Phe Thr Glu Leu Asp Val Ala Ala Glu Lys
1               5                   10

<210> SEQ ID NO 693
<211> LENGTH: 17
<212> TYPE: PRT
<213> ORGANISM: Homo sapiens

<400> SEQUENCE: 693

Val Leu Ser Ala Leu Gln Ala Val Gln Gly Leu Leu Val Ala Gln Gly
1               5                   10                  15

Arg

<210> SEQ ID NO 694
<211> LENGTH: 19
<212> TYPE: PRT
<213> ORGANISM: Homo sapiens

<400> SEQUENCE: 694

Ala Asn Ala Gly Lys Pro Lys Asp Pro Thr Phe Ile Pro Ala Pro Ile
1               5                   10                  15

Gln Ala Lys

<210> SEQ ID NO 695
<211> LENGTH: 10
<212> TYPE: PRT
<213> ORGANISM: Homo sapiens

<400> SEQUENCE: 695

Ala Leu Leu Leu Leu Cys Gly Glu Asp Asp
1               5                   10

<210> SEQ ID NO 696
<211> LENGTH: 17
<212> TYPE: PRT
<213> ORGANISM: Homo sapiens

<400> SEQUENCE: 696

Ala Gln Val Leu Arg Gly Thr Val Thr Asp Phe Pro Gly Phe Asp Glu
1               5                   10                  15

Arg

<210> SEQ ID NO 697
<211> LENGTH: 13
<212> TYPE: PRT
<213> ORGANISM: Homo sapiens

<400> SEQUENCE: 697

Asp Leu Leu Asp Asp Leu Lys Ser Glu Leu Thr Gly Lys
1               5                   10

<210> SEQ ID NO 698
<211> LENGTH: 16
<212> TYPE: PRT
<213> ORGANISM: Homo sapiens

<400> SEQUENCE: 698

Asp Leu Leu Asp Asp Leu Lys Ser Glu Leu Thr Gly Lys Phe Glu Lys
1               5                   10                  15

<210> SEQ ID NO 699
<211> LENGTH: 16
<212> TYPE: PRT
<213> ORGANISM: Homo sapiens

<400> SEQUENCE: 699

Gly Leu Gly Thr Asp Glu Glu Ser Ile Leu Thr Leu Leu Thr Ser Arg
1               5                   10                  15

<210> SEQ ID NO 700
<211> LENGTH: 20
<212> TYPE: PRT
<213> ORGANISM: Homo sapiens

<400> SEQUENCE: 700

Gly Thr Val Thr Asp Phe Pro Gly Phe Asp Glu Arg Ala Asp Ala Glu
1               5                   10                  15

Thr Leu Arg Lys
            20

<210> SEQ ID NO 701
<211> LENGTH: 11
<212> TYPE: PRT
<213> ORGANISM: Homo sapiens

<400> SEQUENCE: 701

Asn Phe Ala Thr Ser Leu Tyr Ser Met Ile Lys
1               5                   10

<210> SEQ ID NO 702
<211> LENGTH: 9
<212> TYPE: PRT
<213> ORGANISM: Homo sapiens

<400> SEQUENCE: 702

Ser Glu Ile Asp Leu Phe Asn Ile Arg
1               5

<210> SEQ ID NO 703
<211> LENGTH: 9
<212> TYPE: PRT
<213> ORGANISM: Homo sapiens

<400> SEQUENCE: 703

Val Leu Thr Glu Ile Ile Ala Ser Arg
1               5

<210> SEQ ID NO 704
<211> LENGTH: 15
<212> TYPE: PRT
<213> ORGANISM: Homo sapiens

<400> SEQUENCE: 704

Trp Gly Thr Asp Glu Glu Lys Phe Ile Thr Ile Phe Gly Thr Arg
1               5                   10                  15

<210> SEQ ID NO 705
<211> LENGTH: 12
<212> TYPE: PRT
<213> ORGANISM: Homo sapiens

<400> SEQUENCE: 705

Gly Thr Val Thr Asp Phe Pro Gly Phe Asp Glu Arg
1               5                   10

<210> SEQ ID NO 706
<211> LENGTH: 10
<212> TYPE: PRT
<213> ORGANISM: Homo sapiens

<400> SEQUENCE: 706

Val Phe Ala Glu Asn Lys Glu Ile Gln Lys
1               5                   10

<210> SEQ ID NO 707
<211> LENGTH: 18
<212> TYPE: PRT
<213> ORGANISM: Homo sapiens

<400> SEQUENCE: 707

Leu Tyr Ala Tyr Glu Pro Ala Asp Thr Ala Leu Leu Leu Asp Asn Met
1               5                   10                  15

Lys Lys

<210> SEQ ID NO 708
<211> LENGTH: 7
<212> TYPE: PRT
<213> ORGANISM: Homo sapiens

<400> SEQUENCE: 708

Leu Pro Gln Thr Leu Ser Arg
1               5

<210> SEQ ID NO 709
<211> LENGTH: 28
<212> TYPE: PRT
<213> ORGANISM: Homo sapiens

<400> SEQUENCE: 709

Leu Ala Glu Gln Phe Val Leu Leu Asn Leu Val Tyr Glu Thr Thr Asp
1               5                   10                  15

Lys His Leu Ser Pro Asp Gly Gln Tyr Val Pro Arg
            20                  25

<210> SEQ ID NO 710
<211> LENGTH: 17
<212> TYPE: PRT
<213> ORGANISM: Homo sapiens

<400> SEQUENCE: 710

Leu Ala Glu Gln Phe Val Leu Leu Asn Leu Val Tyr Glu Thr Thr Asp
1               5                   10                  15

Lys

<210> SEQ ID NO 711
<211> LENGTH: 11
<212> TYPE: PRT
<213> ORGANISM: Homo sapiens

<400> SEQUENCE: 711

Ile Met Phe Val Asp Pro Ser Leu Thr Val Arg
1               5                   10

<210> SEQ ID NO 712
<211> LENGTH: 12
<212> TYPE: PRT
<213> ORGANISM: Homo sapiens

<400> SEQUENCE: 712

Asp Ser Arg Pro Lys Leu Pro Gln Thr Leu Ser Arg
1               5                   10

<210> SEQ ID NO 713
<211> LENGTH: 10
<212> TYPE: PRT
<213> ORGANISM: Homo sapiens

<400> SEQUENCE: 713

Ala Asn Arg Pro Phe Leu Val Phe Ile Arg
1               5                   10

<210> SEQ ID NO 714
<211> LENGTH: 17
<212> TYPE: PRT
<213> ORGANISM: Homo sapiens

<400> SEQUENCE: 714

Ala Thr Glu Asp Glu Gly Ser Glu Gln Lys Ile Pro Glu Ala Thr Asn
1               5                   10                  15
Arg

<210> SEQ ID NO 715
<211> LENGTH: 18
<212> TYPE: PRT
<213> ORGANISM: Homo sapiens

<400> SEQUENCE: 715

Ala Thr Glu Asp Glu Gly Ser Glu Gln Lys Ile Pro Glu Ala Thr Asn
1               5                   10                  15
Arg Arg

<210> SEQ ID NO 716
<211> LENGTH: 12
<212> TYPE: PRT
<213> ORGANISM: Homo sapiens

<400> SEQUENCE: 716

Glu Val Pro Leu Asn Thr Ile Ile Phe Met Gly Arg
1               5                   10

<210> SEQ ID NO 717
<211> LENGTH: 10
<212> TYPE: PRT
<213> ORGANISM: Homo sapiens

<400> SEQUENCE: 717

Phe Arg Ile Glu Asp Gly Phe Ser Leu Lys

<210> SEQ ID NO 718
<211> LENGTH: 25
<212> TYPE: PRT
<213> ORGANISM: Homo sapiens

<400> SEQUENCE: 718

Ile Thr Asp Val Ile Pro Ser Glu Ala Ile Asn Glu Leu Thr Val Leu
1               5                   10                  15

Val Leu Val Asn Thr Ile Tyr Phe Lys
            20                  25

<210> SEQ ID NO 719
<211> LENGTH: 18
<212> TYPE: PRT
<213> ORGANISM: Homo sapiens

<400> SEQUENCE: 719

Lys Ala Thr Glu Asp Glu Gly Ser Glu Gln Lys Ile Pro Glu Ala Thr
1               5                   10                  15

Asn Arg

<210> SEQ ID NO 720
<211> LENGTH: 10
<212> TYPE: PRT
<213> ORGANISM: Homo sapiens

<400> SEQUENCE: 720

Ser Lys Phe Ser Pro Glu Asn Thr Arg Lys
1               5                   10

<210> SEQ ID NO 721
<211> LENGTH: 22
<212> TYPE: PRT
<213> ORGANISM: Homo sapiens

<400> SEQUENCE: 721

Ser Lys Leu Pro Gly Ile Val Ala Glu Gly Arg Asp Asp Leu Tyr Val
1               5                   10                  15

Ser Asp Ala Phe His Lys
            20

<210> SEQ ID NO 722
<211> LENGTH: 11
<212> TYPE: PRT
<213> ORGANISM: Homo sapiens

<400> SEQUENCE: 722

Thr Ser Asp Gln Ile His Phe Phe Phe Ala Lys
1               5                   10

<210> SEQ ID NO 723
<211> LENGTH: 8
<212> TYPE: PRT
<213> ORGANISM: Homo sapiens

<400> SEQUENCE: 723

Ala Glu Leu Gln Glu Gly Ala Arg
1               5

<210> SEQ ID NO 724
<211> LENGTH: 18

```
<212> TYPE: PRT
<213> ORGANISM: Homo sapiens

<400> SEQUENCE: 724

Ala His Val Asp Ala Leu Arg Thr His Leu Ala Pro Tyr Ser Asp Glu
1               5                   10                  15

Leu Arg

<210> SEQ ID NO 725
<211> LENGTH: 11
<212> TYPE: PRT
<213> ORGANISM: Homo sapiens

<400> SEQUENCE: 725

Ala Thr Glu His Leu Ser Thr Leu Ser Glu Lys
1               5                   10

<210> SEQ ID NO 726
<211> LENGTH: 11
<212> TYPE: PRT
<213> ORGANISM: Homo sapiens

<400> SEQUENCE: 726

Asp Leu Ala Thr Val Tyr Val Asp Val Leu Lys
1               5                   10

<210> SEQ ID NO 727
<211> LENGTH: 17
<212> TYPE: PRT
<213> ORGANISM: Homo sapiens

<400> SEQUENCE: 727

Asp Ser Gly Arg Asp Tyr Val Ser Gln Phe Glu Gly Ser Ala Leu Gly
1               5                   10                  15

Lys

<210> SEQ ID NO 728
<211> LENGTH: 13
<212> TYPE: PRT
<213> ORGANISM: Homo sapiens

<400> SEQUENCE: 728

Asp Tyr Val Ser Gln Phe Glu Gly Ser Ala Leu Gly Lys
1               5                   10

<210> SEQ ID NO 729
<211> LENGTH: 16
<212> TYPE: PRT
<213> ORGANISM: Homo sapiens

<400> SEQUENCE: 729

Glu Gln Leu Gly Pro Val Thr Gln Glu Phe Trp Asp Asn Leu Glu Lys
1               5                   10                  15

<210> SEQ ID NO 730
<211> LENGTH: 18
<212> TYPE: PRT
<213> ORGANISM: Homo sapiens

<400> SEQUENCE: 730

Leu Ala Glu Tyr His Ala Lys Ala Thr Glu His Leu Ser Thr Leu Ser
1               5                   10                  15

Glu Lys
```

<210> SEQ ID NO 731
<211> LENGTH: 11
<212> TYPE: PRT
<213> ORGANISM: Homo sapiens

<400> SEQUENCE: 731

Leu Glu Ala Leu Lys Glu Asn Gly Gly Ala Arg
1               5                   10

<210> SEQ ID NO 732
<211> LENGTH: 7
<212> TYPE: PRT
<213> ORGANISM: Homo sapiens

<400> SEQUENCE: 732

Leu His Glu Leu Gln Glu Lys
1               5

<210> SEQ ID NO 733
<211> LENGTH: 14
<212> TYPE: PRT
<213> ORGANISM: Homo sapiens

<400> SEQUENCE: 733

Leu Leu Asp Asn Trp Asp Ser Val Thr Ser Thr Phe Ser Lys
1               5                   10

<210> SEQ ID NO 734
<211> LENGTH: 18
<212> TYPE: PRT
<213> ORGANISM: Homo sapiens

<400> SEQUENCE: 734

Leu Arg Glu Gln Leu Gly Pro Val Thr Gln Glu Phe Trp Asp Asn Leu
1               5                   10                  15

Glu Lys

<210> SEQ ID NO 735
<211> LENGTH: 11
<212> TYPE: PRT
<213> ORGANISM: Homo sapiens

<400> SEQUENCE: 735

Gln Gly Leu Leu Pro Val Leu Glu Ser Phe Lys
1               5                   10

<210> SEQ ID NO 736
<211> LENGTH: 15
<212> TYPE: PRT
<213> ORGANISM: Homo sapiens

<400> SEQUENCE: 736

Gln Lys Val Glu Pro Leu Arg Ala Glu Leu Gln Glu Gly Ala Arg
1               5                   10                  15

<210> SEQ ID NO 737
<211> LENGTH: 11
<212> TYPE: PRT
<213> ORGANISM: Homo sapiens

<400> SEQUENCE: 737

Thr His Leu Ala Pro Tyr Ser Asp Glu Leu Arg
1               5                   10

<210> SEQ ID NO 738
<211> LENGTH: 13
<212> TYPE: PRT
<213> ORGANISM: Homo sapiens

<400> SEQUENCE: 738

Thr His Leu Ala Pro Tyr Ser Asp Glu Leu Arg Gln Arg
1               5                   10

<210> SEQ ID NO 739
<211> LENGTH: 13
<212> TYPE: PRT
<213> ORGANISM: Homo sapiens

<400> SEQUENCE: 739

Val Glu Pro Leu Arg Ala Glu Leu Gln Glu Gly Ala Arg
1               5                   10

<210> SEQ ID NO 740
<211> LENGTH: 13
<212> TYPE: PRT
<213> ORGANISM: Homo sapiens

<400> SEQUENCE: 740

Val Lys Asp Leu Ala Thr Val Tyr Val Asp Val Leu Lys
1               5                   10

<210> SEQ ID NO 741
<211> LENGTH: 11
<212> TYPE: PRT
<213> ORGANISM: Homo sapiens

<400> SEQUENCE: 741

Val Gln Pro Tyr Leu Asp Asp Phe Gln Lys Lys
1               5                   10

<210> SEQ ID NO 742
<211> LENGTH: 12
<212> TYPE: PRT
<213> ORGANISM: Homo sapiens

<400> SEQUENCE: 742

Val Ser Phe Leu Ser Ala Leu Glu Glu Tyr Thr Lys
1               5                   10

<210> SEQ ID NO 743
<211> LENGTH: 13
<212> TYPE: PRT
<213> ORGANISM: Homo sapiens

<400> SEQUENCE: 743

Val Ser Phe Leu Ser Ala Leu Glu Glu Tyr Thr Lys Lys
1               5                   10

<210> SEQ ID NO 744
<211> LENGTH: 11
<212> TYPE: PRT
<213> ORGANISM: Homo sapiens

<400> SEQUENCE: 744

Val Lys Ser Pro Glu Leu Gln Ala Glu Ala Lys
1               5                   10

```
<210> SEQ ID NO 745
<211> LENGTH: 9
<212> TYPE: PRT
<213> ORGANISM: Homo sapiens

<400> SEQUENCE: 745

Ser Pro Glu Leu Gln Ala Glu Ala Lys
1               5

<210> SEQ ID NO 746
<211> LENGTH: 11
<212> TYPE: PRT
<213> ORGANISM: Homo sapiens

<400> SEQUENCE: 746

Ser Lys Glu Gln Leu Thr Pro Leu Ile Lys Lys
1               5                   10

<210> SEQ ID NO 747
<211> LENGTH: 10
<212> TYPE: PRT
<213> ORGANISM: Homo sapiens

<400> SEQUENCE: 747

Ser Lys Glu Gln Leu Thr Pro Leu Ile Lys
1               5                   10

<210> SEQ ID NO 748
<211> LENGTH: 22
<212> TYPE: PRT
<213> ORGANISM: Homo sapiens

<400> SEQUENCE: 748

Ala Gly Thr Glu Leu Val Asn Phe Leu Ser Tyr Phe Val Glu Leu Gly
1               5                   10                  15

Thr Gln Pro Ala Thr Gln
            20

<210> SEQ ID NO 749
<211> LENGTH: 9
<212> TYPE: PRT
<213> ORGANISM: Homo sapiens

<400> SEQUENCE: 749

Ile Ser Ala Ser Ala Glu Glu Leu Arg
1               5

<210> SEQ ID NO 750
<211> LENGTH: 13
<212> TYPE: PRT
<213> ORGANISM: Homo sapiens

<400> SEQUENCE: 750

Leu Gly Glu Val Asn Thr Tyr Ala Gly Asp Leu Gln Lys
1               5                   10

<210> SEQ ID NO 751
<211> LENGTH: 14
<212> TYPE: PRT
<213> ORGANISM: Homo sapiens

<400> SEQUENCE: 751

Ser Glu Leu Thr Gln Gln Leu Asn Ala Leu Phe Gln Asp Lys
1               5                   10
```

<210> SEQ ID NO 752
<211> LENGTH: 17
<212> TYPE: PRT
<213> ORGANISM: Homo sapiens

<400> SEQUENCE: 752

Ser Leu Ala Glu Leu Gly Gly His Leu Asp Gln Gln Val Glu Glu Phe
1               5                   10                  15
Arg

<210> SEQ ID NO 753
<211> LENGTH: 21
<212> TYPE: PRT
<213> ORGANISM: Homo sapiens

<400> SEQUENCE: 753

Ala Thr Phe Gly Cys His Asp Gly Tyr Ser Leu Asp Gly Pro Glu Glu
1               5                   10                  15
Ile Glu Cys Thr Lys
            20

<210> SEQ ID NO 754
<211> LENGTH: 9
<212> TYPE: PRT
<213> ORGANISM: Homo sapiens

<400> SEQUENCE: 754

Ala Thr Val Val Tyr Gln Gly Glu Arg
1               5

<210> SEQ ID NO 755
<211> LENGTH: 12
<212> TYPE: PRT
<213> ORGANISM: Homo sapiens

<400> SEQUENCE: 755

Cys Phe Lys Glu His Ser Ser Leu Ala Phe Trp Lys
1               5                   10

<210> SEQ ID NO 756
<211> LENGTH: 15
<212> TYPE: PRT
<213> ORGANISM: Homo sapiens

<400> SEQUENCE: 756

Phe Ile Cys Pro Leu Thr Gly Leu Trp Pro Ile Asn Thr Leu Lys
1               5                   10                  15

<210> SEQ ID NO 757
<211> LENGTH: 19
<212> TYPE: PRT
<213> ORGANISM: Homo sapiens

<400> SEQUENCE: 757

Lys Cys Ser Tyr Thr Glu Asp Ala Gln Cys Ile Asp Gly Thr Ile Glu
1               5                   10                  15
Val Pro Lys

<210> SEQ ID NO 758
<211> LENGTH: 17
<212> TYPE: PRT
<213> ORGANISM: Homo sapiens

```
<400> SEQUENCE: 758

Thr Cys Pro Lys Pro Asp Asp Leu Pro Phe Ser Thr Val Val Pro Leu
1               5                   10                  15

Lys

<210> SEQ ID NO 759
<211> LENGTH: 9
<212> TYPE: PRT
<213> ORGANISM: Homo sapiens

<400> SEQUENCE: 759

Thr Asp Ala Ser Asp Val Lys Pro Cys
1               5

<210> SEQ ID NO 760
<211> LENGTH: 14
<212> TYPE: PRT
<213> ORGANISM: Homo sapiens

<400> SEQUENCE: 760

Val Cys Pro Phe Ala Gly Ile Leu Glu Asn Gly Ala Val Arg
1               5                   10

<210> SEQ ID NO 761
<211> LENGTH: 21
<212> TYPE: PRT
<213> ORGANISM: Homo sapiens

<400> SEQUENCE: 761

Ser Asp Gly Ala Pro Ala Ser Asp Ser Lys Pro Gly Ser Ser Glu Ala
1               5                   10                  15

Ala Pro Ser Ser Lys
            20

<210> SEQ ID NO 762
<211> LENGTH: 14
<212> TYPE: PRT
<213> ORGANISM: Homo sapiens

<400> SEQUENCE: 762

Glu Thr Pro Ala Ala Thr Glu Ala Pro Ser Ser Thr Pro Lys
1               5                   10

<210> SEQ ID NO 763
<211> LENGTH: 24
<212> TYPE: PRT
<213> ORGANISM: Homo sapiens

<400> SEQUENCE: 763

Ala Glu Pro Pro Lys Ala Pro Glu Gln Glu Gln Ala Ala Pro Gly Pro
1               5                   10                  15

Ala Ala Gly Gly Glu Ala Pro Lys
            20

<210> SEQ ID NO 764
<211> LENGTH: 23
<212> TYPE: PRT
<213> ORGANISM: Homo sapiens

<400> SEQUENCE: 764

Ala Phe Ser Ala Val Asp Thr Asp Gly Asn Gly Thr Ile Asn Ala Gln
1               5                   10                  15
```

Glu Leu Gly Ala Ala Leu Lys
            20

<210> SEQ ID NO 765
<211> LENGTH: 13
<212> TYPE: PRT
<213> ORGANISM: Homo sapiens

<400> SEQUENCE: 765

Ala Gly Glu Leu Thr Pro Glu Glu Ala Gln Tyr Lys
1               5                   10

<210> SEQ ID NO 766
<211> LENGTH: 11
<212> TYPE: PRT
<213> ORGANISM: Homo sapiens

<400> SEQUENCE: 766

Ala Gly Leu Glu Asp Leu Gln Val Ala Phe Arg
1               5                   10

<210> SEQ ID NO 767
<211> LENGTH: 17
<212> TYPE: PRT
<213> ORGANISM: Homo sapiens

<400> SEQUENCE: 767

Glu Ala Asp Val Asp Gln Asp Gly Arg Val Asn Tyr Glu Glu Phe Ala
1               5                   10                  15

Arg

<210> SEQ ID NO 768
<211> LENGTH: 10
<212> TYPE: PRT
<213> ORGANISM: Homo sapiens

<400> SEQUENCE: 768

Tyr Leu Gly Gln Asp Tyr Glu Gln Leu Arg
1               5                   10

<210> SEQ ID NO 769
<211> LENGTH: 11
<212> TYPE: PRT
<213> ORGANISM: Homo sapiens

<400> SEQUENCE: 769

Trp Asn Thr Thr Leu Tyr Glu Gly Thr Trp Arg
1               5                   10

<210> SEQ ID NO 770
<211> LENGTH: 18
<212> TYPE: PRT
<213> ORGANISM: Homo sapiens

<400> SEQUENCE: 770

Arg Pro Thr Glu Leu Leu Ser Asn Pro Gln Phe Ile Val Asp Gly Ala
1               5                   10                  15

Thr Arg

<210> SEQ ID NO 771
<211> LENGTH: 13
<212> TYPE: PRT
<213> ORGANISM: Homo sapiens

```
<400> SEQUENCE: 771

Asn Tyr Pro Ala Thr Phe Trp Val Asn Pro Gln Phe Lys
1               5                   10

<210> SEQ ID NO 772
<211> LENGTH: 24
<212> TYPE: PRT
<213> ORGANISM: Homo sapiens

<400> SEQUENCE: 772

Leu Pro Pro Gly Glu Tyr Val Val Pro Ser Thr Phe Glu Pro Asn
1               5                   10                  15

Lys Glu Gly Asp Phe Val Leu Arg
            20

<210> SEQ ID NO 773
<211> LENGTH: 12
<212> TYPE: PRT
<213> ORGANISM: Homo sapiens

<400> SEQUENCE: 773

Leu Glu Ile Cys Asn Leu Thr Pro Asp Ala Leu Lys
1               5                   10

<210> SEQ ID NO 774
<211> LENGTH: 9
<212> TYPE: PRT
<213> ORGANISM: Homo sapiens

<400> SEQUENCE: 774

Asp Phe Phe Leu Ala Asn Ala Ser Arg
1               5

<210> SEQ ID NO 775
<211> LENGTH: 11
<212> TYPE: PRT
<213> ORGANISM: Homo sapiens

<400> SEQUENCE: 775

Ala Pro Ser Asp Leu Tyr Gln Ile Ile Leu Lys
1               5                   10

<210> SEQ ID NO 776
<211> LENGTH: 13
<212> TYPE: PRT
<213> ORGANISM: Homo sapiens

<400> SEQUENCE: 776

Ala Ala Ala Pro Ala Pro Val Ser Glu Ala Val Cys Arg
1               5                   10

<210> SEQ ID NO 777
<211> LENGTH: 13
<212> TYPE: PRT
<213> ORGANISM: Homo sapiens

<400> SEQUENCE: 777

Cys Gly Glu Asp Asp Glu Thr Ile Pro Ser Glu Tyr Arg
1               5                   10

<210> SEQ ID NO 778
<211> LENGTH: 16
<212> TYPE: PRT
<213> ORGANISM: Homo sapiens
```

<400> SEQUENCE: 778

Glu Glu Ser Thr Glu Val Leu Lys Ala Gln Ser Ala Gly Thr Val Arg
1               5                   10                  15

<210> SEQ ID NO 779
<211> LENGTH: 9
<212> TYPE: PRT
<213> ORGANISM: Homo sapiens

<400> SEQUENCE: 779

Gln Ala Glu Pro Glu Leu Asp Leu Arg
1               5

<210> SEQ ID NO 780
<211> LENGTH: 15
<212> TYPE: PRT
<213> ORGANISM: Homo sapiens

<400> SEQUENCE: 780

Ser Glu Ser Glu Leu Ile Asp Glu Leu Ser Glu Asp Phe Asp Arg
1               5                   10                  15

<210> SEQ ID NO 781
<211> LENGTH: 19
<212> TYPE: PRT
<213> ORGANISM: Homo sapiens

<400> SEQUENCE: 781

Ser Glu Ser Glu Leu Ile Asp Glu Leu Ser Glu Asp Phe Asp Arg Ser
1               5                   10                  15

Glu Cys Lys

<210> SEQ ID NO 782
<211> LENGTH: 15
<212> TYPE: PRT
<213> ORGANISM: Homo sapiens

<400> SEQUENCE: 782

Ile Lys Asp Pro Asp Ala Ser Lys Pro Glu Asp Trp Asp Glu Arg
1               5                   10                  15

<210> SEQ ID NO 783
<211> LENGTH: 22
<212> TYPE: PRT
<213> ORGANISM: Homo sapiens

<400> SEQUENCE: 783

Ile Asp Asn Ser Gln Val Glu Ser Gly Ser Leu Glu Asp Asp Trp Asp
1               5                   10                  15

Phe Leu Pro Pro Lys Lys
            20

<210> SEQ ID NO 784
<211> LENGTH: 18
<212> TYPE: PRT
<213> ORGANISM: Homo sapiens

<400> SEQUENCE: 784

Phe Tyr Gly Asp Glu Glu Lys Asp Lys Gly Leu Gln Thr Ser Gln Asp
1               5                   10                  15

Ala Arg

```
<210> SEQ ID NO 785
<211> LENGTH: 12
<212> TYPE: PRT
<213> ORGANISM: Homo sapiens

<400> SEQUENCE: 785

Glu Gln Phe Leu Asp Gly Asp Gly Trp Thr Ser Arg
1               5                   10

<210> SEQ ID NO 786
<211> LENGTH: 14
<212> TYPE: PRT
<213> ORGANISM: Homo sapiens

<400> SEQUENCE: 786

Phe Tyr Ala Leu Ser Ala Ser Phe Glu Pro Phe Ser Asn Lys
1               5                   10

<210> SEQ ID NO 787
<211> LENGTH: 10
<212> TYPE: PRT
<213> ORGANISM: Homo sapiens

<400> SEQUENCE: 787

Glu Gln Trp Pro Gln Cys Pro Thr Ile Lys
1               5                   10

<210> SEQ ID NO 788
<211> LENGTH: 17
<212> TYPE: PRT
<213> ORGANISM: Homo sapiens

<400> SEQUENCE: 788

Gly Gln Asp His Cys Gly Ile Glu Ser Glu Val Val Ala Gly Ile Pro
1               5                   10                  15

Arg

<210> SEQ ID NO 789
<211> LENGTH: 11
<212> TYPE: PRT
<213> ORGANISM: Homo sapiens

<400> SEQUENCE: 789

Ile Cys Glu Pro Gly Tyr Ser Pro Thr Tyr Lys
1               5                   10

<210> SEQ ID NO 790
<211> LENGTH: 14
<212> TYPE: PRT
<213> ORGANISM: Homo sapiens

<400> SEQUENCE: 790

Ile Cys Glu Pro Gly Tyr Ser Pro Thr Tyr Lys Gln Asp Lys
1               5                   10

<210> SEQ ID NO 791
<211> LENGTH: 19
<212> TYPE: PRT
<213> ORGANISM: Homo sapiens

<400> SEQUENCE: 791

Ile Leu Arg Gly Gln Asp His Cys Gly Ile Glu Ser Glu Val Val Ala
1               5                   10                  15
```

Gly Ile Pro

<210> SEQ ID NO 792
<211> LENGTH: 14
<212> TYPE: PRT
<213> ORGANISM: Homo sapiens

<400> SEQUENCE: 792

Leu Cys Gly Thr Phe Leu Gly Gly Pro Lys Pro Pro Gln Arg
1               5                   10

<210> SEQ ID NO 793
<211> LENGTH: 8
<212> TYPE: PRT
<213> ORGANISM: Homo sapiens

<400> SEQUENCE: 793

Thr Asp Gln Tyr Trp Glu Lys Ile
1               5

<210> SEQ ID NO 794
<211> LENGTH: 10
<212> TYPE: PRT
<213> ORGANISM: Homo sapiens

<400> SEQUENCE: 794

Tyr Val Glu Cys Ser Ala Leu Thr Gln Lys
1               5                   10

<210> SEQ ID NO 795
<211> LENGTH: 17
<212> TYPE: PRT
<213> ORGANISM: Homo sapiens

<400> SEQUENCE: 795

Asn Val Phe Asp Glu Ala Ile Leu Ala Ala Leu Glu Pro Pro Glu Pro
1               5                   10                  15

Lys

<210> SEQ ID NO 796
<211> LENGTH: 20
<212> TYPE: PRT
<213> ORGANISM: Homo sapiens

<400> SEQUENCE: 796

Gly Leu Lys Asn Val Phe Asp Glu Ala Ile Leu Ala Ala Leu Glu Pro
1               5                   10                  15

Pro Glu Pro Lys
            20

<210> SEQ ID NO 797
<211> LENGTH: 21
<212> TYPE: PRT
<213> ORGANISM: Homo sapiens

<400> SEQUENCE: 797

Ala Asp Phe Asp Asn Thr Val Ala Ile His Pro Thr Ser Ser Glu Glu
1               5                   10                  15

Leu Val Thr Leu Arg
            20

<210> SEQ ID NO 798
<211> LENGTH: 12

```
<212> TYPE: PRT
<213> ORGANISM: Homo sapiens

<400> SEQUENCE: 798

Ala Leu Leu Thr Pro Val Ala Ile Ala Ala Gly Arg
1               5                   10

<210> SEQ ID NO 799
<211> LENGTH: 18
<212> TYPE: PRT
<213> ORGANISM: Homo sapiens

<400> SEQUENCE: 799

Gly His Ala Ala Phe Thr Ser Asp Pro Lys Pro Thr Ile Glu Val Ser
1               5                   10                  15

Gly Lys

<210> SEQ ID NO 800
<211> LENGTH: 11
<212> TYPE: PRT
<213> ORGANISM: Homo sapiens

<400> SEQUENCE: 800

Gly Ile Tyr Ala Val Gly Asp Val Cys Gly Lys
1               5                   10

<210> SEQ ID NO 801
<211> LENGTH: 13
<212> TYPE: PRT
<213> ORGANISM: Homo sapiens

<400> SEQUENCE: 801

Leu Gly Gly Thr Cys Val Asn Val Gly Cys Val Pro Lys
1               5                   10

<210> SEQ ID NO 802
<211> LENGTH: 22
<212> TYPE: PRT
<213> ORGANISM: Homo sapiens

<400> SEQUENCE: 802

Leu Gly Ile Gln Thr Asp Asp Lys Gly His Ile Ile Val Asp Glu Phe
1               5                   10                  15

Gln Asn Thr Asn Val Lys
            20

<210> SEQ ID NO 803
<211> LENGTH: 11
<212> TYPE: PRT
<213> ORGANISM: Homo sapiens

<400> SEQUENCE: 803

Leu Asn Ala Ile Tyr Gln Asn Asn Leu Thr Lys
1               5                   10

<210> SEQ ID NO 804
<211> LENGTH: 10
<212> TYPE: PRT
<213> ORGANISM: Homo sapiens

<400> SEQUENCE: 804

Val Ser Glu Glu Ile Glu Asp Ile Ile Lys
1               5                   10
```

<210> SEQ ID NO 805
<211> LENGTH: 11
<212> TYPE: PRT
<213> ORGANISM: Homo sapiens

<400> SEQUENCE: 805

Asn Pro Ser Ala Ala Phe Phe Cys Val Ala Arg
1               5                   10

<210> SEQ ID NO 806
<211> LENGTH: 14
<212> TYPE: PRT
<213> ORGANISM: Homo sapiens

<400> SEQUENCE: 806

Leu Gln Asp Phe Lys Leu Asp Phe Gly Asn Ser Gln Gly Lys
1               5                   10

<210> SEQ ID NO 807
<211> LENGTH: 14
<212> TYPE: PRT
<213> ORGANISM: Homo sapiens

<400> SEQUENCE: 807

Glu Leu Ser Glu Ala Leu Gly Gln Ile Phe Asp Ser Gln Arg
1               5                   10

<210> SEQ ID NO 808
<211> LENGTH: 11
<212> TYPE: PRT
<213> ORGANISM: Homo sapiens

<400> SEQUENCE: 808

Leu Ala Asp Gly Gly Ala Thr Asn Gln Gly Arg
1               5                   10

<210> SEQ ID NO 809
<211> LENGTH: 13
<212> TYPE: PRT
<213> ORGANISM: Homo sapiens

<400> SEQUENCE: 809

Ser Asp Leu Ala Val Pro Ser Glu Leu Ala Leu Leu Lys
1               5                   10

<210> SEQ ID NO 810
<211> LENGTH: 16
<212> TYPE: PRT
<213> ORGANISM: Homo sapiens

<400> SEQUENCE: 810

Ser Thr Ser Ser Phe Pro Cys Pro Ala Gly His Phe Asn Gly Phe Arg
1               5                   10                  15

<210> SEQ ID NO 811
<211> LENGTH: 17
<212> TYPE: PRT
<213> ORGANISM: Homo sapiens

<400> SEQUENCE: 811

Thr Leu Gln Ala Leu Glu Phe His Thr Val Pro Phe Gln Leu Leu Ala
1               5                   10                  15

Arg

```
<210> SEQ ID NO 812
<211> LENGTH: 13
<212> TYPE: PRT
<213> ORGANISM: Homo sapiens

<400> SEQUENCE: 812

Tyr Ser Ser Asp Tyr Phe Gln Ala Pro Ser Asp Tyr Arg
1               5                   10

<210> SEQ ID NO 813
<211> LENGTH: 19
<212> TYPE: PRT
<213> ORGANISM: Homo sapiens

<400> SEQUENCE: 813

Cys Leu Thr Thr Asp Glu Tyr Asp Gly His Ser Thr Tyr Pro Ser His
1               5                   10                  15

Gln Tyr Gln

<210> SEQ ID NO 814
<211> LENGTH: 10
<212> TYPE: PRT
<213> ORGANISM: Homo sapiens

<400> SEQUENCE: 814

Leu Gln Ala Val Thr Asp Asp His Ile Arg
1               5                   10

<210> SEQ ID NO 815
<211> LENGTH: 12
<212> TYPE: PRT
<213> ORGANISM: Homo sapiens

<400> SEQUENCE: 815

Val Thr Asp Ser Ser Val Ser Val Gln Leu Arg Glu
1               5                   10

<210> SEQ ID NO 816
<211> LENGTH: 14
<212> TYPE: PRT
<213> ORGANISM: Homo sapiens

<400> SEQUENCE: 816

Thr Arg Val Thr Asp Ser Ser Val Ser Val Gln Leu Arg Glu
1               5                   10

<210> SEQ ID NO 817
<211> LENGTH: 30
<212> TYPE: PRT
<213> ORGANISM: Homo sapiens

<400> SEQUENCE: 817

Ser Pro Asn Pro Glu Gly Ile Asn Ile Tyr Glu Pro Ala Pro Thr
1               5                   10                  15

Gly Pro Thr Gln Arg Pro Leu Glu Thr Leu Gly Asn Phe Arg
            20                  25                  30

<210> SEQ ID NO 818
<211> LENGTH: 19
<212> TYPE: PRT
<213> ORGANISM: Homo sapiens

<400> SEQUENCE: 818
```

```
Gln Leu Leu Leu Glu Glu Trp Gly Pro Leu Ser Gly Gly Leu Glu Leu
1               5                   10                  15

Pro Gln Arg

<210> SEQ ID NO 819
<211> LENGTH: 15
<212> TYPE: PRT
<213> ORGANISM: Homo sapiens

<400> SEQUENCE: 819

Tyr Gly Thr Cys Ile Tyr Gln Gly Arg Leu Trp Ala Phe Cys Cys
1               5                   10                  15

<210> SEQ ID NO 820
<211> LENGTH: 9
<212> TYPE: PRT
<213> ORGANISM: Homo sapiens

<400> SEQUENCE: 820

Tyr Gly Thr Cys Ile Tyr Gln Gly Arg
1               5

<210> SEQ ID NO 821
<211> LENGTH: 10
<212> TYPE: PRT
<213> ORGANISM: Homo sapiens

<400> SEQUENCE: 821

Arg Tyr Gly Thr Cys Ile Tyr Gln Gly Arg
1               5                   10

<210> SEQ ID NO 822
<211> LENGTH: 6
<212> TYPE: PRT
<213> ORGANISM: Homo sapiens

<400> SEQUENCE: 822

Leu Trp Ala Phe Cys Cys
1               5

<210> SEQ ID NO 823
<211> LENGTH: 10
<212> TYPE: PRT
<213> ORGANISM: Homo sapiens

<400> SEQUENCE: 823

Ile Pro Ala Cys Ile Ala Gly Glu Arg Arg
1               5                   10

<210> SEQ ID NO 824
<211> LENGTH: 9
<212> TYPE: PRT
<213> ORGANISM: Homo sapiens

<400> SEQUENCE: 824

Ile Pro Ala Cys Ile Ala Gly Glu Arg
1               5

<210> SEQ ID NO 825
<211> LENGTH: 11
<212> TYPE: PRT
<213> ORGANISM: Homo sapiens

<400> SEQUENCE: 825
```

```
Ala Leu His Phe Ala Ile Ser Glu Tyr Asn Lys
1               5                   10
```

<210> SEQ ID NO 826
<211> LENGTH: 14
<212> TYPE: PRT
<213> ORGANISM: Homo sapiens

<400> SEQUENCE: 826

```
Ala Leu His Phe Ala Ile Ser Glu Tyr Asn Lys Ala Thr Lys
1               5                   10
```

<210> SEQ ID NO 827
<211> LENGTH: 19
<212> TYPE: PRT
<213> ORGANISM: Homo sapiens

<400> SEQUENCE: 827

```
Ala Arg Gln Gln Thr Val Gly Gly Val Asn Tyr Phe Phe Asp Val Glu
1               5                   10                  15

Val Gly Arg
```

<210> SEQ ID NO 828
<211> LENGTH: 8
<212> TYPE: PRT
<213> ORGANISM: Homo sapiens

<400> SEQUENCE: 828

```
Ala Thr Lys Asp Asp Tyr Tyr Arg
1               5
```

<210> SEQ ID NO 829
<211> LENGTH: 22
<212> TYPE: PRT
<213> ORGANISM: Homo sapiens

<400> SEQUENCE: 829

```
Glu Glu Asp Arg Ile Ile Pro Gly Gly Ile Tyr Asn Ala Asp Leu Asn
1               5                   10                  15

Asp Glu Trp Val Gln Arg
            20
```

<210> SEQ ID NO 830
<211> LENGTH: 17
<212> TYPE: PRT
<213> ORGANISM: Homo sapiens

<400> SEQUENCE: 830

```
Lys Gln Leu Cys Ser Phe Glu Ile Tyr Glu Val Pro Trp Glu Asn Arg
1               5                   10                  15

Arg
```

<210> SEQ ID NO 831
<211> LENGTH: 15
<212> TYPE: PRT
<213> ORGANISM: Homo sapiens

<400> SEQUENCE: 831

```
Gln Leu Cys Ser Phe Glu Ile Tyr Glu Val Pro Trp Glu Asn Arg
1               5                   10                  15
```

<210> SEQ ID NO 832
<211> LENGTH: 16

<212> TYPE: PRT
<213> ORGANISM: Homo sapiens

<400> SEQUENCE: 832

Gln Leu Cys Ser Phe Glu Ile Tyr Glu Val Pro Trp Glu Asn Arg Arg
1               5                   10                  15

<210> SEQ ID NO 833
<211> LENGTH: 17
<212> TYPE: PRT
<213> ORGANISM: Homo sapiens

<400> SEQUENCE: 833

Gln Gln Thr Val Gly Gly Val Asn Tyr Phe Phe Asp Val Glu Val Gly
1               5                   10                  15

Arg

<210> SEQ ID NO 834
<211> LENGTH: 10
<212> TYPE: PRT
<213> ORGANISM: Homo sapiens

<400> SEQUENCE: 834

Ser Leu Val Lys Ser Arg Cys Gln Glu Ser
1               5                   10

<210> SEQ ID NO 835
<211> LENGTH: 18
<212> TYPE: PRT
<213> ORGANISM: Homo sapiens

<400> SEQUENCE: 835

Ser Gln Pro Asn Leu Asp Thr Cys Ala Phe His Glu Gln Pro Glu Leu
1               5                   10                  15

Gln Lys

<210> SEQ ID NO 836
<211> LENGTH: 19
<212> TYPE: PRT
<213> ORGANISM: Homo sapiens

<400> SEQUENCE: 836

Ser Gln Pro Asn Leu Asp Thr Cys Ala Phe His Glu Gln Pro Glu Leu
1               5                   10                  15

Gln Lys Lys

<210> SEQ ID NO 837
<211> LENGTH: 18
<212> TYPE: PRT
<213> ORGANISM: Homo sapiens

<400> SEQUENCE: 837

Ile Ile Pro Gly Gly Ile Tyr Asn Ala Asp Leu Asn Asp Glu Trp Val
1               5                   10                  15

Gln Arg

<210> SEQ ID NO 838
<211> LENGTH: 16
<212> TYPE: PRT
<213> ORGANISM: Homo sapiens

<400> SEQUENCE: 838

```
Val Ser Gln Thr Thr Trp Asp Ser Gly Phe Cys Ala Val Asn Pro Lys
1               5                   10                  15
```

<210> SEQ ID NO 839
<211> LENGTH: 11
<212> TYPE: PRT
<213> ORGANISM: Homo sapiens

<400> SEQUENCE: 839

```
Lys Leu Gln Ala Thr Val Gln Glu Leu Gln Lys
1               5                   10
```

<210> SEQ ID NO 840
<211> LENGTH: 10
<212> TYPE: PRT
<213> ORGANISM: Homo sapiens

<400> SEQUENCE: 840

```
Asp Ala Gly Pro Leu Leu Ile Ser Leu Lys
1               5                   10
```

<210> SEQ ID NO 841
<211> LENGTH: 9
<212> TYPE: PRT
<213> ORGANISM: Homo sapiens

<400> SEQUENCE: 841

```
Ala Asp Gln Cys Tyr Glu Asp Val Arg
1               5
```

<210> SEQ ID NO 842
<211> LENGTH: 16
<212> TYPE: PRT
<213> ORGANISM: Homo sapiens

<400> SEQUENCE: 842

```
Ala Ala Pro Glu Ala Ser Gly Thr Pro Ser Ser Asp Ala Val Ser Arg
1               5                   10                  15
```

<210> SEQ ID NO 843
<211> LENGTH: 13
<212> TYPE: PRT
<213> ORGANISM: Homo sapiens

<400> SEQUENCE: 843

```
Ala Ala Val Tyr His His Phe Ile Ser Asp Gly Val Arg
1               5                   10
```

<210> SEQ ID NO 844
<211> LENGTH: 14
<212> TYPE: PRT
<213> ORGANISM: Homo sapiens

<400> SEQUENCE: 844

```
Ala Ala Val Tyr His His Phe Ile Ser Asp Gly Val Arg Lys
1               5                   10
```

<210> SEQ ID NO 845
<211> LENGTH: 11
<212> TYPE: PRT
<213> ORGANISM: Homo sapiens

<400> SEQUENCE: 845

```
Ala Cys Glu Pro Gly Val Asp Tyr Val Tyr Lys
1               5                   10
```

<210> SEQ ID NO 846
<211> LENGTH: 14
<212> TYPE: PRT
<213> ORGANISM: Homo sapiens

<400> SEQUENCE: 846

Ala Gly Asp Phe Leu Glu Ala Asn Tyr Met Asn Leu Gln Arg
1               5                   10

<210> SEQ ID NO 847
<211> LENGTH: 10
<212> TYPE: PRT
<213> ORGANISM: Homo sapiens

<400> SEQUENCE: 847

Cys Ala Glu Glu Asn Cys Phe Ile Gln Lys
1               5                   10

<210> SEQ ID NO 848
<211> LENGTH: 10
<212> TYPE: PRT
<213> ORGANISM: Homo sapiens

<400> SEQUENCE: 848

Asp Phe Asp Phe Val Pro Pro Val Val Arg
1               5                   10

<210> SEQ ID NO 849
<211> LENGTH: 20
<212> TYPE: PRT
<213> ORGANISM: Homo sapiens

<400> SEQUENCE: 849

Asp Thr Trp Val Glu His Trp Pro Glu Glu Asp Glu Cys Gln Asp Glu
1               5                   10                  15

Glu Asn Gln Lys
            20

<210> SEQ ID NO 850
<211> LENGTH: 8
<212> TYPE: PRT
<213> ORGANISM: Homo sapiens

<400> SEQUENCE: 850

Glu Ala Leu Lys Leu Glu Glu Lys
1               5

<210> SEQ ID NO 851
<211> LENGTH: 25
<212> TYPE: PRT
<213> ORGANISM: Homo sapiens

<400> SEQUENCE: 851

Glu Gly Val Gln Lys Glu Asp Ile Pro Pro Ala Asp Leu Ser Asp Gln
1               5                   10                  15

Val Pro Asp Thr Glu Ser Glu Thr Arg
            20                  25

<210> SEQ ID NO 852
<211> LENGTH: 16
<212> TYPE: PRT
<213> ORGANISM: Homo sapiens

```
<400> SEQUENCE: 852

Glu Tyr Val Leu Pro Ser Phe Glu Val Ile Val Glu Pro Thr Glu Lys
1               5                   10                  15

<210> SEQ ID NO 853
<211> LENGTH: 9
<212> TYPE: PRT
<213> ORGANISM: Homo sapiens

<400> SEQUENCE: 853

Gly Tyr Thr Gln Gln Leu Ala Phe Arg
1               5

<210> SEQ ID NO 854
<211> LENGTH: 20
<212> TYPE: PRT
<213> ORGANISM: Homo sapiens

<400> SEQUENCE: 854

Gly Tyr Thr Gln Gln Leu Ala Phe Arg Gln Pro Ser Ser Ala Phe Ala
1               5                   10                  15

Ala Phe Val Lys
            20

<210> SEQ ID NO 855
<211> LENGTH: 13
<212> TYPE: PRT
<213> ORGANISM: Homo sapiens

<400> SEQUENCE: 855

Ile Phe Thr Val Asn His Lys Leu Leu Pro Val Gly Arg
1               5                   10

<210> SEQ ID NO 856
<211> LENGTH: 20
<212> TYPE: PRT
<213> ORGANISM: Homo sapiens

<400> SEQUENCE: 856

Ile Leu Leu Gln Gly Thr Pro Val Ala Gln Met Thr Glu Asp Ala Val
1               5                   10                  15

Asp Ala Glu Arg
            20

<210> SEQ ID NO 857
<211> LENGTH: 10
<212> TYPE: PRT
<213> ORGANISM: Homo sapiens

<400> SEQUENCE: 857

Ile His Trp Glu Ser Ala Ser Leu Leu Arg
1               5                   10

<210> SEQ ID NO 858
<211> LENGTH: 14
<212> TYPE: PRT
<213> ORGANISM: Homo sapiens

<400> SEQUENCE: 858

Ile Pro Ile Glu Asp Gly Ser Gly Glu Val Val Leu Ser Arg
1               5                   10

<210> SEQ ID NO 859
```

```
<211> LENGTH: 11
<212> TYPE: PRT
<213> ORGANISM: Homo sapiens

<400> SEQUENCE: 859

Ile Arg Tyr Tyr Thr Tyr Leu Ile Met Asn Lys
1               5                   10

<210> SEQ ID NO 860
<211> LENGTH: 12
<212> TYPE: PRT
<213> ORGANISM: Homo sapiens

<400> SEQUENCE: 860

Lys Gln Glu Leu Ser Glu Ala Glu Gln Ala Thr Arg
1               5                   10

<210> SEQ ID NO 861
<211> LENGTH: 14
<212> TYPE: PRT
<213> ORGANISM: Homo sapiens

<400> SEQUENCE: 861

Lys Val Phe Leu Asp Cys Cys Asn Tyr Ile Thr Glu Leu Arg
1               5                   10

<210> SEQ ID NO 862
<211> LENGTH: 15
<212> TYPE: PRT
<213> ORGANISM: Homo sapiens

<400> SEQUENCE: 862

Lys Val Phe Leu Asp Cys Cys Asn Tyr Ile Thr Glu Leu Arg Arg
1               5                   10                  15

<210> SEQ ID NO 863
<211> LENGTH: 11
<212> TYPE: PRT
<213> ORGANISM: Homo sapiens

<400> SEQUENCE: 863

Lys Val Leu Leu Asp Gly Val Gln Asn Pro Arg
1               5                   10

<210> SEQ ID NO 864
<211> LENGTH: 14
<212> TYPE: PRT
<213> ORGANISM: Homo sapiens

<400> SEQUENCE: 864

Leu Asp Lys Ala Cys Glu Pro Gly Val Asp Tyr Val Tyr Lys
1               5                   10

<210> SEQ ID NO 865
<211> LENGTH: 7
<212> TYPE: PRT
<213> ORGANISM: Homo sapiens

<400> SEQUENCE: 865

Leu Pro Tyr Ser Val Val Arg
1               5

<210> SEQ ID NO 866
<211> LENGTH: 17
<212> TYPE: PRT
```

<213> ORGANISM: Homo sapiens

<400> SEQUENCE: 866

Leu Ser Ile Asn Thr His Pro Ser Gln Lys Pro Leu Ser Ile Thr Val
1               5                   10                  15
Arg

<210> SEQ ID NO 867
<211> LENGTH: 14
<212> TYPE: PRT
<213> ORGANISM: Homo sapiens

<400> SEQUENCE: 867

Leu Val Ala Tyr Tyr Thr Leu Ile Gly Ala Ser Gly Gln Arg
1               5                   10

<210> SEQ ID NO 868
<211> LENGTH: 9
<212> TYPE: PRT
<213> ORGANISM: Homo sapiens

<400> SEQUENCE: 868

Asn Thr Leu Ile Ile Tyr Leu Asp Lys
1               5

<210> SEQ ID NO 869
<211> LENGTH: 11
<212> TYPE: PRT
<213> ORGANISM: Homo sapiens

<400> SEQUENCE: 869

Gln Glu Leu Ser Glu Ala Glu Gln Ala Thr Arg
1               5                   10

<210> SEQ ID NO 870
<211> LENGTH: 15
<212> TYPE: PRT
<213> ORGANISM: Homo sapiens

<400> SEQUENCE: 870

Arg Ile Pro Ile Glu Asp Gly Ser Gly Glu Val Val Leu Ser Arg
1               5                   10                  15

<210> SEQ ID NO 871
<211> LENGTH: 10
<212> TYPE: PRT
<213> ORGANISM: Homo sapiens

<400> SEQUENCE: 871

Ser Asp Asp Lys Val Thr Leu Glu Glu Arg
1               5                   10

<210> SEQ ID NO 872
<211> LENGTH: 13
<212> TYPE: PRT
<213> ORGANISM: Homo sapiens

<400> SEQUENCE: 872

Ser Asp Asp Lys Val Thr Leu Glu Glu Arg Leu Asp Lys
1               5                   10

<210> SEQ ID NO 873
<211> LENGTH: 17
<212> TYPE: PRT

<213> ORGANISM: Homo sapiens

<400> SEQUENCE: 873

Ser Glu Glu Thr Lys Glu Asn Glu Gly Phe Thr Val Thr Ala Glu Gly
1               5                   10                  15

Lys

<210> SEQ ID NO 874
<211> LENGTH: 16
<212> TYPE: PRT
<213> ORGANISM: Homo sapiens

<400> SEQUENCE: 874

Ser Gly Ile Pro Ile Val Thr Ser Pro Tyr Gln Ile His Phe Thr Lys
1               5                   10                  15

<210> SEQ ID NO 875
<211> LENGTH: 12
<212> TYPE: PRT
<213> ORGANISM: Homo sapiens

<400> SEQUENCE: 875

Ser Gly Ser Asp Glu Val Gln Val Gly Gln Gln Arg
1               5                   10

<210> SEQ ID NO 876
<211> LENGTH: 16
<212> TYPE: PRT
<213> ORGANISM: Homo sapiens

<400> SEQUENCE: 876

Ser Asn Leu Asp Glu Asp Ile Ile Ala Glu Glu Asn Ile Val Ser Arg
1               5                   10                  15

<210> SEQ ID NO 877
<211> LENGTH: 13
<212> TYPE: PRT
<213> ORGANISM: Homo sapiens

<400> SEQUENCE: 877

Ser Ser Leu Ser Val Pro Tyr Val Ile Val Pro Leu Lys
1               5                   10

<210> SEQ ID NO 878
<211> LENGTH: 22
<212> TYPE: PRT
<213> ORGANISM: Homo sapiens

<400> SEQUENCE: 878

Ser Ser Leu Ser Val Pro Tyr Val Ile Val Pro Leu Lys Thr Gly Leu
1               5                   10                  15

Gln Glu Val Glu Val Lys
            20

<210> SEQ ID NO 879
<211> LENGTH: 8
<212> TYPE: PRT
<213> ORGANISM: Homo sapiens

<400> SEQUENCE: 879

Ser Val Gln Leu Thr Glu Lys Arg
1               5

<210> SEQ ID NO 880
<211> LENGTH: 16
<212> TYPE: PRT
<213> ORGANISM: Homo sapiens

<400> SEQUENCE: 880

Thr Glu Leu Arg Pro Gly Glu Thr Leu Asn Val Asn Phe Leu Leu Arg
1               5                   10                  15

<210> SEQ ID NO 881
<211> LENGTH: 9
<212> TYPE: PRT
<213> ORGANISM: Homo sapiens

<400> SEQUENCE: 881

Thr Gly Leu Gln Glu Val Glu Val Lys
1               5

<210> SEQ ID NO 882
<211> LENGTH: 14
<212> TYPE: PRT
<213> ORGANISM: Homo sapiens

<400> SEQUENCE: 882

Thr Lys Lys Gln Glu Leu Ser Glu Ala Glu Gln Ala Thr Arg
1               5                   10

<210> SEQ ID NO 883
<211> LENGTH: 23
<212> TYPE: PRT
<213> ORGANISM: Homo sapiens

<400> SEQUENCE: 883

Thr Met Gln Ala Leu Pro Tyr Ser Thr Val Gly Asn Ser Asn Asn Tyr
1               5                   10                  15

Leu His Leu Ser Val Leu Arg
            20

<210> SEQ ID NO 884
<211> LENGTH: 12
<212> TYPE: PRT
<213> ORGANISM: Homo sapiens

<400> SEQUENCE: 884

Thr Arg Phe Ile Ser Leu Gly Glu Ala Cys Lys Lys
1               5                   10

<210> SEQ ID NO 885
<211> LENGTH: 16
<212> TYPE: PRT
<213> ORGANISM: Homo sapiens

<400> SEQUENCE: 885

Val Glu Leu Leu His Asn Pro Ala Phe Cys Ser Leu Ala Thr Thr Lys
1               5                   10                  15

<210> SEQ ID NO 886
<211> LENGTH: 13
<212> TYPE: PRT
<213> ORGANISM: Homo sapiens

<400> SEQUENCE: 886

Val Phe Leu Asp Cys Cys Asn Tyr Ile Thr Glu Leu Arg
1               5                   10

-continued

<210> SEQ ID NO 887
<211> LENGTH: 14
<212> TYPE: PRT
<213> ORGANISM: Homo sapiens

<400> SEQUENCE: 887

Val Phe Leu Asp Cys Cys Asn Tyr Ile Thr Glu Leu Arg Arg
1               5                   10

<210> SEQ ID NO 888
<211> LENGTH: 16
<212> TYPE: PRT
<213> ORGANISM: Homo sapiens

<400> SEQUENCE: 888

Val His Gln Tyr Phe Asn Val Glu Leu Ile Gln Pro Gly Ala Val Lys
1               5                   10                  15

<210> SEQ ID NO 889
<211> LENGTH: 10
<212> TYPE: PRT
<213> ORGANISM: Homo sapiens

<400> SEQUENCE: 889

Val Leu Leu Asp Gly Val Gln Asn Pro Arg
1               5                   10

<210> SEQ ID NO 890
<211> LENGTH: 22
<212> TYPE: PRT
<213> ORGANISM: Homo sapiens

<400> SEQUENCE: 890

Val Pro Val Ala Val Gln Gly Glu Asp Thr Val Gln Ser Leu Thr Gln
1               5                   10                  15

Gly Asp Gly Val Ala Lys
            20

<210> SEQ ID NO 891
<211> LENGTH: 12
<212> TYPE: PRT
<213> ORGANISM: Homo sapiens

<400> SEQUENCE: 891

Val Ser His Ser Glu Asp Asp Cys Leu Ala Phe Lys
1               5                   10

<210> SEQ ID NO 892
<211> LENGTH: 11
<212> TYPE: PRT
<213> ORGANISM: Homo sapiens

<400> SEQUENCE: 892

Val Thr Ile Lys Pro Ala Pro Glu Thr Glu Lys
1               5                   10

<210> SEQ ID NO 893
<211> LENGTH: 16
<212> TYPE: PRT
<213> ORGANISM: Homo sapiens

<400> SEQUENCE: 893

Val Val Leu Val Ala Val Asp Lys Gly Val Phe Val Leu Asn Lys Lys
1               5                   10                  15

```
<210> SEQ ID NO 894
<211> LENGTH: 13
<212> TYPE: PRT
<213> ORGANISM: Homo sapiens

<400> SEQUENCE: 894

Val Tyr Ala Tyr Tyr Asn Leu Glu Glu Ser Cys Thr Arg
1               5                   10

<210> SEQ ID NO 895
<211> LENGTH: 9
<212> TYPE: PRT
<213> ORGANISM: Homo sapiens

<400> SEQUENCE: 895

Tyr Tyr Thr Tyr Leu Ile Met Asn Lys
1               5

<210> SEQ ID NO 896
<211> LENGTH: 17
<212> TYPE: PRT
<213> ORGANISM: Homo sapiens

<400> SEQUENCE: 896

Glu Ile Val His Leu Gln Ala Gly Gln Cys Gly Asn Gln Ile Gly Ala
1               5                   10                  15

Lys

<210> SEQ ID NO 897
<211> LENGTH: 18
<212> TYPE: PRT
<213> ORGANISM: Homo sapiens

<400> SEQUENCE: 897

Gly His Tyr Thr Glu Gly Ala Glu Leu Val Asp Ser Val Leu Asp Val
1               5                   10                  15

Val Arg

<210> SEQ ID NO 898
<211> LENGTH: 19
<212> TYPE: PRT
<213> ORGANISM: Homo sapiens

<400> SEQUENCE: 898

Gly His Tyr Thr Glu Gly Ala Glu Leu Val Asp Ser Val Leu Asp Val
1               5                   10                  15

Val Arg Lys

<210> SEQ ID NO 899
<211> LENGTH: 16
<212> TYPE: PRT
<213> ORGANISM: Homo sapiens

<400> SEQUENCE: 899

Ile Asn Val Tyr Tyr Asn Glu Ala Thr Gly Gly Lys Tyr Val Pro Arg
1               5                   10                  15

<210> SEQ ID NO 900
<211> LENGTH: 14
<212> TYPE: PRT
<213> ORGANISM: Homo sapiens
```

```
<400> SEQUENCE: 900

Asn Ser Ser Tyr Phe Val Glu Trp Ile Pro Asn Asn Val Lys
1               5                   10

<210> SEQ ID NO 901
<211> LENGTH: 26
<212> TYPE: PRT
<213> ORGANISM: Homo sapiens

<400> SEQUENCE: 901

Ser Gly Pro Phe Gly Gln Ile Phe Arg Pro Asp Asn Phe Val Phe Gly
1               5                   10                  15

Gln Ser Gly Ala Gly Asn Asn Trp Ala Lys
            20                  25

<210> SEQ ID NO 902
<211> LENGTH: 9
<212> TYPE: PRT
<213> ORGANISM: Homo sapiens

<400> SEQUENCE: 902

Tyr Leu Thr Val Ala Ala Val Phe Arg
1               5

<210> SEQ ID NO 903
<211> LENGTH: 16
<212> TYPE: PRT
<213> ORGANISM: Homo sapiens

<400> SEQUENCE: 903

Phe Ser Gly Ser Asn Ser Gly Asn Thr Ala Thr Leu Thr Ile Ser Arg
1               5                   10                  15

<210> SEQ ID NO 904
<211> LENGTH: 8
<212> TYPE: PRT
<213> ORGANISM: Homo sapiens

<400> SEQUENCE: 904

Leu Thr Val Leu Ser Gln Pro Lys
1               5

<210> SEQ ID NO 905
<211> LENGTH: 18
<212> TYPE: PRT
<213> ORGANISM: Homo sapiens

<400> SEQUENCE: 905

Tyr Val Leu Thr Gln Pro Pro Ser Val Ser Val Ala Pro Gly Glu Thr
1               5                   10                  15

Ala Arg

<210> SEQ ID NO 906
<211> LENGTH: 12
<212> TYPE: PRT
<213> ORGANISM: Homo sapiens

<400> SEQUENCE: 906

Thr Phe Gly Gln Gly Thr Lys Val Glu Ile Lys Arg
1               5                   10

<210> SEQ ID NO 907
<211> LENGTH: 9
```

```
<212> TYPE: PRT
<213> ORGANISM: Homo sapiens

<400> SEQUENCE: 907

Leu Leu Ile Tyr Gly Ala Ser Ser Arg
1               5

<210> SEQ ID NO 908
<211> LENGTH: 16
<212> TYPE: PRT
<213> ORGANISM: Homo sapiens

<400> SEQUENCE: 908

Phe Ser Gly Ser Gly Ser Gly Thr Asp Phe Thr Leu Thr Ile Ser Arg
1               5                   10                  15

<210> SEQ ID NO 909
<211> LENGTH: 23
<212> TYPE: PRT
<213> ORGANISM: Homo sapiens

<400> SEQUENCE: 909

Ala Thr Gly Ile Pro Asp Arg Phe Ser Gly Ser Gly Ser Gly Thr Asp
1               5                   10                  15

Phe Thr Leu Thr Ile Ser Arg
            20

<210> SEQ ID NO 910
<211> LENGTH: 22
<212> TYPE: PRT
<213> ORGANISM: Homo sapiens

<400> SEQUENCE: 910

Ala Ser Gln Ser Val Ser Ser Tyr Leu Ala Trp Tyr Gln Gln Lys
1               5                   10                  15

Pro Gly Gln Ala Pro Arg
            20

<210> SEQ ID NO 911
<211> LENGTH: 11
<212> TYPE: PRT
<213> ORGANISM: Homo sapiens

<400> SEQUENCE: 911

Ala Ser Ser Leu Glu Ser Gly Val Pro Ser Arg
1               5                   10

<210> SEQ ID NO 912
<211> LENGTH: 18
<212> TYPE: PRT
<213> ORGANISM: Homo sapiens

<400> SEQUENCE: 912

Asp Ile Gln Met Thr Gln Ser Pro Ser Thr Leu Ser Ala Ser Val Gly
1               5                   10                  15

Asp Arg

<210> SEQ ID NO 913
<211> LENGTH: 24
<212> TYPE: PRT
<213> ORGANISM: Homo sapiens

<400> SEQUENCE: 913
```

```
Tyr Leu Thr Trp Ala Ser Arg Gln Glu Pro Ser Gln Gly Thr Thr Thr
1               5                   10                  15

Phe Ala Val Thr Ser Ile Leu Arg
            20

<210> SEQ ID NO 914
<211> LENGTH: 7
<212> TYPE: PRT
<213> ORGANISM: Homo sapiens

<400> SEQUENCE: 914

Tyr Leu Thr Trp Ala Ser Arg
1               5

<210> SEQ ID NO 915
<211> LENGTH: 19
<212> TYPE: PRT
<213> ORGANISM: Homo sapiens

<400> SEQUENCE: 915

Trp Leu Gln Gly Ser Gln Glu Leu Pro Arg Glu Lys Tyr Leu Thr Trp
1               5                   10                  15

Ala Ser Arg

<210> SEQ ID NO 916
<211> LENGTH: 12
<212> TYPE: PRT
<213> ORGANISM: Homo sapiens

<400> SEQUENCE: 916

Trp Leu Gln Gly Ser Gln Glu Leu Pro Arg Glu Lys
1               5                   10

<210> SEQ ID NO 917
<211> LENGTH: 8
<212> TYPE: PRT
<213> ORGANISM: Homo sapiens

<400> SEQUENCE: 917

Val Ala Ala Glu Asp Trp Lys Lys
1               5

<210> SEQ ID NO 918
<211> LENGTH: 7
<212> TYPE: PRT
<213> ORGANISM: Homo sapiens

<400> SEQUENCE: 918

Val Ala Ala Glu Asp Trp Lys
1               5

<210> SEQ ID NO 919
<211> LENGTH: 9
<212> TYPE: PRT
<213> ORGANISM: Homo sapiens

<400> SEQUENCE: 919

Thr Pro Leu Thr Ala Thr Leu Ser Lys
1               5

<210> SEQ ID NO 920
<211> LENGTH: 21
<212> TYPE: PRT
<213> ORGANISM: Homo sapiens
```

```
<400> SEQUENCE: 920

Thr Phe Thr Cys Thr Ala Ala Tyr Pro Glu Ser Lys Thr Pro Leu Thr
1               5                   10                  15

Ala Thr Leu Ser Lys
            20

<210> SEQ ID NO 921
<211> LENGTH: 12
<212> TYPE: PRT
<213> ORGANISM: Homo sapiens

<400> SEQUENCE: 921

Thr Phe Thr Cys Thr Ala Ala Tyr Pro Glu Ser Lys
1               5                   10

<210> SEQ ID NO 922
<211> LENGTH: 7
<212> TYPE: PRT
<213> ORGANISM: Homo sapiens

<400> SEQUENCE: 922

Ser Val Thr Cys His Val Lys
1               5

<210> SEQ ID NO 923
<211> LENGTH: 32
<212> TYPE: PRT
<213> ORGANISM: Homo sapiens

<400> SEQUENCE: 923

Ser Gly Asn Thr Phe Arg Pro Glu Val His Leu Leu Pro Pro Pro Ser
1               5                   10                  15

Glu Glu Leu Ala Leu Asn Glu Leu Val Thr Leu Thr Cys Leu Ala Arg
            20                  25                  30

<210> SEQ ID NO 924
<211> LENGTH: 32
<212> TYPE: PRT
<213> ORGANISM: Homo sapiens

<400> SEQUENCE: 924

Ser Ala Val Gln Gly Pro Pro Glu Arg Asp Leu Cys Gly Cys Tyr Ser
1               5                   10                  15

Val Ser Ser Val Leu Pro Gly Cys Ala Glu Pro Trp Asn His Gly Lys
            20                  25                  30

<210> SEQ ID NO 925
<211> LENGTH: 9
<212> TYPE: PRT
<213> ORGANISM: Homo sapiens

<400> SEQUENCE: 925

Ser Ala Val Gln Gly Pro Pro Glu Arg
1               5

<210> SEQ ID NO 926
<211> LENGTH: 17
<212> TYPE: PRT
<213> ORGANISM: Homo sapiens

<400> SEQUENCE: 926

Gln Glu Pro Ser Gln Gly Thr Thr Thr Phe Ala Val Thr Ser Ile Leu
1               5                   10                  15
```

```
1               5                  10                 15

Arg

<210> SEQ ID NO 927
<211> LENGTH: 30
<212> TYPE: PRT
<213> ORGANISM: Homo sapiens

<400> SEQUENCE: 927

Asn Phe Pro Pro Ser Gln Asp Ala Ser Gly Asp Leu Tyr Thr Thr Ser
1               5                   10                  15

Ser Gln Leu Thr Leu Pro Ala Thr Gln Cys Leu Ala Gly Lys
            20                  25                  30

<210> SEQ ID NO 928
<211> LENGTH: 21
<212> TYPE: PRT
<213> ORGANISM: Homo sapiens

<400> SEQUENCE: 928

Lys Gly Asp Thr Phe Ser Cys Met Val Gly His Glu Ala Leu Pro Leu
1               5                   10                  15

Ala Phe Thr Gln Lys
            20

<210> SEQ ID NO 929
<211> LENGTH: 20
<212> TYPE: PRT
<213> ORGANISM: Homo sapiens

<400> SEQUENCE: 929

Gly Phe Ser Pro Lys Asp Val Leu Val Arg Trp Leu Gln Gly Ser Gln
1               5                   10                  15

Glu Leu Pro Arg
            20

<210> SEQ ID NO 930
<211> LENGTH: 10
<212> TYPE: PRT
<213> ORGANISM: Homo sapiens

<400> SEQUENCE: 930

Gly Phe Ser Pro Lys Asp Val Leu Val Arg
1               5                   10

<210> SEQ ID NO 931
<211> LENGTH: 20
<212> TYPE: PRT
<213> ORGANISM: Homo sapiens

<400> SEQUENCE: 931

Gly Asp Thr Phe Ser Cys Met Val Gly His Glu Ala Leu Pro Leu Ala
1               5                   10                  15

Phe Thr Gln Lys
            20

<210> SEQ ID NO 932
<211> LENGTH: 26
<212> TYPE: PRT
<213> ORGANISM: Homo sapiens

<400> SEQUENCE: 932
```

Glu Lys Tyr Leu Thr Trp Ala Ser Arg Gln Glu Pro Ser Gln Gly Thr
1               5                   10                  15

Thr Thr Phe Ala Val Thr Ser Ile Leu Arg
            20                  25

<210> SEQ ID NO 933
<211> LENGTH: 9
<212> TYPE: PRT
<213> ORGANISM: Homo sapiens

<400> SEQUENCE: 933

Glu Lys Tyr Leu Thr Trp Ala Ser Arg
1               5

<210> SEQ ID NO 934
<211> LENGTH: 17
<212> TYPE: PRT
<213> ORGANISM: Homo sapiens

<400> SEQUENCE: 934

Asp Val Leu Val Arg Trp Leu Gln Gly Ser Gln Glu Leu Pro Arg Glu
1               5                   10                  15

Lys

<210> SEQ ID NO 935
<211> LENGTH: 15
<212> TYPE: PRT
<213> ORGANISM: Homo sapiens

<400> SEQUENCE: 935

Asp Val Leu Val Arg Trp Leu Gln Gly Ser Gln Glu Leu Pro Arg
1               5                   10                  15

<210> SEQ ID NO 936
<211> LENGTH: 23
<212> TYPE: PRT
<213> ORGANISM: Homo sapiens

<400> SEQUENCE: 936

Asp Leu Cys Gly Cys Tyr Ser Val Ser Val Leu Pro Gly Cys Ala
1               5                   10                  15

Glu Pro Trp Asn His Gly Lys
            20

<210> SEQ ID NO 937
<211> LENGTH: 15
<212> TYPE: PRT
<213> ORGANISM: Homo sapiens

<400> SEQUENCE: 937

Asp Ala Ser Gly Val Thr Phe Thr Trp Thr Pro Ser Ser Gly Lys
1               5                   10                  15

<210> SEQ ID NO 938
<211> LENGTH: 12
<212> TYPE: PRT
<213> ORGANISM: Homo sapiens

<400> SEQUENCE: 938

Ala Glu Thr Gly Asp Lys Val Tyr Val His Leu Lys
1               5                   10

<210> SEQ ID NO 939

-continued

<211> LENGTH: 12
<212> TYPE: PRT
<213> ORGANISM: Homo sapiens

<400> SEQUENCE: 939

Ala Leu Tyr Leu Gln Tyr Thr Asp Glu Thr Phe Arg
1               5                   10

<210> SEQ ID NO 940
<211> LENGTH: 14
<212> TYPE: PRT
<213> ORGANISM: Homo sapiens

<400> SEQUENCE: 940

Asp Ile Ala Ser Gly Leu Ile Gly Pro Leu Ile Ile Cys Lys
1               5                   10

<210> SEQ ID NO 941
<211> LENGTH: 14
<212> TYPE: PRT
<213> ORGANISM: Homo sapiens

<400> SEQUENCE: 941

Asp Leu Tyr Ser Gly Leu Ile Gly Pro Leu Ile Val Cys Arg
1               5                   10

<210> SEQ ID NO 942
<211> LENGTH: 14
<212> TYPE: PRT
<213> ORGANISM: Homo sapiens

<400> SEQUENCE: 942

Glu Val Gly Pro Thr Asn Ala Asp Pro Val Cys Leu Ala Lys
1               5                   10

<210> SEQ ID NO 943
<211> LENGTH: 10
<212> TYPE: PRT
<213> ORGANISM: Homo sapiens

<400> SEQUENCE: 943

Glu Tyr Thr Asp Ala Ser Phe Thr Asn Arg
1               5                   10

<210> SEQ ID NO 944
<211> LENGTH: 19
<212> TYPE: PRT
<213> ORGANISM: Homo sapiens

<400> SEQUENCE: 944

Phe Asn Lys Asn Asn Glu Gly Thr Tyr Tyr Ser Pro Asn Tyr Asn Pro
1               5                   10                  15

Gln Ser Arg

<210> SEQ ID NO 945
<211> LENGTH: 13
<212> TYPE: PRT
<213> ORGANISM: Homo sapiens

<400> SEQUENCE: 945

Gly Ala Tyr Pro Leu Ser Ile Glu Pro Ile Gly Val Arg
1               5                   10

<210> SEQ ID NO 946

```
<211> LENGTH: 20
<212> TYPE: PRT
<213> ORGANISM: Homo sapiens

<400> SEQUENCE: 946

His Tyr Tyr Ile Gly Ile Ile Glu Thr Thr Trp Asp Tyr Ala Ser Asp
1               5                   10                  15

His Gly Glu Lys
            20

<210> SEQ ID NO 947
<211> LENGTH: 23
<212> TYPE: PRT
<213> ORGANISM: Homo sapiens

<400> SEQUENCE: 947

Lys Ala Glu Glu Glu His Leu Gly Ile Leu Gly Pro Gln Leu His Ala
1               5                   10                  15

Asp Val Gly Asp Lys Val Lys
            20

<210> SEQ ID NO 948
<211> LENGTH: 13
<212> TYPE: PRT
<213> ORGANISM: Homo sapiens

<400> SEQUENCE: 948

Lys Ala Leu Tyr Leu Gln Tyr Thr Asp Glu Thr Phe Arg
1               5                   10

<210> SEQ ID NO 949
<211> LENGTH: 20
<212> TYPE: PRT
<213> ORGANISM: Homo sapiens

<400> SEQUENCE: 949

Lys Leu Ile Ser Val Asp Thr Glu His Ser Asn Ile Tyr Leu Gln Asn
1               5                   10                  15

Gly Pro Asp Arg
            20

<210> SEQ ID NO 950
<211> LENGTH: 19
<212> TYPE: PRT
<213> ORGANISM: Homo sapiens

<400> SEQUENCE: 950

Leu Ile Ser Val Asp Thr Glu His Ser Asn Ile Tyr Leu Gln Asn Gly
1               5                   10                  15

Pro Asp Arg

<210> SEQ ID NO 951
<211> LENGTH: 16
<212> TYPE: PRT
<213> ORGANISM: Homo sapiens

<400> SEQUENCE: 951

Asn Asn Glu Gly Thr Tyr Tyr Ser Pro Asn Tyr Asn Pro Gln Ser Arg
1               5                   10                  15

<210> SEQ ID NO 952
<211> LENGTH: 12
<212> TYPE: PRT
```

<213> ORGANISM: Homo sapiens

<400> SEQUENCE: 952

Gln Ser Glu Asp Ser Thr Phe Tyr Leu Gly Glu Arg
1               5                   10

<210> SEQ ID NO 953
<211> LENGTH: 23
<212> TYPE: PRT
<213> ORGANISM: Homo sapiens

<400> SEQUENCE: 953

Ser Gly Ala Gly Thr Glu Asp Ser Ala Cys Ile Pro Trp Ala Tyr Tyr
1               5                   10                  15

Ser Thr Val Asp Gln Val Lys
            20

<210> SEQ ID NO 954
<211> LENGTH: 23
<212> TYPE: PRT
<213> ORGANISM: Homo sapiens

<400> SEQUENCE: 954

Ser Val Pro Pro Ser Ala Ser His Val Ala Pro Thr Glu Thr Phe Thr
1               5                   10                  15

Tyr Glu Trp Thr Val Pro Lys
            20

<210> SEQ ID NO 955
<211> LENGTH: 21
<212> TYPE: PRT
<213> ORGANISM: Homo sapiens

<400> SEQUENCE: 955

Thr Tyr Cys Ser Glu Pro Glu Lys Val Asp Lys Asp Asn Glu Asp Phe
1               5                   10                  15

Gln Glu Ser Asn Arg
            20

<210> SEQ ID NO 956
<211> LENGTH: 13
<212> TYPE: PRT
<213> ORGANISM: Homo sapiens

<400> SEQUENCE: 956

Val Asn Lys Asp Asp Glu Glu Phe Ile Glu Ser Asn Lys
1               5                   10

<210> SEQ ID NO 957
<211> LENGTH: 7
<212> TYPE: PRT
<213> ORGANISM: Homo sapiens

<400> SEQUENCE: 957

Tyr Thr Val Asn Gln Cys Arg
1               5

<210> SEQ ID NO 958
<211> LENGTH: 15
<212> TYPE: PRT
<213> ORGANISM: Homo sapiens

<400> SEQUENCE: 958

Ala Asp Arg Asp Gln Tyr Glu Leu Leu Cys Leu Asp Asn Thr Arg
1               5                   10                  15

<210> SEQ ID NO 959
<211> LENGTH: 9
<212> TYPE: PRT
<213> ORGANISM: Homo sapiens

<400> SEQUENCE: 959

Ala Pro Asn His Ala Val Val Thr Arg
1               5

<210> SEQ ID NO 960
<211> LENGTH: 8
<212> TYPE: PRT
<213> ORGANISM: Homo sapiens

<400> SEQUENCE: 960

Ala Ser Tyr Leu Asp Cys Ile Arg
1               5

<210> SEQ ID NO 961
<211> LENGTH: 11
<212> TYPE: PRT
<213> ORGANISM: Homo sapiens

<400> SEQUENCE: 961

Cys Asp Glu Trp Ser Val Asn Ser Val Gly Lys
1               5                   10

<210> SEQ ID NO 962
<211> LENGTH: 13
<212> TYPE: PRT
<213> ORGANISM: Homo sapiens

<400> SEQUENCE: 962

Cys Leu Lys Asp Gly Ala Gly Asp Val Ala Phe Val Lys
1               5                   10

<210> SEQ ID NO 963
<211> LENGTH: 12
<212> TYPE: PRT
<213> ORGANISM: Homo sapiens

<400> SEQUENCE: 963

Cys Leu Val Glu Lys Gly Asp Val Ala Phe Val Lys
1               5                   10

<210> SEQ ID NO 964
<211> LENGTH: 13
<212> TYPE: PRT
<213> ORGANISM: Homo sapiens

<400> SEQUENCE: 964

Cys Ser Thr Ser Ser Leu Leu Glu Ala Cys Thr Phe Arg
1               5                   10

<210> SEQ ID NO 965
<211> LENGTH: 15
<212> TYPE: PRT
<213> ORGANISM: Homo sapiens

<400> SEQUENCE: 965

Cys Ser Thr Ser Ser Leu Leu Glu Ala Cys Thr Phe Arg Arg Pro
1               5                   10                  15

```
<210> SEQ ID NO 966
<211> LENGTH: 15
<212> TYPE: PRT
<213> ORGANISM: Homo sapiens

<400> SEQUENCE: 966

Asp Cys His Leu Ala Gln Val Pro Ser His Thr Val Val Ala Arg
1               5                   10                  15

<210> SEQ ID NO 967
<211> LENGTH: 8
<212> TYPE: PRT
<213> ORGANISM: Homo sapiens

<400> SEQUENCE: 967

Asp Asp Thr Val Cys Leu Ala Lys
1               5

<210> SEQ ID NO 968
<211> LENGTH: 10
<212> TYPE: PRT
<213> ORGANISM: Homo sapiens

<400> SEQUENCE: 968

Asp Gly Ala Gly Asp Val Ala Phe Val Lys
1               5                   10

<210> SEQ ID NO 969
<211> LENGTH: 8
<212> TYPE: PRT
<213> ORGANISM: Homo sapiens

<400> SEQUENCE: 969

Asp Lys Glu Ala Cys Val His Lys
1               5

<210> SEQ ID NO 970
<211> LENGTH: 11
<212> TYPE: PRT
<213> ORGANISM: Homo sapiens

<400> SEQUENCE: 970

Asp Lys Glu Ala Cys Val His Lys Ile Leu Arg
1               5                   10

<210> SEQ ID NO 971
<211> LENGTH: 13
<212> TYPE: PRT
<213> ORGANISM: Homo sapiens

<400> SEQUENCE: 971

Asp Leu Leu Phe Lys Asp Ser Ala His Gly Phe Leu Lys
1               5                   10

<210> SEQ ID NO 972
<211> LENGTH: 17
<212> TYPE: PRT
<213> ORGANISM: Homo sapiens

<400> SEQUENCE: 972

Asp Leu Leu Phe Lys Asp Ser Ala His Gly Phe Leu Lys Val Pro Pro
1               5                   10                  15

Arg
```

-continued

<210> SEQ ID NO 973
<211> LENGTH: 13
<212> TYPE: PRT
<213> ORGANISM: Homo sapiens

<400> SEQUENCE: 973

Asp Leu Leu Phe Arg Asp Asp Thr Val Cys Leu Ala Lys
1               5                   10

<210> SEQ ID NO 974
<211> LENGTH: 12
<212> TYPE: PRT
<213> ORGANISM: Homo sapiens

<400> SEQUENCE: 974

Asp Ser Ala His Gly Phe Leu Lys Val Pro Pro Arg
1               5                   10

<210> SEQ ID NO 975
<211> LENGTH: 10
<212> TYPE: PRT
<213> ORGANISM: Homo sapiens

<400> SEQUENCE: 975

Asp Ser Gly Phe Gln Met Asn Gln Leu Arg
1               5                   10

<210> SEQ ID NO 976
<211> LENGTH: 11
<212> TYPE: PRT
<213> ORGANISM: Homo sapiens

<400> SEQUENCE: 976

Asp Tyr Glu Leu Leu Cys Leu Asp Gly Thr Arg
1               5                   10

<210> SEQ ID NO 977
<211> LENGTH: 12
<212> TYPE: PRT
<213> ORGANISM: Homo sapiens

<400> SEQUENCE: 977

Asp Tyr Glu Leu Leu Cys Leu Asp Gly Thr Arg Lys
1               5                   10

<210> SEQ ID NO 978
<211> LENGTH: 24
<212> TYPE: PRT
<213> ORGANISM: Homo sapiens

<400> SEQUENCE: 978

Asp Tyr Glu Leu Leu Cys Leu Asp Gly Thr Arg Lys Pro Val Glu Glu
1               5                   10                  15

Tyr Ala Asn Cys His Leu Ala Arg
            20

<210> SEQ ID NO 979
<211> LENGTH: 14
<212> TYPE: PRT
<213> ORGANISM: Homo sapiens

<400> SEQUENCE: 979

Glu Asp Pro Gln Thr Phe Tyr Tyr Ala Val Ala Val Val Lys

<210> SEQ ID NO 980
<211> LENGTH: 15
<212> TYPE: PRT
<213> ORGANISM: Homo sapiens

<400> SEQUENCE: 980

Glu Asp Pro Gln Thr Phe Tyr Tyr Ala Val Ala Val Val Lys Lys
1               5                   10                  15

<210> SEQ ID NO 981
<211> LENGTH: 11
<212> TYPE: PRT
<213> ORGANISM: Homo sapiens

<400> SEQUENCE: 981

Glu Phe Gln Leu Phe Ser Ser Pro His Gly Lys
1               5                   10

<210> SEQ ID NO 982
<211> LENGTH: 16
<212> TYPE: PRT
<213> ORGANISM: Homo sapiens

<400> SEQUENCE: 982

Glu Phe Gln Leu Phe Ser Ser Pro His Gly Lys Asp Leu Leu Phe Lys
1               5                   10                  15

<210> SEQ ID NO 983
<211> LENGTH: 11
<212> TYPE: PRT
<213> ORGANISM: Homo sapiens

<400> SEQUENCE: 983

Glu Gly Tyr Tyr Gly Tyr Thr Gly Ala Phe Arg
1               5                   10

<210> SEQ ID NO 984
<211> LENGTH: 16
<212> TYPE: PRT
<213> ORGANISM: Homo sapiens

<400> SEQUENCE: 984

Glu Gly Thr Cys Pro Glu Ala Pro Thr Asp Glu Cys Lys Pro Val Lys
1               5                   10                  15

<210> SEQ ID NO 985
<211> LENGTH: 14
<212> TYPE: PRT
<213> ORGANISM: Homo sapiens

<400> SEQUENCE: 985

Phe Asp Glu Phe Phe Ser Glu Gly Cys Ala Pro Gly Ser Lys
1               5                   10

<210> SEQ ID NO 986
<211> LENGTH: 15
<212> TYPE: PRT
<213> ORGANISM: Homo sapiens

<400> SEQUENCE: 986

Phe Asp Glu Phe Phe Ser Glu Gly Cys Ala Pro Gly Ser Lys Lys
1               5                   10                  15

<210> SEQ ID NO 987
<211> LENGTH: 18
<212> TYPE: PRT
<213> ORGANISM: Homo sapiens

<400> SEQUENCE: 987

Gly Asp Val Ala Phe Val Lys His Gln Thr Val Pro Gln Asn Thr Gly
1               5                   10                  15

Gly Lys

<210> SEQ ID NO 988
<211> LENGTH: 21
<212> TYPE: PRT
<213> ORGANISM: Homo sapiens

<400> SEQUENCE: 988

Phe Asp Glu Phe Phe Ser Glu Gly Cys Ala Pro Gly Ser Lys Lys Asp
1               5                   10                  15

Ser Ser Leu Cys Lys
            20

<210> SEQ ID NO 989
<211> LENGTH: 11
<212> TYPE: PRT
<213> ORGANISM: Homo sapiens

<400> SEQUENCE: 989

His Gln Thr Val Pro Gln Asn Thr Gly Gly Lys
1               5                   10

<210> SEQ ID NO 990
<211> LENGTH: 18
<212> TYPE: PRT
<213> ORGANISM: Homo sapiens

<400> SEQUENCE: 990

His Gln Thr Val Pro Gln Asn Thr Gly Gly Lys Asn Pro Asp Pro Trp
1               5                   10                  15

Ala Lys

<210> SEQ ID NO 991
<211> LENGTH: 23
<212> TYPE: PRT
<213> ORGANISM: Homo sapiens

<400> SEQUENCE: 991

His Gln Thr Val Pro Gln Asn Thr Gly Gly Lys Asn Pro Asp Pro Trp
1               5                   10                  15

Ala Lys Asn Leu Asn Glu Lys
            20

<210> SEQ ID NO 992
<211> LENGTH: 11
<212> TYPE: PRT
<213> ORGANISM: Homo sapiens

<400> SEQUENCE: 992

His Ser Thr Ile Phe Glu Asn Leu Ala Asn Lys
1               5                   10

<210> SEQ ID NO 993
<211> LENGTH: 14

-continued

```
<212> TYPE: PRT
<213> ORGANISM: Homo sapiens

<400> SEQUENCE: 993

His Ser Thr Ile Phe Glu Asn Leu Ala Asn Lys Ala Asp Arg
1               5                   10

<210> SEQ ID NO 994
<211> LENGTH: 15
<212> TYPE: PRT
<213> ORGANISM: Homo sapiens

<400> SEQUENCE: 994

Ile Glu Cys Val Ser Ala Glu Thr Thr Glu Asp Cys Ile Ala Lys
1               5                   10                  15

<210> SEQ ID NO 995
<211> LENGTH: 19
<212> TYPE: PRT
<213> ORGANISM: Homo sapiens

<400> SEQUENCE: 995

Ile Asn His Cys Arg Phe Asp Glu Phe Phe Ser Glu Gly Cys Ala Pro
1               5                   10                  15

Gly Ser Lys

<210> SEQ ID NO 996
<211> LENGTH: 20
<212> TYPE: PRT
<213> ORGANISM: Homo sapiens

<400> SEQUENCE: 996

Ile Asn His Cys Arg Phe Asp Glu Phe Phe Ser Glu Gly Cys Ala Pro
1               5                   10                  15

Gly Ser Lys Lys
            20

<210> SEQ ID NO 997
<211> LENGTH: 14
<212> TYPE: PRT
<213> ORGANISM: Homo sapiens

<400> SEQUENCE: 997

Lys Cys Ser Thr Ser Ser Leu Leu Glu Ala Cys Thr Phe Arg
1               5                   10

<210> SEQ ID NO 998
<211> LENGTH: 11
<212> TYPE: PRT
<213> ORGANISM: Homo sapiens

<400> SEQUENCE: 998

Lys Asp Ser Gly Phe Gln Met Asn Gln Leu Arg
1               5                   10

<210> SEQ ID NO 999
<211> LENGTH: 13
<212> TYPE: PRT
<213> ORGANISM: Homo sapiens

<400> SEQUENCE: 999

Lys Pro Val Glu Glu Tyr Ala Asn Cys His Leu Ala Arg
1               5                   10
```

```
<210> SEQ ID NO 1000
<211> LENGTH: 12
<212> TYPE: PRT
<213> ORGANISM: Homo sapiens

<400> SEQUENCE: 1000

Lys Ser Ala Ser Asp Leu Thr Trp Asp Asn Leu Lys
1               5                   10

<210> SEQ ID NO 1001
<211> LENGTH: 15
<212> TYPE: PRT
<213> ORGANISM: Homo sapiens

<400> SEQUENCE: 1001

Leu Cys Met Gly Ser Gly Leu Asn Leu Cys Glu Pro Asn Asn Lys
1               5                   10                  15

<210> SEQ ID NO 1002
<211> LENGTH: 26
<212> TYPE: PRT
<213> ORGANISM: Homo sapiens

<400> SEQUENCE: 1002

Leu Cys Met Gly Ser Gly Leu Asn Leu Cys Glu Pro Asn Asn Lys Glu
1               5                   10                  15

Gly Tyr Tyr Gly Tyr Thr Gly Ala Phe Arg
            20                  25

<210> SEQ ID NO 1003
<211> LENGTH: 17
<212> TYPE: PRT
<213> ORGANISM: Homo sapiens

<400> SEQUENCE: 1003

Leu His Asp Arg Asn Thr Tyr Glu Lys Tyr Leu Gly Glu Glu Tyr Val
1               5                   10                  15

Lys

<210> SEQ ID NO 1004
<211> LENGTH: 13
<212> TYPE: PRT
<213> ORGANISM: Homo sapiens

<400> SEQUENCE: 1004

Leu Lys Cys Asp Glu Trp Ser Val Asn Ser Val Gly Lys
1               5                   10

<210> SEQ ID NO 1005
<211> LENGTH: 28
<212> TYPE: PRT
<213> ORGANISM: Homo sapiens

<400> SEQUENCE: 1005

Leu Lys Cys Asp Glu Trp Ser Val Asn Ser Val Gly Lys Ile Glu Cys
1               5                   10                  15

Val Ser Ala Glu Thr Thr Glu Asp Cys Ile Ala Lys
            20                  25

<210> SEQ ID NO 1006
<211> LENGTH: 12
<212> TYPE: PRT
<213> ORGANISM: Homo sapiens
```

<400> SEQUENCE: 1006

Met Tyr Leu Gly Tyr Glu Tyr Val Thr Ala Ile Arg
1               5                   10

<210> SEQ ID NO 1007
<211> LENGTH: 15
<212> TYPE: PRT
<213> ORGANISM: Homo sapiens

<400> SEQUENCE: 1007

Met Tyr Leu Gly Tyr Glu Tyr Val Thr Ala Ile Arg Asn Leu Arg
1               5                   10                  15

<210> SEQ ID NO 1008
<211> LENGTH: 16
<212> TYPE: PRT
<213> ORGANISM: Homo sapiens

<400> SEQUENCE: 1008

Asn Leu Asn Glu Lys Asp Tyr Glu Leu Leu Cys Leu Asp Gly Thr Arg
1               5                   10                  15

<210> SEQ ID NO 1009
<211> LENGTH: 17
<212> TYPE: PRT
<213> ORGANISM: Homo sapiens

<400> SEQUENCE: 1009

Asn Leu Asn Glu Lys Asp Tyr Glu Leu Leu Cys Leu Asp Gly Thr Arg
1               5                   10                  15

Lys

<210> SEQ ID NO 1010
<211> LENGTH: 19
<212> TYPE: PRT
<213> ORGANISM: Homo sapiens

<400> SEQUENCE: 1010

Asn Leu Arg Glu Gly Thr Cys Pro Glu Ala Pro Thr Asp Glu Cys Lys
1               5                   10                  15

Pro Val Lys

<210> SEQ ID NO 1011
<211> LENGTH: 7
<212> TYPE: PRT
<213> ORGANISM: Homo sapiens

<400> SEQUENCE: 1011

Asn Pro Asp Pro Trp Ala Lys
1               5

<210> SEQ ID NO 1012
<211> LENGTH: 19
<212> TYPE: PRT
<213> ORGANISM: Homo sapiens

<400> SEQUENCE: 1012

Ser Ala Gly Trp Asn Ile Pro Ile Gly Leu Leu Tyr Cys Asp Leu Pro
1               5                   10                  15

Glu Pro Arg

```
<210> SEQ ID NO 1013
<211> LENGTH: 24
<212> TYPE: PRT
<213> ORGANISM: Homo sapiens

<400> SEQUENCE: 1013

Ser Ala Gly Trp Asn Ile Pro Ile Gly Leu Leu Tyr Cys Asp Leu Pro
1               5                   10                  15

Glu Pro Arg Lys Pro Leu Glu Lys
            20

<210> SEQ ID NO 1014
<211> LENGTH: 11
<212> TYPE: PRT
<213> ORGANISM: Homo sapiens

<400> SEQUENCE: 1014

Ser Ala Ser Asp Leu Thr Trp Asp Asn Leu Lys
1               5                   10

<210> SEQ ID NO 1015
<211> LENGTH: 13
<212> TYPE: PRT
<213> ORGANISM: Homo sapiens

<400> SEQUENCE: 1015

Ser Ala Ser Asp Leu Thr Trp Asp Asn Leu Lys Gly Lys
1               5                   10

<210> SEQ ID NO 1016
<211> LENGTH: 14
<212> TYPE: PRT
<213> ORGANISM: Homo sapiens

<400> SEQUENCE: 1016

Ser Ala Ser Asp Leu Thr Trp Asp Asn Leu Lys Gly Lys Lys
1               5                   10

<210> SEQ ID NO 1017
<211> LENGTH: 17
<212> TYPE: PRT
<213> ORGANISM: Homo sapiens

<400> SEQUENCE: 1017

Ser Glu Thr Lys Asp Leu Leu Phe Arg Asp Asp Thr Val Cys Leu Ala
1               5                   10                  15

Lys

<210> SEQ ID NO 1018
<211> LENGTH: 13
<212> TYPE: PRT
<213> ORGANISM: Homo sapiens

<400> SEQUENCE: 1018

Ser Lys Glu Phe Gln Leu Phe Ser Ser Pro His Gly Lys
1               5                   10

<210> SEQ ID NO 1019
<211> LENGTH: 18
<212> TYPE: PRT
<213> ORGANISM: Homo sapiens

<400> SEQUENCE: 1019

Ser Lys Glu Phe Gln Leu Phe Ser Ser Pro His Gly Lys Asp Leu Leu
```

-continued

```
                1               5                  10                 15
Phe Lys

<210> SEQ ID NO 1020
<211> LENGTH: 22
<212> TYPE: PRT
<213> ORGANISM: Homo sapiens

<400> SEQUENCE: 1020

Ser Met Gly Gly Lys Glu Asp Leu Ile Trp Glu Leu Leu Asn Gln Ala
1               5                   10                  15

Gln Glu His Phe Gly Lys
            20

<210> SEQ ID NO 1021
<211> LENGTH: 14
<212> TYPE: PRT
<213> ORGANISM: Homo sapiens

<400> SEQUENCE: 1021

Ser Val Ile Pro Ser Asp Gly Pro Ser Val Ala Cys Val Lys
1               5                   10

<210> SEQ ID NO 1022
<211> LENGTH: 11
<212> TYPE: PRT
<213> ORGANISM: Homo sapiens

<400> SEQUENCE: 1022

Trp Cys Ala Val Ser Glu His Glu Ala Thr Lys
1               5                   10

<210> SEQ ID NO 1023
<211> LENGTH: 14
<212> TYPE: PRT
<213> ORGANISM: Homo sapiens

<400> SEQUENCE: 1023

Thr Ala Gly Trp Asn Ile Pro Met Gly Leu Leu Tyr Asn Lys
1               5                   10

<210> SEQ ID NO 1024
<211> LENGTH: 8
<212> TYPE: PRT
<213> ORGANISM: Homo sapiens

<400> SEQUENCE: 1024

Tyr Leu Gly Glu Glu Tyr Val Lys
1               5

<210> SEQ ID NO 1025
<211> LENGTH: 15
<212> TYPE: PRT
<213> ORGANISM: Homo sapiens

<400> SEQUENCE: 1025

Tyr Leu Gly Glu Glu Tyr Val Lys Ala Val Gly Asn Leu Arg Lys
1               5                   10                  15

<210> SEQ ID NO 1026
<211> LENGTH: 339
<212> TYPE: PRT
<213> ORGANISM: Homo sapiens
```

<400> SEQUENCE: 1026

Met Trp Gln Leu Trp Ala Ser Leu Cys Cys Leu Leu Val Leu Ala Asn
1               5                   10                  15

Ala Arg Ser Arg Pro Ser Phe His Pro Leu Ser Asp Glu Leu Val Asn
            20                  25                  30

Tyr Val Asn Lys Arg Asn Thr Thr Trp Gln Ala Gly His Asn Phe Tyr
        35                  40                  45

Asn Val Asp Met Ser Tyr Leu Lys Arg Leu Cys Gly Thr Phe Leu Gly
    50                  55                  60

Gly Pro Lys Pro Pro Gln Arg Val Met Phe Thr Glu Asp Leu Lys Leu
65                  70                  75                  80

Pro Ala Ser Phe Asp Ala Arg Glu Gln Trp Pro Gln Cys Pro Thr Ile
                85                  90                  95

Lys Glu Ile Arg Asp Gln Gly Ser Cys Gly Ser Cys Trp Ala Phe Gly
            100                 105                 110

Ala Val Glu Ala Ile Ser Asp Arg Ile Cys Ile His Thr Asn Ala His
        115                 120                 125

Val Ser Val Glu Val Ser Ala Glu Asp Leu Leu Thr Cys Cys Gly Ser
    130                 135                 140

Met Cys Gly Asp Gly Cys Asn Gly Gly Tyr Pro Ala Glu Ala Trp Asn
145                 150                 155                 160

Phe Trp Thr Arg Lys Gly Leu Val Ser Gly Gly Leu Tyr Glu Ser His
                165                 170                 175

Val Gly Cys Arg Pro Tyr Ser Ile Pro Pro Cys Glu His His Val Asn
            180                 185                 190

Gly Ser Arg Pro Pro Cys Thr Gly Glu Gly Asp Thr Pro Lys Cys Ser
        195                 200                 205

Lys Ile Cys Glu Pro Gly Tyr Ser Pro Thr Tyr Lys Gln Asp Lys His
    210                 215                 220

Tyr Gly Tyr Asn Ser Tyr Ser Val Ser Asn Ser Glu Lys Asp Ile Met
225                 230                 235                 240

Ala Glu Ile Tyr Lys Asn Gly Pro Val Glu Gly Ala Phe Ser Val Tyr
                245                 250                 255

Ser Asp Phe Leu Leu Tyr Lys Ser Gly Val Tyr Gln His Val Thr Gly
            260                 265                 270

Glu Met Met Gly Gly His Ala Ile Arg Ile Leu Gly Trp Gly Val Glu
        275                 280                 285

Asn Gly Thr Pro Tyr Trp Leu Val Ala Asn Ser Trp Asn Thr Asp Trp
    290                 295                 300

Gly Asp Asn Gly Phe Phe Lys Ile Leu Arg Gly Gln Asp His Cys Gly
305                 310                 315                 320

Ile Glu Ser Glu Val Val Ala Gly Ile Pro Arg Thr Asp Gln Tyr Trp
                325                 330                 335

Glu Lys Ile

<210> SEQ ID NO 1027
<211> LENGTH: 1065
<212> TYPE: PRT
<213> ORGANISM: Homo sapiens

<400> SEQUENCE: 1027

Met Lys Ile Leu Ile Leu Gly Ile Phe Leu Phe Leu Cys Ser Thr Pro
1               5                   10                  15

Ala Trp Ala Lys Glu Lys His Tyr Tyr Ile Gly Ile Ile Glu Thr Thr

-continued

```
             20                  25                  30
Trp Asp Tyr Ala Ser Asp His Gly Glu Lys Leu Ile Ser Val Asp
         35                  40                  45
Thr Glu His Ser Asn Ile Tyr Leu Gln Asn Gly Pro Asp Arg Ile Gly
     50                  55                  60
Arg Leu Tyr Lys Lys Ala Leu Tyr Leu Gln Tyr Thr Asp Glu Thr Phe
 65                  70                  75                  80
Arg Thr Thr Ile Glu Lys Pro Val Trp Leu Gly Phe Leu Gly Pro Ile
                 85                  90                  95
Ile Lys Ala Glu Thr Gly Asp Lys Val Tyr Val His Leu Lys Asn Leu
                100                 105                 110
Ala Ser Arg Pro Tyr Thr Phe His Ser His Gly Ile Thr Tyr Tyr Lys
            115                 120                 125
Glu His Glu Gly Ala Ile Tyr Pro Asp Asn Thr Thr Asp Phe Gln Arg
        130                 135                 140
Ala Asp Asp Lys Val Tyr Pro Gly Glu Gln Tyr Thr Tyr Met Leu Leu
145                 150                 155                 160
Ala Thr Glu Glu Gln Ser Pro Gly Glu Gly Asp Gly Asn Cys Val Thr
                165                 170                 175
Arg Ile Tyr His Ser His Ile Asp Ala Pro Lys Asp Ile Ala Ser Gly
            180                 185                 190
Leu Ile Gly Pro Leu Ile Ile Cys Lys Lys Asp Ser Leu Asp Lys Glu
        195                 200                 205
Lys Glu Lys His Ile Asp Arg Glu Phe Val Val Met Phe Ser Val Val
    210                 215                 220
Asp Glu Asn Phe Ser Trp Tyr Leu Glu Asp Asn Ile Lys Thr Tyr Cys
225                 230                 235                 240
Ser Glu Pro Glu Lys Val Asp Lys Asp Asn Glu Asp Phe Gln Glu Ser
                245                 250                 255
Asn Arg Met Tyr Ser Val Asn Gly Tyr Thr Phe Gly Ser Leu Pro Gly
            260                 265                 270
Leu Ser Met Cys Ala Glu Asp Arg Val Lys Trp Tyr Leu Phe Gly Met
        275                 280                 285
Gly Asn Glu Val Asp Val His Ala Ala Phe Phe His Gly Gln Ala Leu
    290                 295                 300
Thr Asn Lys Asn Tyr Arg Ile Asp Thr Ile Asn Leu Phe Pro Ala Thr
305                 310                 315                 320
Leu Phe Asp Ala Tyr Met Val Ala Gln Asn Pro Gly Glu Trp Met Leu
                325                 330                 335
Ser Cys Gln Asn Leu Asn His Leu Lys Ala Gly Leu Gln Ala Phe Phe
            340                 345                 350
Gln Val Gln Glu Cys Asn Lys Ser Ser Lys Asp Asn Ile Arg Gly
        355                 360                 365
Lys His Val Arg His Tyr Tyr Ile Ala Ala Glu Glu Ile Ile Trp Asn
    370                 375                 380
Tyr Ala Pro Ser Gly Ile Asp Ile Phe Thr Lys Glu Asn Leu Thr Ala
385                 390                 395                 400
Pro Gly Ser Asp Ser Ala Val Phe Phe Glu Gln Gly Thr Thr Arg Ile
                405                 410                 415
Gly Gly Ser Tyr Lys Lys Leu Val Tyr Arg Glu Tyr Thr Asp Ala Ser
            420                 425                 430
Phe Thr Asn Arg Lys Glu Arg Gly Pro Glu Glu Glu His Leu Gly Ile
        435                 440                 445
```

-continued

```
Leu Gly Pro Val Ile Trp Ala Glu Val Gly Asp Thr Ile Arg Val Thr
    450                 455                 460

Phe His Asn Lys Gly Ala Tyr Pro Leu Ser Ile Glu Pro Ile Gly Val
465                 470                 475                 480

Arg Phe Asn Lys Asn Asn Glu Gly Thr Tyr Tyr Ser Pro Asn Tyr Asn
                485                 490                 495

Pro Gln Ser Arg Ser Val Pro Pro Ser Ala Ser His Val Ala Pro Thr
                500                 505                 510

Glu Thr Phe Thr Tyr Glu Trp Thr Val Pro Lys Glu Val Gly Pro Thr
                515                 520                 525

Asn Ala Asp Pro Val Cys Leu Ala Lys Met Tyr Tyr Ser Ala Val Asp
    530                 535                 540

Pro Thr Lys Asp Ile Phe Thr Gly Leu Ile Gly Pro Met Lys Ile Cys
545                 550                 555                 560

Lys Lys Gly Ser Leu His Ala Asn Gly Arg Gln Lys Asp Val Asp Lys
                565                 570                 575

Glu Phe Tyr Leu Phe Pro Thr Val Phe Asp Glu Asn Glu Ser Leu Leu
                580                 585                 590

Leu Glu Asp Asn Ile Arg Met Phe Thr Thr Ala Pro Asp Gln Val Asp
    595                 600                 605

Lys Glu Asp Glu Asp Phe Gln Glu Ser Asn Lys Met His Ser Met Asn
610                 615                 620

Gly Phe Met Tyr Gly Asn Gln Pro Gly Leu Thr Met Cys Lys Gly Asp
625                 630                 635                 640

Ser Val Val Trp Tyr Leu Phe Ser Ala Gly Asn Glu Ala Asp Val His
                645                 650                 655

Gly Ile Tyr Phe Ser Gly Asn Thr Tyr Leu Trp Arg Gly Glu Arg Arg
                660                 665                 670

Asp Thr Ala Asn Leu Phe Pro Gln Thr Ser Leu Thr Leu His Met Trp
    675                 680                 685

Pro Asp Thr Glu Gly Thr Phe Asn Val Glu Cys Leu Thr Thr Asp His
690                 695                 700

Tyr Thr Gly Gly Met Lys Gln Lys Tyr Thr Val Asn Gln Cys Arg Arg
705                 710                 715                 720

Gln Ser Glu Asp Ser Thr Phe Tyr Leu Gly Glu Arg Thr Tyr Tyr Ile
                725                 730                 735

Ala Ala Val Glu Val Glu Trp Asp Tyr Ser Pro Gln Arg Glu Trp Glu
                740                 745                 750

Lys Glu Leu His His Leu Gln Glu Gln Asn Val Ser Asn Ala Phe Leu
    755                 760                 765

Asp Lys Gly Glu Phe Tyr Ile Gly Ser Lys Tyr Lys Lys Val Val Tyr
770                 775                 780

Arg Gln Tyr Thr Asp Ser Thr Phe Arg Val Pro Val Glu Arg Lys Ala
785                 790                 795                 800

Glu Glu Glu His Leu Gly Ile Leu Gly Pro Gln Leu His Ala Asp Val
                805                 810                 815

Gly Asp Lys Val Lys Ile Ile Phe Lys Asn Met Ala Thr Arg Pro Tyr
                820                 825                 830

Ser Ile His Ala His Gly Val Gln Thr Glu Ser Ser Thr Val Thr Pro
    835                 840                 845

Thr Leu Pro Gly Glu Thr Leu Thr Tyr Val Trp Lys Ile Pro Glu Arg
850                 855                 860
```

Ser Gly Ala Gly Thr Glu Asp Ser Ala Cys Ile Pro Trp Ala Tyr Tyr
865                 870                 875                 880

Ser Thr Val Asp Gln Val Lys Asp Leu Tyr Ser Gly Leu Ile Gly Pro
        885                 890                 895

Leu Ile Val Cys Arg Arg Pro Tyr Leu Lys Val Phe Asn Pro Arg Arg
            900                 905                 910

Lys Leu Glu Phe Ala Leu Leu Phe Leu Val Phe Asp Glu Asn Glu Ser
        915                 920                 925

Trp Tyr Leu Asp Asp Asn Ile Lys Thr Tyr Ser Asp His Pro Glu Lys
    930                 935                 940

Val Asn Lys Asp Asp Glu Glu Phe Ile Glu Ser Asn Lys Met His Ala
945                 950                 955                 960

Ile Asn Gly Arg Met Phe Gly Asn Leu Gln Gly Leu Thr Met His Val
            965                 970                 975

Gly Asp Glu Val Asn Trp Tyr Leu Met Gly Met Gly Asn Glu Ile Asp
        980                 985                 990

Leu His Thr Val His Phe His Gly His Ser Phe Gln Tyr Lys His Arg
    995                 1000                1005

Gly Val Tyr Ser Ser Asp Val Phe Asp Ile Phe Pro Gly Thr Tyr
    1010                1015                1020

Gln Thr Leu Glu Met Phe Pro Arg Thr Pro Gly Ile Trp Leu Leu
    1025                1030                1035

His Cys His Val Thr Asp His Ile His Ala Gly Met Glu Thr Thr
    1040                1045                1050

Tyr Thr Val Leu Gln Asn Glu Asp Thr Lys Ser Gly
    1055                1060                1065

<210> SEQ ID NO 1028
<211> LENGTH: 248
<212> TYPE: PRT
<213> ORGANISM: Homo sapiens

<400> SEQUENCE: 1028

Met Glu Arg Ala Ser Leu Ile Gln Lys Ala Lys Leu Ala Glu Gln Ala
1               5                   10                  15

Glu Arg Tyr Glu Asp Met Ala Ala Phe Met Lys Gly Ala Val Glu Lys
            20                  25                  30

Gly Glu Glu Leu Ser Cys Glu Glu Arg Asn Leu Leu Ser Val Ala Tyr
        35                  40                  45

Lys Asn Val Val Gly Gly Gln Arg Ala Ala Trp Arg Val Leu Ser Ser
50                  55                  60

Ile Glu Gln Lys Ser Asn Glu Glu Gly Ser Glu Glu Lys Gly Pro Glu
65                  70                  75                  80

Val Arg Glu Tyr Arg Glu Lys Val Glu Thr Leu Gln Gly Val Cys
            85                  90                  95

Asp Thr Val Leu Gly Leu Leu Asp Ser His Leu Ile Lys Glu Ala Gly
            100                 105                 110

Asp Ala Glu Ser Arg Val Phe Tyr Leu Lys Met Lys Gly Asp Tyr Tyr
        115                 120                 125

Arg Tyr Leu Ala Glu Val Ala Thr Gly Asp Asp Lys Lys Arg Ile Ile
    130                 135                 140

Asp Ser Ala Arg Ser Ala Tyr Gln Glu Ala Met Asp Ile Ser Lys Lys
145                 150                 155                 160

Glu Met Pro Pro Thr Asn Pro Ile Arg Leu Gly Leu Ala Leu Asn Phe
                165                 170                 175

-continued

```
Ser Val Phe His Tyr Glu Ile Ala Asn Ser Pro Glu Ala Ile Ser
            180                 185                 190

Leu Ala Lys Thr Thr Phe Asp Glu Ala Met Ala Asp Leu His Thr Leu
        195                 200                 205

Ser Glu Asp Ser Tyr Lys Asp Ser Thr Leu Ile Met Gln Leu Leu Arg
    210                 215                 220

Asp Asn Leu Thr Leu Trp Thr Ala Asp Asn Ala Gly Glu Glu Gly Gly
225                 230                 235                 240

Glu Ala Pro Gln Glu Pro Gln Ser
                245

<210> SEQ ID NO 1029
<211> LENGTH: 1474
<212> TYPE: PRT
<213> ORGANISM: Homo sapiens

<400> SEQUENCE: 1029

Met Gly Lys Asn Lys Leu Leu His Pro Ser Leu Val Leu Leu Leu Leu
1               5                   10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Thr Glu Lys Gly Cys
        35                  40                  45

Val Leu Leu Ser Tyr Leu Asn Glu Thr Val Thr Val Ser Ala Ser Leu
    50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
    130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205

Lys Lys Ser Gly Gly Arg Thr Glu His Pro Phe Thr Val Glu Glu Phe
    210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
            260                 265                 270

Ser Asp Ala Ser Asp Cys His Gly Glu Asp Ser Gln Ala Phe Cys Glu
        275                 280                 285

Lys Phe Ser Gly Gln Leu Asn Ser His Gly Cys Phe Tyr Gln Gln Val
```

```
                290                 295                 300
Lys Thr Lys Val Phe Gln Leu Lys Arg Lys Glu Tyr Glu Met Lys Leu
305                 310                 315                 320

His Thr Glu Ala Gln Ile Gln Glu Glu Gly Thr Val Val Glu Leu Thr
                325                 330                 335

Gly Arg Gln Ser Ser Glu Ile Thr Arg Thr Ile Thr Lys Leu Ser Phe
                340                 345                 350

Val Lys Val Asp Ser His Phe Arg Gln Gly Ile Pro Phe Phe Gly Gln
                355                 360                 365

Val Arg Leu Val Asp Gly Lys Gly Val Pro Ile Pro Asn Lys Val Ile
                370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
                420                 425                 430

Gly Tyr Gln Trp Val Ser Glu Glu His Glu Glu Ala His His Thr Ala
                435                 440                 445

Tyr Leu Val Phe Ser Pro Ser Lys Ser Phe Val His Leu Glu Pro Met
450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
                485                 490                 495

Tyr Leu Ile Met Ala Lys Gly Gly Ile Val Arg Thr Gly Thr His Gly
                500                 505                 510

Leu Leu Val Lys Gln Glu Asp Met Lys Gly His Phe Ser Ile Ser Ile
                515                 520                 525

Pro Val Lys Ser Asp Ile Ala Pro Val Ala Arg Leu Leu Ile Tyr Ala
530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                565                 570                 575

Ser Leu Pro Ala Ser His Ala His Leu Arg Val Thr Ala Ala Pro Gln
                580                 585                 590

Ser Val Cys Ala Leu Arg Ala Val Asp Gln Ser Val Leu Leu Met Lys
                595                 600                 605

Pro Asp Ala Glu Leu Ser Ala Ser Ser Val Tyr Asn Leu Leu Pro Glu
610                 615                 620

Lys Asp Leu Thr Gly Phe Pro Gly Pro Leu Asn Asp Gln Asp Asn Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
                660                 665                 670

Met Gly Leu Lys Ala Phe Thr Asn Ser Lys Ile Arg Lys Pro Lys Met
                675                 680                 685

Cys Pro Gln Leu Gln Gln Tyr Glu Met His Gly Pro Glu Gly Leu Arg
                690                 695                 700

Val Gly Phe Tyr Glu Ser Asp Val Met Gly Arg Gly His Ala Arg Leu
705                 710                 715                 720
```

```
Val His Val Glu Glu Pro His Thr Glu Thr Val Arg Lys Tyr Phe Pro
            725                 730                 735

Glu Thr Trp Ile Trp Asp Leu Val Val Asn Ser Ala Gly Val Ala
        740                 745                 750

Glu Val Gly Val Thr Val Pro Asp Thr Ile Thr Glu Trp Lys Ala Gly
            755                 760                 765

Ala Phe Cys Leu Ser Glu Asp Ala Gly Leu Gly Ile Ser Ser Thr Ala
    770                 775                 780

Ser Leu Arg Ala Phe Gln Pro Phe Val Glu Leu Thr Met Pro Tyr
785                 790                 795                 800

Ser Val Ile Arg Gly Glu Ala Phe Thr Leu Lys Ala Thr Val Leu Asn
            805                 810                 815

Tyr Leu Pro Lys Cys Ile Arg Val Ser Val Gln Leu Glu Ala Ser Pro
            820                 825                 830

Ala Phe Leu Ala Val Pro Val Glu Lys Glu Gln Ala Pro His Cys Ile
            835                 840                 845

Cys Ala Asn Gly Arg Gln Thr Val Ser Trp Ala Val Thr Pro Lys Ser
    850                 855                 860

Leu Gly Asn Val Asn Phe Thr Val Ser Ala Glu Ala Leu Glu Ser Gln
865                 870                 875                 880

Glu Leu Cys Gly Thr Glu Val Pro Ser Val Pro Glu His Gly Arg Lys
                885                 890                 895

Asp Thr Val Ile Lys Pro Leu Leu Val Glu Pro Glu Gly Leu Glu Lys
            900                 905                 910

Glu Thr Thr Phe Asn Ser Leu Leu Cys Pro Ser Gly Gly Glu Val Ser
            915                 920                 925

Glu Glu Leu Ser Leu Lys Leu Pro Pro Asn Val Val Glu Glu Ser Ala
930                 935                 940

Arg Ala Ser Val Ser Val Leu Gly Asp Ile Leu Gly Ser Ala Met Gln
945                 950                 955                 960

Asn Thr Gln Asn Leu Leu Gln Met Pro Tyr Gly Cys Gly Glu Gln Asn
                965                 970                 975

Met Val Leu Phe Ala Pro Asn Ile Tyr Val Leu Asp Tyr Leu Asn Glu
            980                 985                 990

Thr Gln Gln Leu Thr Pro Glu Ile Lys Ser Lys Ala Ile Gly Tyr Leu
        995                 1000                1005

Asn Thr Gly Tyr Gln Arg Gln Leu Asn Tyr Lys His Tyr Asp Gly
    1010                1015                1020

Ser Tyr Ser Thr Phe Gly Glu Arg Tyr Gly Arg Asn Gln Gly Asn
    1025                1030                1035

Thr Trp Leu Thr Ala Phe Val Leu Lys Thr Phe Ala Gln Ala Arg
    1040                1045                1050

Ala Tyr Ile Phe Ile Asp Glu Ala His Ile Thr Gln Ala Leu Ile
    1055                1060                1065

Trp Leu Ser Gln Arg Gln Lys Asp Asn Gly Cys Phe Arg Ser Ser
    1070                1075                1080

Gly Ser Leu Leu Asn Asn Ala Ile Lys Gly Gly Val Glu Asp Glu
    1085                1090                1095

Val Thr Leu Ser Ala Tyr Ile Thr Ile Ala Leu Leu Glu Ile Pro
    1100                1105                1110

Leu Thr Val Thr His Pro Val Val Arg Asn Ala Leu Phe Cys Leu
    1115                1120                1125
```

-continued

| | | | | | | | | | |
|---|---|---|---|---|---|---|---|---|---|
|Glu|Ser|Ala|Trp|Lys|Thr|Ala|Gln|Glu|Gly|Asp|His|Gly|Ser|His|
|1130| | | |1135| | | |1140| |

Val Tyr Thr Lys Ala Leu Leu Ala Tyr Ala Phe Ala Leu Ala Gly
1145                1150                1155

Asn Gln Asp Lys Arg Lys Glu Val Leu Lys Ser Leu Asn Glu Glu
1160                1165                1170

Ala Val Lys Lys Asp Asn Ser Val His Trp Glu Arg Pro Gln Lys
1175                1180                1185

Pro Lys Ala Pro Val Gly His Phe Tyr Glu Pro Gln Ala Pro Ser
1190                1195                1200

Ala Glu Val Glu Met Thr Ser Tyr Val Leu Leu Ala Tyr Leu Thr
1205                1210                1215

Ala Gln Pro Ala Pro Thr Ser Glu Asp Leu Thr Ser Ala Thr Asn
1220                1225                1230

Ile Val Lys Trp Ile Thr Lys Gln Gln Asn Ala Gln Gly Gly Phe
1235                1240                1245

Ser Ser Thr Gln Asp Thr Val Val Ala Leu His Ala Leu Ser Lys
1250                1255                1260

Tyr Gly Ala Ala Thr Phe Thr Arg Thr Gly Lys Ala Ala Gln Val
1265                1270                1275

Thr Ile Gln Ser Ser Gly Thr Phe Ser Ser Lys Phe Gln Val Asp
1280                1285                1290

Asn Asn Asn Arg Leu Leu Leu Gln Gln Val Ser Leu Pro Glu Leu
1295                1300                1305

Pro Gly Glu Tyr Ser Met Lys Val Thr Gly Glu Gly Cys Val Tyr
1310                1315                1320

Leu Gln Thr Ser Leu Lys Tyr Asn Ile Leu Pro Glu Lys Glu Glu
1325                1330                1335

Phe Pro Phe Ala Leu Gly Val Gln Thr Leu Pro Gln Thr Cys Asp
1340                1345                1350

Glu Pro Lys Ala His Thr Ser Phe Gln Ile Ser Leu Ser Val Ser
1355                1360                1365

Tyr Thr Gly Ser Arg Ser Ala Ser Asn Met Ala Ile Val Asp Val
1370                1375                1380

Lys Met Val Ser Gly Phe Ile Pro Leu Lys Pro Thr Val Lys Met
1385                1390                1395

Leu Glu Arg Ser Asn His Val Ser Arg Thr Glu Val Ser Ser Asn
1400                1405                1410

His Val Leu Ile Tyr Leu Asp Lys Val Ser Asn Gln Thr Leu Ser
1415                1420                1425

Leu Phe Phe Thr Val Leu Gln Asp Val Pro Val Arg Asp Leu Lys
1430                1435                1440

Pro Ala Ile Val Lys Val Tyr Asp Tyr Tyr Glu Thr Asp Glu Phe
1445                1450                1455

Ala Ile Ala Glu Tyr Asn Ala Pro Cys Ser Lys Asp Leu Gly Asn
1460                1465                1470

Ala

<210> SEQ ID NO 1030
<211> LENGTH: 147
<212> TYPE: PRT
<213> ORGANISM: Homo sapiens

<400> SEQUENCE: 1030

```
Met Ala Ser His Arg Leu Leu Leu Cys Leu Ala Gly Leu Val Phe
 1               5                  10                 15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
 65                 70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
130                 135                 140

Pro Lys Glu
145

<210> SEQ ID NO 1031
<211> LENGTH: 527
<212> TYPE: PRT
<213> ORGANISM: Homo sapiens

<400> SEQUENCE: 1031

Met Tyr Ala Leu Phe Leu Leu Ala Ser Leu Leu Gly Ala Ala Leu Ala
 1               5                  10                 15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
 50                 55                  60

Ile Cys Lys Asp Val Val Thr Ala Ala Gly Asp Met Leu Lys Asp Asn
 65                 70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
210                 215                 220
```

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
            245                 250                 255

Met His Met Ser Leu Gln Gln Pro Lys Glu Ile Cys Ala Leu Val Gly
        260                 265                 270

Phe Cys Asp Glu Val Lys Glu Met Pro Met Gln Thr Leu Val Pro Ala
    275                 280                 285

Lys Val Ala Ser Lys Asn Val Ile Pro Ala Leu Glu Leu Val Glu Pro
290                 295                 300

Ile Lys Lys His Glu Val Pro Ala Lys Ser Asp Val Tyr Cys Glu Val
305                 310                 315                 320

Cys Glu Phe Leu Val Lys Glu Val Thr Lys Leu Ile Asp Asn Asn Lys
            325                 330                 335

Thr Glu Lys Glu Ile Leu Asp Ala Phe Asp Lys Met Cys Ser Lys Leu
        340                 345                 350

Pro Lys Ser Leu Ser Glu Glu Cys Gln Glu Val Val Asp Thr Tyr Gly
    355                 360                 365

Ser Ser Ile Leu Ser Ile Leu Leu Glu Glu Val Ser Pro Glu Leu Val
370                 375                 380

Cys Ser Met Leu His Leu Cys Ser Gly Thr Arg Leu Pro Ala Leu Thr
385                 390                 395                 400

Val His Val Thr Gln Pro Lys Asp Gly Gly Phe Cys Glu Val Cys Lys
            405                 410                 415

Lys Leu Val Gly Tyr Leu Asp Arg Asn Leu Glu Lys Asn Ser Thr Lys
        420                 425                 430

Gln Glu Ile Leu Ala Ala Leu Glu Lys Gly Cys Ser Phe Leu Pro Asp
    435                 440                 445

Pro Tyr Gln Lys Gln Cys Asp Gln Phe Val Ala Glu Tyr Glu Pro Val
450                 455                 460

Leu Ile Glu Ile Leu Val Glu Val Met Asp Pro Ser Phe Val Cys Leu
465                 470                 475                 480

Lys Ile Gly Ala Cys Pro Ser Ala His Lys Pro Leu Leu Gly Thr Glu
            485                 490                 495

Lys Cys Ile Trp Gly Pro Ser Tyr Trp Cys Gln Asn Thr Glu Thr Ala
        500                 505                 510

Ala Gln Cys Asn Ala Val Glu His Cys Lys Arg His Val Trp Asn
    515                 520                 525

<210> SEQ ID NO 1032
<211> LENGTH: 426
<212> TYPE: PRT
<213> ORGANISM: Homo sapiens

<400> SEQUENCE: 1032

Met Phe Trp Glu Val Ile Ser Asp Glu His Gly Ile Asp Pro Thr Gly
1               5                   10                  15

Thr Tyr His Gly Asp Ser Asp Leu Gln Leu Asp Arg Ile Ser Val Tyr
            20                  25                  30

Tyr Asn Glu Ala Thr Gly Gly Lys Tyr Val Pro Arg Ala Ile Leu Val
        35                  40                  45

Asp Leu Glu Pro Gly Thr Met Asp Ser Val Arg Ser Gly Pro Phe Gly
    50                  55                  60

Gln Ile Phe Arg Pro Asp Asn Phe Val Phe Gly Gln Ser Gly Ala Gly

```
                65                  70                  75                  80
        Asn Asn Trp Ala Lys Gly His Tyr Thr Glu Gly Ala Glu Leu Val Asp
                        85                  90                  95

Ser Val Leu Asp Val Val Arg Lys Glu Ala Glu Ser Cys Asp Cys Leu
                       100                 105                 110

Gln Gly Phe Gln Leu Thr His Ser Leu Gly Gly Thr Gly Ser Gly
                       115                 120                 125

Met Gly Thr Leu Leu Ile Ser Lys Ile Arg Glu Glu Tyr Pro Asp Arg
                       130                 135                 140

Ile Met Asn Thr Phe Ser Val Val Pro Ser Pro Lys Val Ser Asp Thr
        145                 150                 155                 160

Val Val Glu Pro Tyr Asn Ala Thr Leu Ser Val His Gln Leu Val Glu
                       165                 170                 175

Asn Thr Asp Glu Thr Tyr Cys Ile Asp Asn Glu Ala Leu Tyr Asp Ile
                       180                 185                 190

Cys Phe Arg Thr Leu Lys Leu Thr Thr Pro Thr Tyr Gly Asp Leu Asn
                       195                 200                 205

His Leu Val Ser Ala Thr Met Ser Gly Val Thr Thr Cys Leu Arg Phe
                       210                 215                 220

Pro Gly Gln Leu Asn Ala Asp Leu Arg Lys Leu Ala Val Asn Met Val
        225                 230                 235                 240

Pro Phe Pro Arg Leu His Phe Phe Met Pro Gly Phe Ala Pro Leu Thr
                       245                 250                 255

Ser Arg Gly Ser Gln Gln Tyr Arg Ala Leu Thr Val Pro Glu Leu Thr
                       260                 265                 270

Gln Gln Val Phe Asp Ala Lys Asn Met Met Ala Ala Cys Asp Pro Arg
                       275                 280                 285

His Gly Arg Tyr Leu Thr Val Ala Ala Val Phe Arg Gly Arg Met Ser
                       290                 295                 300

Met Lys Glu Val Asp Glu Gln Met Leu Asn Val Gln Asn Lys Asn Ser
        305                 310                 315                 320

Ser Tyr Phe Val Glu Trp Ile Pro Asn Asn Val Lys Thr Ala Val Cys
                       325                 330                 335

Asp Ile Pro Pro Arg Gly Leu Lys Met Ala Val Thr Phe Ile Gly Asn
                       340                 345                 350

Ser Thr Ala Ile Gln Glu Leu Phe Lys Arg Ile Ser Glu Gln Phe Thr
                       355                 360                 365

Ala Met Phe Arg Arg Lys Ala Phe Leu His Trp Tyr Thr Gly Glu Gly
                       370                 375                 380

Met Asp Glu Met Glu Phe Thr Glu Ala Glu Ser Asn Met Asn Asp Leu
        385                 390                 395                 400

Val Ser Glu Tyr Gln Gln Tyr Gln Asp Ala Thr Ala Glu Glu Glu Glu
                       405                 410                 415

Asp Phe Gly Glu Glu Ala Glu Glu Glu Ala
                       420                 425

<210> SEQ ID NO 1033
<211> LENGTH: 117
<212> TYPE: PRT
<213> ORGANISM: Homo sapiens

<400> SEQUENCE: 1033

Met Ala Trp Thr Val Leu Leu Leu Gly Leu Leu Ser His Cys Thr Gly
        1               5                  10                  15
```

```
Ser Val Thr Ser Tyr Val Leu Thr Gln Pro Ser Val Ser Val Ala
             20                  25                  30

Pro Gly Gln Thr Ala Arg Ile Thr Cys Gly Gly Asn Asn Ile Gly Ser
         35                  40                  45

Lys Ser Val His Trp Tyr Gln Gln Lys Pro Gly Gln Ala Pro Val Leu
 50                  55                  60

Val Val Tyr Asp Asp Ser Asp Arg Pro Ser Gly Ile Pro Glu Arg Phe
 65                  70                  75                  80

Ser Gly Ser Asn Ser Gly Asn Thr Ala Thr Leu Thr Ile Ser Arg Val
                 85                  90                  95

Glu Ala Gly Asp Glu Ala Asp Tyr Tyr Cys Gln Val Trp Asp Ser Ser
                100                 105                 110

Ser Asp His Pro Thr
        115

<210> SEQ ID NO 1034
<211> LENGTH: 109
<212> TYPE: PRT
<213> ORGANISM: Homo sapiens

<400> SEQUENCE: 1034

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Asn Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Asp Asp Phe Ala Val Tyr Tyr Cys Gln Gln Tyr Gly Ser Ser Pro
                 85                  90                  95

Gln Thr Phe Gly Gln Gly Ser Lys Val Glu Ile Lys Arg
                100                 105

<210> SEQ ID NO 1035
<211> LENGTH: 129
<212> TYPE: PRT
<213> ORGANISM: Homo sapiens

<400> SEQUENCE: 1035

Met Glu Thr Pro Ala Gln Leu Leu Phe Leu Leu Leu Leu Trp Leu Pro
 1               5                  10                  15

Asp Thr Thr Gly Glu Ile Val Leu Thr Gln Ser Pro Gly Thr Leu Ser
             20                  25                  30

Leu Ser Pro Gly Glu Arg Ala Thr Leu Ser Cys Arg Ala Ser Gln Ser
         35                  40                  45

Val Ser Ser Ser Tyr Leu Ala Trp Tyr Gln Gln Lys Pro Gly Gln Ala
 50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Tyr
                100                 105                 110
```

Gly Thr Ser Pro Arg Thr Phe Gly Gln Gly Thr Lys Val Glu Ile Lys
            115                 120                 125
Arg

<210> SEQ ID NO 1036
<211> LENGTH: 22
<212> TYPE: PRT
<213> ORGANISM: Homo sapiens

<400> SEQUENCE: 1036

Ala Ser Gln Ser Val Ser Asn Ser Tyr Leu Ala Trp Tyr Gln Gln Lys
1               5                   10                  15

Pro Gly Gln Ala Pro Arg
            20

<210> SEQ ID NO 1037
<211> LENGTH: 23
<212> TYPE: PRT
<213> ORGANISM: Homo sapiens

<400> SEQUENCE: 1037

Ala Thr Gly Ile Pro Asp Arg Phe Ser Gly Ser Gly Ser Gly Thr Asp
1               5                   10                  15

Phe Thr Leu Thr Ile Ser Arg
            20

<210> SEQ ID NO 1038
<211> LENGTH: 18
<212> TYPE: PRT
<213> ORGANISM: Homo sapiens

<400> SEQUENCE: 1038

Glu Ile Val Leu Thr Gln Ser Pro Gly Thr Leu Ser Leu Ser Pro Gly
1               5                   10                  15

Glu Arg

<210> SEQ ID NO 1039
<211> LENGTH: 24
<212> TYPE: PRT
<213> ORGANISM: Homo sapiens

<400> SEQUENCE: 1039

Glu Ile Val Leu Thr Gln Ser Pro Gly Thr Leu Ser Leu Ser Pro Gly
1               5                   10                  15

Glu Arg Ala Thr Leu Ser Cys Arg
            20

<210> SEQ ID NO 1040
<211> LENGTH: 16
<212> TYPE: PRT
<213> ORGANISM: Homo sapiens

<400> SEQUENCE: 1040

Phe Ser Gly Ser Gly Ser Gly Thr Asp Phe Thr Leu Thr Ile Ser Arg
1               5                   10                  15

<210> SEQ ID NO 1041
<211> LENGTH: 9
<212> TYPE: PRT
<213> ORGANISM: Homo sapiens

<400> SEQUENCE: 1041

```
Leu Leu Ile Tyr Gly Ala Ser Ser Arg
1               5

<210> SEQ ID NO 1042
<211> LENGTH: 16
<212> TYPE: PRT
<213> ORGANISM: Homo sapiens

<400> SEQUENCE: 1042

Phe Ser Gly Ser Asn Ser Gly Asn Thr Ala Thr Leu Thr Ile Ser Arg
1               5                   10                  15

<210> SEQ ID NO 1043
<211> LENGTH: 30
<212> TYPE: PRT
<213> ORGANISM: Homo sapiens

<400> SEQUENCE: 1043

Ser Val His Trp Tyr Gln Gln Lys Pro Gly Gln Ala Pro Val Leu Val
1               5                   10                  15

Val Tyr Asp Asp Ser Asp Arg Pro Ser Gly Ile Pro Glu Arg
            20                  25                  30

<210> SEQ ID NO 1044
<211> LENGTH: 15
<212> TYPE: PRT
<213> ORGANISM: Homo sapiens

<400> SEQUENCE: 1044

Ala Leu Thr Val Pro Glu Leu Thr Gln Gln Val Phe Asp Ala Lys
1               5                   10                  15

<210> SEQ ID NO 1045
<211> LENGTH: 19
<212> TYPE: PRT
<213> ORGANISM: Homo sapiens

<400> SEQUENCE: 1045

Gly His Tyr Thr Glu Gly Ala Glu Leu Val Asp Ser Val Leu Asp Val
1               5                   10                  15

Val Arg Lys

<210> SEQ ID NO 1046
<211> LENGTH: 14
<212> TYPE: PRT
<213> ORGANISM: Homo sapiens

<400> SEQUENCE: 1046

Asn Ser Ser Tyr Phe Val Glu Trp Ile Pro Asn Asn Val Lys
1               5                   10

<210> SEQ ID NO 1047
<211> LENGTH: 26
<212> TYPE: PRT
<213> ORGANISM: Homo sapiens

<400> SEQUENCE: 1047

Ser Gly Pro Phe Gly Gln Ile Phe Arg Pro Asp Asn Phe Val Phe Gly
1               5                   10                  15

Gln Ser Gly Ala Gly Asn Asn Trp Ala Lys
            20                  25

<210> SEQ ID NO 1048
```

```
<211> LENGTH: 9
<212> TYPE: PRT
<213> ORGANISM: Homo sapiens

<400> SEQUENCE: 1048

Tyr Leu Thr Val Ala Ala Val Phe Arg
1               5

<210> SEQ ID NO 1049
<211> LENGTH: 12
<212> TYPE: PRT
<213> ORGANISM: Homo sapiens

<400> SEQUENCE: 1049

Asp Ile Ala Pro Thr Leu Thr Leu Tyr Val Gly Lys
1               5                   10

<210> SEQ ID NO 1050
<211> LENGTH: 13
<212> TYPE: PRT
<213> ORGANISM: Homo sapiens

<400> SEQUENCE: 1050

Asp Ile Ala Pro Thr Leu Thr Leu Tyr Val Gly Lys Lys
1               5                   10

<210> SEQ ID NO 1051
<211> LENGTH: 6
<212> TYPE: PRT
<213> ORGANISM: Homo sapiens

<400> SEQUENCE: 1051

Phe Thr Asp His Leu Lys
1               5

<210> SEQ ID NO 1052
<211> LENGTH: 10
<212> TYPE: PRT
<213> ORGANISM: Homo sapiens

<400> SEQUENCE: 1052

His Tyr Glu Gly Ser Thr Val Pro Glu Lys
1               5                   10

<210> SEQ ID NO 1053
<211> LENGTH: 15
<212> TYPE: PRT
<213> ORGANISM: Homo sapiens

<400> SEQUENCE: 1053

Leu Arg Thr Glu Gly Asp Gly Val Tyr Thr Leu Asn Asn Glu Lys
1               5                   10                  15

<210> SEQ ID NO 1054
<211> LENGTH: 20
<212> TYPE: PRT
<213> ORGANISM: Homo sapiens

<400> SEQUENCE: 1054

Leu Arg Thr Glu Gly Asp Gly Val Tyr Thr Leu Asn Asn Glu Lys Gln
1               5                   10                  15

Trp Ile Asn Lys
            20
```

```
<210> SEQ ID NO 1055
<211> LENGTH: 7
<212> TYPE: PRT
<213> ORGANISM: Homo sapiens

<400> SEQUENCE: 1055

Gln Leu Val Glu Ile Glu Lys
1               5

<210> SEQ ID NO 1056
<211> LENGTH: 13
<212> TYPE: PRT
<213> ORGANISM: Homo sapiens

<400> SEQUENCE: 1056

Thr Glu Gly Asp Gly Val Tyr Thr Leu Asn Asn Glu Lys
1               5                   10

<210> SEQ ID NO 1057
<211> LENGTH: 18
<212> TYPE: PRT
<213> ORGANISM: Homo sapiens

<400> SEQUENCE: 1057

Thr Glu Gly Asp Gly Val Tyr Thr Leu Asn Asn Glu Lys Gln Trp Ile
1               5                   10                  15

Asn Lys

<210> SEQ ID NO 1058
<211> LENGTH: 9
<212> TYPE: PRT
<213> ORGANISM: Homo sapiens

<400> SEQUENCE: 1058

Val Gly Tyr Val Ser Gly Trp Gly Arg
1               5

<210> SEQ ID NO 1059
<211> LENGTH: 16
<212> TYPE: PRT
<213> ORGANISM: Homo sapiens

<400> SEQUENCE: 1059

Val Val Leu His Pro Asn Tyr Ser Gln Val Asp Ile Gly Leu Ile Lys
1               5                   10                  15

<210> SEQ ID NO 1060
<211> LENGTH: 8
<212> TYPE: PRT
<213> ORGANISM: Homo sapiens

<400> SEQUENCE: 1060

Tyr Gln Cys Lys Asn Tyr Tyr Lys
1               5

<210> SEQ ID NO 1061
<211> LENGTH: 10
<212> TYPE: PRT
<213> ORGANISM: Homo sapiens

<400> SEQUENCE: 1061

Tyr Gln Cys Lys Asn Tyr Tyr Lys Leu Arg
1               5                   10
```

<210> SEQ ID NO 1062
<211> LENGTH: 14
<212> TYPE: PRT
<213> ORGANISM: Homo sapiens

<400> SEQUENCE: 1062

Tyr Val Met Leu Pro Val Ala Asp Gln Asp Gln Cys Ile Arg
1               5                   10

<210> SEQ ID NO 1063
<211> LENGTH: 222
<212> TYPE: PRT
<213> ORGANISM: Homo sapiens

<400> SEQUENCE: 1063

Met Ser Ala Leu Gly Ala Val Ile Ala Leu Leu Leu Trp Gly Gln Leu
1               5                   10                  15

Phe Ala Val Asp Ser Gly Asn Asp Val Thr Asp Ile Ala Asp Asp Gly
                20                  25                  30

Cys Pro Lys Pro Pro Glu Ile Ala His Gly Tyr Val Glu His Ser Val
            35                  40                  45

Arg Tyr Gln Cys Lys Asn Tyr Tyr Lys Leu Arg Thr Glu Gly Asp Gly
        50                  55                  60

Val Tyr Thr Leu Asn Asn Glu Lys Gln Trp Ile Asn Lys Ala Val Gly
65                  70                  75                  80

Asp Lys Leu Pro Glu Cys Glu Ala Gly Ala Thr Leu Ile Asn Glu Gln
                85                  90                  95

Trp Leu Leu Thr Thr Ala Lys Asn Leu Phe Leu Asn His Ser Glu Asn
            100                 105                 110

Ala Thr Ala Lys Asp Ile Ala Pro Thr Leu Thr Leu Tyr Val Gly Lys
        115                 120                 125

Lys Gln Leu Val Glu Ile Glu Lys Val Val Leu His Pro Asn Tyr Ser
130                 135                 140

Gln Val Asp Ile Gly Leu Ile Lys Leu Lys Gln Lys Val Ser Val Asn
145                 150                 155                 160

Glu Arg Val Met Pro Ile Cys Leu Pro Ser Lys Asp Tyr Ala Glu Val
                165                 170                 175

Gly Arg Val Gly Tyr Val Ser Gly Trp Gly Arg Asn Ala Asn Phe Lys
            180                 185                 190

Phe Thr Asp His Leu Lys Tyr Val Met Leu Pro Val Ala Asp Gln Asp
        195                 200                 205

Gln Cys Ile Arg His Tyr Glu Gly Ser Thr Val Pro Glu Lys
    210                 215                 220

<210> SEQ ID NO 1064
<211> LENGTH: 31
<212> TYPE: PRT
<213> ORGANISM: Homo sapiens

<400> SEQUENCE: 1064

Ala Val Gly Asp Lys Leu Pro Glu Cys Glu Ala Asp Asp Gly Cys Pro
1               5                   10                  15

Lys Pro Pro Glu Ile Ala His Gly Tyr Val Glu His Ser Val Arg
                20                  25                  30

<210> SEQ ID NO 1065
<211> LENGTH: 17
<212> TYPE: PRT
<213> ORGANISM: Homo sapiens

<400> SEQUENCE: 1065

Ala Val Gly Asp Lys Leu Pro Glu Cys Glu Ala Val Cys Gly Lys Pro
1               5                   10                  15
Lys

<210> SEQ ID NO 1066
<211> LENGTH: 12
<212> TYPE: PRT
<213> ORGANISM: Homo sapiens

<400> SEQUENCE: 1066

Asp Ile Ala Pro Thr Leu Thr Leu Tyr Val Gly Lys
1               5                   10

<210> SEQ ID NO 1067
<211> LENGTH: 13
<212> TYPE: PRT
<213> ORGANISM: Homo sapiens

<400> SEQUENCE: 1067

Asp Ile Ala Pro Thr Leu Thr Leu Tyr Val Gly Lys Lys
1               5                   10

<210> SEQ ID NO 1068
<211> LENGTH: 6
<212> TYPE: PRT
<213> ORGANISM: Homo sapiens

<400> SEQUENCE: 1068

Phe Thr Asp His Leu Lys
1               5

<210> SEQ ID NO 1069
<211> LENGTH: 8
<212> TYPE: PRT
<213> ORGANISM: Homo sapiens

<400> SEQUENCE: 1069

Gly Ser Phe Pro Trp Gln Ala Lys
1               5

<210> SEQ ID NO 1070
<211> LENGTH: 10
<212> TYPE: PRT
<213> ORGANISM: Homo sapiens

<400> SEQUENCE: 1070

His Tyr Glu Gly Ser Thr Val Pro Glu Lys
1               5                   10

<210> SEQ ID NO 1071
<211> LENGTH: 11
<212> TYPE: PRT
<213> ORGANISM: Homo sapiens

<400> SEQUENCE: 1071

His Tyr Glu Gly Ser Thr Val Pro Glu Lys Lys
1               5                   10

<210> SEQ ID NO 1072
<211> LENGTH: 9
<212> TYPE: PRT
<213> ORGANISM: Homo sapiens

```
<400> SEQUENCE: 1072

Ile Leu Gly Gly His Leu Asp Ala Lys
1               5

<210> SEQ ID NO 1073
<211> LENGTH: 17
<212> TYPE: PRT
<213> ORGANISM: Homo sapiens

<400> SEQUENCE: 1073

Ile Leu Gly Gly His Leu Asp Ala Lys Gly Ser Phe Pro Trp Gln Ala
1               5                   10                  15

Lys

<210> SEQ ID NO 1074
<211> LENGTH: 14
<212> TYPE: PRT
<213> ORGANISM: Homo sapiens

<400> SEQUENCE: 1074

Leu Arg Thr Glu Gly Asp Gly Val Tyr Thr Leu Asn Asp Lys
1               5                   10

<210> SEQ ID NO 1075
<211> LENGTH: 15
<212> TYPE: PRT
<213> ORGANISM: Homo sapiens

<400> SEQUENCE: 1075

Leu Arg Thr Glu Gly Asp Gly Val Tyr Thr Leu Asn Asp Lys Lys
1               5                   10                  15

<210> SEQ ID NO 1076
<211> LENGTH: 15
<212> TYPE: PRT
<213> ORGANISM: Homo sapiens

<400> SEQUENCE: 1076

Leu Arg Thr Glu Gly Asp Gly Val Tyr Thr Leu Asn Asn Glu Lys
1               5                   10                  15

<210> SEQ ID NO 1077
<211> LENGTH: 20
<212> TYPE: PRT
<213> ORGANISM: Homo sapiens

<400> SEQUENCE: 1077

Leu Arg Thr Glu Gly Asp Gly Val Tyr Thr Leu Asn Asn Glu Lys Gln
1               5                   10                  15

Trp Ile Asn Lys
            20

<210> SEQ ID NO 1078
<211> LENGTH: 8
<212> TYPE: PRT
<213> ORGANISM: Homo sapiens

<400> SEQUENCE: 1078

Asn Pro Ala Asn Pro Val Gln Arg
1               5

<210> SEQ ID NO 1079
```

```
<211> LENGTH: 7
<212> TYPE: PRT
<213> ORGANISM: Homo sapiens

<400> SEQUENCE: 1079

Gln Leu Val Glu Ile Glu Lys
1               5

<210> SEQ ID NO 1080
<211> LENGTH: 12
<212> TYPE: PRT
<213> ORGANISM: Homo sapiens

<400> SEQUENCE: 1080

Ser Cys Ala Val Ala Glu Tyr Gly Val Tyr Val Lys
1               5                   10

<210> SEQ ID NO 1081
<211> LENGTH: 20
<212> TYPE: PRT
<213> ORGANISM: Homo sapiens

<400> SEQUENCE: 1081

Ser Pro Val Gly Val Gln Pro Ile Leu Asn Glu His Thr Phe Cys Ala
1               5                   10                  15

Gly Met Ser Lys
            20

<210> SEQ ID NO 1082
<211> LENGTH: 12
<212> TYPE: PRT
<213> ORGANISM: Homo sapiens

<400> SEQUENCE: 1082

Thr Glu Gly Asp Gly Val Tyr Thr Leu Asn Asp Lys
1               5                   10

<210> SEQ ID NO 1083
<211> LENGTH: 18
<212> TYPE: PRT
<213> ORGANISM: Homo sapiens

<400> SEQUENCE: 1083

Thr Glu Gly Asp Gly Val Tyr Thr Leu Asn Asp Lys Lys Gln Trp Ile
1               5                   10                  15

Asn Lys

<210> SEQ ID NO 1084
<211> LENGTH: 13
<212> TYPE: PRT
<213> ORGANISM: Homo sapiens

<400> SEQUENCE: 1084

Thr Glu Gly Asp Gly Val Tyr Thr Leu Asn Asn Glu Lys
1               5                   10

<210> SEQ ID NO 1085
<211> LENGTH: 18
<212> TYPE: PRT
<213> ORGANISM: Homo sapiens

<400> SEQUENCE: 1085

Thr Glu Gly Asp Gly Val Tyr Thr Leu Asn Asn Glu Lys Gln Trp Ile
1               5                   10                  15
```

Asn Lys

<210> SEQ ID NO 1086
<211> LENGTH: 9
<212> TYPE: PRT
<213> ORGANISM: Homo sapiens

<400> SEQUENCE: 1086

Val Gly Tyr Val Ser Gly Trp Gly Arg
1               5

<210> SEQ ID NO 1087
<211> LENGTH: 17
<212> TYPE: PRT
<213> ORGANISM: Homo sapiens

<400> SEQUENCE: 1087

Glu Ile Val His Leu Gln Ala Gly Gln Cys Gly Asn Gln Ile Gly Ala
1               5                   10                  15

Lys

<210> SEQ ID NO 1088
<211> LENGTH: 18
<212> TYPE: PRT
<213> ORGANISM: Homo sapiens

<400> SEQUENCE: 1088

Gly His Tyr Thr Glu Gly Ala Glu Leu Val Asp Ser Val Leu Asp Val
1               5                   10                  15

Val Arg

<210> SEQ ID NO 1089
<211> LENGTH: 19
<212> TYPE: PRT
<213> ORGANISM: Homo sapiens

<400> SEQUENCE: 1089

Gly His Tyr Thr Glu Gly Ala Glu Leu Val Asp Ser Val Leu Asp Val
1               5                   10                  15

Val Arg Lys

<210> SEQ ID NO 1090
<211> LENGTH: 16
<212> TYPE: PRT
<213> ORGANISM: Homo sapiens

<400> SEQUENCE: 1090

Ile Asn Val Tyr Tyr Asn Glu Ala Thr Gly Gly Lys Tyr Val Pro Arg
1               5                   10                  15

<210> SEQ ID NO 1091
<211> LENGTH: 14
<212> TYPE: PRT
<213> ORGANISM: Homo sapiens

<400> SEQUENCE: 1091

Asn Ser Ser Tyr Phe Val Glu Trp Ile Pro Asn Asn Val Lys
1               5                   10

<210> SEQ ID NO 1092
<211> LENGTH: 26
<212> TYPE: PRT

<213> ORGANISM: Homo sapiens

<400> SEQUENCE: 1092

Ser Gly Pro Phe Gly Gln Ile Phe Arg Pro Asp Asn Phe Val Phe Gly
1               5                   10                  15

Gln Ser Gly Ala Gly Asn Asn Trp Ala Lys
            20                  25

<210> SEQ ID NO 1093
<211> LENGTH: 9
<212> TYPE: PRT
<213> ORGANISM: Homo sapiens

<400> SEQUENCE: 1093

Tyr Leu Thr Val Ala Ala Val Phe Arg
1               5

<210> SEQ ID NO 1094
<211> LENGTH: 445
<212> TYPE: PRT
<213> ORGANISM: Homo sapiens

<400> SEQUENCE: 1094

Met Arg Glu Ile Val His Leu Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Glu Arg Ile Asn
        35                  40                  45

Val Tyr Tyr Asn Glu Ala Thr Gly Gly Lys Tyr Val Pro Arg Ala Val
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

```
Leu Thr Ser Arg Gly Ser Gln Gln Tyr Arg Ala Leu Thr Val Pro Glu
        275                 280                 285

Leu Thr Gln Gln Met Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ser Ala Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Ser Asn Met Asn
                405                 410                 415

Asp Leu Val Ser Glu Tyr Gln Gln Tyr Gln Asp Ala Thr Ala Glu Glu
            420                 425                 430

Glu Gly Glu Phe Glu Glu Glu Ala Glu Glu Val Ala
        435                 440                 445

<210> SEQ ID NO 1095
<211> LENGTH: 15
<212> TYPE: PRT
<213> ORGANISM: Homo sapiens

<400> SEQUENCE: 1095

Asp Ala Ser Gly Ala Thr Phe Thr Trp Thr Pro Ser Ser Gly Lys
1               5                   10                  15

<210> SEQ ID NO 1096
<211> LENGTH: 24
<212> TYPE: PRT
<213> ORGANISM: Homo sapiens

<400> SEQUENCE: 1096

Asp Ala Ser Gly Ala Thr Phe Thr Trp Thr Pro Ser Ser Gly Lys Ser
1               5                   10                  15

Ala Val Gln Gly Pro Pro Glu Arg
            20

<210> SEQ ID NO 1097
<211> LENGTH: 15
<212> TYPE: PRT
<213> ORGANISM: Homo sapiens

<400> SEQUENCE: 1097

Asp Val Leu Val Arg Trp Leu Gln Gly Ser Gln Glu Leu Pro Arg
1               5                   10                  15

<210> SEQ ID NO 1098
<211> LENGTH: 17
<212> TYPE: PRT
<213> ORGANISM: Homo sapiens

<400> SEQUENCE: 1098

Asp Val Leu Val Arg Trp Leu Gln Gly Ser Gln Glu Leu Pro Arg Glu
```

Lys

<210> SEQ ID NO 1099
<211> LENGTH: 9
<212> TYPE: PRT
<213> ORGANISM: Homo sapiens

<400> SEQUENCE: 1099

Glu Lys Tyr Leu Thr Trp Ala Ser Arg
1               5

<210> SEQ ID NO 1100
<211> LENGTH: 26
<212> TYPE: PRT
<213> ORGANISM: Homo sapiens

<400> SEQUENCE: 1100

Glu Lys Tyr Leu Thr Trp Ala Ser Arg Gln Glu Pro Ser Gln Gly Thr
1               5                   10                  15

Thr Thr Phe Ala Val Thr Ser Ile Leu Arg
            20                  25

<210> SEQ ID NO 1101
<211> LENGTH: 20
<212> TYPE: PRT
<213> ORGANISM: Homo sapiens

<400> SEQUENCE: 1101

Gly Asp Thr Phe Ser Cys Met Val Gly His Glu Ala Leu Pro Leu Ala
1               5                   10                  15

Phe Thr Gln Lys
            20

<210> SEQ ID NO 1102
<211> LENGTH: 20
<212> TYPE: PRT
<213> ORGANISM: Homo sapiens

<400> SEQUENCE: 1102

Gly Phe Ser Pro Lys Asp Val Leu Val Arg Trp Leu Gln Gly Ser Gln
1               5                   10                  15

Glu Leu Pro Arg
            20

<210> SEQ ID NO 1103
<211> LENGTH: 25
<212> TYPE: PRT
<213> ORGANISM: Homo sapiens

<400> SEQUENCE: 1103

His Tyr Thr Asn Pro Ser Gln Asp Val Thr Val Pro Cys Pro Val Pro
1               5                   10                  15

Pro Pro Pro Pro Cys Cys His Pro Arg
            20                  25

<210> SEQ ID NO 1104
<211> LENGTH: 21
<212> TYPE: PRT
<213> ORGANISM: Homo sapiens

<400> SEQUENCE: 1104

```
Lys Gly Asp Thr Phe Ser Cys Met Val Gly His Glu Ala Leu Pro Leu
1               5                   10                  15

Ala Phe Thr Gln Lys
            20
```

<210> SEQ ID NO 1105
<211> LENGTH: 30
<212> TYPE: PRT
<213> ORGANISM: Homo sapiens

<400> SEQUENCE: 1105

```
Asn Phe Pro Pro Ser Gln Asp Ala Ser Gly Asp Leu Tyr Thr Thr Ser
1               5                   10                  15

Ser Gln Leu Thr Leu Pro Ala Thr Gln Cys Pro Asp Gly Lys
            20                  25                  30
```

<210> SEQ ID NO 1106
<211> LENGTH: 17
<212> TYPE: PRT
<213> ORGANISM: Homo sapiens

<400> SEQUENCE: 1106

```
Gln Glu Pro Ser Gln Gly Thr Thr Phe Ala Val Thr Ser Ile Leu
1               5                   10                  15

Arg
```

<210> SEQ ID NO 1107
<211> LENGTH: 9
<212> TYPE: PRT
<213> ORGANISM: Homo sapiens

<400> SEQUENCE: 1107

```
Ser Ala Val Gln Gly Pro Pro Glu Arg
1               5
```

<210> SEQ ID NO 1108
<211> LENGTH: 32
<212> TYPE: PRT
<213> ORGANISM: Homo sapiens

<400> SEQUENCE: 1108

```
Ser Gly Asn Thr Phe Arg Pro Glu Val His Leu Leu Pro Pro Ser
1               5                   10                  15

Glu Glu Leu Ala Leu Asn Glu Leu Val Thr Leu Thr Cys Leu Ala Arg
            20                  25                  30
```

<210> SEQ ID NO 1109
<211> LENGTH: 7
<212> TYPE: PRT
<213> ORGANISM: Homo sapiens

<400> SEQUENCE: 1109

```
Ser Val Thr Cys His Val Lys
1               5
```

<210> SEQ ID NO 1110
<211> LENGTH: 10
<212> TYPE: PRT
<213> ORGANISM: Homo sapiens

<400> SEQUENCE: 1110

```
Gly Phe Ser Pro Lys Asp Val Leu Val Arg
1               5                   10
```

<210> SEQ ID NO 1111
<211> LENGTH: 13
<212> TYPE: PRT
<213> ORGANISM: Homo sapiens

<400> SEQUENCE: 1111

Ala Gly Lys Gly Met His Gly Gly Val Pro Gly Gly Lys
1               5                   10

<210> SEQ ID NO 1112
<211> LENGTH: 10
<212> TYPE: PRT
<213> ORGANISM: Homo sapiens

<400> SEQUENCE: 1112

Gly Met His Gly Gly Val Pro Gly Gly Lys
1               5                   10

<210> SEQ ID NO 1113
<211> LENGTH: 7
<212> TYPE: PRT
<213> ORGANISM: Homo sapiens

<400> SEQUENCE: 1113

Gln Glu Leu Asn Pro Leu Lys
1               5

<210> SEQ ID NO 1114
<211> LENGTH: 10
<212> TYPE: PRT
<213> ORGANISM: Homo sapiens

<400> SEQUENCE: 1114

Gln Phe Ile Glu Ser Glu Cys Ile Pro Arg
1               5                   10

<210> SEQ ID NO 1115
<211> LENGTH: 85
<212> TYPE: PRT
<213> ORGANISM: Homo sapiens

<400> SEQUENCE: 1115

Pro Ala Gln Glu Ala Gly Thr Ser Lys Pro Asn Glu Glu Ile Ser Gly
1               5                   10                  15

Pro Ala Glu Pro Ala Ser Pro Pro Glu Thr Thr Thr Thr Ala Gln Glu
            20                  25                  30

Thr Ser Ala Ala Ala Val Gln Gly Thr Ala Lys Val Thr Ser Ser Arg
        35                  40                  45

Gln Glu Leu Asn Pro Leu Lys Gln Ala Leu Ala Lys Ala Gly Lys Gly
    50                  55                  60

Met His Gly Gly Val Pro Gly Gly Lys Gln Phe Ile Glu Ser Glu Cys
65                  70                  75                  80

Ile Pro Arg Trp Lys
                85

<210> SEQ ID NO 1116
<211> LENGTH: 21
<212> TYPE: PRT
<213> ORGANISM: Homo sapiens

<400> SEQUENCE: 1116

```
Val Phe Ser Asn Gly Ala Asp Leu Ser Gly Val Thr Glu Glu Ala Pro
1               5                   10                  15

Leu Lys Leu Ser Lys
            20

<210> SEQ ID NO 1117
<211> LENGTH: 7
<212> TYPE: PRT
<213> ORGANISM: Homo sapiens

<400> SEQUENCE: 1117

Ser Pro Leu Phe Met Gly Lys
1               5

<210> SEQ ID NO 1118
<211> LENGTH: 22
<212> TYPE: PRT
<213> ORGANISM: Homo sapiens

<400> SEQUENCE: 1118

Gly Phe Tyr Pro Ser Asp Ile Ser Val Glu Trp Glu Ser Asn Gly Gln
1               5                   10                  15

Pro Glu Asn Asn Tyr Lys
            20

<210> SEQ ID NO 1119
<211> LENGTH: 11
<212> TYPE: PRT
<213> ORGANISM: Homo sapiens

<400> SEQUENCE: 1119

Asp Leu Ala Thr Val Tyr Val Asp Val Leu Lys
1               5                   10

<210> SEQ ID NO 1120
<211> LENGTH: 15
<212> TYPE: PRT
<213> ORGANISM: Homo sapiens

<400> SEQUENCE: 1120

Ala Gly Val Glu Thr Thr Thr Pro Ser Lys Gln Ser Asn Asn Lys
1               5                   10                  15

<210> SEQ ID NO 1121
<211> LENGTH: 8
<212> TYPE: PRT
<213> ORGANISM: Homo sapiens

<400> SEQUENCE: 1121

Ser Glu Gln Phe Ile Asn Leu Arg
1               5

<210> SEQ ID NO 1122
<211> LENGTH: 8
<212> TYPE: PRT
<213> ORGANISM: Homo sapiens

<400> SEQUENCE: 1122

Leu Pro Ala Ser Phe Asp Ala Arg
1               5

<210> SEQ ID NO 1123
<211> LENGTH: 17
<212> TYPE: PRT
```

-continued

<213> ORGANISM: Homo sapiens

<400> SEQUENCE: 1123

Thr Thr Ile Glu Lys Pro Val Trp Leu Gly Phe Leu Gly Pro Ile Ile
1               5                   10                  15

Lys

<210> SEQ ID NO 1124
<211> LENGTH: 11
<212> TYPE: PRT
<213> ORGANISM: Homo sapiens

<400> SEQUENCE: 1124

Asn Ser Lys Ile Glu Ile Ser Glu Leu Asn Arg
1               5                   10

<210> SEQ ID NO 1125
<211> LENGTH: 16
<212> TYPE: PRT
<213> ORGANISM: Homo sapiens

<400> SEQUENCE: 1125

Ile Pro Glu Pro Gly Cys Thr Lys Val Pro Glu Pro Gly Cys Thr Lys
1               5                   10                  15

<210> SEQ ID NO 1126
<211> LENGTH: 23
<212> TYPE: PRT
<213> ORGANISM: Homo sapiens

<400> SEQUENCE: 1126

Glu Glu Pro Trp Val Asp Pro Asn Ser Pro Val Leu Leu Glu Asp Pro
1               5                   10                  15

Val Leu Cys Ala Leu Ala Lys
            20

<210> SEQ ID NO 1127
<211> LENGTH: 11
<212> TYPE: PRT
<213> ORGANISM: Homo sapiens

<400> SEQUENCE: 1127

Val Ala Phe Thr Gly Ser Thr Glu Val Gly Lys
1               5                   10

<210> SEQ ID NO 1128
<211> LENGTH: 24
<212> TYPE: PRT
<213> ORGANISM: Homo sapiens

<400> SEQUENCE: 1128

Asp Ala Ser Gly Val Thr Phe Thr Trp Thr Pro Ser Ser Gly Lys Ser
1               5                   10                  15

Ala Val Gln Gly Pro Pro Glu Arg
            20

<210> SEQ ID NO 1129
<211> LENGTH: 732
<212> TYPE: PRT
<213> ORGANISM: Homo sapiens

<400> SEQUENCE: 1129

Met Pro Glu Glu Thr Gln Thr Gln Asp Gln Pro Met Glu Glu Glu Glu

-continued

```
1               5                   10                  15
Val Glu Thr Phe Ala Phe Gln Ala Glu Ile Ala Gln Leu Met Ser Leu
        20                  25                  30

Ile Ile Asn Thr Phe Tyr Ser Asn Lys Glu Ile Phe Leu Arg Glu Leu
        35                  40                  45

Ile Ser Asn Ser Ser Asp Ala Leu Asp Lys Ile Arg Tyr Glu Ser Leu
        50                  55                  60

Thr Asp Pro Ser Lys Leu Asp Ser Gly Lys Glu Leu His Ile Asn Leu
65                  70                  75                  80

Ile Pro Asn Lys Gln Asp Arg Thr Leu Thr Ile Val Asp Thr Gly Ile
                    85                  90                  95

Gly Met Thr Lys Ala Asp Leu Ile Asn Asn Leu Gly Thr Ile Ala Lys
                    100                 105                 110

Ser Gly Thr Lys Ala Phe Met Glu Ala Leu Gln Ala Gly Ala Asp Ile
                    115                 120                 125

Ser Met Ile Gly Gln Phe Gly Val Gly Phe Tyr Ser Ala Tyr Leu Val
        130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                    165                 170                 175

Gly Glu Pro Met Gly Arg Gly Thr Lys Val Ile Leu His Leu Lys Glu
                    180                 185                 190

Asp Gln Thr Glu Tyr Leu Glu Glu Arg Arg Ile Lys Glu Ile Val Lys
            195                 200                 205

Lys His Ser Gln Phe Ile Gly Tyr Pro Ile Thr Leu Phe Val Glu Lys
        210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                    245                 250                 255

Glu Ile Glu Asp Val Gly Ser Asp Glu Glu Glu Glu Lys Lys Asp Gly
                    260                 265                 270

Asp Lys Lys Lys Lys Lys Ile Lys Glu Lys Tyr Ile Asp Gln Glu
            275                 280                 285

Glu Leu Asn Lys Thr Lys Pro Ile Trp Thr Arg Asn Pro Asp Asp Ile
        290                 295                 300

Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu
                    325                 330                 335

Phe Arg Ala Leu Leu Phe Val Pro Arg Arg Ala Pro Phe Asp Leu Phe
                    340                 345                 350

Glu Asn Arg Lys Lys Lys Asn Asn Ile Lys Leu Tyr Val Arg Arg Val
                    355                 360                 365

Phe Ile Met Asp Asn Cys Glu Glu Leu Ile Pro Glu Tyr Leu Asn Phe
                    370                 375                 380

Ile Arg Gly Val Val Asp Ser Glu Asp Leu Pro Leu Asn Ile Ser Arg
385                 390                 395                 400

Glu Met Leu Gln Gln Ser Lys Ile Leu Lys Val Ile Arg Lys Asn Leu
                    405                 410                 415

Val Lys Lys Cys Leu Glu Leu Phe Thr Glu Leu Ala Glu Asp Lys Glu
                    420                 425                 430
```

```
Asn Tyr Lys Lys Phe Tyr Glu Gln Phe Ser Lys Asn Ile Lys Leu Gly
        435                 440                 445
Ile His Glu Asp Ser Gln Asn Arg Lys Lys Leu Ser Glu Leu Leu Arg
    450                 455                 460
Tyr Tyr Thr Ser Ala Ser Gly Asp Glu Met Val Ser Leu Lys Asp Tyr
465                 470                 475                 480
Cys Thr Arg Met Lys Glu Asn Gln Lys His Ile Tyr Tyr Ile Thr Gly
                485                 490                 495
Glu Thr Lys Asp Gln Val Ala Asn Ser Ala Phe Val Glu Arg Leu Arg
                500                 505                 510
Lys His Gly Leu Glu Val Ile Tyr Met Ile Glu Pro Ile Asp Glu Tyr
            515                 520                 525
Cys Val Gln Gln Leu Lys Glu Phe Glu Gly Lys Thr Leu Val Ser Val
        530                 535                 540
Thr Lys Glu Gly Leu Glu Leu Pro Glu Asp Glu Glu Lys Lys
545                 550                 555                 560
Gln Glu Glu Lys Lys Thr Lys Phe Glu Asn Leu Cys Lys Ile Met Lys
                565                 570                 575
Asp Ile Leu Glu Lys Lys Val Glu Lys Val Val Ser Asn Arg Leu
            580                 585                 590
Val Thr Ser Pro Cys Cys Ile Val Thr Ser Thr Tyr Gly Trp Thr Ala
        595                 600                 605
Asn Met Glu Arg Ile Met Lys Ala Gln Ala Leu Arg Asp Asn Ser Thr
    610                 615                 620
Met Gly Tyr Met Ala Ala Lys Lys His Leu Glu Ile Asn Pro Asp His
625                 630                 635                 640
Ser Ile Ile Glu Thr Leu Arg Gln Lys Ala Glu Ala Asp Lys Asn Asp
                645                 650                 655
Lys Ser Val Lys Asp Leu Val Ile Leu Leu Tyr Glu Thr Ala Leu Leu
            660                 665                 670
Ser Ser Gly Phe Ser Leu Glu Asp Pro Gln Thr His Ala Asn Arg Ile
        675                 680                 685
Tyr Arg Met Ile Lys Leu Gly Leu Gly Ile Asp Glu Asp Pro Thr
    690                 695                 700
Ala Asp Asp Thr Ser Ala Ala Val Thr Glu Glu Met Pro Pro Leu Glu
705                 710                 715                 720
Gly Asp Asp Asp Thr Ser Arg Met Glu Glu Val Asp
                725                 730

<210> SEQ ID NO 1130
<211> LENGTH: 724
<212> TYPE: PRT
<213> ORGANISM: Homo sapiens

<400> SEQUENCE: 1130

Met Pro Glu Glu Val His His Gly Glu Glu Val Glu Thr Phe Ala
1               5                   10                  15
Phe Gln Ala Glu Ile Ala Gln Leu Met Ser Leu Ile Ile Asn Thr Phe
                20                  25                  30
Tyr Ser Asn Lys Glu Ile Phe Leu Arg Glu Leu Ile Ser Asn Ala Ser
            35                  40                  45
Asp Ala Leu Asp Lys Ile Arg Tyr Glu Ser Leu Thr Asp Pro Ser Lys
        50                  55                  60
Leu Asp Ser Gly Lys Glu Leu Lys Ile Asp Ile Ile Pro Asn Pro Gln
```

```
                65                  70                  75                  80
        Glu Arg Thr Leu Thr Leu Val Asp Thr Gly Ile Gly Met Thr Lys Ala
                        85                  90                  95

Asp Leu Ile Asn Asn Leu Gly Thr Ile Ala Lys Ser Gly Thr Lys Ala
                        100                 105                 110

Phe Met Glu Ala Leu Gln Ala Gly Ala Asp Ile Ser Met Ile Gly Gln
                        115                 120                 125

Phe Gly Val Gly Phe Tyr Ser Ala Tyr Leu Val Ala Glu Lys Val Val
                        130                 135                 140

Val Ile Thr Lys His Asn Asp Asp Glu Gln Tyr Ala Trp Glu Ser Ser
        145                 150                 155                 160

Ala Gly Gly Ser Phe Thr Val Arg Ala Asp His Gly Glu Pro Ile Gly
                        165                 170                 175

Arg Gly Thr Lys Val Ile Leu His Leu Lys Glu Asp Gln Thr Glu Tyr
                        180                 185                 190

Leu Glu Glu Arg Arg Val Lys Glu Val Val Lys Lys His Ser Gln Phe
                        195                 200                 205

Ile Gly Tyr Pro Ile Thr Leu Tyr Leu Glu Lys Glu Arg Glu Lys Glu
                        210                 215                 220

Ile Ser Asp Asp Glu Ala Glu Glu Lys Gly Glu Lys Glu Glu Glu
        225                 230                 235                 240

Asp Lys Asp Asp Glu Glu Lys Pro Lys Ile Glu Asp Val Gly Ser Asp
                        245                 250                 255

Glu Glu Asp Asp Ser Gly Lys Asp Lys Lys Lys Thr Lys Lys Ile
                        260                 265                 270

Lys Glu Lys Tyr Ile Asp Gln Glu Glu Leu Asn Lys Thr Lys Pro Ile
                        275                 280                 285

Trp Thr Arg Asn Pro Asp Asp Ile Thr Gln Glu Glu Tyr Gly Glu Phe
                        290                 295                 300

Tyr Lys Ser Leu Thr Asn Asp Trp Glu Asp His Leu Ala Val Lys His
        305                 310                 315                 320

Phe Ser Val Glu Gly Gln Leu Glu Phe Arg Ala Leu Leu Phe Ile Pro
                        325                 330                 335

Arg Arg Ala Pro Phe Asp Leu Phe Glu Asn Lys Lys Lys Asn Asn
                        340                 345                 350

Ile Lys Leu Tyr Val Arg Arg Val Phe Ile Met Asp Ser Cys Asp Glu
                        355                 360                 365

Leu Ile Pro Glu Tyr Leu Asn Phe Ile Arg Gly Val Val Asp Ser Glu
                        370                 375                 380

Asp Leu Pro Leu Asn Ile Ser Arg Glu Met Leu Gln Gln Ser Lys Ile
        385                 390                 395                 400

Leu Lys Val Ile Arg Lys Asn Ile Val Lys Cys Leu Glu Leu Phe
                        405                 410                 415

Ser Glu Leu Ala Glu Asp Lys Glu Asn Tyr Lys Lys Phe Tyr Glu Ala
                        420                 425                 430

Phe Ser Lys Asn Leu Lys Leu Gly Ile His Glu Asp Ser Thr Asn Arg
                        435                 440                 445

Arg Arg Leu Ser Glu Leu Leu Arg Tyr His Thr Ser Gln Ser Gly Asp
                        450                 455                 460

Glu Met Thr Ser Leu Ser Glu Tyr Val Ser Arg Met Lys Glu Thr Gln
        465                 470                 475                 480

Lys Ser Ile Tyr Tyr Ile Thr Gly Glu Ser Lys Glu Gln Val Ala Asn
                        485                 490                 495
```

-continued

Ser Ala Phe Val Glu Arg Val Arg Lys Arg Gly Phe Glu Val Val Tyr
                500                 505                 510

Met Thr Glu Pro Ile Asp Glu Tyr Cys Val Gln Gln Leu Lys Glu Phe
                515                 520                 525

Asp Gly Lys Ser Leu Val Ser Val Thr Lys Glu Gly Leu Glu Leu Pro
                530                 535                 540

Glu Asp Glu Glu Glu Lys Lys Lys Met Glu Glu Ser Lys Ala Lys Phe
545                 550                 555                 560

Glu Asn Leu Cys Lys Leu Met Lys Glu Ile Leu Asp Lys Lys Val Glu
                565                 570                 575

Lys Val Thr Ile Ser Asn Arg Leu Val Ser Ser Pro Cys Cys Ile Val
                580                 585                 590

Thr Ser Thr Tyr Gly Trp Thr Ala Asn Met Glu Arg Ile Met Lys Ala
                595                 600                 605

Gln Ala Leu Arg Asp Asn Ser Thr Met Gly Tyr Met Met Ala Lys Lys
                610                 615                 620

His Leu Glu Ile Asn Pro Asp His Pro Ile Val Glu Thr Leu Arg Gln
625                 630                 635                 640

Lys Ala Glu Ala Asp Lys Asn Asp Lys Ala Val Lys Asp Leu Val Val
                645                 650                 655

Leu Leu Phe Glu Thr Ala Leu Leu Ser Ser Gly Phe Ser Leu Glu Asp
                660                 665                 670

Pro Gln Thr His Ser Asn Arg Ile Tyr Arg Met Ile Lys Leu Gly Leu
                675                 680                 685

Gly Ile Asp Glu Asp Glu Val Ala Ala Glu Glu Pro Asn Ala Ala Val
                690                 695                 700

Pro Asp Glu Ile Pro Pro Leu Glu Gly Asp Glu Asp Ala Ser Arg Met
705                 710                 715                 720

Glu Glu Val Asp

<210> SEQ ID NO 1131
<211> LENGTH: 9
<212> TYPE: PRT
<213> ORGANISM: Homo sapiens

<400> SEQUENCE: 1131

Ala Pro Phe Asp Leu Phe Glu Asn Arg
1               5

<210> SEQ ID NO 1132
<211> LENGTH: 17
<212> TYPE: PRT
<213> ORGANISM: Homo sapiens

<400> SEQUENCE: 1132

Cys Leu Glu Leu Phe Thr Glu Leu Ala Glu Asp Lys Glu Asn Tyr Lys
1               5                   10                  15

Lys

<210> SEQ ID NO 1133
<211> LENGTH: 27
<212> TYPE: PRT
<213> ORGANISM: Homo sapiens

<400> SEQUENCE: 1133

Asp Leu Val Ile Leu Leu Tyr Glu Thr Ala Leu Leu Ser Ser Gly Phe
1               5                   10                  15

```
Ser Leu Glu Asp Pro Gln Thr His Ala Asn Arg
            20                  25

<210> SEQ ID NO 1134
<211> LENGTH: 11
<212> TYPE: PRT
<213> ORGANISM: Homo sapiens

<400> SEQUENCE: 1134

Asp Gln Val Ala Asn Ser Ala Phe Val Glu Arg
1               5                   10

<210> SEQ ID NO 1135
<211> LENGTH: 12
<212> TYPE: PRT
<213> ORGANISM: Homo sapiens

<400> SEQUENCE: 1135

Glu Leu Ile Ser Asn Ser Ser Asp Ala Leu Asp Lys
1               5                   10

<210> SEQ ID NO 1136
<211> LENGTH: 14
<212> TYPE: PRT
<213> ORGANISM: Homo sapiens

<400> SEQUENCE: 1136

Gly Val Val Asp Ser Glu Asp Leu Pro Leu Asn Ile Ser Arg
1               5                   10

<210> SEQ ID NO 1137
<211> LENGTH: 10
<212> TYPE: PRT
<213> ORGANISM: Homo sapiens

<400> SEQUENCE: 1137

His Ile Tyr Tyr Ile Thr Gly Glu Thr Lys
1               5                   10

<210> SEQ ID NO 1138
<211> LENGTH: 15
<212> TYPE: PRT
<213> ORGANISM: Homo sapiens

<400> SEQUENCE: 1138

His Leu Glu Ile Asn Pro Asp His Ser Ile Ile Glu Thr Leu Arg
1               5                   10                  15

<210> SEQ ID NO 1139
<211> LENGTH: 15
<212> TYPE: PRT
<213> ORGANISM: Homo sapiens

<400> SEQUENCE: 1139

His Ser Gln Phe Ile Gly Tyr Pro Ile Thr Leu Phe Val Glu Lys
1               5                   10                  15

<210> SEQ ID NO 1140
<211> LENGTH: 10
<212> TYPE: PRT
<213> ORGANISM: Homo sapiens

<400> SEQUENCE: 1140

Leu Gly Ile His Glu Asp Ser Gln Asn Arg
```

```
1               5                   10
```

<210> SEQ ID NO 1141
<211> LENGTH: 15
<212> TYPE: PRT
<213> ORGANISM: Homo sapiens

<400> SEQUENCE: 1141

```
Asn Pro Asp Asp Ile Thr Asn Glu Glu Tyr Gly Glu Phe Tyr Lys
1               5                   10                  15
```

<210> SEQ ID NO 1142
<211> LENGTH: 13
<212> TYPE: PRT
<213> ORGANISM: Homo sapiens

<400> SEQUENCE: 1142

```
Ser Leu Thr Asn Asp Trp Glu Asp His Leu Ala Val Lys
1               5                   10
```

<210> SEQ ID NO 1143
<211> LENGTH: 16
<212> TYPE: PRT
<213> ORGANISM: Homo sapiens

<400> SEQUENCE: 1143

```
Val Ile Leu His Leu Lys Glu Asp Gln Thr Glu Tyr Leu Glu Glu Arg
1               5                   10                  15
```

<210> SEQ ID NO 1144
<211> LENGTH: 9
<212> TYPE: PRT
<213> ORGANISM: Homo sapiens

<400> SEQUENCE: 1144

```
Tyr Ile Asp Gln Glu Glu Leu Asn Lys
1               5
```

<210> SEQ ID NO 1145
<211> LENGTH: 11
<212> TYPE: PRT
<213> ORGANISM: Homo sapiens

<400> SEQUENCE: 1145

```
Glu Gln Val Ala Asn Ser Ala Phe Val Glu Arg
1               5                   10
```

<210> SEQ ID NO 1146
<211> LENGTH: 14
<212> TYPE: PRT
<213> ORGANISM: Homo sapiens

<400> SEQUENCE: 1146

```
Gly Val Val Asp Ser Glu Asp Leu Pro Leu Asn Ile Ser Arg
1               5                   10
```

<210> SEQ ID NO 1147
<211> LENGTH: 15
<212> TYPE: PRT
<213> ORGANISM: Homo sapiens

<400> SEQUENCE: 1147

```
Asn Pro Asp Asp Ile Thr Gln Glu Glu Tyr Gly Glu Phe Tyr Lys
1               5                   10                  15
```

-continued

```
<210> SEQ ID NO 1148
<211> LENGTH: 10
<212> TYPE: PRT
<213> ORGANISM: Homo sapiens

<400> SEQUENCE: 1148

Ser Ile Tyr Tyr Ile Thr Gly Glu Ser Lys
1               5                   10

<210> SEQ ID NO 1149
<211> LENGTH: 13
<212> TYPE: PRT
<213> ORGANISM: Homo sapiens

<400> SEQUENCE: 1149

Ser Leu Thr Asn Asp Trp Glu Asp His Leu Ala Val Lys
1               5                   10

<210> SEQ ID NO 1150
<211> LENGTH: 16
<212> TYPE: PRT
<213> ORGANISM: Homo sapiens

<400> SEQUENCE: 1150

Val Ile Leu His Leu Lys Glu Asp Gln Thr Glu Tyr Leu Glu Glu Arg
1               5                   10                  15

<210> SEQ ID NO 1151
<211> LENGTH: 9
<212> TYPE: PRT
<213> ORGANISM: Homo sapiens

<400> SEQUENCE: 1151

Tyr Ile Asp Gln Glu Glu Leu Asn Lys
1               5

<210> SEQ ID NO 1152
<211> LENGTH: 17
<212> TYPE: PRT
<213> ORGANISM: Homo sapiens

<400> SEQUENCE: 1152

Ala Asp Gly Ser Pro Val Lys Ala Gly Val Glu Thr Thr Lys Pro Ser
1               5                   10                  15

Lys

<210> SEQ ID NO 1153
<211> LENGTH: 10
<212> TYPE: PRT
<213> ORGANISM: Homo sapiens

<400> SEQUENCE: 1153

Ala Gly Val Glu Thr Thr Lys Pro Ser Lys
1               5                   10

<210> SEQ ID NO 1154
<211> LENGTH: 19
<212> TYPE: PRT
<213> ORGANISM: Homo sapiens

<400> SEQUENCE: 1154

Ala Asn Pro Thr Val Thr Leu Phe Pro Pro Ser Ser Glu Glu Leu Gln
1               5                   10                  15
```

-continued

Ala Asn Lys

<210> SEQ ID NO 1155
<211> LENGTH: 20
<212> TYPE: PRT
<213> ORGANISM: Homo sapiens

<400> SEQUENCE: 1155

Gln Ser Asn Asn Lys Tyr Ala Ala Ser Ser Tyr Leu Ser Leu Thr Pro
1               5                   10                  15

Glu Gln Trp Lys
            20

<210> SEQ ID NO 1156
<211> LENGTH: 13
<212> TYPE: PRT
<213> ORGANISM: Homo sapiens

<400> SEQUENCE: 1156

Arg Pro Ser Gly Val Pro Asp Arg Phe Ser Gly Ser Lys
1               5                   10

<210> SEQ ID NO 1157
<211> LENGTH: 18
<212> TYPE: PRT
<213> ORGANISM: Homo sapiens

<400> SEQUENCE: 1157

Ser His Arg Ser Tyr Ser Cys Gln Val Thr His Glu Gly Ser Thr Val
1               5                   10                  15

Glu Lys

<210> SEQ ID NO 1158
<211> LENGTH: 15
<212> TYPE: PRT
<213> ORGANISM: Homo sapiens

<400> SEQUENCE: 1158

Ser Tyr Ser Cys Gln Val Thr His Glu Gly Ser Thr Val Glu Lys
1               5                   10                  15

<210> SEQ ID NO 1159
<211> LENGTH: 23
<212> TYPE: PRT
<213> ORGANISM: Homo sapiens

<400> SEQUENCE: 1159

Ser Tyr Ser Cys Gln Val Thr His Glu Gly Ser Thr Val Glu Lys Thr
1               5                   10                  15

Val Ala Pro Thr Glu Cys Ser
            20

<210> SEQ ID NO 1160
<211> LENGTH: 8
<212> TYPE: PRT
<213> ORGANISM: Homo sapiens

<400> SEQUENCE: 1160

Thr Val Ala Pro Thr Glu Cys Ser
1               5

<210> SEQ ID NO 1161
<211> LENGTH: 13

-continued

```
<212> TYPE: PRT
<213> ORGANISM: Homo sapiens

<400> SEQUENCE: 1161

Ile Tyr Gly Asn Gln Asp Thr Ser Ser Gln Leu Lys Lys
1               5                   10

<210> SEQ ID NO 1162
<211> LENGTH: 11
<212> TYPE: PRT
<213> ORGANISM: Homo sapiens

<400> SEQUENCE: 1162

Glu Pro Gln Val Tyr Thr Leu Pro Pro Ser Arg
1               5                   10
```